US010632185B2

United States Patent
Kinney

(10) Patent No.: US 10,632,185 B2
(45) Date of Patent: Apr. 28, 2020

(54) CHIMERIC WEST NILE/ZIKA VIRUSES AND METHODS OF USE

(71) Applicant: The United States of America, as represented by the Secretary, Department of Health and Human Services, Bethesda, MD (US)

(72) Inventor: Claire Y. H. Kinney, Fort Collins, CO (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/315,897

(22) PCT Filed: Jul. 6, 2017

(86) PCT No.: PCT/US2017/040818
§ 371 (c)(1),
(2) Date: Jan. 7, 2019

(87) PCT Pub. No.: WO2018/009603
PCT Pub. Date: Jan. 11, 2018

(65) Prior Publication Data
US 2019/0298818 A1    Oct. 3, 2019

Related U.S. Application Data

(60) Provisional application No. 62/359,807, filed on Jul. 8, 2016.

(51) Int. Cl.
| | | |
|---|---|---|
| *A61K 39/12* | (2006.01) | |
| *A61K 39/00* | (2006.01) | |
| *C07K 14/005* | (2006.01) | |
| *C12N 7/00* | (2006.01) | |
| *A61K 39/295* | (2006.01) | |
| *G01N 33/533* | (2006.01) | |

(52) U.S. Cl.
CPC ............ *A61K 39/12* (2013.01); *C07K 14/005* (2013.01); *C12N 7/00* (2013.01); *G01N 33/533* (2013.01); *A61K 2039/525* (2013.01); *A61K 2039/5252* (2013.01); *A61K 2039/5254* (2013.01); *A61K 2039/53* (2013.01); *C12N 2770/24122* (2013.01); *C12N 2770/24134* (2013.01); *C12N 2770/24141* (2013.01); *C12N 2770/24144* (2013.01); *Y02A 50/392* (2018.01); *Y02A 50/394* (2018.01)

(58) Field of Classification Search
CPC ............ C12N 7/00; C12N 2770/24122; C07K 14/005; Y02A 50/386; Y02A 50/388
See application file for complete search history.

(56) References Cited

U.S. PATENT DOCUMENTS

| 8,715,689 B2 | 5/2014 | Kinney et al. |
|---|---|---|
| 2017/0114330 A1 | 4/2017 | Kinney |

FOREIGN PATENT DOCUMENTS

| WO | WO2015196094 | * 12/2005 |
|---|---|---|
| WO | WO 2015/1960954 | 12/2015 |
| WO | WO2015196094 | * 12/2015 |

OTHER PUBLICATIONS

Chao et al. "Zika virus: diagnosis, therapeutics, and vaccine", ACS infectious diseases, 2(3), 2016:170-172.*
Cohen, "The race for a Zika vaccine is on," *Science*, vol. 351:543-544, 2016.
Faria et al., "Zika Virus in the Americas: Early Epidemiological and Genetic Findings," *Science*, vol. 352:345-349, 2016.
Heymann et al., "Zika Virus and Microcephaly: Why is this Situation a PHEIC?" *Lancet*, vol. 387:719-721, 2016.
Shan et al "Zika Virus: Diagnosis, Therapeutics, and Vaccine," *ACS Infect. Dis.*, vol. 2:170-172, 2016.
Shan et al., "An Infectious cDNA Clone of Zika Virus to Study Viral Virulence, Mosquito Transmission, and Antiviral Inhibitors," *Cell Host & Microbe*, vol. 19:891-900, 2016.
Shan et al., "A Rapid Zika Diagnostic Assay to Measure Neutralizing Antibodies in Patients," *EBioMed.*, vol. 17:157-162, 2017.
Suzuki et al., "Construction and Characterization of a Single-Cycle Chimeric Flavivirus Vaccine Candidate that Protects Mice Against Lethal Challenge with Dengue Virus Type 2," *J. Virol.*, vol. 83:1870-1880, 2009.
Weaver et al., "Zika Virus: History, Emergence, Biology, and Prospects for Control," *Antiviral Res.*, vol. 130:69-80, 2016.

* cited by examiner

*Primary Examiner* — Barry A Chestnut
(74) *Attorney, Agent, or Firm* — Klarquist Sparkman, LLP

(57) ABSTRACT

Chimeric flaviviruses that include non-coding regions, non-structural proteins, a capsid (C) protein and a portion of a premembrane (prM) signal sequence from West Nile virus (WNV), and a portion of a prM signal sequence, a prM protein and an E protein from Zika virus (VIKV) are described. Also described are compositions and methods for eliciting an immune response in a subject, such as an immune response directed against ZIKV. Diagnostic assays that utilize chimeric West Nile/Zika viruses are further described.

39 Claims, 6 Drawing Sheets
Specification includes a Sequence Listing.

FIG. 1

NS2B-3 protease cleavage        Signalase cleavage
              C    PrM Signal Sequence (SS)    PrM WNV NY99      AAGAAAAGA GGAGGAAAGA CCGGAATTGC AGTCATGATT GGCTGGCTTG TGGGAGGAAA CACCATGCAG AGAGTGGTGT TTGTCGTGCT ATTGCTATTG GTGGCCCCAG CCTACAGCTT CAACTGCCTT GGAATGTCAA
              K K R    G G K    T G I A V M I G L I A S V G A    G V T L S N F G G ZIKV R103451  AAGAAAACGA GGAGGAAAGA CCGGAGTTCA TTGGTCGTGC TGCTGCTGCT AGTTGCCATG GTGCTGAAGT ACAAGCTGCT GACCAGTGGG GCAACCAGTG AGAAGACCTG AACCAGTGGG GCAGCGGAGG
              K R R    G A D T S V G I V G L L L T A M A    A E V T R R G S Chimeric WN/ZKVs:

WN/ZKV-Z3     AAGAAAAAGA GGAGGAAAGA CCGGAATTGC AGTCATGATT GGCTGGCTTA GCCTGAATGC CATGGCAGCG GAGGTCACTA GACGTGGAAG T
              K K R    G G K    T G I A V M I G L I A S    A M A    A E V T R R G S

WN/ZKV-Z5     AAGAAAAAGA GGAGGAAAGA CCGGAATTGC AGTCATGATT GGCGGCTTAT TACCAGCAAT GGCAGCGGAG GTCACTAGAC GTGGAAGT
              K K R    G G K    T G I A V M I G L I I T A M A    A E V T R R G S

WN/ZKV-Z15    AAGAAAAAGA GGAGGAAAAG ACTAGTGTCG GAATTGTTGG TCTGCTGCTG ACCGCAATGG CAGCGGAGGT CACTAGACGT GGAAGT
              K K R    G G K    T S V G I V G L L L T A M A    A E V T R R G S

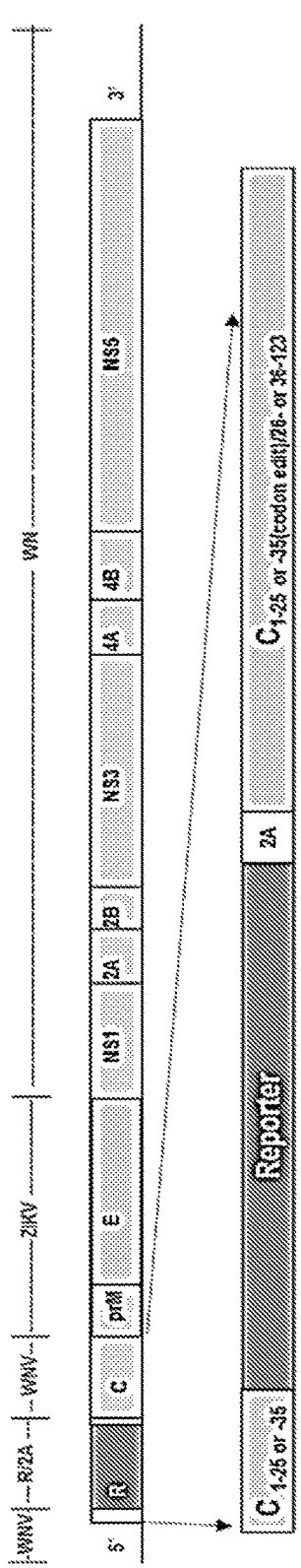
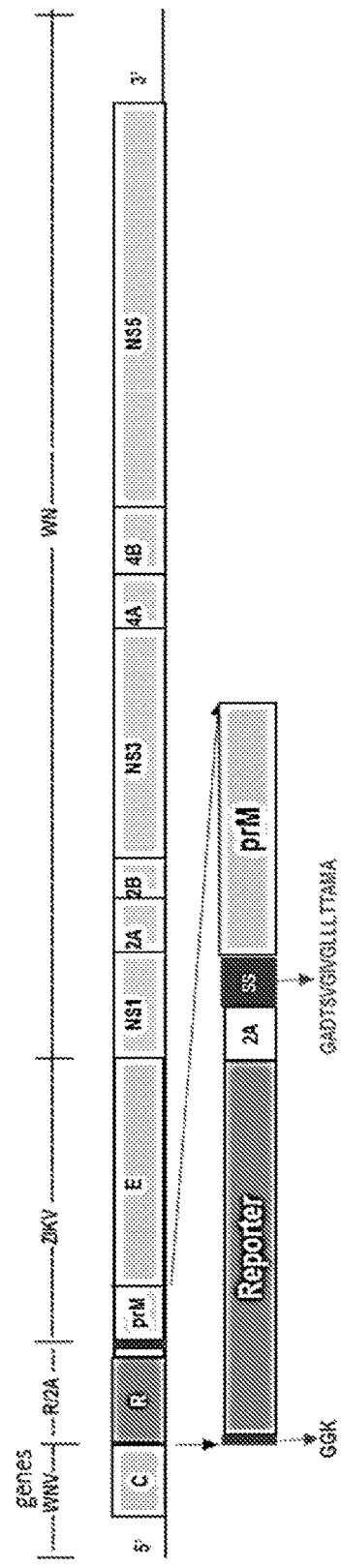
FIG. 2

FIG. 6

Comparison of Neutralization Assays

| | PRNT | Immuno-mFRNT | Fluoro-mFRNT |
|---|---|---|---|
| Detection | Plaque | Immunospot | Fluorospot |
| Processing | 1-2 overlays<br>Plaque staining<br>Plaque visualization | 1 overlay<br>Fixation and Immunostaining<br>Foci image | none<br>Live cell image (w/o fixation) |
| Plate Format | 6-, 12-, 24-well | 96-, 384-well | 96-, 384-well |
| Labor-intensive | High | High | Low |
| Estimated minimal time* | WN/ZKV: 72 hours<br>(wt ZKV: 120 hours) | WN/ZKV: 28 hours<br>(wt ZKV: 28/40 hours**) | R-WN/ZKV: 25 hours |
| Summary | Slow and labor-intensive | Fast and automatic readout, but labor-intensive | Fast and automatic readout, minimum procedures (high-throughput) |

* Minimal duration starts from cell infection with virus-Ab complex and ends at result readout
** 40 hours is better than 28 hours

CHIMERIC WEST NILE/ZIKA VIRUSES AND METHODS OF USE

CROSS REFERENCE TO RELATED APPLICATIONS

This application is the U.S. National Stage of International Application No. PCT/US2017/040818, file Jul. 6, 2017, published in English under PCT Article 21(2), which claims the benefit of U.S. Provisional Application No. 62/359,807, filed Jul. 8, 2016, which is herein incorporated by reference in its entirety.

FIELD

This disclosure concerns chimeric flaviviruses, particularly chimeric West Nile virus/Zika virus constructs. Further, it relates to methods of using the chimeric viruses for therapeutic and diagnostic applications.

BACKGROUND

Zika virus, a flavivirus classified within the Flaviviridae with other important mosquito-borne viruses, including yellow fever, dengue, West Nile and Japanese encephalitis viruses, has spread rapidly in a hemispheric-wide epidemic since the virus was introduced to Brazil in 2015, reaching Central and North Americas, including territories of the United States and now threatening the continental U.S. Initially isolated in 1947 in Uganda, the virus was first linked to human disease in 1952 and has been recognized sporadically as a cause of mild, self-limited febrile illness in Africa and Southeast Asia (Weaver et al., *Antiviral Res* 130:69-80, 2016; Faria et al., *Science* 352(6283):345-349, 2016). However, in 2007, an outbreak appeared in the North Pacific island of Yap, transferred there presumably from Asia, and subsequently disseminated from island to island across the Pacific, leading to an extensive outbreak in 2013-2014 in French Polynesia, with subsequent spread to New Caledonia, the Cook Islands, and ultimately to Easter Island, far to the East. An Asian lineage virus subsequently was transferred to the Western Hemisphere by routes that remain undetermined (Faria et al., *Science* 352(6283):345-349, 2016). The virus is transmitted anthropontically by *Aedes aegypti, A. albopictus* and possibly *A. hensilli* and *A. polynieseinsis* (Weaver et al., *Antiviral Res* 130:69-80, 2016).

In late 2015, a significant increase in fetal abnormalities (e.g. microcephaly) and Guillain-Barré syndrome (GBS) in areas of widespread Zika virus infection raised concerns that Zika virus might be much more virulent than originally thought and prompted the World Health Organization (WHO) to declare a Public Health Emergency of International Concern (PHEIC) (Heymann et al., *Lancet* 387 (10020):719-721, 2016).

SUMMARY

Disclosed herein are chimeric flaviviruses that include non-coding regions, a capsid (C) protein, a portion of a premembrane (prM) signal sequence, and non-structural proteins from West Nile virus (WNV); and a portion of a prM signal sequence, a prM protein and an envelope (E) protein from Zika virus (ZIKV). Also disclosed are compositions and methods for eliciting an immune response directed against ZIKV in a subject. Diagnostic assays that utilize the disclosed chimeric West Nile/Zika viruses are further described.

Provided herein is a nucleic acid chimera that includes nucleic acid sequence from a WNV and nucleic acid sequence from a ZIKV. In some embodiments, the nucleic acid chimera includes a first nucleic acid molecule comprising a 5' non-coding region, a nucleic acid encoding a C protein and non-structural proteins, and a 3' non-coding region, each from a WNV genome, wherein the C protein comprises a portion of a prM signal sequence from the WNV genome and a portion of a prM signal sequence from a ZIKV genome; and a second nucleic acid molecule operably linked to the first nucleic acid molecule, encoding a prM protein and an E protein from the ZIKV genome. In some examples, the portion of the prM signal sequence from the WNV genome includes the first 15 amino acids of the WNV prM signal sequence and the portion of the prM signal sequence from the ZIKV genome includes the last three amino acids of the ZIKV prM signal sequence. In other examples, the portion of the prM signal sequence from the WNV genome includes the first 13 amino acids of the WNV prM signal sequence and the portion of the prM signal sequence from the ZIKV genome includes the last five amino acids of the ZIKV prM signal sequence. In yet other examples, the portion of the prM signal sequence from the WNV genome includes the first three amino acids of the WNV prM signal sequence and the portion of the prM signal sequence from the ZIKV genome includes the last 15 amino acids of the ZIKV prM signal sequence.

Also provided herein is an immunogenic composition that includes an inactivated virus comprising a nucleic acid chimera disclosed herein, and a pharmaceutically acceptable carrier. Further provided is a method of eliciting an immune response against ZIKV in a subject by administering the immunogenic composition.

A method that includes inactivating a virus comprising a nucleic chimera disclosed herein is further provided by the present disclosure. The virus can be inactivated using any means known in the art, such as, but not limited to treating the virus with a chemical inactivation agent, high pressure, ultraviolet irradiation, gamma irradiation, or any combination thereof.

Further provided herein is a nucleic acid chimera that includes a first nucleic acid molecule comprising a 5' non-coding region, a nucleic acid encoding a C protein and non-structural proteins, and a 3' non-coding region, each from a WNV genome, wherein the C protein comprises a portion of a prM signal sequence from the WNV genome and a portion of a prM signal sequence from a ZIKV genome; and a second nucleic acid molecule operably linked to the first nucleic acid molecule, encoding a prM protein and an E protein from the ZIKV genome, and further includes a reporter gene, such as a reporter gene encoding a light-emitting protein, such as a fluorescent or bioluminescent protein.

Further provided herein are chimeric viruses that include a nucleic acid chimera disclosed herein.

Methods of detecting ZIKV-specific antibodies in a sample are also provided herein. In some embodiments, the method includes contacting the sample with a chimeric virus disclosed herein under conditions sufficient to form virus-antibody complexes if ZIKV antibodies are present in the sample; and detecting the virus-antibody complexes, thereby detecting ZIKV-specific antibodies in the sample.

In some embodiments, the method includes contacting the sample with a chimeric virus disclosed herein to form a virus-sample mixture, wherein virus-antibody complexes are formed in the virus-sample mixture if ZIKV-specific antibodies are present in the sample; inoculating a cell culture with the virus-sample mixture under conditions sufficient to allow plaque formation or micro-focus formation in the cell culture; and detecting a decrease in plaque formation or micro-focus formation in the cell culture as compared to a control cell culture, such as a control cell culture infected with virus only.

In some embodiments, the method includes providing a chimeric virus disclosed herein bound to a solid support; contacting the chimeric virus-bound solid support with the sample under conditions sufficient to form virus-antibody complexes if ZIKV-specific antibodies are present in the sample; contacting the virus-antibody complexes with a secondary antibody; and detecting binding of the secondary antibody to the virus-antibody complexes.

In some embodiments, the method includes providing a secondary antibody bound to a solid support; contacting the secondary antibody-bound solid support with the sample under conditions sufficient to allow binding of the secondary antibody to any ZIKV-specific antibodies present in the sample, thereby forming antibody-antibody complexes; contacting the antibody-antibody complexes with a chimeric virus disclosed herein under conditions sufficient for the chimeric virus to bind the ZIKV-specific antibodies, thereby forming immune complexes; and detecting the presence of the immune complexes.

In some embodiments, the method includes providing a ZIKV-specific antibody bound to a solid support; contacting the antibody-bound solid support with a chimeric virus disclosed herein under conditions sufficient for the chimeric virus to bind the ZIKV-specific antibody to form antibody-virus complexes; contacting the antibody-virus complexes with the sample to allow binding of any ZIKV-specific antibodies present in the sample to the chimeric virus, thereby forming immune complexes; contacting the immune complexes with a secondary antibody; and detecting binding of the secondary antibody to the immune complexes, thereby detecting ZIKV-specific antibodies present in the sample.

The foregoing and other objects, features, and advantages of the invention will become more apparent from the following detailed description, which proceeds with reference to the accompanying figures.

BRIEF DESCRIPTION OF THE DRAWINGS

FIG. 1 shows the genomic structure of chimeric West Nile/Zika viruses. Chimeric viruses contain prM-E of ZIKV in the genomic backbone of WNV. The chimeric C/prM junction site is enlarged to show the 3 different junction strategies. The NS2B-3 protease cleavage and signalase cleavage sites are indicated. WNV (NY99) and ZIKV (R103451; also referred to as "103451" in the GenBank database) nucleotide and amino acid sequences are shown. For the three chimeric viruses, boxes indicate the ZIKV portion of the sequence. The sequences shown include WNV NY99 (nucleotides 403-489 of SEQ ID NO: 17; amino acids 103-131 of SEQ ID NO: 18), ZIKV R103451 (nucleotides 411-497 of SEQ ID NO: 13 and amino acids 102-130 of SEQ ID NO: 14), WN/ZKV-Z3 (nucleotides 403-489 of SEQ ID NO: 3; amino acids 103-131 of SEQ ID NO: 4), WN/ZKV-Z5 (nucleotides 403-489 of SEQ ID NO: 5; amino acids 103-131 of SEQ ID NO: 6) and WN/ZKV-Z15 (nucleotides 403-489 of SEQ ID NO: 7; amino acids 103-131 of SEQ ID NO: 8).

FIG. 2 shows the genomic structure of chimeric West Nile/Zika reporter viruses. Two construct strategies (Type I and Type II) are shown in the figure. For Type I reporter constructs, the reporter cassette (including the reporter gene and a 2A peptide encoding sequence) is inserted 5' of the complete C gene, and a partial C gene encoding the first 25 or 35 amino acids is added 5' of the reporter cassette. The partial C gene provides a critical cyclization sequence connected to the 5' non-coding region for competent virus replication. The first 25 or 35 amino acids in the complete C gene is codon edited with silent mutations to minimize homologous recombination potential with the partial C gene. The reporter viruses WN/ZKV-ZsG0 (SEQ ID NOs: 9 and 10) and WN/ZKV-ZsG1 (SEQ ID NOs: 11 and 12) are examples of Type 1 constructs with ZsGreen and P2A as the reporter cassette for both. For Type II reporter constructs, the reporter cassette is inserted in the signal sequence region at the 3' end of the C gene. The first three amino acids (GGK) of the WNV signal sequence are retained in front of the reporter for correct NS2B-NS3 cleavage, and the entire 18 amino acids of the ZIKV signal sequence (residues 105-122 of SEQ ID NO: 14) are included between the 2A peptide and Zika virus prM for proper prM protein processing.

FIG. 6 is a table showing a comparison of PRNT, immuno-mFRNT and fluoro-mFRNT assays when using WN/ZKV, R-WN/ZKV or wild-type Zika virus.

SEQUENCE LISTING

Figure 3:
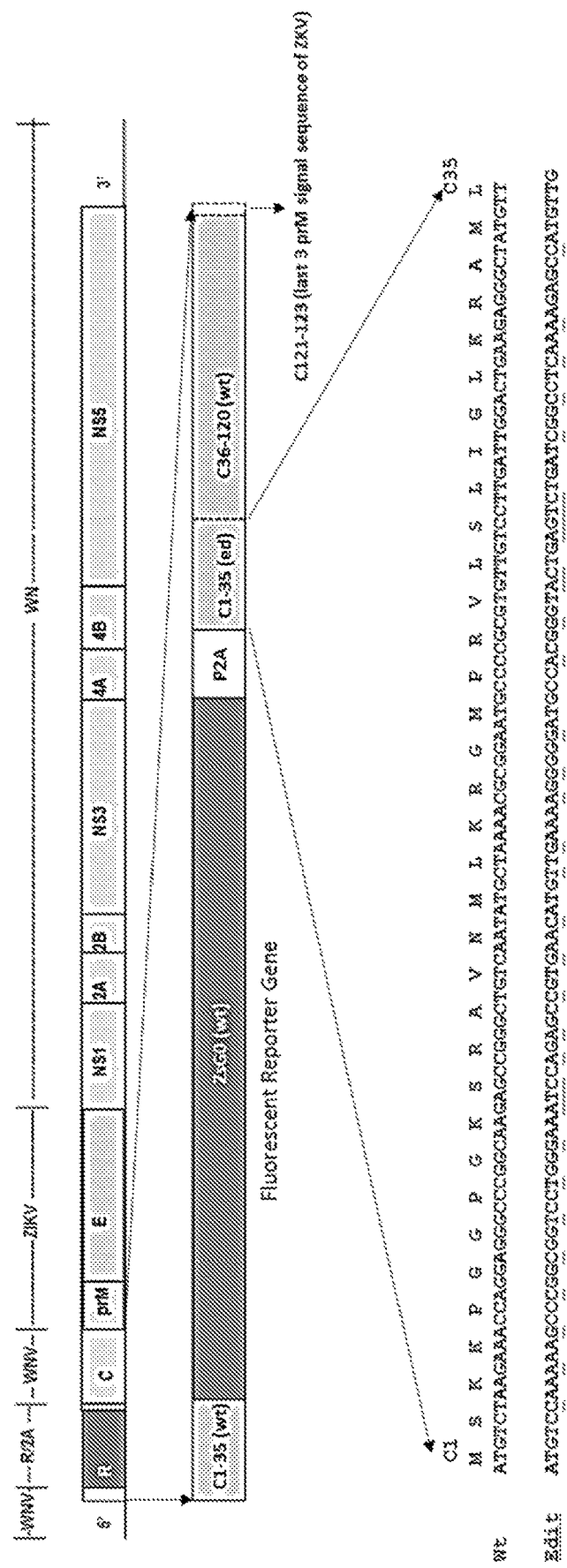
FIG. 3 is a schematic of the R-WN/ZKV-PR chimeric reporter virus. R-WN/ZKV-PR (also referred to as R-WN/ZKV) is a Type I reporter construct with ZsG0/P2A inserted after C1-35 of WNV and includes a complete WNV C gene downstream of P2A. In order to minimize homologous recombination between the partial C gene (C1-35(wt)) proceeding the reporter insert and the complete C gene following the reporter insert, the first 35 amino acids of the downstream C protein (C1-35(ed)) was edited to substitute specific nucleotides (indicated by underline) while maintaining the amino acid sequence.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 2, 2019 448 KB, which is incorporated by reference herein. In the accompanying sequence listing:

SEQ ID NOs: 1 and 2 are WN/ZKV-3PR nucleotide and amino acid sequences, respectively.

SEQ ID NOs: 3 and 4 are WN/ZKV-3SPH nucleotide and amino acid sequences, respectively.

SEQ ID NOs: 5 and 6 are WN/ZKV-5SPH nucleotide and amino acid sequences, respectively.

SEQ ID NOs: 7 and 8 are WN/ZKV-15SPH nucleotide and amino acid sequences, respectively.

SEQ ID NOs: 9 and 10 are WN/ZKV-ZsG0 reporter nucleotide and amino acid sequences, respectively.

SEQ ID NOs: 11 and 12 are WN/ZKV-ZsG1 reporter nucleotide and amino acid sequences, respectively.

SEQ ID NOs: 13 and 14 are the nucleotide and amino acid sequences of Zika virus strain R103451.

SEQ ID NOs: 15 and 16 are the nucleotide and amino acid sequences of Zika virus strain PRVABC59.

SEQ ID NOs: 17 and 18 are the nucleotide and amino acid sequences of West Nile virus strain NY99, deposited under Genbank Accession No. AF196835.

SEQ ID NOs: 19 and 20 are R-WN/ZKV-PR reporter nucleotide and amino acid sequences, respectively.

DETAILED DESCRIPTION

I. Abbreviations

AST average survival time
C capsid protein
C(ss) prM signal sequence portion of C protein
CPE cytopathic effect
E envelope glycoprotein
ELISA enzyme-linked immunosorbent assay
GBS Guillain-Barré syndrome
mAb monoclonal antibody
mFRNT microfocus reduction neutralization test
NCR non-coding region
NS non-structural
Nt Abs neutralization antibodies
pfu plaque forming unit
p.i. post-infection
prM premembrane protein
PHEIC Public Health Emergency of International Concern
PRNT plaque reduction neutralization test
WHO World Health Organization
WNV West Nile virus
WN/ZKV West Nile/Zika virus chimera
ZIKV Zika virus

II. Terms and Methods

Unless otherwise noted, technical terms are used according to conventional usage. Definitions of common terms in molecular biology may be found in *Lewin's Genes X*, ed. Krebs et al, Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics,* 3rd Edition, Springer, 2008 (ISBN: 1402067534).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes (lengths) or amino acid sizes (lengths), and all molecular weight or molecular mass values, given for nucleic acids or polypeptides are approximate, and are provided for description. All publications, patent applications, patents, and other references mentioned herein are incorporated by reference in their entirety for all purposes. All GenBank Accession Nos. mentioned herein are incorporated by reference in their entirety. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition, such as a chimeric virus) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope. In one example, antibody binding affinity is measured by end-point titration in an Ag-ELISA assay.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a flavivirus E protein.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Capsid protein (C protein): A flavivirus structural protein that functions to package viral RNA into the nucleocapsid core during virus assembly. The C-terminal portion of the C protein includes an internal signal sequence (referred to herein as either C(ss) or prM signal sequence) for translocation of the prM protein into the endoplasmic reticulum, where cleavage of the C and prM proteins occurs. This signal sequence varies in length among different flaviviruses. For example, the C(ss) of both WNV and ZIKV is 18 amino acids, while the C(ss) of DEN viruses is 14 amino acids.

Chimera: A molecule (e.g., nucleic acid or protein) composed of parts that are of different origin (such as at least two nucleic acids or polypeptides) that, while typically unjoined in their native state, are joined or linked to form a single continuous molecule. A chimera may include nucleic acids or polypeptides that are joined end-to-end (for example, the amino-terminus of one sequence is joined to the carboxyl-terminus of a second sequence) or may include a sequence from one molecule that is embedded within that of another molecule (for example, the amino-terminus and carboxyl-terminus of the chimera are from one molecule, while an intervening sequence comes from another molecule).

A chimera may include a chimeric protein, for example a protein that is composed of amino acids from more than one protein. A chimera may also include a chimeric nucleic acid composed of nucleic acid sequences from more than one source, such as a chimeric nucleic acid which encodes a chimeric protein. In other examples, a chimera may include a chimeric genome, such as a flavivirus genome, which is composed of sequences from two or more flaviviruses. For example, a chimeric flavivirus genome may comprise nucleic acid sequences from more than one flavivirus genome, such as a West Nile virus and a Zika virus. In some examples, a chimeric flavivirus includes nucleic acids encoding one or more proteins from a first flavivirus and nucleic acids encoding one or more proteins from a second flavivirus. In particular examples, a chimeric flavivirus is composed of a nucleic acid encoding the non-structural proteins and a C protein or a portion thereof from a West Nile virus genome linked to a nucleic acid encoding a prM protein and E protein (and optionally a portion of a C protein) from a Zika virus genome.

Conservative substitution: A substitution of one amino acid residue in a protein sequence for a different amino acid residue having similar biochemical properties. Typically, conservative substitutions have little to no impact on the activity of a resulting polypeptide. For example, ideally, a flavivirus protein (such as a prM, E, or non-structural protein) including one or more conservative substitutions (for example 1-10, 2-5, or 10-20, or no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by infecting cells with a virus containing a variant protein and determining its ability to replicate, by producing virus containing a variant protein and determining its neurovirulence or neuroinvasion properties, and/or by testing antibody cross-reactivity.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Control: A reference standard, for example a positive control or negative control. A positive control is known to provide a positive test result. A negative control is known to provide a negative test result. However, the reference standard can be a theoretical or computed result, for example a result obtained in a population.

Envelope glycoprotein (E protein): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222:159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B. NS2A is involved in RNA replication and virus particle assembly and secretion and NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., *The Togaviruses: Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Fluorescent protein: A protein that emits light of a certain wavelength when exposed to a particular wavelength of light. Fluorescent proteins include, but are not limited to, green fluorescent proteins (such as GFP, EGFP, AcGFP1, Emerald, Superfolder GFP, Azami Green, mWasabi, TagGFP, TurboGFP and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyanl, Midori-Ishi Cyan, mTurquoise and mTFP1), yellow fluorescent proteins (EYFP, Topaz, Venus, mCitrine, YPet, TagYFP, PhiYFP, ZsYellow1 and mBanana), orange fluorescent proteins (Kusabira Orange, Kusabira Orange2, mOrange, mOrange2 and mTangerine), red fluorescent proteins (mRuby, mApple, mStrawberry, AsRed2, mRFPI, JRed, mCherry, HcRed1, mRaspberry, dKeima-Tandem, HcRed-Tandem, mPlum, AQ143, tdTomato and E2-Crimson), orange/red fluorescence proteins (dTomato, dTomato-Tandem, TagRFP, TagRFP-T, DsRed, DsRed2, DsRed-Express (TI) and DsRed-Monomer) and modified versions thereof.

Heterologous: Originating from a different genetic sources or species. For example, a chimeric nucleic acid including nucleic acid from two (or more) different genetic sources or from two (or more) otherwise separated segments of sequence from a single genetic source is considered a heterologous nucleic acid. Similarly, a polypeptide including peptides from two (or more) different proteins from a single genetic source or two (or more) proteins from different genetic sources (such as a fusion protein) is considered a heterologous polypeptide. For example, a nucleic acid comprising portions of a WNV genome operably linked to a nucleic acid comprising portions of a ZIKV genome is a heterologous nucleic acid. Similarly, a polypeptide including a WNV polypeptide or portion thereof linked to a ZIKV polypeptide or portion thereof is a heterologous polypeptide.

In another example of use of the term heterologous, a nucleic acid that is heterologous to a cell originates from an organism or species other than the cell in which it is expressed. In one specific, non-limiting example, a heterologous nucleic acid includes a flavivirus nucleic acid that is present or expressed in a bacterial cell (such as an *E. coli* cell) or in an algal, plant, insect (e.g. C6/36), or mammalian (e.g., Vero) cell. Methods for introducing a heterologous nucleic acid into bacterial, algal, plant, insect, and mammalian cells are well known in the art, including infection of a cell with a viral nucleic acid, or transformation with a nucleic acid, for example electroporation, lipofection, and particle gun acceleration.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunize: To render a subject protected from an infectious disease, such as by vaccination.

Inactivated virus: A virus (such as a viral vaccine) that has been rendered incapable of replication in host cells (and is thus not virulent), but can elicit an immune response. Methods of inactivating a virus (such as a virus including a nucleic acid chimera described herein) include chemical treatment (for example, formaldehyde), physical treatment (such as heat), irradiation, or combinations thereof.

Isolated: An "isolated" or "purified" biological component (such as a nucleic acid, peptide, protein, protein complex, or particle) has been substantially separated, produced apart from, or purified away from other components in a preparation or other biological components in the cell of the organism in which the component occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Light-emitting protein: Any protein that is capable of emitting light or inducing the emission of light by acting on a particular substrate. Light-emitting proteins include, for example, fluorescent proteins and bioluminescent proteins. Fluorescent proteins include, for example, green fluorescent proteins and variants thereof (including blue, cyan, yellow, orange and red fluorescent proteins) and phycobiliproteins, such as B-phycoerythrin (B-PE), R-phycoerythrin (R-PE) and allophycocyanin (APC). Bioluminescent proteins include, for example, aequorin and luciferase (which acts on the substrate luciferin to emit light).

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Operably linked: A first nucleic acid is operably linked to a second nucleic acid when the first nucleic acid is placed in a functional relationship with the second nucleic acid. Generally, operably linked DNA sequences are contiguous and, where necessary to join two protein coding regions, in the same reading frame. Operably linked nucleic acids include a first nucleic acid contiguous with the 5' or 3' end of a second nucleic acid. In other examples, a second nucleic acid is operably linked to a first nucleic acid when it is embedded within the first nucleic acid, for example, where the nucleic acid construct includes (in order) a portion of the first nucleic acid, the second nucleic acid, and the remainder of the first nucleic acid.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic compositions, such as a chimeric virus, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: Fields Virology, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Purified: The term purified does not require absolute purity; rather, it is intended as a relative term. Thus, for example, a purified nucleic acid preparation is one in which the nucleic acid is more enriched than the nucleic acid is in its natural environment (such as within a cell) or in a preparation or production vessel. In other examples, a purified virus preparation is one in which the virus is more enriched than in a cell or organism, a preparation, or a production vessel. A purified nucleic acid or virus also includes one that is substantially free of undesired components, such as an inactivating agent. Preferably, a preparation is purified such that the nucleic acid or virus represents at least 50% of the total content of the preparation. In some embodiments, a purified preparation contains at least 60%, at least 70%, at least 80%, at least 85%, at least 90%, at least 95%, at least 98%, at least 99%, or more of the nucleic acid or virus.

Recombinant nucleic add: A nucleic acid molecule (or protein or virus) that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual, $2^{nd}$* ed., vol. 1-3, Cold Spring Harbor Laboratory Press, Cold Spring Harbor, N.Y., 1989. The term recombinant includes nucleic acids and proteins that have been altered solely by addition, substitution, or deletion of a portion of a natural nucleic acid molecule or protein.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (Gene, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Serum: The fluid portion of the blood that separates out from clotted blood. Serum contains many proteins, including antibodies, but does not contain clotting factors.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as a chimeric virus) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a Zika virus vaccine, for example, is an amount sufficient to increase resistance to, prevent, ameliorate, and/or treat infection caused by Zika virus in a subject without causing a substantial cytotoxic effect in the subject. The effective amount of a Zika virus vaccine (or Zika virus immunogenic composition) useful for increasing resistance to, preventing, ameliorating, and/or treating infection in a subject will be dependent on, for example, the subject being treated, the manner of administration of the therapeutic composition and other factors.

Transformed: A "transformed" cell is a cell into which has been introduced a nucleic acid molecule (such as a heterologous nucleic acid) by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, inhibition, amelioration, or treatment of infectious or other types of disease. The immunogenic material may include attenuated or inactivated (killed) microorganisms (such as bacteria or viruses), or antigenic proteins, peptides or DNA derived from them. An attenuated virus is a virulent organism that has been modified to produce a less virulent form, but nevertheless retains the ability to elicit antibodies and cell-mediated immunity against the virulent form. An inactivated (killed) virus is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

West Nile virus (WNV): A member of the virus family Flaviviridae and the genus Flavivirus. Other members of this genus include dengue virus, yellow fever virus, Japanese encephalitis virus (JEV), Zika virus and Spondweni virus. WNV was first isolated from a woman in the West Nile district of Uganda in 1937. The virus was later identified in birds in the Nile delta region in 1953. Human infections attributable to WNV have been reported in many countries for over 50 years. In 1999, a WNV circulating in Israel and Tunisia was imported into New York, producing a large and dramatic outbreak that spread throughout the continental United States in the following years. Human infection is most often the result of bites from infected mosquitoes, but may also be transmitted through contact with other infection animals, their blood or other tissues. Infection with WNV is asymptomatic in about 80% of infected people, but about 20% develop West Nile fever. Symptoms include fever, headache, fatigue, body aches, nausea, vomiting, swollen lymph glands and in some cases, a skin rash. Approximately 1 in 150 of infected individuals develop severe, neuroinvasive disease, such as encephalitis, meningitis or poliomyelitis. Treatment of WNV infection is supportive, such as administration of intravenous fluids, respiratory support and prevention of secondary infections. There is currently no approved vaccine available for humans.

Zika virus (ZIKV): A member of the virus family Flaviviridae and the genus Flavivirus. Other members of this genus include dengue virus, yellow fever virus, Japanese encephalitis virus (JEV), West Nile virus and Spondweni virus. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-

2014, resulting in ZIKV outbreaks in Oceania to French Polynesia, New Caledonia, the Cook Islands, and Easter Island. In 2015, ZIKV spread to Mexico, Central America, the Caribbean and South America, where ZIKV has reached pandemic levels. Infection by ZIKV generally causes either no symptoms are mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk. There are currently no available medical countermeasures for the treatment or prevention of Zika virus infection (Malone et al., *PLoS Negl Trop Dis* 10(3):e0004530, 2016).

III. West Nile/Zika Virus Chimeras

Although both ZIKV and WNV are flaviviruses, ZIKV replicates more slowly and to lower titers than WNV in cell cultures. This makes production of Zika viruses or viral antigens (for example for development of ZIKV vaccines) more difficult than for WNV. The chimeric West Nile/Zika viruses described herein contain ZIKV antigenic structures on the surface of the virus particles while retaining certain WNV features (such as replication to high titer). The disclosed chimeras can thus be used in the development of immunogenic compositions, such as inactivated virus vaccines, for eliciting an immune response to Zika viruses. Due to their fast and more robust growth than the wild type Zika viruses in cell cultures, these chimeras can be produced in large quantity more efficiently than the wild-type ZIKV for making inactivated virus. The chimeric viruses disclosed herein can also be used as a challenge virus to assess the efficacy of ZIKV candidate vaccines. Furthermore, the chimeric viruses can be used for more rapid and effective ZIKV diagnostic assays.

Disclosed herein are chimeric flaviviruses that include non-coding regions, a C protein, a portion of a prM signal sequence, and non-structural proteins, from WNV; and include a portion of a prM signal sequence, a prM protein and an E protein from ZIKV. Tables 1 and 2 below provide start and stop positions of the particular genes and proteins in exemplary West Nile and Zika viruses. These sequences can serve as reference sequences and may be used to identify particular nucleotide or amino acid positions that correspond to positions referred to in the chimeric nucleic acids disclosed herein, or proteins encoded by the chimeric nucleic acids disclosed herein, for example by producing an alignment of a chimera and one of the virus sequences provided herein.

TABLE 1

Start and stop positions of noncoding regions (NCRs), structural proteins and nonstructural proteins in WNV NY99 (Genbank Accession No. AF196835)

| Region | Nucleotide start/stop position (SEQ ID NO: 17) | Amino acid start/stop position (SEQ ID NO: 18) |
| --- | --- | --- |
| 5' NCR | 1-96 | — |
| C | 97-465 | 1-123 |
| C(ss) | 412-465 | 106-123 |
| prM | 466-966 | 124-290 |
| M | 742-966 | 216-290 |
| E | 967-2469 | 291-791 |
| NS1 | 2470-3525 | 792-1143 |
| NS2A | 3526-4218 | 1144-1374 |
| NS2B | 4219-4611 | 1375-1505 |
| NS3 | 4612-6468 | 1506-2124 |
| NS4A | 6469-6915 | 2125-2273 |
| NS4B | 6916-7680 | 2274-2528 |
| NS5 | 7681-10395 | 2529-3433 |
| Stop | 10396-10398 | — |
| 3' NCR | 10399-11029 | — |

TABLE 2

Start and stop positions of NCRs, structural proteins and nonstructural proteins in ZIKV strain R103451

| Region | Nucleotide start/stop position (SEQ ID NO: 13) | Amino acid start/stop position (SEQ ID NO: 14) |
| --- | --- | --- |
| 5' NCR | 1-107 | — |
| C | 108-473 | 1-122 |
| C(ss) | 420-473 | 105-122 |
| prM | 474-977 | 123-290 |
| M | 753-977 | 216-290 |
| E | 978-2489 | 291-794 |
| NS1 | 2490-3545 | 795-1146 |
| NS2A | 3546-4223 | 1147-1372 |
| NS2B | 4224-4613 | 1373-1502 |
| NS3 | 4614-6464 | 1503-2119 |
| NS4A | 6465-6914 | 2119-2269 |
| NS4B | 6915-7667 | 2270-2520 |
| NS5 | 7668-10376 | 2521-3423 |
| Stop | 10377-10379 | — |
| 3' NCR | 10380-100807 | — |

In some examples disclosed herein, the WNV genome used in the chimera is derived from a particular WNV strain, such as NY99 or KEN-3829. Additional WNV strains are known in the art (see, e.g., Ebel et al. *Emerg. Infect. Dis.* 7:650-653, 2001; American Type Culture Collection (ATCC) catalog numbers VR-82, VR-1267, VR-1507, VR-1510). In particular examples, the WNV genome is WN NY99, for example, SEQ ID NO: 17 (GenBank Accession No. AF196835, incorporated by reference as included in GenBank on Jun. 14, 2016), or with mutations as described in Kinney et al. (*J. Gen. Virol.* 87:3611-3622, 2006), U.S. Pat. No. 8,715,689 and/or PCT Publication No. WO 2015/196094, each of which are incorporated by reference herein in their entirety. In some examples, the WNV genome sequence is modified, for example to introduce restriction sites for cloning purposes. These modifications can be silent mutations (for example, nucleotide sequence changes that do not alter amino acid sequence) or they may change the amino acid sequence.

WNV genome sequences are publicly available. For example, GenBank Accession Nos. AF196835, AY278441, AF202541, AF404754, AF260967, AY660002, AY481864, AY268133, AF404757, AY268132, AF260969, AF317203, AY262283, AY490240, AF260968, AY603654, D00246, M12294, EU068667, AY765264, and AY277251 disclose WNV genomic nucleic acid sequences, all of which are incorporated by reference as included in GenBank on Jun. 14, 2016. In further examples, the WNV genome, or the non-coding regions, C protein and/or non-structural proteins of the WNV genome are at least 90%, at least 95%, at least 96%, at least 97%, at least 98%, or at least 99% identical to a publicly available WNV genome sequence.

In the disclosed nucleic acid chimeras, the ZIKV genome can be from any strain of ZIKV, including an African genotype strain or an Asian genotype strain. In some embodiments, the ZIKV is an African genotype strain, such as MR-766. In other embodiments, the ZIKV is an Asian genotype strain, such as SPH2015, PRVABC59, R103451, P6-740 or FSS 13025. In some embodiments, the ZIKV genome is from strain R103451 (SEQ ID NO: 13). The ZIKV genome may be a wild type strain or an attenuated (or vaccine) strain. In some examples, the ZIKV genome sequence is modified, for example to introduce restriction sites for cloning purposes. These modifications can be silent mutations (for example, nucleotide sequence changes that do not alter amino acid sequence) or they may change the amino acid sequence.

ZIKV sequences are publicly available. For example GenBank Accession Nos. KU321639.1, KU955595.1, KU955594.1, KU955593.1, KU955592.1, KU955591.1, KU681082.3, KU681081.3 and KX247646.1, all of which are incorporated by reference as included in GenBank on Jun. 14, 2016. In additional examples, the ZIKV genome (or the C signal sequence, prM, and/or E protein from the ZIKV genome) are at least 90%, at least 95%, at least 96%, at least 97%, at least 98%, or at least 99% identical to a publicly available ZIKV sequence.

In some examples, the disclosed WN/ZKV chimeras include one or more nucleic acid substitutions that result in an amino acid substitution that provides a desirable characteristic, for example, increased stability or replication in cell culture (such as Vero or C6/36 cells), or decreased infectivity or transmission in mosquitoes, compared to the unsubstituted virus or chimera.

The viruses containing the disclosed nucleic acid chimeras can readily be produced by replication in host cells in culture. Methods of producing viruses are well known in the art (see e.g. *Fields Virology*, Knipe and Howley, eds., Lippincott, Williams, and Wilkins, 2001; Flint et al., *Principles of Virology*, ASM Press, 2000). Host cell lines are generally selected to be easy to infect with virus or transfect with viral genomic RNA, capable of stably maintaining foreign RNA with an unarranged sequence, and have the necessary cellular components for efficient transcription, translation, post-translation modification, virus assembly, and secretion of the protein or virus particle. In addition, cells are typically those having simple media component requirements which can be adapted for growth in suspension culture. In some examples, the host cell line is a mammalian cell line that is adapted to growth in low serum or serum-free medium. Exemplary suitable host cell lines include Vero (monkey), C6/36 (mosquito), BHK21 (hamster), LLC-MK2 (monkey) SK6 (swine), L292 (mouse), HeLa (human), HEK (human), 2fTGH cells (human), HepG2 (human), and PDK (dog) cells. Suitable cell lines can be obtained from the American Type Culture Collection (ATCC), Manassas, Va.

In some examples, the disclosed chimeric WN/ZKV replicate in cell culture more rapidly than wild type Zika viruses. In some examples, plaques formed by WN/ZKV chimeric viruses form on cell cultures (such as Vero, LLC-MK2 or BHK21 cells) sooner than ZIKVs (such as at least one day, two days, three days, four days, or five days post-infection sooner). In other examples, WN/ZKV chimeric viruses form larger plaques than ZIKVs, for example, plaques that are at least 25% larger to about 10 times larger than Zika viruses (such as at least 50% larger, two-fold, three-fold, four-fold, five-fold, or up to 10-fold larger).

The disclosure also provides WN/ZKV chimeras having one or more nucleic acid or amino acid substitutions, insertions, deletions, or combinations thereof, such that the resulting chimera has improved characteristics. In some examples, the improved characteristic of the chimera includes but is not limited to increased virus titer, increased replication rate, increased plaque size, or increased stability in cell culture compared to a wild type virus. In additional examples, the improved characteristic of the chimera includes increased infectivity or virulence in a subject (such as mice or non-human primates) or decreased infectivity or transmissibility in mosquitoes as compared to a wild type virus. For example, to decrease infectivity or transmissibility in mosquitoes, the WN/ZKV chimeras may include one or more miRNAs specific to mosquito cells, such as but not limited to, miRNA-14, miRNA-184 or miRNA-1175.

Manipulation of the nucleotide sequence of the disclosed chimeric flaviviruses by standard procedures, including for instance site-directed mutagenesis or PCR and M13 primer mutagenesis, can be used to produce variants with improved characteristics (such as increased virus titer or stability in cell culture). Details of these techniques are well known. For instances, protocols are provided in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The simplest modifications involve the substitution of one or more amino acids for amino acids having similar physiochemical and/or structural properties. These so-called conservative substitutions are likely to have minimal impact on the activity and/or structure of the resultant protein. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl (or vice versa); (b) a cysteine or proline is substituted for (or by) any other residue; (c) a residue having an electropositive side chain, for example, lysyl, arginyl, or histadyl, is substituted for (or by) an electronegative residue, for example, glutamyl or asparty (or vice versa); or (d) a residue having a bulky side chain, for example, phenylalanine, is substituted for (or by) one not having a side chain, for example, glycine (or vice versa).

In addition to targeted mutagenesis to produce variants of the disclosed WN/ZKV chimeras, mutations may accrue upon passage in cell culture that result in variants, some with desirable characteristics. Nucleic acid and amino acid substitutions, insertions, and/or deletions that accrue in chimeric viruses during cell culture passages are readily determined by sequence analysis of the virus amplified from isolated plaques of the virus seed, and can be engineered into infectious clones to generate WN/ZKV chimera variants that have improved characteristics (such as replication to high titer or production of uniform large plaques in cells). Consistent mutations identified from multiple seeds or isolated plaques are one indication of a desirable substitution of the chimera in the cell type. Previous studies have successfully identified substitutions which occurred in cell culture and engineered these into different chimeric virus constructs to produce chimeric viruses with improved characteristics (e.g., Huang et al., *J. Virol.* 77:11436-11447, 2003; Huang et al., *J. Virol.* 12:7300-7310, 2005; U.S. Pat. No. 8,715,689; and WO 2015/196094).

A. Nucleic Acid Chimeras

Provided herein are flavivirus nucleic acid chimeras. In some embodiments, the nucleic acid chimera includes a first nucleic acid molecule comprising a 5' non-coding region, a nucleic acid encoding a C protein and non-structural proteins, and a 3' non-coding region, each from a West Nile virus genome, wherein the C protein comprises a portion of a prM signal sequence from the West Nile virus genome and a portion of a prM signal sequence from a Zika virus genome; and a second nucleic acid molecule operably linked to the first nucleic acid molecule, encoding a prM protein and an E protein from the Zika virus genome.

In some examples, the portion of the prM signal sequence from the West Nile virus genome includes the first 15 amino acids of the West Nile virus prM signal sequence and the portion of the prM signal sequence from the Zika virus genome includes the last three amino acids of the Zika virus prM signal sequence. In specific non-limiting examples, the first 15 amino acids of the West Nile virus prM signal sequence includes amino acids 106-120 of SEQ ID NOs: 2 and 4 and/or the last three amino acids of the Zika virus prM signal sequence includes AMA (amino acids 121-123 of SEQ ID NOs: 2 and 4).

In other examples, the portion of the prM signal sequence from the West Nile virus genome includes the first 13 amino acids of the West Nile virus prM signal sequence and the portion of the prM signal sequence from the Zika virus genome includes the last five amino acids of the Zika virus prM signal sequence. In specific non-limiting examples, the first 13 amino acids of the West Nile virus prM signal sequence includes amino acids 106-118 of SEQ ID NO: 6 and/or the last five amino acids of the Zika virus prM signal sequence includes amino acids 119-123 of SEQ ID NO: 6.

In yet other examples, the portion of the prM signal sequence from the West Nile virus genome includes the first three amino acids of the West Nile virus prM signal sequence and the portion of the prM signal sequence from the Zika virus genome includes the last 15 amino acids of the Zika virus prM signal sequence. In specific non-limiting examples, the first three amino acids of the West Nile virus prM signal sequence includes amino acids GGK (amino acids 106-108 of SEQ ID NO: 8) and/or the last 15 amino acids of the Zika virus prM signal sequence includes amino acids 109-123 of SEQ ID NO: 8.

In some embodiments, the West Nile virus is strain NY99 or KEN-3829.

In some embodiments, the Zika virus is an African genotype virus, such as strain MR-766. In other embodiments, the Zika virus is an Asian genotype virus, such as strain SPH2015, PRVABC59, R103451, P6-740 or FSS 13025.

In some embodiments, the nucleic acid chimera includes a nucleic acid sequence at least 80%, at least 85%, at least 90%, at least 95%, at least 96%, at least 97%, at least 98% or at least 99% identical to SEQ ID NO: 1, SEQ ID NO: 3, SEQ ID NO: 5 or SEQ ID NO: 7. In some examples, the nucleic acid chimera includes the nucleic acid sequence of SEQ ID NO: 1, SEQ ID NO: 3, SEQ ID NO: 5 or SEQ ID NO: 7.

In some embodiments, the nucleic acid chimera encodes an amino acid sequence at least 80%, at least 85%, at least 90%, at least 95%, at least 96%, at least 97%, at least 98% or at least 99% identical to SEQ ID NO: 2, SEQ ID NO: 4, SEQ ID NO: 6 or SEQ ID NO: 8. In some examples, the nucleic acid chimera encodes the amino acid sequence of SEQ ID NO: 2, SEQ ID NO: 4, SEQ ID NO: 6 or SEQ ID NO: 8.

In some embodiments, the nucleic acid chimera further includes a reporter gene. In some examples, the reporter gene encodes a light-emitting protein. In some examples, the light-emitting protein is a fluorescent protein, such as a green, blue, cyan, yellow, orange or red fluorescent protein. In other examples, the light-emitting protein is a bioluminescent protein, such as luciferase. In particular non-limiting examples, the reporter gene encodes a green fluorescent protein, such as ZsGreen or mWasabi.

In some examples, the reporter gene is inserted upstream (5') of a complete C gene, and an additional nucleic acid sequence encoding a portion of the C protein (such as the first 25 or 35 amino acids of the C protein) is inserted between the 5' non-coding region and the reporter gene (see FIG. 2, Type I reporter construct). In specific non-limiting examples, the nucleic acid sequence encoding the portion of the C protein is human codon optimized or modified with multiple silent mutations to enhance the genetic stability of the reporter virus by decreasing homologous sequences between the complete and partial C genes. In particular examples, the nucleic acid sequence of the reporter gene (such as ZsGreen) is human codon optimized.

In some examples, a nucleic acid sequence encoding a self-cleaving 2A peptide (such as F2A or P2A) is placed at the 3' end of the reporter gene (see FIG. 2, Type II reporter construct). In particular examples, the reporter gene and 2A peptide coding sequence are inserted in the signal sequence region at the 3' end of the C gene. In specific non-limiting examples, the reporter gene and 2A peptide coding sequence are flanked by a nucleic acid sequence encoding the first three amino acids (GGK) of the WNV signal sequence at the 5' end and a nucleic acid sequence encoding the 18 amino acid ZIKV signal sequence at the 3' end (see FIG. 2, Type II reporter construct).

In some examples, the nucleic acid sequence encoding the report construct is human codon optimized.

In some examples, the nucleic acid chimera includes a nucleic acid sequence at least 80%, at least 85%, at least 90%, at least 95%, at least 96%, at least 97%, at least 98% or at least 99% identical to SEQ ID NO: 9, SEQ ID NO: 11 or SEQ ID NO: 19. In specific examples, the nucleic acid chimera includes the nucleic acid sequence of SEQ ID NO: 9, SEQ ID NO: 11 or SEQ ID NO: 19.

In some examples, the nucleic acid chimera encodes an amino acid sequence at least 80%, at least 85%, at least 90%, at least 95%, at least 96%, at least 97%, at least 98% or at least 99% identical to SEQ ID NO: 10, SEQ ID NO: 12 or SEQ ID NO: 20. In specific examples, the nucleic acid chimera encodes the amino acid sequence of SEQ ID NO: 10, SEQ ID NO: 12 or SEQ ID NO: 20.

Also provided herein are chimeric flaviviruses that comprise a nucleic acid chimera disclosed herein. Compositions, such as immunogenic compositions, that include the chimeric flaviviruses are also provided by the present disclosure.

B. Inactivated Virus, Methods of Use and Methods of Making

Further provided herein are inactivated chimeric flaviviruses. In particular, provided are chimeric West Nile/Zika viruses that have been inactivated using any method known to one of skill in the art. The chimeric West/Nile Zika viruses have a chimeric nucleic acid that includes a first nucleic acid molecule comprising a 5' non-coding region, a nucleic acid encoding a C protein and non-structural proteins, and a 3' non-coding region, each from a West Nile virus genome, wherein the C protein comprises a portion of a prM signal sequence from the West Nile virus genome and a portion of a prM signal sequence from a Zika virus genome; and a second nucleic acid molecule operably linked to the first nucleic acid molecule, encoding a prM protein and an E protein from the Zika virus genome, as described in the above section.

Also provided are immunogenic compositions that include an inactivated flavivirus comprising a nucleic acid chimera disclosed herein and a pharmaceutically acceptable carrier. In some embodiments, the inactivated virus is purified.

In some embodiments, the inactivated virus is inactivated by one or more of chemical inactivation, high pressure inactivation, ultraviolet or gamma irradiation, or any combination thereof.

Further provided herein is a method of eliciting an immune response against Zika virus in a subject by administering to the subject an inactivated virus or immunogenic composition disclosed herein. The immune response may include, for example, induction of ZIKV-specific antibodies (such as IgM and/or IgG antibodies) or induction of a virus-specific T cell response. In some examples, the immune response is a protective immune response.

In some embodiments, the subject is a human.

In some embodiments, the method includes administering one to five doses (such as 1, 2, 3, 4 or 5 doses) of the immunogenic composition to the subject. In some examples, the method further includes administering one or more adjuvants to the subject.

Also provided is a method of immunizing a subject against ZIKV by administering to the subject an inactivated virus or immunogenic composition disclosed herein. In some embodiments, the subject is a human.

Further provided is a method that includes inactivating a virus that includes a nucleic acid chimera disclosed herein. In some embodiments, inactivating the virus includes treating the virus with a chemical inactivation agent, high pressure, ultraviolet irradiation, gamma irradiation, or any combination thereof. In some examples, the method further includes purifying the inactivated virus. In some examples, the method further includes administering the inactivated virus to a subject

C. Methods of Detecting Zika Virus Infection

Methods of detecting ZIKV-specific antibodies in a sample are also provided herein. In some embodiments, the method includes contacting the sample with a chimeric virus disclosed herein under conditions sufficient to form virus-antibody complexes if ZIKV antibodies are present in the sample; and detecting the virus-antibody complexes, thereby detecting ZIKV-specific antibodies in the sample.

In some embodiments, the method includes contacting the sample with a chimeric virus disclosed herein to form a virus-sample mixture, wherein virus-antibody complexes are formed in the virus-sample mixture if ZIKV-specific antibodies are present in the sample; inoculating a cell culture with the virus-sample mixture under conditions sufficient to allow plaque formation or micro-focus formation in the cell culture; and detecting a decrease in plaque formation or micro-focus formation in the cell culture as compared to a virus-infected control cell culture.

In some embodiments, the method includes providing a chimeric virus disclosed herein bound to a solid support; contacting the chimeric virus-bound solid support with the sample under conditions sufficient to form virus-antibody complexes if ZIKV-specific antibodies are present in the sample; contacting the virus-antibody complexes with a secondary antibody; and detecting binding of the secondary antibody to the virus-antibody complexes.

In some embodiments, the method includes providing a secondary antibody bound to a solid support; contacting the secondary antibody-bound solid support with the sample under conditions sufficient to allow binding of the secondary antibody to any ZIKV-specific antibodies present in the sample, thereby forming antibody-antibody complexes; contacting the antibody-antibody complexes with a chimeric virus disclosed herein under conditions sufficient for the chimeric virus to bind the ZIKV-specific antibodies, thereby forming immune complexes; and detecting the presence of the immune complexes. In some examples, detecting the presence of the immune complexes includes contacting the immune complexes with an antibody that specifically binds the chimeric virus and comprises a detectable label.

In some embodiments, the method includes providing a ZIKV-specific antibody bound to a solid support; contacting the antibody-bound solid support with a chimeric virus disclosed herein under conditions sufficient for the chimeric virus to bind the ZIKV-specific antibody to form antibody-virus complexes; contacting the antibody-virus complexes with the sample to allow binding of any ZIKV-specific antibodies present in the sample to the chimeric virus, thereby forming immune complexes; contacting the immune complexes with a secondary antibody; and detecting binding of the secondary antibody to the immune complexes, thereby detecting ZIKV-specific antibodies present in the sample.

In some examples of the detection methods, the secondary antibody is an anti-IgM antibody. In other examples, the secondary antibody is an anti-IgG antibody. In specific examples, the secondary antibody includes an anti-human IgM antibody or an anti-human IgG antibody.

In some examples, the sample includes a biological fluid samples, such as serum, blood or plasma. In particular non-limiting examples, the sample includes serum.

In some examples, the ZIKV-specific antibody is cross-reactive with other flaviviruses.

In some examples, the ZIKV-specific antibody is a neutralizing antibody.

IV. Compositions and Methods for Eliciting an Immune Response

Due to its robust replication in Vero cells, the chimeric viruses disclosed herein can be readily utilized for producing inactivated virus vaccine from vaccine-production certified Vero cells. Inactivated flavivirus vaccines, such as Japanese encephalitis virus vaccine and tick-borne encephalitis vaccine, have previously been used successfully in humans. An inactivated ZIKV vaccine may be a safe vaccine option for pregnant woman to prevent ZIKV-caused microcephaly in the fetus. Large quantities of virus are required for purification and inactivation procedures to make an inactivated vaccine. Thus, the chimeric West Nile/Zika viruses disclosed herein are advantageous due to their ability to produce very high titers for many days, which will significantly enhance Zika virus vaccine production.

Provided herein are methods of eliciting an immune response in a subject by administering an inactivated viruses including a WN/ZKV chimeric nucleic acid to the subject. In a particular example, the subject is a human. The inactivated virus comprising a WN/ZKV nucleic acid chimera is used to produce an immune response that prevents or inhibits infection with a ZIKV, and can also be used to treat or inhibit infection with ZIKV.

In some examples, the method further includes selecting a subject in need of enhanced immunity to ZIKV. Subjects in need of enhanced immunity to ZIKV include subjects who are at risk of ZIKV infection, and subjects who have been previously vaccinated with a ZIKV vaccine. Residents of, or travelers to, countries or regions where ZIKV is endemic are at risk of contracting ZIKV. Additional factors that contribute to risk of infection with ZIKV include the characteristics of the area, presence of ZIKV in the area, exposure to mosquitos, and lack of preventive measures (such as insect repellant).

In some examples, the chimeric virus is inactivated, for example, using chemical inactivation, high pressure inactivation, ultraviolet or gamma irradiation, or any combination thereof. For example, chemical inactivation includes exposing the virus to one or more of formaldehyde (e.g., formalin), β-propiolactone, aziridines, hydrogen peroxide, organic solvents, surfactants (e.g., sarkosyl) or non-ionic detergents (e.g., Triton®-X100), or ascorbic acid for a time sufficient to inactivate the virus. In one example, the virus is inactivated using an oxidizing agent such as hydrogen peroxide, for example, treatment with about 0.05-5% hydrogen peroxide (such as about 0.1-1% about 0.5-3%, about 1-5%) at room temperature for about 1-24 hours (such as about 1-16 hours, about 2-12 hours, about 4-8 hours, about 1-6 hours, for example, about 1 hour, about 2 hours, about 3 hours, about 4 hours, about 6 hours, about 8 hours, about 12 hours, about 16 hours, or about 24 hours). See, e.g., WO 2008/039171; Amanna et al., *Nat. Med* 18:974-979, 2012; Pinto et al., *J. Virol.* 87:1926-1936, 2013. One of ordinary skill in the art can determine optimal hydrogen peroxide concentrations and conditions for inactivation for different starting viral titers or volumes.

In a particular, non-limiting example, the virus is treated with about 0.001-0.5% sarkosyl (such as about 0.005-0.4%, about 0.025-0.2%, or about 0.01-0.4% sarkosyl, for example, about 0.005%, about 0.01%, about 0.025%, about 0.05%, about 0.1%, about 0.2%, about 0.3%, about 0.4%, or about 0.5% sarkosyl) at about 20-37° C. (for example, about 20-37° C., about 22-30° C., about 30-37° C., or about room temperature) for a sufficient time to inactivate the virus (such as about 15 minutes to 3 hours, about 30 minutes to 2 hours, about 1-2 hours or about 30 minutes to 90 minutes). One of ordinary skill in the art can determine optimal detergent concentrations and conditions for inactivation for other detergents and/or different starting viral titers or volumes. In some examples, longer inactivation times are used at lower temperatures (such as room temperature) than at higher temperatures (such as 37° C.). One of ordinary skill in the art can determine inactivation times based on the temperature of treatment and routine experimentation.

In other examples, the virus is exposed to an ultraviolet light source (such as a UV-C light source of 254 nm) or a radioactive source (such as cobalt-60) for a time sufficient to inactivate the virus. In some examples, the virus (such as a WN/ZIKV chimera disclosed herein) is exposed to about 350-700 µW/cm$^2$ (such as about 350-680 µW/cm$^2$, about 400-670 µW/cm$^2$, about 670-685 µW/cm$^2$, or about 350 µW/cm$^2$, about 670 µW/cm$^2$, or about 680 µW/cm$^2$) of UV-254 nm for about 10 minutes to 2 hours (such as about 15 minutes to 1 hour, about 15-45 minutes, about 1-2 hours, about 15 minutes, about 30 minutes, about 45 minutes, about 1 hour, or more). In other examples, the virus is exposed to about 0.1-200 mW/cm$^2$ (such as about 0.5-5 mW/cm$^2$, about 1-10 mW/cm$^2$, about 10-50 mW/cm$^2$, about 25-100 mW/cm$^2$, about 100-200 mW/cm$^2$, for example, about 2 mW/cm$^2$, about 5 mW/cm$^2$, about 10 mW/cm$^2$, about 50 mW/cm2, about 100 mW/cm$^2$, about 150 mW/cm$^2$, or about 200 mW/cm$^2$) for about 10 minutes to 8 hours (such as about 30 minutes to 1 hour, about 1-6 hours, about 2-4 hours, about 15 minutes, about 30 minutes, about 1 hour, about 2 hours, about 3 hours, about 4 hours, about 6 hours, about 8 hours). In some examples, the virus in kept cool (for example at 4° C. or on ice) during UV treatment. In particular examples, small volumes (such as less than about 1 ml) are treated at 670 µW/cm$^2$ for 15 minutes or 350 µW/cm$^2$ for 45 minutes and larger volumes (such as about 1 ml or more, for example about 2-5 ml, about 1-3 ml, or more) are treated at 680 µW/cm$^2$ for 45 minutes or more. One of ordinary skill in the art can determine optimal UV power and conditions for inactivation for other volumes or different starting viral titers.

In additional examples, the virus is inactivated by photochemical inactivation. The methods include exposure of the virus to UV radiation (365 nm) in the presence of photo-activatable chemicals, such as 1,5-indonaphthylazide (INA), 4'-aminomethyl-trioxsalen (AMT), 8-methoxypsoralen (MOP), 4,5',8-trimethylpsoralen (TMP), or psoralen. See, e.g., Raviprakash et al., *Hum Vaccines Immunother.* 9:2336-2341, 2013; Raviv et al., *J. Virol.* 82:4612-4619, 2008; Sharma et al., *Vaccine* 29:953-959, 2011; Hanson et al., *J. Gen. Virol.* 40:345-358, 1978. In particular examples, the virus is exposed to about 0.1-200 mW/cm$^2$ (such as about 0.1-1 mW/cm$^2$, about 0.5-5 mW/cm$^2$, about 1-100 mW/cm$^2$, about 100-200 mW/cm$^2$, for example, about 2 mW/cm$^2$, about 100 mW/cm$^2$, about 145 mW/cm$^2$, about 180 mW/cm$^2$, or about 200 mW/cm$^2$) of UV-365 nm for about 1 minute to about 6 hours (such as about 2-15 minutes, about 5-30 minutes, about 15 minutes to 1 hour, about 15-45 minutes, about 1-2 hours, about 90 minutes to 4 hours, about 2-6 hours, about 2 minutes, about 5 minutes, about 10 minutes, about 15 minutes, about 30 minutes, about 45 minutes, about 1 hour, about 2 hours, about 4 hours, about 6 hours, or more) in the presence of INA, ANT, MOP, TMP, or psoralen. One of ordinary skill in the art can determine optimal UV power and conditions for inactivation using particular compounds, virus volumes, or starting viral titers.

Before or after the chimeric virus has been inactivated, the virus may be purified. Purification methods include filtration or diafiltration, chromatography (e.g., size exclusion, ion exchange, or immunoaffinity chromatography), density-gradient centrifugation, glycerol-cushion centrifugation, or Cellufine® sulfate media chromatography. In other examples, the chimeric virus is purified prior to inactivation. If purified virus is inactivated, an additional purification step may be included following inactivation, for example, to remove a chemical inactivation agent (such as detergent), for example using filtration or buffer exchange. Preparations of purified inactivated WN/ZIKV chimeras may include both inactivated whole virus and inactivated virus-like particles.

In some examples, chimeras are purified (for example, through polyethylene glycol 8000 (PEG8000) precipitation and gradient-density centrifugation, glycerol cushion centrifugation, and/or Cellufine® sulfate media chromatography) before inactivation. Inactivated viruses may be further purified by filtration to remove inactivating reagent, for example, if necessary. In particular examples, detergent (such as sarkosyl) is removed after inactivation by filtration, detergent removal spin columns (such as Millipore Detergent-OUT™ kits), dialysis, or ion-exchange chromatography. Final product may be tested for infectivity in cell cultures, antigenicity (for example, by ELISA; as discussed in Section VI, below), and/or protein concentration (for example, by Bradford or bicinchoninic acid protein assay).

One or more purified inactivated viruses comprising a WN/ZKV nucleic acid chimera (for example in the form of a pharmaceutical or immunogenic composition) are administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In some examples, the compositions disclosed herein include one or more adjuvants. In other examples, an adjuvant is not included in the composition, but is separately administered to a subject (for example, in combination with a composition disclosed herein) before, after, or substantially simultaneously with administration of one or more of the compositions disclosed herein. Adjuvants are agents that increase or enhance an immune response in a subject administered an antigen, compared to administration of the antigen in the absence of an adjuvant. One example of an adjuvant is an aluminum salt, such as aluminum hydroxide, aluminum phosphate, aluminum potassium sulfate, or aluminum hydroxyphosphate. Other adjuvants include biological adjuvants, such as cytokines (for example, IL-2, IL-6, IL-12, RANTES, GM-CSF, TNF-α, or IFN-γ), growth factors (for example, GM-CSF or G-CSF), one or more molecules such as OX-40L or 4-1 BBL, immunostimulatory oligonucleotides (for example, CpG oligonucleotides), Toll-like receptor agonists (for example, TLR2, TLR4, TLR7/8, or TLR9 agonists), and bacterial lipopolysaccharides or their derivatives (such as 3D-MPL). Additional adjuvants include oil and water emulsions, squalene, or other agents. In one example, the adjuvant is a mixture of stabilizing detergents, micelle-forming agent, and oil available under the name PROVAX® (IDEC Pharmaceuticals, San Diego, Calif.). One of skill in the art can select a suitable adjuvant or combination of adjuvants to be included in the compositions disclosed herein or administered to a subject in combination with the compositions disclosed herein.

Administration is accomplished by single or multiple doses. The dose administered to a subject in the context of the present disclosure should be sufficient to induce a beneficial therapeutic response in a subject over time, or to inhibit or prevent ZIKV infection. The dose required will vary from subject to subject depending on the species, age, weight and general condition of the subject, the severity of the infection being treated, the particular immunogenic composition being used, and its mode of administration. An appropriate dose can be determined by one of ordinary skill in the art using only routine experimentation. In some examples, the dose of inactivated virus (such as in an immunogenic composition) administered to the subject is about 0.1 µg to about 100 µg. For example, a dose of the immunogenic composition can contains at least 0.1 µg, at least 0.2 µg, at least 0.25 µg, at least 0.3 µg, at least 0.33 µg, at least 0.4 µg, at least 0.5 µg, at least 1.0 µg, at least 2.0 µg, at least 3.0 µg, at least 5.0 µg, at least 10.0 µg, at least 20 µg, at least 40 µg, at least 80 µg, or at least 100 µg (or any amount between 0.1 and 10.0 µg) of inactivated chimeric virus.

Repeated immunizations may be necessary to produce an immune response in a subject. When administered in multiple doses, the booster doses are administered at various time intervals, such as weeks or months to years. In other examples, the inactivated WN/ZKV chimeric viruses are used as a booster following administration of one or more ZIKV vaccines. In one example, a subject is administered a prime dose of a live-attenuated ZIKV vaccine followed by at least one boost dose of the inactivated WN/ZKV chimeric viruses disclosed herein. In some examples, the boost dose is administered about 14, 30, 60, 90, or more days after administration of the prime dose. Additional boosters (of live-attenuated ZIKV or inactivated WN/ZKV chimeras) can be administered at subsequent time points, if determined to be necessary or beneficial. Immunization protocols (such as amount of immunogen, number of doses and timing of administration) can be determined experimentally, for example by using animal models (such as mice or non-human primates), followed by clinical testing in humans.

V. Preparation of Viruses

Methods of cell culture, viral replication, plaque titration, and virus or virus particle purification are well known in the art. See e.g. Obijeski et al., *J. Gen. Virol.* 22:21-33, 1974; Beaty et al., *Diagnostic Procedures for Viral, Ricksettial, and Chlamydial Infections*, pp. 189-212, Lennette et al. (eds.), 7<sup>th</sup> Edition, American Public Health Association, 1995; *Virology Methods Manual*, Mahy and Kangro (eds.), Academic Press, 1996.

The chimeric viruses of the present disclosure can be made using standard methods known and recognized in the art. For example, an RNA molecule corresponding to the genome of a virus, or a chimeric virus, can be introduced into primary cells, chick embryos, or diploid cell lines, from which (or the supernatants of which) progeny virus can then be purified. Another method that can be used to produce the viruses employs heteroploid cells, such as Vero cells (Yasumura et al., *Nihon Rinsho* 21:1201-1215, 1963) or C6/36 cells. In this method, a nucleic acid molecule (e.g., an RNA molecule) corresponding to the genome of a virus or chimeric virus is introduced into the heteroploid cells and virus is harvested from the medium in which the cells have been cultured. The harvested virus can be further amplified in cell cultures and then concentrated (e.g., by PEG 8000 precipitation, use of ultrafiltration, such as a filter having a molecular weight cut-off of, e.g., 50-500 kDa (e.g., Amicon ultracentrifugal filter, tangential flow filtration cassette, or Pellicon-2 Mini ultrafilter cassette)), diafiltered against MEME without phenol red or FBS, formulated by the addition of lactose, and filtered into a sterile container. Details of a method of virus production are provided in WO 03/060088. Viruses optionally are further purified, for example by density gradient centrifugation, glycerol cushion centrifugation, and/or Cellufine® sulfate media chromatography.

VI. Detection of Flavivirus Antibodies

The present disclosure further provides a method of detecting a Zika virus-reactive antibody in a sample (such as a sample from a subject, for example, a blood or serum sample), including contacting the sample with a chimeric virus disclosed herein under conditions sufficient to form virus-antibody complexes if Zika virus antibodies are present in the sample; and detecting formation of the complexes, thereby detecting Zika virus antibody in the sample. An advantage of the disclosed WN/ZKV chimeras is that they grow faster and to higher titers and produce larger and more well-defined plaques or micro-foci than wild type ZIKV. It is disclosed herein that chimeric WN/ZIKV expresses authentic ZIKV neutralization epitopes that result in neutralization assay results that are equivalent to the neutralization assay using wt ZIKV (Table 3). In addition, the chimeric virus can speed up the traditional PRNT from 5-6 days to 3-4 days, and plaque morphology of the WN/ZIKV is more uniform for consistent counting. Therefore, the disclosure provides methods of detecting ZIKV-reactive antibody in a sample that are faster and more accurate (consistent) than methods utilizing wild type ZIKV.

The methods of detecting Zika virus-specific antibodies in a sample are performed, for example, by contacting a fluid or tissue sample from a subject with a chimeric virus of this disclosure and detecting the binding of at least one polypeptide encoded by the virus to the antibody. A fluid sample of this method includes any biological fluid which could contain the antibody, such as cerebrospinal fluid, blood, bile plasma, serum, saliva and urine. Other possible examples of body fluids include sputum, mucus and the like.

In one example, the presence of a ZIKV antibody is detected in a sample from a subject utilizing a disclosed chimeric flavivirus in a plaque-reduction neutralization test (PRNT) or micro-focus reduction neutralization test (mFRNT). In the PRNT or mFRNT assay, a sample is contacted with a virus encoded by a chimeric flavivirus disclosed herein. A suitable cell culture (such as Vero, C6/36, LLC-MK2 or BHK cells) is inoculated with the virus-sample mixture to infect the cells. The cell culture is incubated under conditions sufficient to allow plaque or micro-focus formation and the number of plaques or micro-foci formed in a culture inoculated with the chimeric virus-sample mixture is compared to the number of plaques or micro-foci formed in a control culture (such as cells inoculated with virus alone). A reduction in the number of plaques or micro-foci in the cell culture inoculated with the chimeric virus-sample mixture as compared to the control culture (for example a decrease of at least 50%, 60%, 70%, 80%, 90%, 95%, or 99% compared with the control sample) indicates the presence of a ZIKV antibody, such as a neutralizing antibody, in the sample.

Chimeric WN/ZKVs encoding a fluorescent reporter (Zs-Green) are also disclosed herein (referred to as WN/ZKV-ZsG0 and WN/ZKV-ZsG1). The reporter viruses can be used to improve the micro-neutralization assay because the viral foci (infected cells) can be directly imaged and automatically counted, for example, by an ELISPOT reader. This eliminates the time-consuming and labor-intensive procedure required for immunostaining of viral foci.

The robust growth characteristics of the chimeric virus disclosed herein can also be useful in the production of ZIKV particles for use in a variety of diagnostic assays. For example, viral particles and/or antigens are required in various serology assays, such as traditional IgM antibody capture (MAC)-ELISA or IgG antibody capture (GAC)-ELISA, indicted ELISA and rapid lateral flow assays. Other immunoassays, such as immunofluorescence assay and immunoblotting can also be readily adapted for the detection of Zika virus antibodies in a sample according to the methods of this disclosure. An ELISA method effective for the detection of the antibodies includes, for example, binding the chimeric virus or virus particles to a substrate; contacting the bound chimeric virus with a fluid or tissue sample containing the antibody; contacting the above with a secondary antibody, which is reactive with the bound antibody, bound to a detectable moiety (for example, horseradish peroxidase enzyme or alkaline phosphatase enzyme); contacting the above with the substrate for the enzyme; contacting the above with a color reagent; and observing/measuring color change or development.

The immune response following a flavivirus infection includes the production of IgM and IgG antibodies, which are primarily directed against the flavivirus E protein. IgM antibody capture (MAC) or IgG antibody capture (GAC) ELISAs are commonly used to detect the level of IgM or IgG (respectively) in serum samples of patients suspected of having a flavivirus (such as a Zika virus) infection. In these assays, anti-human IgM or anti-human IgG serves as a capture antibody and is coated onto an appropriate assay plate, such as a multi-well plate. After blocking of the plate, such as with nonfat dry milk, diluted human sera are reacted with the anti-human IgM or IgG. In the context of the present disclosure, chimeric virus, which serves as the antigen, is added to the plates. A ZIKV antigen-specific antibody conjugated to a detectable label (for example, an enzyme or fluorophore) is then reacted with the immobilized virus. The detectable label is then measured to detect the presence of ZIKV-specific antibodies that were present in the serum sample. Serial dilutions of positive sera can be evaluated. The maximum dilution that exhibits positive signal is the titer for the serum. The titer of the MAC-ELISA or GAC-ELISA can be compared with the titers of other tests, such as hemagglutination inhibition tests (HIT) or PRNT. Serum samples can also be tested on control antigen in addition to viral antigen, to reduce the number of false-positive results due to non-specific binding of the serum or other factors (U.S. Patent Application Publication No. 2006/0115896).

Indirect ELISAs to detect the presence of virus-specific antibodies are typically carried out by coating a microtiter plate with an antigen-specific antibody (such as a flavivirus-cross reactive or ZIKV-specific antibody), blocking the plates to prevent non-specific binding to the plate surface, and adding virus antigen (such as a chimeric virus disclosed herein) to allow binding of the antigen to the virus-specific antibody. After several washes, diluted human sera is added to allow binding of any antibodies present in the sample to the immobilized viral antigens (e.g. the chimeric virus antigens). IgM or IgG antibodies that were present in the sample are then detected using a labelled secondary antibody, such as anti-human IgG or anti-human IgM conjugated to a detectable label (such as an enzyme or fluorophore). The presence of ZIKV-specific antibody is detected by measuring the detectable label (for example, by measuring fluorescence, optical density or colorimetric absorbance).

In some embodiments herein, detection of Zika virus-specific antibodies in a sample is performed by providing a chimeric virus disclosed herein bound to a solid support; contacting the chimeric virus-bound solid support with the sample under conditions sufficient to form virus-antibody complexes if Zika virus-specific antibodies are present in the sample; contacting the virus-antibody complexes with a secondary antibody; and detecting binding of the secondary antibody to the virus-antibody complexes.

In other embodiments herein, detection Zika virus-specific antibodies in a sample is carried out by providing a secondary antibody bound to a solid support; contacting the secondary antibody-bound solid support with the sample under conditions sufficient to allow binding of the secondary antibody to any Zika virus-specific antibodies present in the sample, thereby forming antibody-antibody complexes; contacting the antibody-antibody complexes with a chimeric virus disclosed herein under conditions sufficient for the chimeric virus to bind the Zika virus-specific antibodies, thereby forming immune complexes; and detecting the presence of the immune complexes, thereby detecting Zika virus-specific antibodies in the sample. In some examples, detecting the presence of the immune complexes includes contacting the immune complexes with an antibody that specifically binds the chimeric virus and comprises a detectable label.

In yet other embodiments, detection of Zika virus-specific antibodies in a sample includes the steps of providing a Zika virus-specific antibody bound to a solid support; contacting the antibody-bound solid support with a chimeric virus disclosed herein under conditions sufficient for the chimeric virus to bind the Zika virus-specific antibody to form antibody-virus complexes; contacting the antibody-virus complexes with the sample to allow binding of any Zika virus-specific antibodies present in the sample to the chimeric virus, thereby forming immune complexes; contacting the immune complexes with a secondary antibody; and detecting binding of the secondary antibody to the immune complexes, thereby detecting Zika virus-specific antibodies present in the sample.

A detectable moiety allows for visual detection of a precipitate or a color change, visual detection by microscopy (such as a chromogenic deposit or fluorescence), or automated detection by spectrometry, radiometric measurement or the like. Examples of detectable moieties include fluorescein, fluorescein isothiocyanate, rhodamine, Cy5, and Cy3 (for fluorescence microscopy and/or the microsphere-based immunoassay), horseradish peroxidase (for either light or electron microscopy and biochemical detection), biotin-streptavidin (for light or electron microscopy) and alkaline phosphatase (for biochemical detection by color change).

Another immunologic technique that can be useful in the detection of flavivirus antibodies uses mAbs for detection of antibodies specifically reactive with flavivirus polypeptides in a competitive inhibition assay. Briefly, a sample is contacted with a chimeric flavivirus or virus particle of the present disclosure which is bound to a substrate (for example, a 96-well plate). Excess sample is thoroughly washed away. A labeled (for example, enzyme-linked, fluorescent, radioactive, etc.) mAb is then contacted with any previously formed polypeptide-antibody complexes and the amount of mAb binding is measured. The amount of inhibition of mAb binding is measured relative to a control (no antibody), allowing for detection and measurement of antibody in the sample. The degree of mAb binding inhibition can be a very specific assay for detecting a particular flavivirus variety or strain, when based on mAb binding specificity for a particular variety or strain of flavivirus. mAbs can also be used for direct detection of flavivirus in cells by, for example, immunofluorescence assays according to standard methods.

As a further example, a micro-agglutination test can be used to detect the presence of Zika virus antibodies in a sample. Briefly, latex beads, red blood cells or other agglutinable particles are coated with a chimeric flavivirus or virus particles of this disclosure and mixed with a sample, such that antibodies in the sample that are specifically reactive with the antigen crosslink with the antigen, causing agglutination. The agglutinated antigen-antibody complexes form a precipitate, visible with the naked eye or measurable by spectrophotometer.

In yet another example, a microsphere-based immunoassay can be used to detect the presence of flavivirus antibodies in a sample. Microsphere immunoassays (MIAs) are becoming increasingly popular for laboratory diagnosis of many diseases (Earley et al., *Cytometry* 50:239-242, 2002; Kellar et al., *Cytometry* 45:27-36, 2001). The technology involves the detection and analysis of a reaction (such as an antibody or other ligand) attached to microspheres or beads. The detecting instrument is a simplified flow cytometer, and lasers simultaneously identify the microsphere sets and measure the fluorescence associated with the reaction. The speed at which these tests can be performed and the ability to multiplex make this methodology particularly useful.

A MIA can be used to detect the presence of Zika virus-specific antibodies in a sample. In some embodiments, microsphere beads are coated with a ZIKV-specific antibody and contacted with a chimeric virus (as disclosed herein) such that the chimeric viruses bind to the microsphere-bound Zika virus-specific antibodies. The microsphere immune complexes are mixed with a serum sample such that antibodies in the sample that are specifically reactive with the chimeric viruses bind the viruses bound (indirectly) to the microsphere. The bead-bound immune complexes are allowed to react with fluorescent-dye labeled anti-species antibody (such as PE-labeled anti-human IgM or anti-human IgG), and are measured using a microsphere reader (such as a Luminex instrument). In an alternative embodiment, microsphere beads are coated directly with the chimeric viruses and virus-bound microspheres are contacted with the serum samples.

Lateral flow assays (LFAs) are another method by which antigen-specific antibodies (or pathogen-specific antigens) can be detected in biological samples. These assays are generally very rapid and enable point of care testing. LFA is performed over a strip, different parts of which are assembled on a plastic backing. These parts are sample application pad, conjugate pad, nitrocellulose membrane and adsorption pad. Nitrocellulose membrane is further divided into test and control lines. Pre-immobilized reagents at different parts of the strip become active upon flow of liquid sample. LFA combines the unique advantages of biorecognition probes and chromatography.

Several designs have been developed for lateral flow assays. Generally LFAs include a porous support strip (such as a strip of cellulose) with a number of separate regions spaced horizontally along the support. The solid support need not be identical in all regions of a strip. Typically, the first region is a sample pad where a biological fluid is applied to flow laterally through the support to the remaining regions. The second region generally contains a labeling moiety that can be bound to the analyte of interest (such as an antibody or protein) in the sample if present. Downstream of the labeling region is a capture or "test" region where the labeled analyte (for example, antibody or peptide) is retained in the strip. It is in this test region where detection is generally performed. In addition to the test region, the strip may contain a control region either in the same flow path as that of the test region, or in a parallel path on the strip. There may also be a reservoir downstream of the various regions to absorb the sample that has traversed the test strip.

LFAs can be direct assays, forming sandwiches in proportion to the level of analyte present, or may be competition assays where analyte in the sample diminishes the amount of label detected in the detection zone. In direct sandwich assays, for example, the sample may be labeled by colored particles that are coupled to affinity reagents such as secondary antibodies that bind ZIKV-specific antibodies present in the sample, forming complexes which are then carried to the test region for capture by an additional reagent. The detectable label in the test region will be directly proportional to the level of peptide in the sample.

In competitive assays, the labeling region may contain labeled reagents, for example, that are already coupled to the target analyte (e.g. antibody) or an analog thereof, and the analytes in the sample compete with this labeled material for capture by the capture reagent in the test region. In this case, the detectable label in the test region will be inversely proportional to the quantity of analyte in the sample itself.

Simple visual detection is the most common means of reading an LFA, however, there are commercially available lateral flow readers that can quantitate the detectable label in the test region.

LFAs can be used, for example, to detect antigen-specific antibodies present in a biological sample (such as a serum sample) that specifically recognize ZIKV.

VII. Peripheral Challenge Model and Evaluation of Candidate Vaccine Efficacy

The chimeric viruses disclosed herein can also be used in the development of a peripheral challenge mouse model for ZIKV vaccine evaluation. It has been shown that mouse models established for ZIKV infection have limitations. In particular, many strains of mice are not susceptible to most wt ZIKV challenge by peripheral injection routes. Since the chimeric WN/ZKV disclosed herein are based on the WNV genetic backbone that is highly infective in many strains of mouse at any age, the chimeric viruses could be used as challenge viruses that are virulent in some of the mouse strain that are resistant to wt ZIKV infection.

Thus, the chimeric flaviviruses disclosed herein may be used in methods to assess the efficacy of candidate vaccines, such as ZIKV vaccine candidates. In some examples, the efficacy of candidate ZIKV vaccines are tested by inoculating subjects (for example, mice or non-human primates (such as rhesus monkeys)) with a candidate vaccine, followed by challenge with a virulent ZIKV strain. The disclosed WN/ZKV chimeras are virulent and/or generate significant viremia in non-immunized mice, therefore they can be used as the challenge dose in previously inoculated subjects.

In one particular embodiment, a set of subjects (such as mice) is inoculated with a candidate ZIKV vaccine. Administration of the candidate vaccine strain virus may be carried out by any suitable means, including by parenteral injection (such as intraperitoneal, subcutaneous, or intramuscular injection). In a particular example, the subjects are inoculated intraperitoneally with candidate vaccine virus in a vehicle such as phosphate buffered saline. Multiple inoculations (such as boosters) may be carried out, separated by a suitable period of time, such as at least two weeks, four weeks, eight weeks, twelve weeks, or more.

Subjects that have been test vaccinated with the candidate vaccine are challenged with a virulent or lethal dose of a WN/ZKV chimera disclosed herein following a suitable period of time to allow immunity based on the vaccination to develop (such as at least two weeks, four weeks, eight weeks, twelve weeks, or more). The challenge dose is administered by any suitable route including those above, and optionally is administered by the same or a different route as the vaccinating dose. Following the challenge dose, subjects are monitored for development of morbidity (such as fever, rash, vomiting, loss of appetite, rough fur, hunched back, lethargy, unbalanced or irritable movement, dehydration, weight loss, or signs of paralysis) or mortality. In addition, blood is collected from subjects after challenge for measurement of viremia levels. A decrease in viremia levels, signs of morbidity and/or mortality compared to a set of control subjects which is not inoculated with the candidate vaccine (for example, a decrease of at least 10%, 20%, 30%, 40%, 50%, 60%, 70%, 80%, 90%, 95%, or 99% in a test vaccinated population compared with a control population) indicates the effectiveness of the candidate vaccine.

The following examples are provided to illustrate certain particular features and/or embodiments. These examples should not be construed to limit the disclosure to the particular features or embodiments described.

EXAMPLES

Example 1: Construction of Chimeric West Nile/Zika Viruses

This example describes the construction of chimeric West Nile/Zika viruses (WN/ZKVs) that include the prM and E genes from Zika virus in a WNV backbone.

Engineering and Deriving Chimeric WN/ZKVs

Using previously engineered infectious clones of WNV (Kinney et al., *J Gen Virol* 87: 3611-3622, 2006), several chimeric WN/ZKVs that contain the prM and E genes of a Zika virus (ZIKV) in the genomic background of the WNV NY99 virus were engineered. The chimeric WN/ZKV expresses the entire ZIKV viral envelope on the virion surface, and can be used as a surrogate for ZIKV for multiple applications.

Flaviviruses encode a signal sequence (SS) at the C-terminal end of the capsid protein that serves as a signal peptide for prM during protein processing. The junction site of the chimeric constructs within the SS requires empirical investigation to obtain the most viable and stable chimeric virus. The amino acid (AA) sequences of the SS between WNV and ZIKV are not highly conserved, but both are 18 AA in length (FIG. 1). Based in part on knowledge obtained from the previous construction of various chimeric flaviviruses (U.S. Pat. No. 8,715,689 and PCT Publication No. WO 2015/196094, which are herein incorporated by reference in their entirety), three junction strategies were designed for the chimeric constructs (FIG. 1). The Z3 chimeric construct contains 15 AA of the SS from WNV and 3 AA of the SS from ZIKV; the Z5 construct contains 13 AA of the SS from WNV and 5AA from ZIKV; and the Z15 construct contain 3 AA of the SS from WNV and 15 AA from ZIKV.

All three chimeric viruses were successfully recovered from C6/36 cells transfected with chimeric viral RNA which was in vitro transcribed from engineered chimeric cDNA. Virus seeds were designated as C6/36-0 seeds when recovered from transfected C6/36 cells, and were amplified one more time in C6/36 and Vero cells to obtain the working virus seeds, C6/36-1 and C6/36-0/Vero-1, for further characterization.

Genome Sequencing of Chimeric WN/ZKVs

Initial chimeric constructs (WN/ZKV-3SPH, WN/ZKV-5SPH, and WN/ZKV-15SPH) were made using the prM-E gene sequence of the ZIKV SPH2015 strain obtained from Genbank (Accession No. KU321639.1), prior to when the PRVABC59 and R103451 strains were isolated from travelers acquiring ZIKV infection during the 2015 outbreak by the CDC diagnostic lab at Fort Collins, Colo. The R103451 (GenBank Accession No. KX262887.1; SEQ ID NO: 13) and PRVABC59 (GenBank Access No. KU501215.1; SEQ ID NO: 15) strains were available as wild-type (wt) ZIKV controls to CDC labs, but the SPH2015 strain was not. There is only 1 amino acid residue that differs between SPH2015 and R103451/PRVABC59 within the prM-E gene region included in the WN/ZIKV chimeric constructs. The difference is at E protein amino acid position 23 (E23), with an isoleucine (Ile) in the SPH2015 strain and a valine (Val) in the PRVABC59 and R103451 strains. Although the difference from Ile to Val is quite conserved, the E23 amino acid was changed to Val in one of the Z3 chimeric constructs (WN/ZKV-3PR) to make the entire prM-E amino acid sequence identical to the R103451 and PRVABC59 strains that will be used as wt ZIKV controls. For the nucleotide sequences of the prM-E, there is one nucleotide that differs (silent) between the chimeras and strain R103251, and six silent differences between the chimeras and the PRVABC59 strain. Except for the 5' and 3' 24-base termini of the viral genome, the genomes of the chimeric virus working seeds have been sequenced, and it has been verified that all of the seeds contain the correct recombinant genome sequences. The following constructs have been sequenced:

WN/ZKV-3PR (SEQ ID NOs: 1 and 2)—contains 15 AA of the SS from WNV and 3 AA of the SS from ZIKV; the nucleotide and amino sequences of this construct were modified to substitute Ile for Val at position 23 of the E protein (E23; residue 314 of SEQ ID NO: 2) to correspond to the sequence of strain PRVABC59 and R103451.

WN/ZKV-3SPH (SEQ ID NOs: 3 and 4)—contains 15 AA of the SS from WNV and 3 AA of the SS from ZIKV; includes Ile at position E23 (residue 314 of SEQ ID NO: 4), which corresponds to strain SPH2015.

WN/ZKV-5SPH (SEQ ID NOs: 5 and 6)—contains 13 AA of the SS from WNV and 5 AA of the SS from ZIKV; includes Ile at position E23 (residue 314 of SEQ ID NO: 6), which corresponds to strain SPH2015.

WN/ZKV-15SPH (SEQ ID NOs: 7 and 8)—contains 3 AA of the SS from WNV and 15 AA of the SS from ZIKV; includes Ile at position E23 (residue 314 of SEQ ID NO: 8), which corresponds to strain SPH2015.

Chimeric Virus Growth in Cells

All three types of chimeric constructs yielded viable viruses that replicated competently and reached very high titers (ranging from $10^8$-$10^9$ pfu/ml) in C6/36 cells as early as day 3 post-infection (p.i.). In C6/36 cell cultures, rapid replication to high titer permitted the chimeric viruses to be harvested daily from day 3 to day 14. In Vero cells, the chimeric viruses caused significant cytopathic effect (CPE) starting at day 3, but still achieved high virus titers ($10^7$-$10^8$ pfu/ml) that could be harvested daily from day 2 to day 10 p.i. All three types of chimeric constructs demonstrated similar infectivity and replication efficiency in cell cultures.

When comparing plaque size of chimeric WN/ZKV with its wt ZIKV, the chimeric plaques were significantly larger and more uniform than wt ZIKV plaques. Plaques of chimeric WN/ZKV could be clearly counted on day 3 p.i., while wt ZIKV R103451 plaques could not be readily counted until day 5-6 p.i.

PRNT Titers of Human Serum Against Chimeric WN/ZKV

In view of the faster replication rate of chimeric WN/ZKV compared to wt ZIKV, the chimeric viruses were evaluated as a ZIKV surrogate for the development of faster neutralization assays. Wild type ZIKV and chimeric WN/ZKV-3SPH were compared in the traditional plaque reduction neutralization test (PRNT). The results confirmed that chimeric WN/ZKV expressed authentic ZIKV neutralization epitopes that resulted in neutralization assay results that were equivalent to the neutralization assay using wt ZIKV (Table 3). The chimeric virus can speed up the traditional PRNT from 5-6 days to 3-4 days.

TABLE 3

Similar PRNT (90% virus reduction) titers of 13 human serum samples against chimeric WN/ZKV-3SPH virus and wt ZIKV PRVABC59

| | PRNT90 | |
|---|---|---|
| Serum ID | wt ZIKV (PRVABC59) | WN/ZKV |
| 1 | 5120 | 5120 |
| 2 | 10 | 20 |
| 3 | 2560 | 2560 |
| 4 | 320 | 640 |
| 5 | 10,240 | 10240 |
| 6 | 40 | 80 |
| 7 | 2560 | 2560 |
| 8 | 640 | 1280 |
| 9 | <10 | <10 |
| 10 | <10 | <10 |
| 13 | 160 | 640 |
| 14 | 160 | 320 |
| 15 | 320 | 640 |

Live Chimeric Reporter Viruses

A fluorescent reporter gene (ZsGreen) was inserted into the chimeric WN/ZKV virus construct to generate live chimeric WN/ZKV reporter viruses. Reporter viruses were successfully generated for WN/ZKV-3SPH by insertion of the ZsGreen linked with P2A using strategy 1 (FIG. 2, Type I reporter construct). The nucleotide and amino acid sequences of two reporter viruses (WN/ZKV-ZsG0 and WN/ZKV-ZsG1) are set forth herein as SEQ ID NOs: 9-12. The nucleotide sequence of the ZsGreen in WN/ZKV-ZsG1 (SEQ ID NO: 11) is codon-optimized for expression in human cells. The first 35 amino acid codons of the C gene immediately after ZsGreen-P2A in both chimeric constructs were edited (not human codon optimized) to make multiple silent mutations in order to minimize homologous recombination potential with the partial C35 gene upstream of ZsGreen. The C sequence was edited instead of human codon optimized because the codon optimization could result in more homologous recombination potential with the human optimized ZsGreen gene. Decreasing homologous recombination potential is expected to enhance the genetic stability of the reporter viruses. An alternative reporter virus strategy is shown in FIG. 2 (see Type II reporter construct).

Genetic Stability

Chimeric viruses are passaged serially in Vero cell cultures to determine their genetic stability. The chimeric virus exhibiting the greatest genetic stability are chosen for applications that require serial cell passages during virus production (for example, production of inactivated vaccine).

Example 2: Characterization of Chimeric WN/ZKV and R-WN/ZKV Constructs

This example describes the generation and characterization of an additional WN/ZKV reporter virus (R-WN/ZKV).

Stability of WN/ZKV and R-WN/ZKV Constructs

Example 1 describes the successful recovery of chimeric WN/ZKVs using all three of the strategies illustrated in FIG. 1. All three types of chimeric viruses replicated efficiently in both Vero and C6/36 cells and, based on their similar plaque phenotypes in Vero cells between 1 to 10 serial passages, all three chimeric constructs appeared to be similarly stable in Vero cells. The chimeric WN/ZKV-Z3 constructs WN/ZKV-3SPH and WN/ZKV-3PR were genome sequenced after serial passages in Vero cells. Both chimeric viral genomes were quite stable after serial passage. The WN/ZKV-3SPH acquired 3 amino acid (AA) mutations, and WN/ZKV-3PR acquired only 2 AA mutations after the 10 passages.

The reporter chimeric virus constructs disclosed herein are based on WN/ZKV-3SPH or WN/ZKV-3PR. First, two reporter viruses (WN/ZKV-ZsG0 and WN/ZKV-ZsG1) based on WN/ZKV-3SPH were recovered. After genome sequencing both reporter chimeras recovered from transfection and 1 more passage in C6/36 cells, WN/ZKV-ZsG0 was found to have the expected sequence, including the full ZsGreen gene, while a small portion of the WN/ZKV-ZsG1 reporter seed lost the ZsGreen gene. After RT-PCR analysis, it was estimated that about 10% of the WN/ZKV-ZsG1 suffered deletion of the ZsGreen gene. Therefore, the WN/ZKV-ZsG0 construct was used to make the reporter chimera R-WN/ZKV-PR (based on WN/ZKV-3PR).

Figure 4:
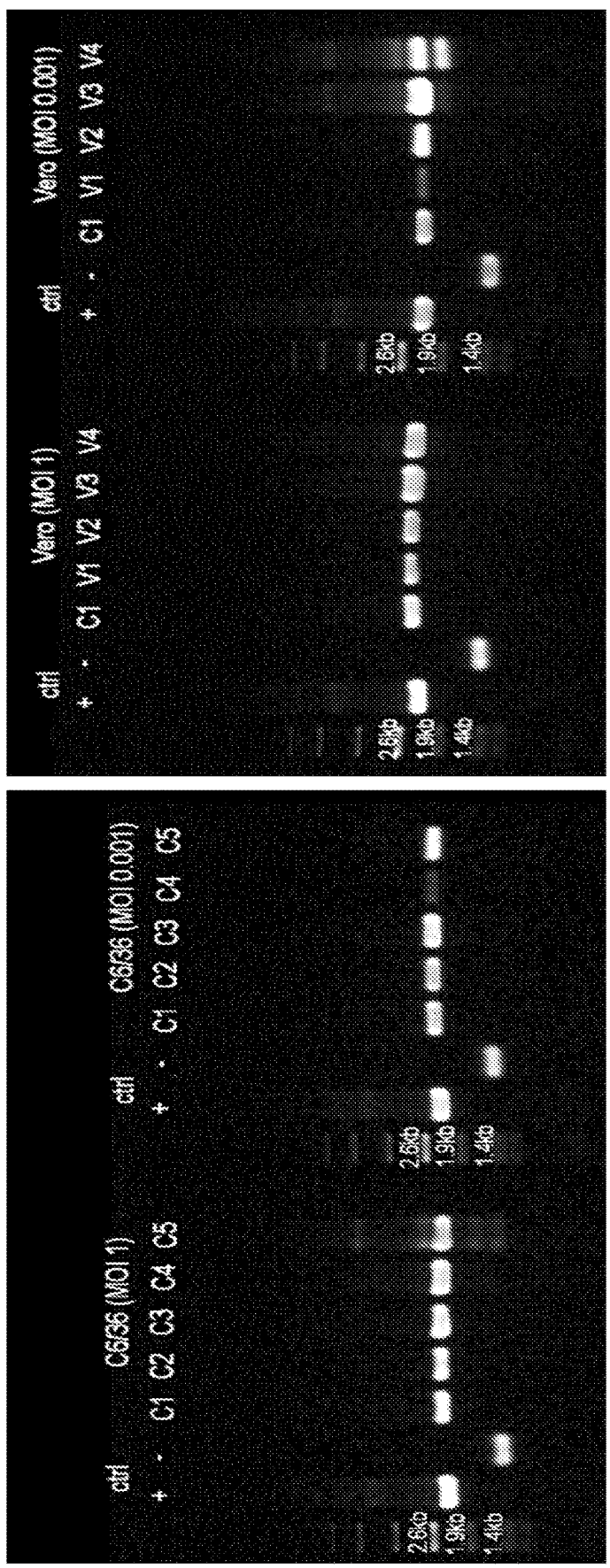
FIG. 4 shows the genetic stability of ZsG0 in R-WN/ZKV-PR virus. R-WN/ZKV-PR was serially passaged in C6/36 cells (left) or Vero cells (right) at an MOI of 1 or an MOI of 0.001. ZsG0 gene was analyzed by RT-PCR with a primer set for amplifying a 2.27 kb cDNA fragment (nucleotides 1-2272 of R-WN/ZKV-PR), including the full ZsG0 and P2A. The reporter gene was intact after 5 passages in C6/36 cells at an MOI of 0.001, but showed deletion in a portion of the stock at an MOI of 1. In Vero cells, the reporter gene was stable up to 4 passages at an MOI of 1, but a significant portion of the 0.001 MOI passage-4 stock showed partial gene deletion.
Figure 5:
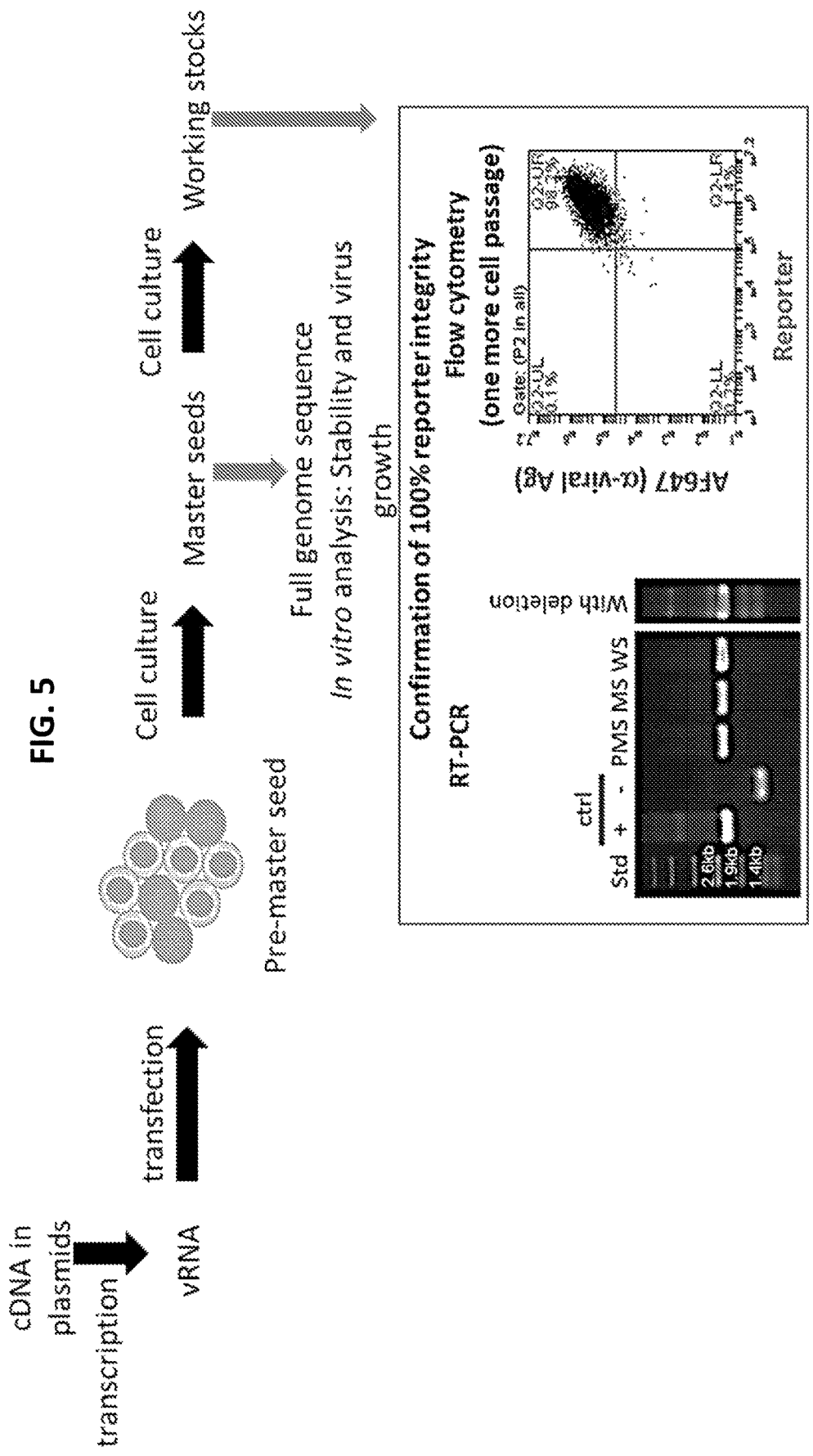
FIG. 5 includes a schematic of the production of R-WN/ZKV reporter virus seed lots. Also shown are RT-PCR and flow cytometry analysis of the integrity of the R-WN/ZKV reporter virus.

Similar to WN/ZKV-ZsG0, R-WN/ZKV-PR was constructed with the type 1 reporter construct shown in FIG. 2. The reporter genome contains WNV 5'NCR, WNV partial C gene (first 35 AA with wt sequence), ZsGreen gene (wt) linked with a self-cleavage 2A peptide from porcine teschovirus-1 (P2A), a full WNV C gene with its first 35 AA codon edited, the first 15 AA of the WNV prM signal sequence and the last 3 AA of the ZIKV prM signal sequence, the prM and E genes of ZIKV, and all of the NS genes and the 3'NCR of WNV (FIG. 3). The nucleotide and amino acid sequences of R-WN/ZKV-PR are set forth herein as SEQ ID NO: 19 and SEQ ID NO: 20, respectively. Serial passaging of R-WN/ZKV-PR indicated that the ZsG0 gene in the construct was stable up to 4 passages in Vero cells and 5 passages in C6/36 cells (FIG. 4). Therefore, it was determined that the working stock of the reporter virus should be limited to low cell passage levels, less than a total of three passages after deriving the virus from transfection of the in vitro transcribed recombinant viral RNA (FIG. 5).

In addition, every reporter virus lot generated is confirmed for ZsGreen gene stability and expression by dual-fluorescent flow cytometry analysis. Cells infected with pre-master seed (PMS), master seed (MS), or working stock (WS) of the R-WN/ZKV-PR were immunostained with a rabbit monoclonal WNV capsid Ab followed by a goat anti-rabbit Ab conjugated with Alexa Fluor 647 (AF647) fluorophore after 24-48 hours of infection. Flow cytometry results in FIG. 5 show an example in which 98% of infected cells co-expressed both WNV C protein (AF647) and ZsG0 protein (ZsGreen), while only 0.1% of cells showed low positivity to WNV C protein only, and only 1.4% of cells showed positivity to ZsG0 only. Using RT-PCR and flow cytometry, the PMS, MS, and WS lots of R-WN/ZKV-PR were analyzed, and all three lots had an intact ZsG0 gene and showed a high level of co-expression of WNV C and ZsG0 proteins in the infected cells. These two assays serve as quality control assays for each lot of reporter virus generated.

Chimeric WN/ZKV and WN/DENVs for Fast and Synchronized PRNT and mFRNT to ZIKV and DENVs The WNV NY99 strain replicates significantly faster than wt DENV and ZIKV in multiple cell cultures, including Vero, LLC-MK2, and BHK-21 cells that are widely used for cell based neutralization antibody assays. Unlike ELISA that measures all types of antibodies, the neutralization test measures antibodies capable of neutralizing the viruses. Because it is more specific than ELISA, the neutralization test has been used as a confirmative serological assay after positive results of ELISA in diagnosis.

Upon binding to viruses, the neutralization antibodies (Nt Abs) block virus infection of cells (mostly during virus entry stage) and are the most important B cell immune response product in directly fighting many viral infections. Therefore, the neutralization test is also one of the most important functional immunological assays in analyses of vaccine efficacy. However, most of the cell-based neutralization tests are time-consuming and labor-intensive. The traditional gold-standard plaque-reduction neutralization test (PRNT) used in detecting Nt Abs to many flaviviruses typically has used 6- to 24-well plates, and required multiple days of cell infection before the virus plaques formed on the infected cell sheet under an agarose medium overlay can be stained and become visible for counting. The faster micro-focus neutralization test (mFRNT) typically uses 96-well micro plates, and the viral micro-foci can be detected and counted by microplate reader (such as ELISPOT reader or image-based cytometry reader) after immunostaining by viral Abs of the cell sheet within 1-2 days post infection.

Because ZIKV and DENVs are transmitted by the same mosquito vectors, Ae. aegypti and Ae. albopictus, most recent ZIKV outbreaks happen in areas that are also endemic for DENVs. Due to significant cross-reactivity of flavivirus antibodies, it is very difficult to differentiate infection among ZIKV and the four types of DENV in secondary ZIKV- or DENV-infected cases. For example, during confirmative diagnosis by PRNT for recent ZIKV outbreaks, it is necessary to conduct a PRNT assay against ZIKV and multiple types (typically at least 2) of DENV for the same clinical samples. Because DENVs and ZIKV have different replication rates in Vero cells, the duration of PRNT for each virus is different. Such differential testing schedule complicates the streaming of diagnostic effort. By using chimeric WN/DENVs and WN/ZKV for the PRNT, it is possible to synchronize the assay duration to three days post infection (pi). As indicated in the Table 4, wt DENVs require 6 to 9 days, depending on the DENV strain, to produce visible plaques, while the wt ZIKV takes at least 5 days p.i. to show countable plaques. On the other hand, all chimeric WN/DENVs and WN/ZKV produced clear plaques by 3 days p.i. Therefore, using the chimeric viruses, it was possible to decrease the PRNT duration by approximately 50% and obtain results for all viruses on the same day. A panel of human serum specimens were tested to confirm that use of the chimeric WN/DENVs and WN/ZIKV resulted in similar PRNT titers as those that were obtained when using wt DENVs and wt ZIKV (Table 3 shows WN/ZKV vs ZIKV results).

TABLE 4

Chimeric viruses form plaques faster than wt parental viruses in Vero cells
Visible Plaques (day p.i.)

| WNV | 3 | | |
|---|---|---|---|
| DENV-1 | 6-8 | WN/DENV-1 | 3 |
| DENV-2 | 7-9 | WN/DENV-2 | 3 |
| DENV-3 | 6-8 | WN/DENV-3 | 3 |
| DENV-4 | 6-8 | WN/DENV-4 | 3 |
| ZIKV | 5-7 | WN/ZIKV | 3 |

R-WN/ZKV-PR for Fast, Easy, and High-Throughput Fluoro-mFRNT or Cell Infection Rate Reduction Assay Although much faster and higher throughput than the PRNT, the typical mFRNT is still labor intensive. The procedures include adding and removing the carboxyl methyl cellulose overlays from cell plates, cell fixation, and multiple immunostaining procedures. R-WN/ZKV-PR was used to largely simplify and optimize the mFRNT to a fluoro-mFRNT that can be live-imaged by an image-based cytometry plate reader to detect the fluorescent viral foci on infected cell sheets. Due to the fast replication efficiency of the WN/ZKV and strong ZsG0 reporter signal, the infected cells can be measured within 24 hours p.i. With a live-imaging capable cytometry plate reader, it was possible to directly read the infected 96-well plate without any CMC overly, cell fixation, or immunostaining process. FIG. 6 shows a comparison of the PRNT, mFRNT, and fluoro-mFRNT procedures.

A small panel of human serum specimens were tested with the fluoro-mFRNT using R-WN/ZKV-PR. The neutralizing Ab titer results were very comparable to the traditional gold-standard PRNT using wt ZIKV (Table 5). In addition to the fluoro-mFRNT, R-WN/ZKV-PR can also be used in other cytometry-based neutralization assays, which measure reduction of the percent cell infection rate instead of the reduction in viral foci formation. The same image-cytometry plate reader was used to evaluate such an assay with R-WN/ZKV-PR, and the results indicated that a wide linear range of the cell infection rate can be easily achieved by R-WN/ZKV-PR, suggesting its utility for the percent cell infection reduction-based Nt assay.

TABLE 5

Comparable results between PRNT using wt ZIKV and Fluoro-mFRNT using R-WN/ZKV

| Serum ID | wt ZIKV PRNT90* | R-WN/ZKV F-mFRNT90* |
|---|---|---|
| 20 | 1280 | 640/1280 |
| 21 | 10240 | 2560/5120 |
| 22 | 2560 | 1280 |
| 23 | 5120 | 1280/2860 |
| 30 | 160 | 320/640 |
| 32 | 2560 | 1280 |
| 33 | 20480 | 10240/20480 |
| 38 | 640 | 640/1280 |
| 39 | 1280 | 2560 |
| 44 | 320 | 640 |

*At least 90% reduction

Mouse Challenge Study

WN/ZKV-3PR was tested in CD-1 and AG129 mice. The results showed that the CD-1 immune competent, outbred mice were not susceptible to WN/ZKV-3PR or wt ZIKV, but were highly susceptible to wt WNV (Table 6). In the interferon-α, -β, -γ receptor knockout AG129 mice, WN/ZKV was also attenuated relative to WNV, but caused a mortality rate similar to or somewhat higher than that of wt ZIKV (Table 7). AG129 mice infected with WN/ZKV had significantly shorter survival time than wt ZIKV-infected AG129. Overall, the results showed that WN/ZKV was more similar to the BSL-2 wt ZIKV in mice than the BSL-3 WNV. Therefore, these results support laboratory containment at BSL-2 when working with chimeric WN/ZKV.

TABLE 6

Three week-old CD-1 mice by intra-peritoneal challenge

| Virus/dose (pfu) | Survival | AST* ± SD |
|---|---|---|
| ZIKV PRVABC59/$10^6$ | 100% | NA |
| WN/ZIKV-3PR/$10^6$ | 100% | NA |
| WN/ZIKV-3PR/$10^5$ | 100% | NA |
| WN/ZIKV-3PR/$10^4$ | 100% | NA |
| WN/ZIKV-3PR/$10^3$ | 100% | NA |
| WN NY99/$10^3$ | 0% | 8 ± 0 |

*AST = Average Survival Time

TABLE 7

AG129 mice (≥20 week-old) by intraperitoneal challenge

| Virus/dose (pfu) | Survival | AST* ± SD |
|---|---|---|
| ZIKV PRVABC59/$10^4$ | 0% | 13.6 ± 1.2 |
| ZIKV PRVABC59/$10^3$ | 0% | 18.6 ± 3.5 |
| ZIKV PRVABC59/$10^2$ | 40% | 19.7 ± 1.89 |
| WN/ZIKV-3PR/$10^3$ | 0% | 5.2 ± 0.4 |
| WN/ZIKV-3PR/$10^2$ | 20% | 6 ± 0 |
| WN/ZIKV-3PR/10 | 40% | 7.3 ± 2.6 |
| WN NY99/$10^2$ | 0% | 3.1 ± 0.4 |
| WN NY99/10 | 20% | 3.8 ± 0.4 |

*AST = Average Survival Time

Mosquito Study

A mosquito infection experiment was initiated with the chimeric viruses WN/ZKV-3PR and R-WN/ZKV-PR. Results from a small number of infected mosquitoes have shown an absence of infectivity or very low infectivity of the chimeric viruses for the Culex mosquito vector of WNV. To further reduce the potential for infection of mosquitos, miRNAs specific to mosquito cells are incorporated into WN/ZKV and R-WN/ZKV to evaluate whether such miRNA can be used to eliminate any potential of mosquito transmission of the virus. Specifically, miRNA-14, miRNA-184, and miRNA-1175 are investigated.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A nucleic acid chimera comprising:

a first nucleic acid molecule comprising a 5' non-coding region, a nucleic acid encoding a capsid (C) protein and non-structural proteins, and a 3' non-coding region, each from a West Nile virus genome, wherein the C protein comprises a portion of a premembrane (prM) signal sequence from the West Nile virus genome and a portion of a prM signal sequence from a Zika virus genome; and a second nucleic acid molecule operably linked to the first nucleic acid molecule, encoding a prM protein and an envelope (E) protein from the Zika virus genome.

2. The nucleic acid chimera of claim 1, wherein:

(i) the portion of the prM signal sequence from the West Nile virus genome comprises the first 15 amino acids of the West Nile virus prM signal sequence and the portion of the prM signal sequence from the Zika virus genome comprises the last three amino acids of the Zika virus prM signal sequence;

(ii) the portion of the prM signal sequence from the West Nile virus genome comprises the first 13 amino acids of the West Nile virus prM signal sequence and the portion of the prM signal sequence from the Zika virus genome comprises the last five amino acids of the Zika virus prM signal sequence; or (iii) the portion of the prM signal sequence from the West Nile virus genome comprises the first three amino acids of the West Nile virus prM signal sequence and the portion of the prM signal sequence from the Zika virus genome comprises the last 15 amino acids of the Zika virus prM signal sequence.

3. The nucleic acid chimera of claim 2(i), wherein:
the first 15 amino acids of the West Nile virus prM signal sequence comprises amino acids 106-120 of SEQ ID NO: 2 or SEQ ID NO: 4;
the last three amino acids of the Zika virus prM signal sequence comprises AMA; or
the first 15 amino acids of the West Nile virus prM signal sequence comprises amino acids 106-120 of SEQ ID NO: 2 or SEQ ID NO: 4, and the last three amino acids of the Zika virus prM signal sequence comprises AMA.

4. The nucleic acid chimera of claim 2(ii), wherein:
the first 13 amino acids of the West Nile virus prM signal sequence comprises amino acids 106-118 of SEQ ID NO: 6;
the last five amino acids of the Zika virus prM signal sequence comprises amino acids 119-123 of SEQ ID NO: 6; or
the first 13 amino acids of the West Nile virus prM signal sequence comprises amino acids 106-118 of SEQ ID NO: 6 and the last five amino acids of the Zika virus prM signal sequence comprises amino acids 119-123 of SEQ ID NO: 6.

5. The nucleic acid chimera of claim 2(iii), wherein:
the first three amino acids of the West Nile virus prM signal sequence comprises amino acids 106-108 of SEQ ID NO: 8;
the last 15 amino acids of the Zika virus prM signal sequence comprises amino acids 109-123 of SEQ ID NO: 8; or
the first three amino acids of the West Nile virus prM signal sequence comprises amino acids 106-108 of SEQ ID NO: 8 and the last 15 amino acids of the Zika virus prM signal sequence comprises amino acids 109-123 of SEQ ID NO: 8.

6. The nucleic acid chimera of claim 1, wherein the West Nile virus is strain NY99.

7. The nucleic acid chimera of claim 1, wherein the Zika virus is strain SPH2015, PRVABC59 or R103451.

8. The nucleic acid chimera of claim 1, comprising a nucleic acid sequence at least 95% identical to SEQ ID NO: 1, SEQ ID NO: 3, SEQ ID NO: 5 or SEQ ID NO: 7.

9. The nucleic acid chimera of claim 8, comprising the nucleic acid sequence of SEQ ID NO: 1, SEQ ID NO: 3, SEQ ID NO: 5 or SEQ ID NO: 7.

10. The nucleic acid chimera of claim 1, wherein the nucleic acid chimera encodes an amino acid sequence at least 95% identical to SEQ ID NO: 2, SEQ ID NO: 4, SEQ ID NO: 6 or SEQ ID NO: 8.

11. The nucleic acid chimera of claim 10, wherein the nucleic acid chimera encodes the amino acid sequence of SEQ ID NO: 2, SEQ ID NO: 4, SEQ ID NO: 6 or SEQ ID NO: 8.

12. An immunogenic composition comprising an inactivated virus comprising the nucleic acid chimera of claim 1 and a pharmaceutically acceptable carrier.

13. The immunogenic composition of claim 12, wherein the inactivated virus is inactivated by one or more of chemical treatment, physical treatment and irradiation.

14. A method of eliciting an immune response against Zika virus in a subject, comprising administering to the subject the immunogenic composition of claim 12.

15. A method, comprising inactivating a virus comprising a nucleic acid chimera of claim 1.

16. The method of claim 15, wherein inactivating the virus comprises treating the virus with a chemical inactivation agent, high pressure, ultraviolet irradiation, gamma irradiation, or any combination thereof.

17. The method of claim 15, further comprising administering the inactivated virus to a subject.

18. The nucleic acid chimera of claim 1, further comprising a reporter gene.

19. The nucleic acid chimera of claim 18, wherein the reporter gene encodes a fluorescent protein or a bioluminescent protein.

20. The nucleic acid chimera of claim 18, wherein the reporter gene is human codon optimized.

21. The nucleic acid chimera of claim 18, comprising a nucleic acid sequence at least 95% identical to SEQ ID NO: 9, SEQ ID NO: 11 or SEQ ID NO: 19.

22. The nucleic acid chimera of claim 21, comprising the nucleic acid sequence of SEQ ID NO: 9, SEQ ID NO: 11 or SEQ ID NO: 19.

23. A chimeric virus, comprising the nucleic acid chimera of claim 18.

24. A method of detecting Zika virus-specific antibodies in a sample, comprising:
contacting the sample with the chimeric virus of claim 23 under conditions sufficient to form virus-antibody complexes if Zika virus antibodies are present in the sample; and
detecting the virus-antibody complexes, thereby detecting Zika virus-specific antibodies in the sample.

25. A method of detecting Zika virus-specific antibodies in a sample, comprising:
contacting the sample with the chimeric virus of claim 23 to form a virus-sample mixture, wherein virus-antibody complexes are formed in the virus-sample mixture if Zika virus-specific antibodies are present in the sample;
inoculating a cell culture with the virus-sample mixture under conditions sufficient to allow plaque formation or micro-focus formation in the cell culture; and
detecting a decrease in plaque formation or micro-focus formation in the cell culture as compared to a control cell culture, thereby detecting a Zika virus-specific antibody in the sample.

26. A method of detecting Zika virus-specific antibodies in a sample, comprising:
providing the chimeric virus of claim 23 bound to a solid support;
contacting the chimeric virus-bound solid support with the sample under conditions sufficient to form virus-antibody complexes if Zika virus-specific antibodies are present in the sample;
contacting the virus-antibody complexes with a secondary antibody; and
detecting binding of the secondary antibody to the virus-antibody complexes, thereby detecting Zika virus-specific antibodies in the sample.

27. A method of detecting Zika virus-specific antibodies in a sample, comprising:

providing a secondary antibody bound to a solid support;
contacting the secondary antibody-bound solid support with the sample under conditions sufficient to allow binding of the secondary antibody to any Zika virus-specific antibodies present in the sample, thereby forming antibody-antibody complexes;
contacting the antibody-antibody complexes with the chimeric virus of claim 23 under conditions sufficient for the chimeric virus to bind the Zika virus-specific antibodies, thereby forming immune complexes; and
detecting the presence of the immune complexes, thereby detecting Zika virus-specific antibodies in the sample.

28. The method of claim 27, wherein detecting the presence of the immune complexes comprises contacting the immune complexes with an antibody that specifically binds the chimeric virus and comprises a detectable label.

29. A method of detecting Zika virus-specific antibodies in a sample, comprising:
providing a Zika virus-specific antibody bound to a solid support;
contacting the antibody-bound solid support with the chimeric virus of claim 23 under conditions sufficient for the chimeric virus to bind the Zika virus-specific antibody to form antibody-virus complexes;
contacting the antibody-virus complexes with the sample to allow binding of any Zika virus-specific antibodies present in the sample to the chimeric virus, thereby forming immune complexes;
contacting the immune complexes with a secondary antibody; and
detecting binding of the secondary antibody to the immune complexes, thereby detecting Zika virus-specific antibodies present in the sample.

30. The method of claim 26, wherein the secondary antibody comprises an anti-IgM antibody or an anti-IgG antibody.

31. The method of claim 24, wherein the sample comprises a biological fluid sample.

32. The method of claim 31, wherein the biological fluid sample comprises serum, blood or plasma.

33. A chimeric virus, comprising the nucleic acid chimera of claim 1.

34. A method of detecting Zika virus-specific antibodies in a sample, comprising:
contacting the sample with the chimeric virus of claim 33 under conditions sufficient to form virus-antibody complexes if Zika virus antibodies are present in the sample; and
detecting the virus-antibody complexes, thereby detecting Zika virus-specific antibodies in the sample.

35. A method of detecting Zika virus-specific antibodies in a sample, comprising:
contacting the sample with the chimeric virus of claim 33 to form a virus-sample mixture, wherein virus-antibody complexes are formed in the virus-sample mixture if Zika virus-specific antibodies are present in the sample;
inoculating a cell culture with the virus-sample mixture under conditions sufficient to allow plaque formation or micro-focus formation in the cell culture; and
detecting a decrease in plaque formation or micro-focus formation in the cell culture as compared to a control cell culture, thereby detecting a Zika virus-specific antibody in the sample.

36. A method of detecting Zika virus-specific antibodies in a sample, comprising:
providing the chimeric virus of claim 33 bound to a solid support;
contacting the chimeric virus-bound solid support with the sample under conditions sufficient to form virus-antibody complexes if Zika virus-specific antibodies are present in the sample;
contacting the virus-antibody complexes with a secondary antibody; and
detecting binding of the secondary antibody to the virus-antibody complexes, thereby detecting Zika virus-specific antibodies in the sample.

37. A method of detecting Zika virus-specific antibodies in a sample, comprising:
providing a secondary antibody bound to a solid support;
contacting the secondary antibody-bound solid support with the sample under conditions sufficient to allow binding of the secondary antibody to any Zika virus-specific antibodies present in the sample, thereby forming antibody-antibody complexes;
contacting the antibody-antibody complexes with the chimeric virus of claim 33 under conditions sufficient for the chimeric virus to bind the Zika virus-specific antibodies, thereby forming immune complexes; and
detecting the presence of the immune complexes, thereby detecting Zika virus-specific antibodies in the sample.

38. The method of claim 37, wherein detecting the presence of the immune complexes comprises contacting the immune complexes with an antibody that specifically binds the chimeric virus and comprises a detectable label.

39. A method of detecting Zika virus-specific antibodies in a sample, comprising:
providing a Zika virus-specific antibody bound to a solid support;
contacting the antibody-bound solid support with the chimeric virus of claim 33 under conditions sufficient for the chimeric virus to bind the Zika virus-specific antibody to form antibody-virus complexes;
contacting the antibody-virus complexes with the sample to allow binding of any Zika virus-specific antibodies present in the sample to the chimeric virus, thereby forming immune complexes;
contacting the immune complexes with a secondary antibody; and
detecting binding of the secondary antibody to the immune complexes, thereby detecting Zika virus-specific antibodies present in the sample.

* * * * *

SEQUENCE LISTING

```
<160> NUMBER OF SEQ ID NOS: 20

<210> SEQ ID NO 1
<211> LENGTH: 11041
<212> TYPE: DNA
<213> ORGANISM: Artificial Sequence
<220> FEATURE:
<223> OTHER INFORMATION: Synthetic construct

<400> SEQUENCE: 1
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agttcgaaac aaaagaaaag aggaggaaag     420
accggaattg cagtcatgat tggcctgatc gccagcgcta tggcagcgga ggtcactaga     480
cgtgggagtg catactatat gtacttggac agaaacgatg ctggggaggc catatctttt     540
ccaaccacat tggggatgaa taagtgttat atacagatca tggatcttgg acacatgtgt     600
gatgccacca tgagctatga atgccctatg ctggatgagg gggtggaacc agatgacgtc     660
gattgttggt gcaacacgac gtcaacttgg gttgtgtacg gaacctgcca tcacaaaaaa     720
ggtgaagcac ggagaagtag aagagctgtg acgctcccct cccattccac taggaagctg     780
caaacgcggt cgcaaacctg gttggaatca agagaataca caaagcactt gattagagtc     840
gaaaattgga tattcaggaa ccctggcttc gcgttagcag cagctgccat cgcttggctt     900
ttgggaagct caacgagcca aaaagtcata tacttggtca tgatactgct gattgccccg     960
gcatacagca tcaggtgcat aggagtcagc aatagggact ttgtggaagg tatgtcaggt    1020
gggacttggg ttgatgttgt cttggaacat ggaggttgtg tcaccgtaat ggcacaggac    1080
aaaccgactg tcgacataga gctggttaca caacagtca gcaacatggc ggaggtaaga    1140
tcctactgct atgaggcatc aatatcagac atggcttcgg cagccgctg cccaacacaa    1200 ggtgaagcct accttgacaa gcaatcagac actcaatatg tctgcaaaag aacgttagtg    1260
gacagaggct ggggaaatgg atgtggactt tttggcaaag ggagtctggt gacatgcgct    1320
aagtttgcat gctccaagaa aatgaccggg aagagcatcc agccagagaa tctggagtac    1380
cggataatgc tgtcagttca tggctcccag cacagtggga tgatcgttaa tgacacagga    1440
catgaaactg atgagaatag agcgaaggtt gagataacgc ccaattcacc aagagccgaa    1500
gccacactgg ggggttttgg aagcctagga cttgattgtg aaccgaggac aggccttgac    1560
ttttcagatt tgtattactt gactatgaat aacaagcact ggttggttca caaggagtgg    1620
ttccacgaca ttccattacc ttggcacgct ggggcagaca ccggaactcc acactggaac    1680
aacaaagaag cactggtaga gttcaaggac gcacatgcca aaaggcaaac tgtcgtggtt    1740
ctagggagtc aagaaggagc agttcacacg gcccttgctg gagctctgga ggctgagatg    1800
```

```
gatggtgcaa agggaaggct gtcctctggc cacttgaaat gtcgcctgaa aatggataaa    1860
cttagattga agggcgtgtc atactccttg tgtaccgcag cgttcacatt caccaagatc    1920
ccggctgaaa cactgcacgg gacagtcaca gtggaggtac agtacgcagg gacagatgga    1980
ccttgcaagg ttccagctca gatggcggtg gacatgcaaa ctctgacccc agttgggagg    2040
ttgataaccg ctaaccccgt aatcactgaa agcactgaga actctaagat gatgctggaa    2100
cttgatccac catttgggga ctcttacatt gtcataggag tcggggagaa gaagatcacc    2160
caccactggc acaggagtgg cagcaccatt ggaaaagcat ttgaagccac tgtgagaggt    2220
gccaagagaa tggcagtctt gggagacaca gcctgggact ttggatcagt tggaggcgct    2280
ctcaactcat tgggcaaggg catccatcaa atttttggag cagctttcaa atcattgttt    2340
ggaggaatgt cctggttctc acaaattctc attggaacgt tgctgatgtg gttgggtctg    2400
aacacaaaga atggatctat ttcccttatg tgcttggcct tagggggagt gttgatcttc    2460
ttatccacag ccgtctctgc tgattccgga tgtgccatag acatcagccg gcaagagctg    2520
agatgtggaa gtggagtgtt catacacaat gatgtggagg cttggatgga ccggtacaag    2580
tattaccctg aaacgccaca aggcctagcc aagatcattc agaaagctca taaggaagga    2640
gtgtgcggtc tacgatcagt ttccagactg gagcatcaaa tgtgggaagc agtgaaggac    2700
gagctgaaca ctcttttgaa ggagaatggt gtggaccttag tgtcgtggt tgagaaacag    2760 gagggaatgt acaagtcagc acctaaacgc ctcaccgcca ccacggaaaa attggaaatt    2820
ggctggaagg cctggggaaa gagtatttta tttgcaccag aactcgccaa caacaccttt    2880
gtggttgatg gtccggagac caaggaatgt ccgactcaga atcgcgcttg gaatagctta    2940
gaagtggagg attttggatt tggtctcacc agcactcgga tgttcctgaa ggtcagagag    3000
agcaacacaa ctgaatgtga ctcgaagatc attggaacgg ctgtcaagaa caacttggcg    3060
atccacagtg acctgtccta ttggattgaa agcaggctca atgatacgtg gaagcttgaa    3120
agggcagttc tgggtgaagt caaatcatgt acgtggcctg agacgcatac cttgtggggc    3180
gatggaatcc ttgagagtga cttgataata ccagtcacac tggcgggacc acgaagcaat    3240
cacaatcgga gacctgggta caagacacaa aaccagggcc catgggacga aggccgggta    3300
gagattgact tcgattactg cccaggaact acggtcaccc tgagtgagag ctgcggacac    3360
cgtggacctg ccactcgcac caccacagag agcggaaagt tgataacaga ttggtgctgc    3420
aggagctgca ccttaccacc actgcgctac caaactgaca gcggctgttg gtatggtatg    3480
gagatcagac cacagagaca tgatgaaaag accctcgtgc agtcacaagt gaatgcttat    3540
aatgctgata tgattgaccc ttttcagttg ggccttctgg tcgtgttctt ggccacccag    3600
gaggtccttc gcaagaggtg gacagccaag atcagcatgc agctatact gattgctctg    3660 ctagtcctgg tgtttggggg cattacttac actgatgtgt acgctatgt catcttggtg    3720 ggggcagctt tcgcagaatc taattcggga ggagacgtgg tacacttggc gctcatggcg    3780
accttcaaga tacaaccagt gtttatggtg gcatcgtttc tcaaagcgag atggaccaac    3840
caggagaaca ttttgttgat gttggcggct gtttttcttc aaatggctta ttacgatgcc    3900
cgccaaattc tgctctggga gatccctgat gtgttgaatt cactggcggt agcttggatg    3960
atactgagag ccataacatt cacaacgaca tcaaacgtgg ttgttccgct gctagccctg    4020
ctaacacccg gctgagatg cttgaatctg gatgtgtaca ggatactgct gttgatggtc    4080
ggaataggca gcttgatcag ggagaagagg agtgcagctg caaaaaagaa aggagcaagt    4140
```

```
ctgctatgct tggctctagc ctcaacagga cttttcaacc ccatgatcct tgctgctgga    4200
ctgattgcat gtgatcccaa ccgtaaacgc ggatggcccg caactgaagt gatgacagct    4260
gtcggcctaa tgtttgccat cgtcggaggg ctggcagagc ttgacattga ctccatggcc    4320
attccaatga ctatcgcggg gctcatgttt gctgctttcg tgatttctgg gaaatcaaca    4380
gatatgtgga ttgagagaac ggcggacatt tcctgggaaa gtgatgcaga aattacaggc    4440
tcgagcgaaa gagttgatgt gcggcttgat gatgatggaa acttccagct catgaatgat    4500
ccaggagcac cttggaagat atggatgctc agaatggtct gtctcgcgat tagtgcgtac    4560
accccctggg caatcttgcc ctcagtagtt ggattttgga taactctcca atacacaaag    4620
agaggaggcg tgttgtggga cactccctca ccaaaggagt acaaaaaggg ggacacgacc    4680
accggcgtct acaggatcat gactcgtggg ctgctcggca gttatcaagc aggagcgggc    4740
gtgatggttg aaggtgtttt ccacaccctt tggcatacaa caaaggagc cgctttgatg    4800
agcggagagg gccgcctgga cccatactgg ggcagtgtca aggaggatcg actttgttac    4860
ggaggaccct ggaaattgca gcacaagtgg aacgggcagg atgaggtgca gatgattgtg    4920
gtggaacctg gcaggaacgt taagaacgtc cagacgaaac caggggtgtt caaaacacct    4980
gaaggagaaa tcggggccgt gactttggac ttccccactg gaacatcagg ctcaccaata    5040
gtggacaaaa acgtgatgt gattgggctt tatggcaatg gagtcataat gcccaacggc    5100
tcatacataa gcgcgatagt gcagggtgaa aggatggatg agccaatccc agccggattc    5160
gaacctgaga tgctgaggaa aaaacagatc actgtactgg atctccatcc cggcgccggt    5220
aaaacaagga ggattctgcc acagatcatc aaagaggcca taaacagaag actgagaaca    5280
gccgtgctag caccaaccag ggttgtggct gctgagatgg ctgaagcact gagaggactg    5340
cccatccggt accagacatc cgcagtgccc agagaacata tggaaatga gattgttgat    5400
gtcatgtgtc atgctaccct cacccacagg ctgatgtctc ctcacagggt gccgaactac    5460
aacctgttcg tgatggatga ggctcatttc accgacccag ctagcattgc agcaagaggt    5520
tacatttcca caaaggtcga gctaggggag gcggcggcaa tattcatgac agccacccca    5580
ccaggcactt cagatccatt cccagagtcc aattcaccaa tttccgactt acagactgag    5640
atcccggatc gagcttggaa ctctggatac gaatggatca cagaatacac cgggaagacg    5700
gtttggtttg tgcctagtgt caagatgggg aatgagattg cccttttgcct acaacgtgct    5760
ggaaagaaag tagtccaatt gaacagaaag tcgtacgaga cggagtaccc aaaatgtaag    5820
aacgatgatt gggactttgt tatcacaaca gacatatctg aaatggggc taacttcaag    5880
gcgagcaggg tgattgacag ccggaagagt gtgaaaccaa ccatcataac agaaggagaa    5940
gggagagtga tcctgggaga accatctgca gtgacagcag ctagtgccgc ccagagacgt    6000
ggacgtatcg gtagaaatcc gtcgcaagtt ggtgatgagt actgttatgg ggggcacacg    6060
aatgaagacg actcgaactt cgcccattgg actgaggcac gaatcatgct ggacaacatc    6120
aacatgccaa acggactgat cgctcaattc taccaaccag agcgtgagaa ggtatatacc    6180
atggatgggg aataccggct cagaggagaa gagagaaaaa actttctgga actgttgagg    6240
actgcagatc tgccagtttg gctggcttac aaggttgcag cggctggagt gtcataccac    6300
gaccggaggt ggtgctttga tggtcctagg acaaacacaa ttttagaaga caacaacgaa    6360
gtggaagtca tcacgaagct tggtgaaagg aagattctga ggccgcgctg gattgacgcc    6420
agggtgtact cggatcacca ggcactaaag gcgttcaagg acttcgcctc gggaaaacgt    6480
tctcagatag ggctcattga ggttctggga agatgcctg agcacttcat ggggaagaca    6540
```

```
tgggaagcac ttgacaccat gtacgttgtg gccactgcag agaaaggagg aagagctcac    6600
agaatggccc tggaggaact gccagatgct cttcagacaa ttgccttgat tgccttattg    6660
agtgtgatga ccatgggagt attcttcctc tcatgcagc ggaagggcat tggaaagata    6720
ggtttgggag gcgctgtctt gggagtcgcg acctttttct gttggatggc tgaagttcca    6780
ggaacgaaga tcgccggaat gttgctgctc tcccttctct tgatgattgt gctaattcct    6840
gagccagaga agcaacgttc gcagacagac aaccagctag ccgtgttcct gatttgtgtc    6900
atgacccttg tgagcgcagt ggcagccaac gagatgggtt ggctagataa gaccaagagt    6960
gacataagca gtttgtttgg gcaaagaatt gaggtcaagg agaatttcag catgggagag    7020
tttcttttgg acttgaggcc tgcaacagcc tggtcactgt acgctgtgac aacagcggtc    7080
ctcactccac tgctaaagca tttgatcacg tcagattaca tcaacacctc attgacctca    7140
ataaacgttc aggcaagtgc actattcaca ctcgcgcgag gcttccccttt cgtcgatgtt    7200 ggagtgtcgg ctctcctgct agcagccgga tgctggggac aagtcaccct caccgttacg    7260
gtaacagcgg caacactcct ttttgccac tatgcctaca tggttcccgg ttggcaagct    7320
gaggcaatgc gctcagccca gcggcggaca gcggccggaa tcatgaagaa cgctgtagtg    7380
gatggcatcg tggccacgga cgtcccagaa ttagagcgca ccacacccat catgcagaag    7440
aaagttggac agatcatgct gatcttggtg tctctagctg cagtagtagt gaacccgtct    7500
gtgaagacag tacgagaagc cggaatttttg atcacggccg cagcggtgac gctttgggag    7560
aatggagcaa gctctgtttg gaacgcaaca actgccatcg gactctgcca catcatgcgt    7620
gggggttggt tgtcatgtct atccataaca tggacactca taagaacat ggaaaaacca    7680 ggactaaaaa gaggtggggc aaaaggacgc accttgggag aggtttggaa agaaagactc    7740
aaccagatga caaaagaaga gttcactagg taccgcaaag aggccatcat cgaagtcgat    7800
cgctcagcgg caaaacacgc caggaaagaa ggcaatgtca ctggagggca tccagtctct    7860
aggggcacag caaaactgag atggctggtc gaacggaggt ttctcgaacc ggtcggaaaa    7920
gtgattgacc ttggatgtgg aagaggcggt tggtgttact atatggcaac caaaaaaga    7980 gtccaagaag tcagagggta cacaaagggc ggtcccggac atgaagagcc caactagtg    8040 caaagttatg gatggaacat tgtcaccatg aagagtggag tggatgtgtt ctacagacct    8100
tctgagtgtt gtgacaccct cctttgtgac atcggagagt cctcgtcaag tgctgaggtt    8160
gaagagcata ggacgattcg ggtccttgaa atggttgagg actggctgca ccgagggcca    8220
agggaatttt gcgtgaaggt gctctgcccc tacatgccga aagtcataga gaagatggag    8280
ctgctccaac gccggtatgg gggggactg gtcagaaacc cactctcacg gaattccacg    8340
cacgagatgt attgggtgag tcgagcttca ggcaatgtgg tacattcagt gaatatgacc    8400
agccaggtgc tcctaggaag aatggaaaaa aggacctgga agggaccca atacgaggaa    8460 gatgtaaact tgggaagtgg aaccagggcg gtggaaaaac ccctgctcaa ctcagacacc    8520
agtaaaatca gaacaggat tgaacgactc aggcgtgagt acagttcgac gtggcaccac    8580
gatgagaacc acccatatag aacctggaac tatcacggca gttatgatgt gaagcccaca    8640
ggctccgcca gttcgctggt caatggagtg gtcaggctcc tctcaaaacc atgggacacc    8700
atcacgaatg ttaccaccat ggccatgact gacactactc ccttcgggca gcagcgagtg    8760
ttcaaagaga aggtggacac gaaagctcct gaaccgccag aaggagtgaa gtacgtgctc    8820
aacgagacca ccaactggtt gtgggcgttt ttggccagag aaaaacgtcc cagaatgtgc    8880
```

| | |
|---|---|
| tctcgagagg aattcataag aaaggtcaac agcaatgcag ctttgggtgc catgtttgaa | 8940 |
| gagcagaatc aatggaggag cgccagagaa gcagttgaag atccaaaatt ttgggagatg | 9000 |
| gtggatgagg agcgcgaggc acatctgcgg ggggaatgtc acacttgcat ttacaacatg | 9060 |
| atgggaaaga gagagaaaaa acccggagag ttcggaaagg ccaagggaag cagagccatt | 9120 |
| tggttcatgt ggctcggagc tcgctttctg gagttcgagg ctctgggttt tctcaatgaa | 9180 |
| gaccactggc ttgaagaaa gaactcagga ggaggtgtcg agggcttggg cctccaaaaa | 9240 |
| ctgggttaca tcctgcgtga agttggcacc cggcctgggg gcaagatcta tgctgatgac | 9300 |
| acagctggct gggacacccg catcacgaga gctgacttgg aaaatgaagc taaggtgctt | 9360 |
| gagctgcttg atggggaaca tcggcgtctt gccagggcca tcattgagct cacctatcgt | 9420 |
| cacaaagttg tgaaagtgat gcgcccggct gctgatggaa gaaccgtcat ggatgttatc | 9480 |
| tccagagaag atcagagggg gagtggacaa gttgtcacct acgccctaaa cactttcacc | 9540 |
| aacctggccg tccagctggt gaggatgatg aaggggaag gagtgattgg cccagatgat | 9600 |
| gtggagaaac tcacaaaagg gaaaggaccc aaagtcagga cctggctgtt tgagaatggg | 9660 |
| gaagaaagac tcagccgcat ggctgtcagt ggagatgact gtgtggtaaa gcccctggac | 9720 |
| gatcgctttg ccacctcgct ccacttcctc aatgctatgt caaaggttcg caaagacatc | 9780 |
| caagagtgga aaccgtcaac tggatggtat gattggcagc aggttccatt ttgctcaaac | 9840 |
| catttcactg aattgatcat gaaagatgga agaacactgg tggttccatg ccgaggacag | 9900 |
| gatgaattgg taggcagagc tcgcatatct ccaggggccg gatgaacgt ccgcgacact | 9960 |
| gcttgtctgc ctaagtctta tgcccagatg tggctgcttc tgtacttcca cagaagagac | 10020 |
| ctgcggctca tggccaacgc catttgctcc gctgtccctg tgaattgggt ccctaccgga | 10080 |
| agaaccacgt ggtccatcca tgcaggagga gagtggatga caacagagga catgttggag | 10140 |
| gtctggaacc gtgtttggat agaggagaat gaatggatgg aagacaaaac cccagtggag | 10200 |
| aaatggagtg acgtcccata ttcaggaaaa cgagaggaca tctggtgtgg cagcctgatt | 10260 |
| ggcacaagag cccgagccac gtgggcagaa acatccagg tggctatcaa ccaagtcaga | 10320 |
| gcaatcatcg gagatgagaa gtatgtggat tacatgagtt cactaaagag atatgaagac | 10380 |
| acaactttgg ttgaggacac agtactgtag atatttaatc aattgtaaat agacaatata | 10440 |
| agtatgcata aaagtgtagt tttatagtag tatttagtgg tgttagtgta aatagttaag | 10500 |
| aaaattttga ggagaaagtc aggccgggaa gttcccgcca ccggaagttg agtagacggt | 10560 |
| gctgcctgcg actcaacccc aggaggactg ggtgaacaaa gccgcgaagt gatccatgta | 10620 |
| agccctcaga accgtctcgg aaggaggacc ccacatgttg taacttcaaa gcccaatgtc | 10680 |
| agaccacgct acggcgtgct actctgcgga gagtgcagtc tgcgatagtg ccccaggagg | 10740 |
| actgggttaa caaaggcaaa ccaacgcccc acgcggccct agccccggta atggtgttaa | 10800 |
| ccagggcgaa aggactagag gttagaggag accccgcggt ttaaagtgca cggcccagcc | 10860 |
| tggctgaagc tgtaggtcag gggaaggact agaggttagt ggagacccg tgccacaaaa | 10920 |
| caccacaaca aaacagcata ttgacacctg ggatagacta ggagatcttc tgctctgcac | 10980 |
| aaccagccac acggcacagt gcgccgacaa tggtggctgg tggtgcgaga acacaggatc | 11040 |
| t | 11041 |

<210> SEQ ID NO 2
<211> LENGTH: 3437
<212> TYPE: PRT
<213> ORGANISM: Artificial Sequence

```
<220> FEATURE:
<223> OTHER INFORMATION: Synthetic polypeptide

<400> SEQUENCE: 2

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
                20                  25                  30

Ala Met Leu Ser Leu Ile Asp Gly Lys Gly Pro Ile Arg Phe Val Leu
            35                  40                  45

Ala Leu Leu Ala Phe Phe Arg Phe Thr Ala Ile Ala Pro Thr Arg Ala
        50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
                100                 105                 110

Val Met Ile Gly Leu Ile Ala Ser Ala Met Ala Ala Glu Val Thr Arg
            115                 120                 125

Arg Gly Ser Ala Tyr Tyr Met Tyr Leu Asp Arg Asn Asp Ala Gly Glu
        130                 135                 140

Ala Ile Ser Phe Pro Thr Thr Leu Gly Met Asn Lys Cys Tyr Ile Gln
145                 150                 155                 160

Ile Met Asp Leu Gly His Met Cys Asp Ala Thr Met Ser Tyr Glu Cys
                165                 170                 175

Pro Met Leu Asp Glu Gly Val Glu Pro Asp Asp Val Asp Cys Trp Cys
                180                 185                 190

Asn Thr Thr Ser Thr Trp Val Val Tyr Gly Thr Cys His His Lys Lys
            195                 200                 205

Gly Glu Ala Arg Arg Ser Arg Arg Ala Val Thr Leu Pro Ser His Ser
        210                 215                 220

Thr Arg Lys Leu Gln Thr Arg Ser Gln Thr Trp Leu Glu Ser Arg Glu
225                 230                 235                 240

Tyr Thr Lys His Leu Ile Arg Val Glu Asn Trp Ile Phe Arg Asn Pro
                245                 250                 255

Gly Phe Ala Leu Ala Ala Ala Ile Ala Trp Leu Leu Gly Ser Ser
                260                 265                 270

Thr Ser Gln Lys Val Ile Tyr Leu Val Met Ile Leu Leu Ile Ala Pro
        275                 280                 285

Ala Tyr Ser Ile Arg Cys Ile Gly Val Ser Asn Arg Asp Phe Val Glu
        290                 295                 300

Gly Met Ser Gly Gly Thr Trp Val Asp Val Val Leu Glu His Gly Gly
305                 310                 315                 320

Cys Val Thr Val Met Ala Gln Asp Lys Pro Thr Val Asp Ile Glu Leu
                325                 330                 335

Val Thr Thr Thr Val Ser Asn Met Ala Glu Val Arg Ser Tyr Cys Tyr
                340                 345                 350

Glu Ala Ser Ile Ser Asp Met Ala Ser Asp Ser Arg Cys Pro Thr Gln
        355                 360                 365

Gly Glu Ala Tyr Leu Asp Lys Gln Ser Asp Thr Gln Tyr Val Cys Lys
        370                 375                 380

Arg Thr Leu Val Asp Arg Gly Trp Gly Asn Gly Cys Gly Leu Phe Gly
385                 390                 395                 400
```

-continued

```
Lys Gly Ser Leu Val Thr Cys Ala Lys Phe Ala Cys Ser Lys Met
            405                 410                 415
Thr Gly Lys Ser Ile Gln Pro Glu Asn Leu Glu Tyr Arg Ile Met Leu
            420                 425                 430
Ser Val His Gly Ser Gln His Ser Gly Met Ile Val Asn Asp Thr Gly
            435                 440                 445
His Glu Thr Asp Glu Asn Arg Ala Lys Val Glu Ile Thr Pro Asn Ser
450                 455                 460
Pro Arg Ala Glu Ala Thr Leu Gly Gly Phe Gly Ser Leu Gly Leu Asp
465                 470                 475                 480
Cys Glu Pro Arg Thr Gly Leu Asp Phe Ser Asp Leu Tyr Tyr Leu Thr
            485                 490                 495
Met Asn Asn Lys His Trp Leu Val His Lys Glu Trp Phe His Asp Ile
            500                 505                 510
Pro Leu Pro Trp His Ala Gly Ala Asp Thr Gly Thr Pro His Trp Asn
            515                 520                 525
Asn Lys Glu Ala Leu Val Glu Phe Lys Asp Ala His Ala Lys Arg Gln
            530                 535                 540
Thr Val Val Leu Gly Ser Gln Glu Gly Ala Val His Thr Ala Leu
545                 550                 555                 560
Ala Gly Ala Leu Glu Ala Glu Met Asp Gly Ala Lys Gly Arg Leu Ser
            565                 570                 575
Ser Gly His Leu Lys Cys Arg Leu Lys Met Asp Lys Leu Arg Leu Lys
            580                 585                 590
Gly Val Ser Tyr Ser Leu Cys Thr Ala Ala Phe Thr Phe Thr Lys Ile
            595                 600                 605
Pro Ala Glu Thr Leu His Gly Thr Val Thr Val Glu Val Gln Tyr Ala
610                 615                 620
Gly Thr Asp Gly Pro Cys Lys Val Pro Ala Gln Met Ala Val Asp Met
625                 630                 635                 640
Gln Thr Leu Thr Pro Val Gly Arg Leu Ile Thr Ala Asn Pro Val Ile
            645                 650                 655
Thr Glu Ser Thr Glu Asn Ser Lys Met Met Leu Glu Leu Asp Pro Pro
            660                 665                 670
Phe Gly Asp Ser Tyr Ile Val Ile Gly Val Gly Glu Lys Lys Ile Thr
            675                 680                 685
His His Trp His Arg Ser Gly Ser Thr Ile Gly Lys Ala Phe Glu Ala
            690                 695                 700
Thr Val Arg Gly Ala Lys Arg Met Ala Val Leu Gly Asp Thr Ala Trp
705                 710                 715                 720
Asp Phe Gly Ser Val Gly Gly Ala Leu Asn Ser Leu Gly Lys Gly Ile
            725                 730                 735
His Gln Ile Phe Gly Ala Ala Phe Lys Ser Leu Phe Gly Gly Met Ser
            740                 745                 750
Trp Phe Ser Gln Ile Leu Ile Gly Thr Leu Leu Met Trp Leu Gly Leu
            755                 760                 765
Asn Thr Lys Asn Gly Ser Ile Ser Leu Met Cys Leu Ala Leu Gly Gly
            770                 775                 780
Val Leu Ile Phe Leu Ser Thr Ala Val Ser Ala Asp Ser Gly Cys Ala
785                 790                 795                 800
Ile Asp Ile Ser Arg Gln Glu Leu Arg Cys Gly Ser Gly Val Phe Ile
            805                 810                 815
```

-continued

```
His Asn Asp Val Glu Ala Trp Met Asp Arg Tyr Lys Tyr Tyr Pro Glu
            820                 825                 830

Thr Pro Gln Gly Leu Ala Lys Ile Ile Gln Lys Ala His Lys Glu Gly
            835                 840                 845

Val Cys Gly Leu Arg Ser Val Ser Arg Leu Glu His Gln Met Trp Glu
            850                 855                 860

Ala Val Lys Asp Glu Leu Asn Thr Leu Leu Lys Glu Asn Gly Val Asp
865                 870                 875                 880

Leu Ser Val Val Glu Lys Gln Glu Gly Met Tyr Lys Ser Ala Pro
                885                 890                 895

Lys Arg Leu Thr Ala Thr Thr Glu Lys Leu Glu Ile Gly Trp Lys Ala
            900                 905                 910

Trp Gly Lys Ser Ile Leu Phe Ala Pro Glu Leu Ala Asn Asn Thr Phe
            915                 920                 925

Val Val Asp Gly Pro Glu Thr Lys Glu Cys Pro Thr Gln Asn Arg Ala
            930                 935                 940

Trp Asn Ser Leu Glu Val Glu Asp Phe Gly Phe Gly Leu Thr Ser Thr
945                 950                 955                 960

Arg Met Phe Leu Lys Val Arg Glu Ser Asn Thr Thr Glu Cys Asp Ser
                965                 970                 975

Lys Ile Ile Gly Thr Ala Val Lys Asn Asn Leu Ala Ile His Ser Asp
            980                 985                 990

Leu Ser Tyr Trp Ile Glu Ser Arg  Leu Asn Asp Thr Trp  Lys Leu Glu
                995                 1000                1005

Arg Ala  Val Leu Gly Glu Val  Lys Ser Cys Thr Trp  Pro Glu Thr
    1010                1015                1020

His Thr  Leu Trp Gly Asp Gly  Ile Leu Glu Ser Asp  Leu Ile Ile
    1025                1030                1035

Pro Val  Thr Leu Ala Gly Pro  Arg Ser Asn His Asn  Arg Arg Pro
    1040                1045                1050

Gly Tyr  Lys Thr Gln Asn Gln  Gly Pro Trp Asp Glu  Gly Arg Val
    1055                1060                1065

Glu Ile  Asp Phe Asp Tyr Cys  Pro Gly Thr Thr Val  Thr Leu Ser
    1070                1075                1080

Glu Ser  Cys Gly His Arg Gly  Pro Ala Thr Arg Thr  Thr Thr Glu
    1085                1090                1095

Ser Gly  Lys Leu Ile Thr Asp  Trp Cys Cys Arg Ser  Cys Thr Leu
    1100                1105                1110

Pro Pro  Leu Arg Tyr Gln Thr  Asp Ser Gly Cys Trp  Tyr Gly Met
    1115                1120                1125

Glu Ile  Arg Pro Gln Arg His  Asp Glu Lys Thr Leu  Val Gln Ser
    1130                1135                1140

Gln Val  Asn Ala Tyr Asn Ala  Asp Met Ile Asp Pro  Phe Gln Leu
    1145                1150                1155

Gly Leu  Leu Val Val Phe Leu  Ala Thr Gln Glu Val  Leu Arg Lys
    1160                1165                1170

Arg Trp  Thr Ala Lys Ile Ser  Met Pro Ala Ile Leu  Ile Ala Leu
    1175                1180                1185

Leu Val  Leu Val Phe Gly Gly  Ile Thr Tyr Thr Asp  Val Leu Arg
    1190                1195                1200

Tyr Val  Ile Leu Val Gly Ala  Ala Phe Ala Glu Ser  Asn Ser Gly
    1205                1210                1215

Gly Asp  Val Val His Leu Ala  Leu Met Ala Thr Phe  Lys Ile Gln
```

```
                1220                1225                1230

Pro Val Phe Met Val Ala Ser Phe Leu Lys Ala Arg Trp Thr Asn
        1235                1240                1245

Gln Glu Asn Ile Leu Leu Met Leu Ala Ala Val Phe Phe Gln Met
        1250                1255                1260

Ala Tyr Tyr Asp Ala Arg Gln Ile Leu Leu Trp Glu Ile Pro Asp
        1265                1270                1275

Val Leu Asn Ser Leu Ala Val Ala Trp Met Ile Leu Arg Ala Ile
        1280                1285                1290

Thr Phe Thr Thr Thr Ser Asn Val Val Pro Leu Leu Ala Leu
        1295                1300                1305

Leu Thr Pro Gly Leu Arg Cys Leu Asn Leu Asp Val Tyr Arg Ile
        1310                1315                1320

Leu Leu Leu Met Val Gly Ile Gly Ser Leu Ile Arg Glu Lys Arg
        1325                1330                1335

Ser Ala Ala Ala Lys Lys Lys Gly Ala Ser Leu Leu Cys Leu Ala
        1340                1345                1350

Leu Ala Ser Thr Gly Leu Phe Asn Pro Met Ile Leu Ala Ala Gly
        1355                1360                1365

Leu Ile Ala Cys Asp Pro Asn Arg Lys Arg Gly Trp Pro Ala Thr
        1370                1375                1380

Glu Val Met Thr Ala Val Gly Leu Met Phe Ala Ile Val Gly Gly
        1385                1390                1395

Leu Ala Glu Leu Asp Ile Asp Ser Met Ala Ile Pro Met Thr Ile
        1400                1405                1410

Ala Gly Leu Met Phe Ala Ala Phe Val Ile Ser Gly Lys Ser Thr
        1415                1420                1425

Asp Met Trp Ile Glu Arg Thr Ala Asp Ile Ser Trp Glu Ser Asp
        1430                1435                1440

Ala Glu Ile Thr Gly Ser Ser Glu Arg Val Asp Val Arg Leu Asp
        1445                1450                1455

Asp Asp Gly Asn Phe Gln Leu Met Asn Asp Pro Gly Ala Pro Trp
        1460                1465                1470

Lys Ile Trp Met Leu Arg Met Val Cys Leu Ala Ile Ser Ala Tyr
        1475                1480                1485

Thr Pro Trp Ala Ile Leu Pro Ser Val Val Gly Phe Trp Ile Thr
        1490                1495                1500

Leu Gln Tyr Thr Lys Arg Gly Gly Val Leu Trp Asp Thr Pro Ser
        1505                1510                1515

Pro Lys Glu Tyr Lys Lys Gly Asp Thr Thr Gly Val Tyr Arg
        1520                1525                1530

Ile Met Thr Arg Gly Leu Leu Gly Ser Tyr Gln Ala Gly Ala Gly
        1535                1540                1545

Val Met Val Glu Gly Val Phe His Thr Leu Trp His Thr Thr Lys
        1550                1555                1560

Gly Ala Ala Leu Met Ser Gly Glu Gly Arg Leu Asp Pro Tyr Trp
        1565                1570                1575

Gly Ser Val Lys Glu Asp Arg Leu Cys Tyr Gly Gly Pro Trp Lys
        1580                1585                1590

Leu Gln His Lys Trp Asn Gly Gln Asp Glu Val Gln Met Ile Val
        1595                1600                1605

Val Glu Pro Gly Arg Asn Val Lys Asn Val Gln Thr Lys Pro Gly
        1610                1615                1620
```

```
Val Phe Lys Thr Pro Glu Gly Glu Ile Gly Ala Val Thr Leu Asp
1625                1630                1635

Phe Pro Thr Gly Thr Ser Gly Ser Pro Ile Val Asp Lys Asn Gly
1640                1645                1650

Asp Val Ile Gly Leu Tyr Gly Asn Gly Val Ile Met Pro Asn Gly
1655                1660                1665

Ser Tyr Ile Ser Ala Ile Val Gln Gly Glu Arg Met Asp Glu Pro
1670                1675                1680

Ile Pro Ala Gly Phe Glu Pro Glu Met Leu Arg Lys Lys Gln Ile
1685                1690                1695

Thr Val Leu Asp Leu His Pro Gly Ala Gly Lys Thr Arg Arg Ile
1700                1705                1710

Leu Pro Gln Ile Ile Lys Glu Ala Ile Asn Arg Arg Leu Arg Thr
1715                1720                1725

Ala Val Leu Ala Pro Thr Arg Val Val Ala Ala Glu Met Ala Glu
1730                1735                1740

Ala Leu Arg Gly Leu Pro Ile Arg Tyr Gln Thr Ser Ala Val Pro
1745                1750                1755

Arg Glu His Asn Gly Asn Glu Ile Val Asp Val Met Cys His Ala
1760                1765                1770

Thr Leu Thr His Arg Leu Met Ser Pro His Arg Val Pro Asn Tyr
1775                1780                1785

Asn Leu Phe Val Met Asp Glu Ala His Phe Thr Asp Pro Ala Ser
1790                1795                1800

Ile Ala Ala Arg Gly Tyr Ile Ser Thr Lys Val Glu Leu Gly Glu
1805                1810                1815

Ala Ala Ala Ile Phe Met Thr Ala Thr Pro Pro Gly Thr Ser Asp
1820                1825                1830

Pro Phe Pro Glu Ser Asn Ser Pro Ile Ser Asp Leu Gln Thr Glu
1835                1840                1845

Ile Pro Asp Arg Ala Trp Asn Ser Gly Tyr Glu Trp Ile Thr Glu
1850                1855                1860

Tyr Thr Gly Lys Thr Val Trp Phe Val Pro Ser Val Lys Met Gly
1865                1870                1875

Asn Glu Ile Ala Leu Cys Leu Gln Arg Ala Gly Lys Lys Val Val
1880                1885                1890

Gln Leu Asn Arg Lys Ser Tyr Glu Thr Glu Tyr Pro Lys Cys Lys
1895                1900                1905

Asn Asp Asp Trp Asp Phe Val Ile Thr Thr Asp Ile Ser Glu Met
1910                1915                1920

Gly Ala Asn Phe Lys Ala Ser Arg Val Ile Asp Ser Arg Lys Ser
1925                1930                1935

Val Lys Pro Thr Ile Ile Thr Glu Gly Glu Gly Arg Val Ile Leu
1940                1945                1950

Gly Glu Pro Ser Ala Val Thr Ala Ala Ser Ala Ala Gln Arg Arg
1955                1960                1965

Gly Arg Ile Gly Arg Asn Pro Ser Gln Val Gly Asp Glu Tyr Cys
1970                1975                1980

Tyr Gly Gly His Thr Asn Glu Asp Asp Ser Asn Phe Ala His Trp
1985                1990                1995

Thr Glu Ala Arg Ile Met Leu Asp Asn Ile Asn Met Pro Asn Gly
2000                2005                2010
```

```
Leu Ile Ala Gln Phe Tyr Gln Pro Glu Arg Glu Lys Val Tyr Thr
2015                2020                2025

Met Asp Gly Glu Tyr Arg Leu Arg Gly Glu Glu Arg Lys Asn Phe
2030                2035                2040

Leu Glu Leu Leu Arg Thr Ala Asp Leu Pro Val Trp Leu Ala Tyr
2045                2050                2055

Lys Val Ala Ala Ala Gly Val Ser Tyr His Asp Arg Arg Trp Cys
2060                2065                2070

Phe Asp Gly Pro Arg Thr Asn Thr Ile Leu Glu Asp Asn Asn Glu
2075                2080                2085

Val Glu Val Ile Thr Lys Leu Gly Glu Arg Lys Ile Leu Arg Pro
2090                2095                2100

Arg Trp Ile Asp Ala Arg Val Tyr Ser Asp His Gln Ala Leu Lys
2105                2110                2115

Ala Phe Lys Asp Phe Ala Ser Gly Lys Arg Ser Gln Ile Gly Leu
2120                2125                2130

Ile Glu Val Leu Gly Lys Met Pro Glu His Phe Met Gly Lys Thr
2135                2140                2145

Trp Glu Ala Leu Asp Thr Met Tyr Val Val Ala Thr Ala Glu Lys
2150                2155                2160

Gly Gly Arg Ala His Arg Met Ala Leu Glu Glu Leu Pro Asp Ala
2165                2170                2175

Leu Gln Thr Ile Ala Leu Ile Ala Leu Leu Ser Val Met Thr Met
2180                2185                2190

Gly Val Phe Phe Leu Leu Met Gln Arg Lys Gly Ile Gly Lys Ile
2195                2200                2205

Gly Leu Gly Gly Ala Val Leu Gly Val Ala Thr Phe Phe Cys Trp
2210                2215                2220

Met Ala Glu Val Pro Gly Thr Lys Ile Ala Gly Met Leu Leu Leu
2225                2230                2235

Ser Leu Leu Leu Met Ile Val Leu Ile Pro Glu Pro Glu Lys Gln
2240                2245                2250

Arg Ser Gln Thr Asp Asn Gln Leu Ala Val Phe Leu Ile Cys Val
2255                2260                2265

Met Thr Leu Val Ser Ala Val Ala Ala Asn Glu Met Gly Trp Leu
2270                2275                2280

Asp Lys Thr Lys Ser Asp Ile Ser Ser Leu Phe Gly Gln Arg Ile
2285                2290                2295

Glu Val Lys Glu Asn Phe Ser Met Gly Glu Phe Leu Leu Asp Leu
2300                2305                2310

Arg Pro Ala Thr Ala Trp Ser Leu Tyr Ala Val Thr Thr Ala Val
2315                2320                2325

Leu Thr Pro Leu Leu Lys His Leu Ile Thr Ser Asp Tyr Ile Asn
2330                2335                2340

Thr Ser Leu Thr Ser Ile Asn Val Gln Ala Ser Ala Leu Phe Thr
2345                2350                2355

Leu Ala Arg Gly Phe Pro Phe Val Asp Val Gly Val Ser Ala Leu
2360                2365                2370

Leu Leu Ala Ala Gly Cys Trp Gly Gln Val Thr Leu Thr Val Thr
2375                2380                2385

Val Thr Ala Ala Thr Leu Leu Phe Cys His Tyr Ala Tyr Met Val
2390                2395                2400

Pro Gly Trp Gln Ala Glu Ala Met Arg Ser Ala Gln Arg Arg Thr
```

```
            2405                2410                2415

Ala Ala Gly Ile Met Lys Asn Ala Val Val Asp Gly Ile Val Ala
    2420                2425                2430

Thr Asp Val Pro Glu Leu Glu Arg Thr Thr Pro Ile Met Gln Lys
    2435                2440                2445

Lys Val Gly Gln Ile Met Leu Ile Leu Val Ser Leu Ala Ala Val
    2450                2455                2460

Val Val Asn Pro Ser Val Lys Thr Val Arg Glu Ala Gly Ile Leu
    2465                2470                2475

Ile Thr Ala Ala Ala Val Thr Leu Trp Glu Asn Gly Ala Ser Ser
    2480                2485                2490

Val Trp Asn Ala Thr Thr Ala Ile Gly Leu Cys His Ile Met Arg
    2495                2500                2505

Gly Gly Trp Leu Ser Cys Leu Ser Ile Thr Trp Thr Leu Ile Lys
    2510                2515                2520

Asn Met Glu Lys Pro Gly Leu Lys Arg Gly Gly Ala Lys Gly Arg
    2525                2530                2535

Thr Leu Gly Glu Val Trp Lys Glu Arg Leu Asn Gln Met Thr Lys
    2540                2545                2550

Glu Glu Phe Thr Arg Tyr Arg Lys Glu Ala Ile Ile Glu Val Asp
    2555                2560                2565

Arg Ser Ala Ala Lys His Ala Arg Lys Glu Gly Asn Val Thr Gly
    2570                2575                2580

Gly His Pro Val Ser Arg Gly Thr Ala Lys Leu Arg Trp Leu Val
    2585                2590                2595

Glu Arg Arg Phe Leu Glu Pro Val Gly Lys Val Ile Asp Leu Gly
    2600                2605                2610

Cys Gly Arg Gly Gly Trp Cys Tyr Tyr Met Ala Thr Gln Lys Arg
    2615                2620                2625

Val Gln Glu Val Arg Gly Tyr Thr Lys Gly Gly Pro Gly His Glu
    2630                2635                2640

Glu Pro Gln Leu Val Gln Ser Tyr Gly Trp Asn Ile Val Thr Met
    2645                2650                2655

Lys Ser Gly Val Asp Val Phe Tyr Arg Pro Ser Glu Cys Cys Asp
    2660                2665                2670

Thr Leu Leu Cys Asp Ile Gly Glu Ser Ser Ser Ala Glu Val
    2675                2680                2685

Glu Glu His Arg Thr Ile Arg Val Leu Glu Met Val Glu Asp Trp
    2690                2695                2700

Leu His Arg Gly Pro Arg Glu Phe Cys Val Lys Val Leu Cys Pro
    2705                2710                2715

Tyr Met Pro Lys Val Ile Glu Lys Met Glu Leu Leu Gln Arg Arg
    2720                2725                2730

Tyr Gly Gly Gly Leu Val Arg Asn Pro Leu Ser Arg Asn Ser Thr
    2735                2740                2745

His Glu Met Tyr Trp Val Ser Arg Ala Ser Gly Asn Val Val His
    2750                2755                2760

Ser Val Asn Met Thr Ser Gln Val Leu Leu Gly Arg Met Glu Lys
    2765                2770                2775

Arg Thr Trp Lys Gly Pro Gln Tyr Glu Glu Asp Val Asn Leu Gly
    2780                2785                2790

Ser Gly Thr Arg Ala Val Gly Lys Pro Leu Leu Asn Ser Asp Thr
    2795                2800                2805
```

-continued

```
Ser Lys Ile Lys Asn Arg Ile Glu Arg Leu Arg Glu Tyr Ser
2810             2815             2820

Ser Thr Trp His His Asp Glu Asn His Pro Tyr Arg Thr Trp Asn
2825             2830             2835

Tyr His Gly Ser Tyr Asp Val Lys Pro Thr Gly Ser Ala Ser Ser
2840             2845             2850

Leu Val Asn Gly Val Val Arg Leu Leu Ser Lys Pro Trp Asp Thr
2855             2860             2865

Ile Thr Asn Val Thr Thr Met Ala Met Thr Asp Thr Thr Pro Phe
2870             2875             2880

Gly Gln Gln Arg Val Phe Lys Glu Lys Val Asp Thr Lys Ala Pro
2885             2890             2895

Glu Pro Pro Glu Gly Val Lys Tyr Val Leu Asn Glu Thr Thr Asn
2900             2905             2910

Trp Leu Trp Ala Phe Leu Ala Arg Glu Lys Arg Pro Arg Met Cys
2915             2920             2925

Ser Arg Glu Glu Phe Ile Arg Lys Val Asn Ser Asn Ala Ala Leu
2930             2935             2940

Gly Ala Met Phe Glu Glu Gln Asn Gln Trp Arg Ser Ala Arg Glu
2945             2950             2955

Ala Val Glu Asp Pro Lys Phe Trp Glu Met Val Asp Glu Glu Arg
2960             2965             2970

Glu Ala His Leu Arg Gly Glu Cys His Thr Cys Ile Tyr Asn Met
2975             2980             2985

Met Gly Lys Arg Glu Lys Lys Pro Gly Glu Phe Gly Lys Ala Lys
2990             2995             3000

Gly Ser Arg Ala Ile Trp Phe Met Trp Leu Gly Ala Arg Phe Leu
3005             3010             3015

Glu Phe Glu Ala Leu Gly Phe Leu Asn Glu Asp His Trp Leu Gly
3020             3025             3030

Arg Lys Asn Ser Gly Gly Gly Val Glu Gly Leu Gly Leu Gln Lys
3035             3040             3045

Leu Gly Tyr Ile Leu Arg Glu Val Gly Thr Arg Pro Gly Gly Lys
3050             3055             3060

Ile Tyr Ala Asp Asp Thr Ala Gly Trp Asp Thr Arg Ile Thr Arg
3065             3070             3075

Ala Asp Leu Glu Asn Glu Ala Lys Val Leu Glu Leu Leu Asp Gly
3080             3085             3090

Glu His Arg Arg Leu Ala Arg Ala Ile Ile Glu Leu Thr Tyr Arg
3095             3100             3105

His Lys Val Val Lys Val Met Arg Pro Ala Ala Asp Gly Arg Thr
3110             3115             3120

Val Met Asp Val Ile Ser Arg Glu Asp Gln Arg Gly Ser Gly Gln
3125             3130             3135

Val Val Thr Tyr Ala Leu Asn Thr Phe Thr Asn Leu Ala Val Gln
3140             3145             3150

Leu Val Arg Met Met Glu Gly Glu Gly Val Ile Gly Pro Asp Asp
3155             3160             3165

Val Glu Lys Leu Thr Lys Gly Lys Gly Pro Lys Val Arg Thr Trp
3170             3175             3180

Leu Phe Glu Asn Gly Glu Glu Arg Leu Ser Arg Met Ala Val Ser
3185             3190             3195
```

| | | | | | | | | | | | |
|---|---|---|---|---|---|---|---|---|---|---|---|
| Gly | Asp | Asp | Cys | Val | Val | Lys | Pro | Leu | Asp | Asp | Arg | Phe | Ala | Thr |
| | 3200 | | | | 3205 | | | | 3210 | | |

Gly Asp Asp Cys Val Val Lys Pro Leu Asp Asp Arg Phe Ala Thr
    3200                3205                3210

Ser Leu His Phe Leu Asn Ala Met Ser Lys Val Arg Lys Asp Ile
    3215                3220                3225

Gln Glu Trp Lys Pro Ser Thr Gly Trp Tyr Asp Trp Gln Gln Val
    3230                3235                3240

Pro Phe Cys Ser Asn His Phe Thr Glu Leu Ile Met Lys Asp Gly
    3245                3250                3255

Arg Thr Leu Val Val Pro Cys Arg Gly Gln Asp Glu Leu Val Gly
    3260                3265                3270

Arg Ala Arg Ile Ser Pro Gly Ala Gly Trp Asn Val Arg Asp Thr
    3275                3280                3285

Ala Cys Leu Ala Lys Ser Tyr Ala Gln Met Trp Leu Leu Leu Tyr
    3290                3295                3300

Phe His Arg Arg Asp Leu Arg Leu Met Ala Asn Ala Ile Cys Ser
    3305                3310                3315

Ala Val Pro Val Asn Trp Val Pro Thr Gly Arg Thr Thr Trp Ser
    3320                3325                3330

Ile His Ala Gly Gly Glu Trp Met Thr Thr Glu Asp Met Leu Glu
    3335                3340                3345

Val Trp Asn Arg Val Trp Ile Glu Glu Asn Glu Trp Met Glu Asp
    3350                3355                3360

Lys Thr Pro Val Glu Lys Trp Ser Asp Val Pro Tyr Ser Gly Lys
    3365                3370                3375

Arg Glu Asp Ile Trp Cys Gly Ser Leu Ile Gly Thr Arg Ala Arg
    3380                3385                3390

Ala Thr Trp Ala Glu Asn Ile Gln Val Ala Ile Asn Gln Val Arg
    3395                3400                3405

Ala Ile Ile Gly Asp Glu Lys Tyr Val Asp Tyr Met Ser Ser Leu
    3410                3415                3420

Lys Arg Tyr Glu Asp Thr Thr Leu Val Glu Asp Thr Val Leu
    3425                3430                3435

<210> SEQ ID NO 3
<211> LENGTH: 11041
<212> TYPE: DNA
<213> ORGANISM: Artificial Sequence
<220> FEATURE:
<223> OTHER INFORMATION: Synthetic construct

<400> SEQUENCE: 3

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc ccgcgtgtt gtccttgatt      180 ggactgaaga gggctatgtt gagcctgatc gacggcaagg gccaatacg atttgtgttg     240 gctctcttgg cgttcttcag gttcacagca attgctccga cccgagcagt gctggatcga    300
tggagaggtg tgaacaaaca aacagcgatg aaacaccttc tgagttttaa gaggaactaa   360
gggaccttga ccagtgctat caatcggcgg agttcgaaac aaaagaaaag aggaggaaag  420
accggaattg cagtcatgat tggcctgatc gccagcgcta tggcagcgga ggtcactaga   480
cgtgggagtg catactatat gtacttggac agaaacgatg ctggggaggc catatctttt   540
ccaaccacat tggggatgaa taagtgttat atacagatca tggatcttgg acacatgtgt   600
gatgccacca tgagctatga atgccctatg ctggatgagg gggtggaacc agatgacgtc   660
```

-continued

```
gattgttggt gcaacacgac gtcaacttgg gttgtgtacg gaacctgcca tcacaaaaaa    720
ggtgaagcac ggagaagtag aagagctgtg acgctcccct cccattccac taggaagctg    780
caaacgcggt cgcaaacctg gttggaatca agagaataca caaagcactt gattagagtc    840
gaaaattgga tattcaggaa ccctggcttc gcgttagcag cagctgccat cgcttggctt    900
ttgggaagct caacgagcca aaaagtcata tacttggtca tgatactgct gattgccccg    960
gcatacagca tcaggtgcat aggagtcagc aataggact ttgtggaagg tatgtcaggt    1020
gggacttggg ttgatattgt cttggaacat ggaggttgtg tcaccgtaat ggcacaggac   1080
aaaccgactg tcgacataga gctggttaca acaacagtca gcaacatggc ggaggtaaga   1140
tcctactgct atgaggcatc aatatcagac atggcttcgg acagccgctg cccaacacaa   1200
ggtgaagcct accttgacaa gcaatcgac actcaatatg tctgcaaaag aacgttagtg     1260
gacagaggct ggggaaatgg atgtggactt tttggcaaag ggagtctggt gacatgcgct   1320
aagtttgcat gctccaagaa aatgaccggg aagagcatcc agccagagaa tctggagtac   1380
cggataatgc tgtcagttca tggctcccag cacagtggga tgatcgttaa tgacacagga   1440
catgaaactg atgagaatag agcgaaggtt gagataacgc ccaattcacc aagagccgaa   1500
gccaccctgg ggggttttgg aagcctagga cttgattgtg aaccgaggac aggccttgac   1560
tttttcagatt tgtattactt gactatgaat aacaagcact ggttggttca aaggagtgg   1620
ttccacgaca ttccattacc ttggcacgct ggggcagaca ccggaactcc acactggaac   1680
aacaaagaag cactggtaga gttcaaggac gcacatgcca aaaggcaaac tgtcgtggtt   1740
ctagggagtc aagaaggagc agttcacacg gcccttgctg gagctctgga ggctgagatg   1800
gatggtgcaa agggaaggct gtcctctggc cacttgaaat gtcgcctgaa aatggataaa   1860
cttagattga agggcgtgtc atactccttg tgtaccgcag cgttcacatt caccaagatc   1920
ccggctgaaa cactgcacgg gacagtcaca gtggaggtac agtacgcagg acagatggga   1980
ccttgcaagg ttccagctca gatggcggtg gacatgcaaa ctctgacccc agttgggagg   2040
ttgataaccg ctaaccccgt aatcactgaa agcactgaga actctaagat gatgctggaa   2100
cttgatccac catttgggga ctcttacatt gtcataggag tcggggagaa gaagatcacc   2160
caccactggc acaggagtgg cagcaccatt ggaaaagcat ttgaagccac tgtgagaggt   2220
gccaagagaa tggcagtctt gggagacaca gcctgggact ttggatcagt tggaggcgct   2280
ctcaactcat tgggcaaggg catccatcaa atttttggag cagctttcaa atcattgttt   2340
ggaggaatgt cctggttctc acaaattctc attggaacgt tgctgatgtg gttgggtctg   2400
aacacaaaga atggatctat ttcccttatg tgcttggcct taggggagt gttgatcttc   2460
ttatccacag ccgtctctgc tgattccgga tgtgccatag acatcagccg gcaagagctg   2520
agatgtggaa gtggagtgtt catacacaat gatgtggagg cttggatgga ccggtacaag   2580
tattaccctg aaacgccaca aggcctagcc aagatcattc agaaagctca taaggaagga   2640
gtgtgcggtc tacgatcagt ttccagactg gagcatcaaa tgtgggaagc agtgaaggac   2700
gagctgaaca ctcttttgaa ggagaatggt gtggacctta gtcgtggt tgagaaacag   2760
gagggaatgt acaagtcagc acctaaacgc ctcaccgcca ccacgaaaa attgaaaatt   2820
ggctggaagg cctggggaaa gagtatttta tttgcaccag aactcgccaa caacacctt    2880
gtggttgatg gtccggagac caaggaatgt ccgactcaga atcgcgcttg aatagctta    2940
gaagtggagg attttggatt tggtctcacc agcactcgga tgttcctgaa ggtcagagag   3000
```

-continued

```
agcaacacaa ctgaatgtga ctcgaagatc attggaacgg ctgtcaagaa caacttggcg    3060
atccacagtg acctgtccta ttggattgaa agcaggctca atgatacgtg gaagcttgaa    3120
agggcagttc tgggtgaagt caaatcatgt acgtggcctg agacgcatac cttgtggggc    3180
gatggaatcc ttgagagtga cttgataata ccagtcacac tggcgggacc acgaagcaat    3240
cacaatcgga gacctgggta caagacacaa aaccagggcc catgggacga aggccgggta    3300
gagattgact tcgattactg cccaggaact acggtcaccc tgagtgagag ctgcggacac    3360
cgtggacctg ccactcgcac caccacagag agcggaaagt tgataacaga ttggtgctgc    3420
aggagctgca ccttaccacc actgcgctac caaactgaca gcggctgttg gtatggtatg    3480
gagatcagac cacagagaca tgatgaaaag accctcgtgc agtcacaagt gaatgcttat    3540
aatgctgata tgattgaccc ttttcagttg ggccttctgg tcgtgttctt ggccacccag    3600
gaggtccttc gcaagaggtg gacagccaag atcagcatgc cagctatact gattgctctg    3660
ctagtcctgg tgtttggggg cattacttac actgatgtgt tacgctatgt catcttggtg    3720
ggggcagctt tcgcagaatc taattcggga ggagacgtgg tacacttggc gctcatggcg    3780
accttcaaga tacaaccagt gtttatggtg gcatcgtttc tcaaagcgag atggaccaac    3840
caggagaaca ttttgttgat gttggcggct gttttctttc aaatggctta ttacgatgcc    3900
cgccaaattc tgctctggga gatccctgat gtgttgaatt cactggcggt agcttggatg    3960
atactgagag ccataacatt cacaacgaca tcaaacgtgg ttgttccgct gctagccctg    4020
ctaacacccg ggctgagatg cttgaatctg gatgtgtaca ggatactgct gttgatggtc    4080
ggaataggca gcttgatcag ggagaagagg agtgcagctg caaaaaagaa aggagcaagt    4140
ctgctatgct tggctctagc ctcaacagga cttttcaacc ccatgatcct tgctgctgga    4200
ctgattgcat gtgatcccaa ccgtaaacgc ggatggcccg caactgaagt gatgacagct    4260
gtcggcctaa tgtttgccat cgtcggaggg ctggcagagc ttgacattga ctccatggcc    4320
attccaatga ctatcgcggg gctcatgttt gctgctttcg tgatttctgg gaaatcaaca    4380
gatatgtgga ttgagagaac ggcggacatt tcctgggaaa gtgatgcaga aattacaggc    4440
tcgagcgaaa gagttgatgt gcggcttgat gatgatggaa acttccagct catgaatgat    4500
ccaggagcac cttggaagat atggatgctc agaatggtct gtctcgcgat tagtgcgtac    4560
accccctggg caatcttgcc ctcagtagtt ggattttgga taactctcca atacacaaag    4620
agaggaggcg tgttgtggga cactccctca ccaaaggagt acaaaaaggg ggacacgacc    4680
accgcgtctc acaggatcat gactcgtggg ctgctcggca gttatcaagc aggagcgggc    4740
gtgatggttg aaggtgtttt ccacacccct tggcatacaa caaaggagc cgctttgatg    4800 agcggagagg gccgcctgga cccatactgg ggcagtgtca aggaggatcg actttgttac    4860
ggaggaccct ggaaattgca gcacaagtgg aacgggcagg atgaggtgca gatgattgtg    4920
gtggaacctg gcaggaacgt taagaacgtc cagacgaaac cagggggtgtt caaaacacct    4980 gaaggagaaa tcggggccgt gactttggac ttccccactg aacatcagg ctcaccaata    5040 gtggacaaaa acgtgatgt gattgggctt tatggcaatg gagtcataat gcccaacggc    5100
tcatacataa gcgcgatagt gcagggtgaa aggatggatg agccaatccc agccggattc    5160
gaacctgaga tgctgaggaa aaaacagatc actgtactgg atctccatcc cggcgccggt    5220
aaaacaagga ggattctgcc acagatcatc aaagaggcca taaacagaag actgagaaca    5280
gccgtgctag caccaaccag ggttgtggct gctgagatgc tgaagcact gagaggactg    5340 cccatccggt accagacatc cgcagtgccc agagaacata atggaaatga gattgttgat    5400
```

```
gtcatgtgtc atgctaccct cacccacagg ctgatgtctc ctcacagggt gccgaactac    5460
aacctgttcg tgatggatga ggctcatttc accgacccag ctagcattgc agcaagaggt    5520
tacatttcca caaggtcga gctaggggag gcggcggcaa tattcatgac agccacccca    5580
ccaggcactt cagatccatt cccagagtcc aattcaccaa tttccgactt acagactgag    5640
atcccggatc gagcttggaa ctctggatac gaatggatca cagaatacac cgggaagacg    5700
gtttggtttg tgcctagtgt caagatgggg aatgagattg ccctttgcct acaacgtgct    5760
ggaaagaaag tagtccaatt gaacagaaag tcgtacgaga cggagtaccc aaaatgtaag    5820
aacgatgatt gggactttgt tatcacaaca gacatatctg aaatgggggc taacttcaag    5880
gcgagcaggg tgattgacag ccggaagagt gtgaaaccaa ccatcataac agaaggagaa    5940
gggagagtga tcctgggaga accatctgca gtgacagcag ctagtgccgc ccagagacgt    6000
ggacgtatcg gtagaaatcc gtcgcaagtt ggtgatgagt actgttatgg ggggcacacg    6060
aatgaagacg actcgaactt cgcccattgg actgaggcac gaatcatgct ggacaacatc    6120
aacatgccaa acggactgat cgctcaattc taccaaccag agcgtgagaa ggtatatacc    6180
atggatgggg aataccggct cagaggagaa gagagaaaaa actttctgga actgttgagg    6240
actgcagatc tgccagtttg gctggcttac aaggttgcag cggctggagt gtcataccac    6300
gaccggaggt ggtgctttga tggtcctagg acaaacacaa ttttagaaga caacaacgaa    6360
gtggaagtca tcacgaagct tggtgaaagg aagattctga ggccgcgctg gattgacgcc    6420
agggtgtact cggatcacca ggcactaaag gcgttcaagg acttcgcctc gggaaaacgt    6480
tctcagatag ggctcattga ggttctggga agatgcctg agcacttcat ggggaagaca    6540
tgggaagcac ttgacaccat gtacgttgtg ccactgcag agaaaggagg aagagctcac    6600
agaatggccc tggaggaact gccagatgct cttcagacaa ttgccttgat tgccttattg    6660
agtgtgatga ccatgggagt attcttcctc ctcatgcagc ggaagggcat tggaaagata    6720
ggtttgggag gcgctgtctt gggagtcgcg accttttct gttggatggc tgaagttcca    6780
ggaacgaaga tcgccggaat gttgctgctc tcccttctct tgatgattgt gctaattcct    6840
gagccagaga agcaacgttc gcagacagac aaccagctag ccgtgttcct gatttgtgtc    6900
atgacccttg tgagcgcagt ggcagccaac gagatgggtt ggctagataa gaccaagagt    6960
gacataagca gtttgttgg gcaaagaatt gaggtcaagg agaatttcag catgggagag    7020
tttcttttgg acttgaggcc tgcaacagcc tggtcactgt acgctgtgac aacagcggtc    7080
ctcactccac tgctaaagca tttgatcacg tcagattaca tcaacacctc attgacctca    7140
ataaacgttc aggcaagtgc actattcaca ctcgcgcgag gcttccccctt cgtcgatgtt    7200 ggagtgtcgc tctcctgct agcagccgga tgctggggac aagtcaccct caccgttacg    7260
gtaacagcgg caacactcct tttttgccac tatgcctaca tggttccggg ttggcaagct    7320
gaggcaatgc gctcagccca gcggcggaca gcggccggaa tcatgaagaa cgctgtagtg    7380
gatggcatcg tggccacgga cgtcccagaa ttagagcgca ccacacccat catgcagaag    7440
aaagttggac agatcatgct gatcttggtg tctctagctg cagtagtagt gaacccgtct    7500
gtgaagacag tacgagaagc cggaattttg atcacggccg cagcggtgac gctttgggag    7560
aatggagcaa gctctgtttg gaacgcaaca actgccatcg gactctgcca catcatgcgt    7620
gggggttggt tgtcatgtct atccataaca tggacactca taaagaacat ggaaaaacca    7680
ggactaaaaa gaggtgggc aaaaggacgc accttgggag aggtttggaa agaaagactc    7740
```

```
aaccagatga caaaagaaga gttcactagg taccgcaaag aggccatcat cgaagtcgat    7800
cgctcagcgg caaaacacgc caggaaagaa ggcaatgtca ctggagggca tccagtctct    7860
aggggcacag caaaactgag atggctggtc gaacggaggt ttctcgaacc ggtcggaaaa    7920
gtgattgacc ttggatgtgg aagaggcggt tggtgttact atatggcaac ccaaaaaaga    7980
gtccaagaag tcagagggta cacaaagggc ggtcccggac atgaagagcc ccaactagtg    8040
caaagttatg gatggaacat tgtcaccatg aagagtggag tggatgtgtt ctacagacct    8100
tctgagtgtt gtgacaccct cctttgtgac atcggagagt cctcgtcaag tgctgaggtt    8160
gaagagcata ggacgattcg ggtccttgaa atggttgagg actggctgca ccagggggcca   8220 agggaattt gcgtgaaggt gctctgcccc tacatgccga aagtcataga gaagatggag     8280
ctgctccaac gccggtatgg ggggggactg gtcagaaacc cactctcacg gaattccacg    8340
cacgagatgt attgggtgag tcgagcttca ggcaatgtgg tacattcagt gaatatgacc    8400
agccaggtgc tcctaggaag aatgaaaaaa aggacctgga agggacccca atacgaggaa    8460
gatgtaaact tgggaagtgg aaccagggcg gtgggaaaaac ccctgctcaa ctcagacacc    8520
agtaaaatca agaacaggat tgaacgactc aggcgtgagt acagttcgac gtggcaccac    8580
gatgagaacc acccatatag aacctggaac tatcacggca gttatgatgt gaagcccaca    8640
ggctccgcca gttcgctggt caatggagtg gtcaggctcc tctcaaaacc atgggacacc    8700
atcacgaatg ttaccaccat ggccatgact gacactactc ccttcgggca gcagcgagtg    8760
ttcaaagaga aggtggacac gaaagctcct gaaccgccag aaggagtgaa gtacgtgctc    8820
aacgagacca ccaactggtt gtgggcgttt ttggccagag aaaaacgtcc cagaatgtgc    8880
tctcgagagg aattcataag aaaggtcaac agcaatgcag ctttgggtgc catgtttgaa    8940
gagcagaatc aatggaggag cgccagagaa gcagttgaag atccaaaatt ttgggagatg    9000
gtggatgagg agcgcgaggc acatctgcgg ggggaatgtc acacttgcat ttacaacatg    9060
atgggaaaga gagagaaaaa acccggagag ttcggaaagg ccaagggaag cagagccatt    9120
tggttcatgt ggctcggagc tcgctttctg gagttcgagg ctctgggttt tctcaatgaa    9180
gaccactggc ttgaagaaaa gaactcagga ggaggtgtcg agggcttggg cctccaaaaa    9240
ctgggttaca tcctgcgtga agttggcacc cggcctgggg gcaagatcta tgctgatgac    9300
acagctggct gggacacccg catcacgaga gctgacttgg aaaatgaagc taaggtgctt    9360
gagctgcttg atgggggaaca tcggcgtctt gccagggcca tcattgagct cacctatcgt    9420
cacaaagttg tgaaagtgat gcgccccggct gctgatggaa gaaccgtcat ggatgttatc    9480
tccagagaag atcagagggg gagtggacaa gttgtcacct acgccctaaa cacttttcacc    9540 aacctggccg tccagctggt gaggatgatg gaaggggaag gagtgattgg cccagatgat    9600
gtggagaaac tcacaaaagg gaaaggaccc aaagtcagga cctggctgtt tgagaatggg    9660
gaagaaagac tcagccgcat ggctgtcagt ggagatgact gtgtggtaaa gccctggac    9720 gatcgctttg ccacctcgct ccacttcctc aatgctatgt caaaggttcg caaagacatc    9780
caagagtgga aaccgtcaac tggatggtat gattggcagc aggttccatt ttgctcaaac    9840
catttcactg aattgatcat gaaagatgga agaaacactgg tggttccatg ccgaggacag    9900
gatgaattgg taggcagagc tcgcatatct ccaggggccg gatggaacgt ccgcgacact    9960
gcttgtctgg ctaagtctta tgcccagatg tggctgcttc tgtacttcca cagaagagac    10020
ctgcggctca tggccaacgc catttgctcc gctgtccctg tgaattgggt ccctaccgga    10080
agaaccacgt ggtccatcca tgcaggagga gagtggatga caacagagga catgttggag    10140
```

```
gtctggaacc gtgtttggat agaggagaat gaatggatgg aagacaaaac cccagtggag  10200
aaatggagtg acgtcccata ttcaggaaaa cgagaggaca tctggtgtgg cagcctgatt  10260
ggcacaagag cccgagccac gtgggcagaa acatccagg tggctatcaa ccaagtcaga  10320
gcaatcatcg gagatgagaa gtatgtggat tacatgagtt cactaaagag atatgaagac  10380
acaactttgg ttgaggacac agtactgtag atatttaatc aattgtaaat agacaatata  10440
agtatgcata aaagtgtagt tttatagtag tatttagtgg tgttagtgta aatagttaag  10500
aaaattttga ggagaaagtc aggccgggaa gttcccgcca ccggaagttg agtagacggt  10560
gctgcctgcg actcaacccc aggaggactg ggtgaacaaa gccgcgaagt gatccatgta  10620
agccctcaga accgtctcgg aaggaggacc ccacatgttg taacttcaaa gcccaatgtc  10680
agaccacgct acggcgtgct actctgcgga gagtgcagtc tgcgatagtg ccccaggagg  10740
actgggttaa caaaggcaaa ccaacgcccc acgcggccct agccccggta atggtgttaa  10800
ccagggcgaa aggactagag gttagaggag accccgcggt ttaaagtgca cggcccagcc  10860
tggctgaagc tgtaggtcag gggaaggact agaggttagt ggagaccccg tgccacaaaa  10920
caccacaaca aaacagcata ttgacacctg ggatagacta ggagatcttc tgctctgcac  10980
aaccagccac acggcacagt gcgccgacaa tggtggctgg tggtgcgaga acacaggatc  11040
t                                                                11041
```

<210> SEQ ID NO 4
<211> LENGTH: 3437
<212> TYPE: PRT
<213> ORGANISM: Artificial Sequence
<220> FEATURE:
<223> OTHER INFORMATION: Synthetic polypeptide

<400> SEQUENCE: 4

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Ala Met Ala Ala Glu Val Thr Arg
        115                 120                 125

Arg Gly Ser Ala Tyr Tyr Met Tyr Leu Asp Arg Asn Asp Ala Gly Glu
    130                 135                 140

Ala Ile Ser Phe Pro Thr Thr Leu Gly Met Asn Lys Cys Tyr Ile Gln
145                 150                 155                 160

Ile Met Asp Leu Gly His Met Cys Asp Ala Thr Met Ser Tyr Glu Cys
                165                 170                 175

Pro Met Leu Asp Glu Gly Val Glu Pro Asp Asp Val Asp Cys Trp Cys
            180                 185                 190
```

-continued

Asn Thr Thr Ser Thr Trp Val Val Tyr Gly Thr Cys His His Lys Lys
            195                 200                 205

Gly Glu Ala Arg Arg Ser Arg Arg Ala Val Thr Leu Pro Ser His Ser
210                 215                 220

Thr Arg Lys Leu Gln Thr Arg Ser Gln Thr Trp Leu Glu Ser Arg Glu
225                 230                 235                 240

Tyr Thr Lys His Leu Ile Arg Val Glu Asn Trp Ile Phe Arg Asn Pro
                245                 250                 255

Gly Phe Ala Leu Ala Ala Ala Ala Ile Ala Trp Leu Leu Gly Ser Ser
                260                 265                 270

Thr Ser Gln Lys Val Ile Tyr Leu Val Met Ile Leu Leu Ile Ala Pro
            275                 280                 285

Ala Tyr Ser Ile Arg Cys Ile Gly Val Ser Asn Arg Asp Phe Val Glu
290                 295                 300

Gly Met Ser Gly Gly Thr Trp Val Asp Ile Val Leu Glu His Gly Gly
305                 310                 315                 320

Cys Val Thr Val Met Ala Gln Asp Lys Pro Thr Val Asp Ile Glu Leu
                325                 330                 335

Val Thr Thr Thr Val Ser Asn Met Ala Glu Val Arg Ser Tyr Cys Tyr
                340                 345                 350

Glu Ala Ser Ile Ser Asp Met Ala Ser Asp Ser Arg Cys Pro Thr Gln
            355                 360                 365

Gly Glu Ala Tyr Leu Asp Lys Gln Ser Asp Thr Gln Tyr Val Cys Lys
370                 375                 380

Arg Thr Leu Val Asp Arg Gly Trp Gly Asn Gly Cys Gly Leu Phe Gly
385                 390                 395                 400

Lys Gly Ser Leu Val Thr Cys Ala Lys Phe Ala Cys Ser Lys Lys Met
                405                 410                 415

Thr Gly Lys Ser Ile Gln Pro Glu Asn Leu Glu Tyr Arg Ile Met Leu
            420                 425                 430

Ser Val His Gly Ser Gln His Ser Gly Met Ile Val Asn Asp Thr Gly
            435                 440                 445

His Glu Thr Asp Glu Asn Arg Ala Lys Val Glu Ile Thr Pro Asn Ser
450                 455                 460

Pro Arg Ala Glu Ala Thr Leu Gly Gly Phe Gly Ser Leu Gly Leu Asp
465                 470                 475                 480

Cys Glu Pro Arg Thr Gly Leu Asp Phe Ser Asp Leu Tyr Tyr Leu Thr
                485                 490                 495

Met Asn Asn Lys His Trp Leu Val His Lys Glu Trp Phe His Asp Ile
            500                 505                 510

Pro Leu Pro Trp His Ala Gly Ala Asp Thr Gly Thr Pro His Trp Asn
515                 520                 525

Asn Lys Glu Ala Leu Val Glu Phe Lys Asp Ala His Ala Lys Arg Gln
530                 535                 540

Thr Val Val Leu Gly Ser Gln Glu Gly Ala Val His Thr Ala Leu
545                 550                 555                 560

Ala Gly Ala Leu Glu Ala Glu Met Asp Gly Ala Lys Gly Arg Leu Ser
                565                 570                 575

Ser Gly His Leu Lys Cys Arg Leu Lys Met Asp Lys Leu Arg Leu Lys
            580                 585                 590

Gly Val Ser Tyr Ser Leu Cys Thr Ala Ala Phe Thr Phe Thr Lys Ile
            595                 600                 605

Pro Ala Glu Thr Leu His Gly Thr Val Thr Val Glu Val Gln Tyr Ala

-continued

```
            610                 615                 620

Gly Thr Asp Gly Pro Cys Lys Val Pro Ala Gln Met Ala Val Asp Met
625                 630                 635                 640

Gln Thr Leu Thr Pro Val Gly Arg Leu Ile Thr Ala Asn Pro Val Ile
                645                 650                 655

Thr Glu Ser Thr Glu Asn Ser Lys Met Met Leu Glu Leu Asp Pro Pro
                660                 665                 670

Phe Gly Asp Ser Tyr Ile Val Ile Gly Val Gly Glu Lys Lys Ile Thr
                675                 680                 685

His His Trp His Arg Ser Gly Ser Thr Ile Gly Lys Ala Phe Glu Ala
            690                 695                 700

Thr Val Arg Gly Ala Lys Arg Met Ala Val Leu Gly Asp Thr Ala Trp
705                 710                 715                 720

Asp Phe Gly Ser Val Gly Gly Ala Leu Asn Ser Leu Gly Lys Gly Ile
                725                 730                 735

His Gln Ile Phe Gly Ala Ala Phe Lys Ser Leu Phe Gly Gly Met Ser
                740                 745                 750

Trp Phe Ser Gln Ile Leu Ile Gly Thr Leu Leu Met Trp Leu Gly Leu
            755                 760                 765

Asn Thr Lys Asn Gly Ser Ile Ser Leu Met Cys Leu Ala Leu Gly Gly
770                 775                 780

Val Leu Ile Phe Leu Ser Thr Ala Val Ser Ala Asp Ser Gly Cys Ala
785                 790                 795                 800

Ile Asp Ile Ser Arg Gln Glu Leu Arg Cys Gly Ser Gly Val Phe Ile
                805                 810                 815

His Asn Asp Val Glu Ala Trp Met Asp Arg Tyr Lys Tyr Tyr Pro Glu
                820                 825                 830

Thr Pro Gln Gly Leu Ala Lys Ile Ile Gln Lys Ala His Lys Glu Gly
                835                 840                 845

Val Cys Gly Leu Arg Ser Val Ser Arg Leu Glu His Gln Met Trp Glu
850                 855                 860

Ala Val Lys Asp Glu Leu Asn Thr Leu Leu Lys Glu Asn Gly Val Asp
865                 870                 875                 880

Leu Ser Val Val Val Glu Lys Gln Glu Gly Met Tyr Lys Ser Ala Pro
                885                 890                 895

Lys Arg Leu Thr Ala Thr Thr Glu Lys Leu Glu Ile Gly Trp Lys Ala
                900                 905                 910

Trp Gly Lys Ser Ile Leu Phe Ala Pro Glu Leu Ala Asn Asn Thr Phe
            915                 920                 925

Val Val Asp Gly Pro Glu Thr Lys Glu Cys Pro Thr Gln Asn Arg Ala
930                 935                 940

Trp Asn Ser Leu Glu Val Glu Asp Phe Gly Phe Gly Leu Thr Ser Thr
945                 950                 955                 960

Arg Met Phe Leu Lys Val Arg Glu Ser Asn Thr Thr Glu Cys Asp Ser
                965                 970                 975

Lys Ile Ile Gly Thr Ala Val Lys Asn Asn Leu Ala Ile His Ser Asp
                980                 985                 990

Leu Ser Tyr Trp Ile Glu Ser Arg Leu Asn Asp Thr Trp Lys Leu Glu
            995                 1000                1005

Arg Ala Val Leu Gly Glu Val Lys Ser Cys Thr Trp Pro Glu Thr
            1010                1015                1020

His Thr Leu Trp Gly Asp Gly Ile Leu Glu Ser Asp Leu Ile Ile
            1025                1030                1035
```

-continued

Pro Val Thr Leu Ala Gly Pro Arg Ser Asn His Asn Arg Arg Pro
1040              1045                1050

Gly Tyr Lys Thr Gln Asn Gln Gly Pro Trp Asp Glu Gly Arg Val
1055              1060                1065

Glu Ile Asp Phe Asp Tyr Cys Pro Gly Thr Thr Val Thr Leu Ser
1070              1075                1080

Glu Ser Cys Gly His Arg Gly Pro Ala Thr Arg Thr Thr Thr Glu
1085              1090                1095

Ser Gly Lys Leu Ile Thr Asp Trp Cys Cys Arg Ser Cys Thr Leu
1100              1105                1110

Pro Pro Leu Arg Tyr Gln Thr Asp Ser Gly Cys Trp Tyr Gly Met
1115              1120                1125

Glu Ile Arg Pro Gln Arg His Asp Glu Lys Thr Leu Val Gln Ser
1130              1135                1140

Gln Val Asn Ala Tyr Asn Ala Asp Met Ile Asp Pro Phe Gln Leu
1145              1150                1155

Gly Leu Leu Val Val Phe Leu Ala Thr Gln Glu Val Leu Arg Lys
1160              1165                1170

Arg Trp Thr Ala Lys Ile Ser Met Pro Ala Ile Leu Ile Ala Leu
1175              1180                1185

Leu Val Leu Val Phe Gly Gly Ile Thr Tyr Thr Asp Val Leu Arg
1190              1195                1200

Tyr Val Ile Leu Val Gly Ala Ala Phe Ala Glu Ser Asn Ser Gly
1205              1210                1215

Gly Asp Val Val His Leu Ala Leu Met Ala Thr Phe Lys Ile Gln
1220              1225                1230

Pro Val Phe Met Val Ala Ser Phe Leu Lys Ala Arg Trp Thr Asn
1235              1240                1245

Gln Glu Asn Ile Leu Leu Met Leu Ala Ala Val Phe Phe Gln Met
1250              1255                1260

Ala Tyr Tyr Asp Ala Arg Gln Ile Leu Leu Trp Glu Ile Pro Asp
1265              1270                1275

Val Leu Asn Ser Leu Ala Val Ala Trp Met Ile Leu Arg Ala Ile
1280              1285                1290

Thr Phe Thr Thr Thr Ser Asn Val Val Val Pro Leu Leu Ala Leu
1295              1300                1305

Leu Thr Pro Gly Leu Arg Cys Leu Asn Leu Asp Val Tyr Arg Ile
1310              1315                1320

Leu Leu Leu Met Val Gly Ile Gly Ser Leu Ile Arg Glu Lys Arg
1325              1330                1335

Ser Ala Ala Lys Lys Lys Gly Ala Ser Leu Leu Cys Leu Ala
1340              1345                1350

Leu Ala Ser Thr Gly Leu Phe Asn Pro Met Ile Leu Ala Ala Gly
1355              1360                1365

Leu Ile Ala Cys Asp Pro Asn Arg Lys Arg Gly Trp Pro Ala Thr
1370              1375                1380

Glu Val Met Thr Ala Val Gly Leu Met Phe Ala Ile Val Gly Gly
1385              1390                1395

Leu Ala Glu Leu Asp Ile Asp Ser Met Ala Ile Pro Met Thr Ile
1400              1405                1410

Ala Gly Leu Met Phe Ala Ala Phe Val Ile Ser Gly Lys Ser Thr
1415              1420                1425

-continued

Asp Met Trp Ile Glu Arg Thr Ala Asp Ile Ser Trp Glu Ser Asp
1430                1435                1440

Ala Glu Ile Thr Gly Ser Ser Glu Arg Val Asp Val Arg Leu Asp
1445                1450                1455

Asp Asp Gly Asn Phe Gln Leu Met Asn Asp Pro Gly Ala Pro Trp
1460                1465                1470

Lys Ile Trp Met Leu Arg Met Val Cys Leu Ala Ile Ser Ala Tyr
1475                1480                1485

Thr Pro Trp Ala Ile Leu Pro Ser Val Val Gly Phe Trp Ile Thr
1490                1495                1500

Leu Gln Tyr Thr Lys Arg Gly Gly Val Leu Trp Asp Thr Pro Ser
1505                1510                1515

Pro Lys Glu Tyr Lys Lys Gly Asp Thr Thr Gly Val Tyr Arg
1520                1525                1530

Ile Met Thr Arg Gly Leu Leu Gly Ser Tyr Gln Ala Gly Ala Gly
1535                1540                1545

Val Met Val Glu Gly Val Phe His Thr Leu Trp His Thr Thr Lys
1550                1555                1560

Gly Ala Ala Leu Met Ser Gly Glu Gly Arg Leu Asp Pro Tyr Trp
1565                1570                1575

Gly Ser Val Lys Glu Asp Arg Leu Cys Tyr Gly Gly Pro Trp Lys
1580                1585                1590

Leu Gln His Lys Trp Asn Gly Gln Asp Glu Val Gln Met Ile Val
1595                1600                1605

Val Glu Pro Gly Arg Asn Val Lys Asn Val Gln Thr Lys Pro Gly
1610                1615                1620

Val Phe Lys Thr Pro Glu Gly Glu Ile Gly Ala Val Thr Leu Asp
1625                1630                1635

Phe Pro Thr Gly Thr Ser Gly Ser Pro Ile Val Asp Lys Asn Gly
1640                1645                1650

Asp Val Ile Gly Leu Tyr Gly Asn Gly Val Ile Met Pro Asn Gly
1655                1660                1665

Ser Tyr Ile Ser Ala Ile Val Gln Gly Glu Arg Met Asp Glu Pro
1670                1675                1680

Ile Pro Ala Gly Phe Glu Pro Glu Met Leu Arg Lys Lys Gln Ile
1685                1690                1695

Thr Val Leu Asp Leu His Pro Gly Ala Gly Lys Thr Arg Arg Ile
1700                1705                1710

Leu Pro Gln Ile Ile Lys Glu Ala Ile Asn Arg Arg Leu Arg Thr
1715                1720                1725

Ala Val Leu Ala Pro Thr Arg Val Val Ala Ala Glu Met Ala Glu
1730                1735                1740

Ala Leu Arg Gly Leu Pro Ile Arg Tyr Gln Thr Ser Ala Val Pro
1745                1750                1755

Arg Glu His Asn Gly Asn Glu Ile Val Asp Val Met Cys His Ala
1760                1765                1770

Thr Leu Thr His Arg Leu Met Ser Pro His Arg Val Pro Asn Tyr
1775                1780                1785

Asn Leu Phe Val Met Asp Glu Ala His Phe Thr Asp Pro Ala Ser
1790                1795                1800

Ile Ala Ala Arg Gly Tyr Ile Ser Thr Lys Val Glu Leu Gly Glu
1805                1810                1815

Ala Ala Ala Ile Phe Met Thr Ala Thr Pro Pro Gly Thr Ser Asp

```
               1820              1825              1830
Pro Phe Pro Glu Ser Asn Ser Pro Ile Ser Asp Leu Gln Thr Glu
        1835              1840              1845
Ile Pro Asp Arg Ala Trp Asn Ser Gly Tyr Glu Trp Ile Thr Glu
        1850              1855              1860
Tyr Thr Gly Lys Thr Val Trp Phe Val Pro Ser Val Lys Met Gly
        1865              1870              1875
Asn Glu Ile Ala Leu Cys Leu Gln Arg Ala Gly Lys Lys Val Val
        1880              1885              1890
Gln Leu Asn Arg Lys Ser Tyr Glu Thr Glu Tyr Pro Lys Cys Lys
        1895              1900              1905
Asn Asp Asp Trp Asp Phe Val Ile Thr Thr Asp Ile Ser Glu Met
        1910              1915              1920
Gly Ala Asn Phe Lys Ala Ser Arg Val Ile Asp Ser Arg Lys Ser
        1925              1930              1935
Val Lys Pro Thr Ile Ile Thr Glu Gly Glu Gly Arg Val Ile Leu
        1940              1945              1950
Gly Glu Pro Ser Ala Val Thr Ala Ala Ser Ala Ala Gln Arg Arg
        1955              1960              1965
Gly Arg Ile Gly Arg Asn Pro Ser Gln Val Gly Asp Glu Tyr Cys
        1970              1975              1980
Tyr Gly Gly His Thr Asn Glu Asp Asp Ser Asn Phe Ala His Trp
        1985              1990              1995
Thr Glu Ala Arg Ile Met Leu Asp Asn Ile Asn Met Pro Asn Gly
        2000              2005              2010
Leu Ile Ala Gln Phe Tyr Gln Pro Glu Arg Glu Lys Val Tyr Thr
        2015              2020              2025
Met Asp Gly Glu Tyr Arg Leu Arg Gly Glu Glu Arg Lys Asn Phe
        2030              2035              2040
Leu Glu Leu Leu Arg Thr Ala Asp Leu Pro Val Trp Leu Ala Tyr
        2045              2050              2055
Lys Val Ala Ala Ala Gly Val Ser Tyr His Asp Arg Arg Trp Cys
        2060              2065              2070
Phe Asp Gly Pro Arg Thr Asn Thr Ile Leu Glu Asp Asn Asn Glu
        2075              2080              2085
Val Glu Val Ile Thr Lys Leu Gly Glu Arg Lys Ile Leu Arg Pro
        2090              2095              2100
Arg Trp Ile Asp Ala Arg Val Tyr Ser Asp His Gln Ala Leu Lys
        2105              2110              2115
Ala Phe Lys Asp Phe Ala Ser Gly Lys Arg Ser Gln Ile Gly Leu
        2120              2125              2130
Ile Glu Val Leu Gly Lys Met Pro Glu His Phe Met Gly Lys Thr
        2135              2140              2145
Trp Glu Ala Leu Asp Thr Met Tyr Val Val Ala Thr Ala Glu Lys
        2150              2155              2160
Gly Gly Arg Ala His Arg Met Ala Leu Glu Glu Leu Pro Asp Ala
        2165              2170              2175
Leu Gln Thr Ile Ala Leu Ile Ala Leu Leu Ser Val Met Thr Met
        2180              2185              2190
Gly Val Phe Phe Leu Leu Met Gln Arg Lys Gly Ile Gly Lys Ile
        2195              2200              2205
Gly Leu Gly Gly Ala Val Leu Gly Val Ala Thr Phe Phe Cys Trp
        2210              2215              2220
```

```
Met Ala Glu Val Pro Gly Thr Lys Ile Ala Gly Met Leu Leu Leu
2225                2230                2235

Ser Leu Leu Leu Met Ile Val Leu Ile Pro Glu Pro Glu Lys Gln
2240                2245                2250

Arg Ser Gln Thr Asp Asn Gln Leu Ala Val Phe Leu Ile Cys Val
2255                2260                2265

Met Thr Leu Val Ser Ala Val Ala Ala Asn Glu Met Gly Trp Leu
2270                2275                2280

Asp Lys Thr Lys Ser Asp Ile Ser Ser Leu Phe Gly Gln Arg Ile
2285                2290                2295

Glu Val Lys Glu Asn Phe Ser Met Gly Glu Phe Leu Leu Asp Leu
2300                2305                2310

Arg Pro Ala Thr Ala Trp Ser Leu Tyr Ala Val Thr Thr Ala Val
2315                2320                2325

Leu Thr Pro Leu Leu Lys His Leu Ile Thr Ser Asp Tyr Ile Asn
2330                2335                2340

Thr Ser Leu Thr Ser Ile Asn Val Gln Ala Ser Ala Leu Phe Thr
2345                2350                2355

Leu Ala Arg Gly Phe Pro Phe Val Asp Val Gly Val Ser Ala Leu
2360                2365                2370

Leu Leu Ala Ala Gly Cys Trp Gly Gln Val Thr Leu Thr Val Thr
2375                2380                2385

Val Thr Ala Ala Thr Leu Leu Phe Cys His Tyr Ala Tyr Met Val
2390                2395                2400

Pro Gly Trp Gln Ala Glu Ala Met Arg Ser Ala Gln Arg Arg Thr
2405                2410                2415

Ala Ala Gly Ile Met Lys Asn Ala Val Val Asp Gly Ile Val Ala
2420                2425                2430

Thr Asp Val Pro Glu Leu Glu Arg Thr Thr Pro Ile Met Gln Lys
2435                2440                2445

Lys Val Gly Gln Ile Met Leu Ile Leu Val Ser Leu Ala Ala Val
2450                2455                2460

Val Val Asn Pro Ser Val Lys Thr Val Arg Glu Ala Gly Ile Leu
2465                2470                2475

Ile Thr Ala Ala Ala Val Thr Leu Trp Glu Asn Gly Ala Ser Ser
2480                2485                2490

Val Trp Asn Ala Thr Thr Ala Ile Gly Leu Cys His Ile Met Arg
2495                2500                2505

Gly Gly Trp Leu Ser Cys Leu Ser Ile Thr Trp Thr Leu Ile Lys
2510                2515                2520

Asn Met Glu Lys Pro Gly Leu Lys Arg Gly Gly Ala Lys Gly Arg
2525                2530                2535

Thr Leu Gly Glu Val Trp Lys Glu Arg Leu Asn Gln Met Thr Lys
2540                2545                2550

Glu Glu Phe Thr Arg Tyr Arg Lys Glu Ala Ile Ile Glu Val Asp
2555                2560                2565

Arg Ser Ala Ala Lys His Ala Arg Lys Glu Gly Asn Val Thr Gly
2570                2575                2580

Gly His Pro Val Ser Arg Gly Thr Ala Lys Leu Arg Trp Leu Val
2585                2590                2595

Glu Arg Arg Phe Leu Glu Pro Val Gly Lys Val Ile Asp Leu Gly
2600                2605                2610
```

-continued

Cys Gly Arg Gly Gly Trp Cys Tyr Tyr Met Ala Thr Gln Lys Arg
2615                2620                2625

Val Gln Glu Val Arg Gly Tyr Thr Lys Gly Gly Pro Gly His Glu
2630                2635                2640

Glu Pro Gln Leu Val Gln Ser Tyr Gly Trp Asn Ile Val Thr Met
2645                2650                2655

Lys Ser Gly Val Asp Val Phe Tyr Arg Pro Ser Glu Cys Cys Asp
2660                2665                2670

Thr Leu Leu Cys Asp Ile Gly Glu Ser Ser Ser Ala Glu Val
2675                2680                2685

Glu Glu His Arg Thr Ile Arg Val Leu Glu Met Val Glu Asp Trp
2690                2695                2700

Leu His Arg Gly Pro Arg Glu Phe Cys Val Lys Val Leu Cys Pro
2705                2710                2715

Tyr Met Pro Lys Val Ile Glu Lys Met Glu Leu Leu Gln Arg Arg
2720                2725                2730

Tyr Gly Gly Gly Leu Val Arg Asn Pro Leu Ser Arg Asn Ser Thr
2735                2740                2745

His Glu Met Tyr Trp Val Ser Arg Ala Ser Gly Asn Val Val His
2750                2755                2760

Ser Val Asn Met Thr Ser Gln Val Leu Leu Gly Arg Met Glu Lys
2765                2770                2775

Arg Thr Trp Lys Gly Pro Gln Tyr Glu Glu Asp Val Asn Leu Gly
2780                2785                2790

Ser Gly Thr Arg Ala Val Gly Lys Pro Leu Leu Asn Ser Asp Thr
2795                2800                2805

Ser Lys Ile Lys Asn Arg Ile Glu Arg Leu Arg Arg Glu Tyr Ser
2810                2815                2820

Ser Thr Trp His His Asp Glu Asn His Pro Tyr Arg Thr Trp Asn
2825                2830                2835

Tyr His Gly Ser Tyr Asp Val Lys Pro Thr Gly Ser Ala Ser Ser
2840                2845                2850

Leu Val Asn Gly Val Val Arg Leu Leu Ser Lys Pro Trp Asp Thr
2855                2860                2865

Ile Thr Asn Val Thr Thr Met Ala Met Thr Asp Thr Thr Pro Phe
2870                2875                2880

Gly Gln Gln Arg Val Phe Lys Glu Lys Val Asp Thr Lys Ala Pro
2885                2890                2895

Glu Pro Pro Glu Gly Val Lys Tyr Val Leu Asn Glu Thr Thr Asn
2900                2905                2910

Trp Leu Trp Ala Phe Leu Ala Arg Glu Lys Arg Pro Arg Met Cys
2915                2920                2925

Ser Arg Glu Glu Phe Ile Arg Lys Val Asn Ser Asn Ala Ala Leu
2930                2935                2940

Gly Ala Met Phe Glu Glu Gln Asn Gln Trp Arg Ser Ala Arg Glu
2945                2950                2955

Ala Val Glu Asp Pro Lys Phe Trp Glu Met Val Asp Glu Glu Arg
2960                2965                2970

Glu Ala His Leu Arg Gly Glu Cys His Thr Cys Ile Tyr Asn Met
2975                2980                2985

Met Gly Lys Arg Glu Lys Lys Pro Gly Glu Phe Gly Lys Ala Lys
2990                2995                3000

Gly Ser Arg Ala Ile Trp Phe Met Trp Leu Gly Ala Arg Phe Leu

-continued

```
            3005                3010                3015
Glu Phe Glu Ala Leu Gly Phe Leu Asn Glu Asp His Trp Leu Gly
    3020                3025                3030
Arg Lys Asn Ser Gly Gly Gly Val Glu Gly Leu Gly Leu Gln Lys
    3035                3040                3045
Leu Gly Tyr Ile Leu Arg Glu Val Gly Thr Arg Pro Gly Gly Lys
    3050                3055                3060
Ile Tyr Ala Asp Asp Thr Ala Gly Trp Asp Thr Arg Ile Thr Arg
    3065                3070                3075
Ala Asp Leu Glu Asn Glu Ala Lys Val Leu Glu Leu Leu Asp Gly
    3080                3085                3090
Glu His Arg Arg Leu Ala Arg Ala Ile Ile Glu Leu Thr Tyr Arg
    3095                3100                3105
His Lys Val Val Lys Val Met Arg Pro Ala Ala Asp Gly Arg Thr
    3110                3115                3120
Val Met Asp Val Ile Ser Arg Glu Asp Gln Arg Gly Ser Gly Gln
    3125                3130                3135
Val Val Thr Tyr Ala Leu Asn Thr Phe Thr Asn Leu Ala Val Gln
    3140                3145                3150
Leu Val Arg Met Met Glu Gly Glu Gly Val Ile Gly Pro Asp Asp
    3155                3160                3165
Val Glu Lys Leu Thr Lys Gly Lys Gly Pro Lys Val Arg Thr Trp
    3170                3175                3180
Leu Phe Glu Asn Gly Glu Glu Arg Leu Ser Arg Met Ala Val Ser
    3185                3190                3195
Gly Asp Asp Cys Val Val Lys Pro Leu Asp Asp Arg Phe Ala Thr
    3200                3205                3210
Ser Leu His Phe Leu Asn Ala Met Ser Lys Val Arg Lys Asp Ile
    3215                3220                3225
Gln Glu Trp Lys Pro Ser Thr Gly Trp Tyr Asp Trp Gln Gln Val
    3230                3235                3240
Pro Phe Cys Ser Asn His Phe Thr Glu Leu Ile Met Lys Asp Gly
    3245                3250                3255
Arg Thr Leu Val Val Pro Cys Arg Gly Gln Asp Glu Leu Val Gly
    3260                3265                3270
Arg Ala Arg Ile Ser Pro Gly Ala Gly Trp Asn Val Arg Asp Thr
    3275                3280                3285
Ala Cys Leu Ala Lys Ser Tyr Ala Gln Met Trp Leu Leu Leu Tyr
    3290                3295                3300
Phe His Arg Arg Asp Leu Arg Leu Met Ala Asn Ala Ile Cys Ser
    3305                3310                3315
Ala Val Pro Val Asn Trp Val Pro Thr Gly Arg Thr Thr Trp Ser
    3320                3325                3330
Ile His Ala Gly Gly Glu Trp Met Thr Thr Glu Asp Met Leu Glu
    3335                3340                3345
Val Trp Asn Arg Val Trp Ile Glu Glu Asn Glu Trp Met Glu Asp
    3350                3355                3360
Lys Thr Pro Val Glu Lys Trp Ser Asp Val Pro Tyr Ser Gly Lys
    3365                3370                3375
Arg Glu Asp Ile Trp Cys Gly Ser Leu Ile Gly Thr Arg Ala Arg
    3380                3385                3390
Ala Thr Trp Ala Glu Asn Ile Gln Val Ala Ile Asn Gln Val Arg
    3395                3400                3405
```

```
Ala Ile Ile Gly Asp Glu Lys Tyr Val Asp Tyr Met Ser Ser Leu
    3410            3415                3420
Lys Arg Tyr Glu Asp Thr Thr Leu Val Glu Asp Thr Val Leu
    3425            3430                3435

<210> SEQ ID NO 5
<211> LENGTH: 11041
<212> TYPE: DNA
<213> ORGANISM: Artificial Sequence
<220> FEATURE:
<223> OTHER INFORMATION: Synthetic construct

<400> SEQUENCE: 5
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agttcgaaac aaaagaaaag aggaggaaag     420
accggaattg cagtcatgat tggcctgatc accacagcta tggcagcgga ggtcactaga     480
cgtgggagtg catactatat gtacttggac agaaacgatg ctggggaggc catatctttt     540
ccaaccacat tggggatgaa taagtgttat atacagatca tggatcttgg acacatgtgt     600
gatgccacca tgagctatga atgccctatg ctggatgagg gggtggaacc agatgacgtc     660
gattgttggt gcaacacgac gtcaacttgg gttgtgtacg gaacctgcca tcacaaaaaa     720
ggtgaagcac ggagaagtag aagagctgtg acgctcccct cccattccac taggaagctg     780
caaacgcggt cgcaaacctg gttggaatca agagaataca caaagcactt gattagagtc     840
gaaaattgga tattcaggaa ccctggcttc gcgttagcag cagctgccat cgcttggctt     900
ttgggaagct caacgagcca aaaagtcata tacttggtca tgatactgct gattgccccg     960
gcatacagca tcaggtgcat aggagtcagc aataggact ttgtggaagg tatgtcaggt    1020
gggacttggg ttgatattgt cttggaacat ggaggttgtg tcaccgtaat ggcacaggac    1080
aaaccgactg tcgacataga gctggttaca acaacagtca gcaacatggc ggaggtaaga    1140
tcctactgct atgaggcatc aatatcagac atggcttcgg acagccgctg cccaacacaa    1200
ggtgaagcct accttgacaa gcaatcagac actcaatatg tctgcaaaag aacgttagtg    1260
gacagaggct ggggaaatgg atgtggactt tttggcaaag ggagtctggt gacatgcgct    1320
aagtttgcat gctccaagaa aatgaccggg aagagcatcc agccagagaa tctggagtac    1380
cggataatgc tgtcagttca tggctcccag cacagtggga tgatcgttaa tgacacagga    1440
catgaaactg atgagaatag agcgaaggtt gagataacgc ccaattcacc aagagccgaa    1500
gccaccctgg ggggttttgg aagcctagga cttgattgtg aaccgaggac aggccttgac    1560
ttttcagatt tgtattactt gactatgaat aacaagcact ggttggttca aggagtgg    1620
ttccacgaca ttccattacc ttggcacgct ggggcagaca ccggaactcc acactggaac    1680
aacaaagaag cactggtaga gttcaaggac gcacatgcca aaaggcaaac tgtcgtggtt    1740
ctagggagtc aagaaggagc agttcacacg gcccttgctg gagctctgga ggctgagatg    1800
gatggtgcaa agggaaggct gtcctctggc cacttgaaat gtcgcctgaa aatggataaa    1860
```

```
cttagattga agggcgtgtc atactccttg tgtaccgcag cgttcacatt caccaagatc    1920
ccggctgaaa cactgcacgg gacagtcaca gtggaggtac agtacgcagg gacagatgga    1980
ccttgcaagg ttccagctca gatggcggtg gacatgcaaa ctctgacccc agttgggagg    2040
ttgataaccg ctaaccccgt aatcactgaa agcactgaga actctaagat gatgctggaa    2100
cttgatccac catttgggga ctcttacatt gtcataggag tcggggagaa gaagatcacc    2160
caccactggc acaggagtgg cagcaccatt ggaaaagcat ttgaagccac tgtgagaggt    2220
gccaagagaa tggcagtctt gggagacaca gcctgggact ttggatcagt tggaggcgct    2280
ctcaactcat tgggcaaggg catccatcaa attttttggag cagctttcaa atcattgttt    2340
ggaggaatgt cctggttctc acaaattctc attggaacgt tgctgatgtg gttgggtctg    2400
aacacaaaga atggatctat ttcccttatg tgcttggcct taggggagt gttgatcttc    2460 ttatccacag ccgtctctgc tgattccgga tgtgccatag acatcagccg gcaagagctg    2520
agatgtggaa gtggagtgtt catacacaat gatgtggagg cttggatgga ccggtacaag    2580
tattaccctg aaacgccaca aggcctagcc aagatcattc agaaagctca taggaagga    2640 gtgtgcggtc tacgatcagt ttccagactg gagcatcaaa tgtgggaagc agtgaaggac    2700
gagctgaaca ctcttttgaa ggagaatggt gtggacctta tgtcgtggt tgagaaacag    2760 gagggaatgt acaagtcagc acctaaacgc ctcaccgcca ccacggaaaa attggaaatt    2820
ggctggaagg cctggggaaa gagtatttta tttgcaccag aactcgccaa caacaccttt    2880
gtggttgatg gtccggagac caaggaatgt ccgactcaga atcgcgcttg gaatagctta    2940
gaagtggagg attttggatt tggtctcacc agcactcgga tgttcctgaa ggtcagagag    3000
agcaacacaa ctgaatgtga ctcgaagatc attggaacgg ctgtcaagaa caacttggcg    3060
atccacagtg acctgtccta ttggattgaa agcaggctca atgatacgtg gaagcttgaa    3120
agggcagttc tgggtgaagt caaatcatgt acgtggcctg agacgcatac cttgtggggc    3180
gatggaatcc ttgagagtga cttgataata ccagtcacac tggcgggacc acgaagcaat    3240
cacaatcgga gacctgggta aagacacaa aaccagggcc catgggacga aggccgggta    3300
gagattgact tcgattactg cccaggaact acggtcaccc tgagtgagag ctgcggacac    3360
cgtggacctg ccactcgcac caccacagag agcggaaagt tgataacaga ttggtgctgc    3420
aggagctgca ccttaccacc actgcgctac caaactgaca gcggctgttg gtatggtatg    3480
gagatcagac cacagagaca tgatgaaaag accctcgtgc agtcacaagt gaatgcttat    3540
aatgctgata tgattgaccc tttttcagttg ggccttctgg tcgtgttctt ggccacccag    3600
gaggtccttc gcaagaggtg gacagccaag atcagcatgc cagctatact gattgctctg    3660
ctagtcctgg tgtttgggg cattacttac actgatgtgt tacgctatgt catcttggtg    3720
ggggcagctt tcgcagaatc taattcggga ggagacgtgg tacacttggc gctcatggcg    3780
accttcaaga taaccagt gtttatggtg gcatcgtttc tcaaagcgag atggaccaac    3840
caggagaaca tttgtgttgat gttggcggct gttttctttc aaatggctta ttacgatgcc    3900
cgccaaattc tgctctggga gatccctgat gtgttgaatt cactggcggt agcttggatg    3960
atactgagag ccataacatt cacaacgaca tcaaacgtgg ttgttccgct gctagccctg    4020
ctaacacccg gctgagatg cttgaatctg gatgtgtaca ggatactgct gttgatggtc    4080
ggaataggca gcttgatcag ggagaagagg agtgcagctg caaaaaagaa aggagcaagt    4140
ctgctatgct tggctctagc ctcaacagga cttttcaacc ccatgatcct tgctgctgga    4200
ctgattgcat gtgatcccaa ccgtaaacgc ggatggcccg caactgaagt gatgacagct    4260
```

```
gtcggcctaa tgtttgccat cgtcggaggg ctggcagagc ttgacattga ctccatggcc   4320
attccaatga ctatcgcggg gctcatgttt gctgctttcg tgatttctgg gaaatcaaca   4380
gatatgtgga ttgagagaac ggcggacatt tcctgggaaa gtgatgcaga aattacaggc   4440
tcgagcgaaa gagttgatgt gcggcttgat gatgatggaa acttccagct catgaatgat   4500
ccaggagcac cttggaagat atggatgctc agaatggtct gtctcgcgat tagtgcgtac   4560
accccctggg caatcttgcc ctcagtagtt ggattttgga taactctcca atacacaaag   4620
agaggaggcg tgttgtggga cactccctca ccaaaggagt acaaaaaggg ggacacgacc   4680
accggcgtct acaggatcat gactcgtggg ctgctcggca gttatcaagc aggagcgggc   4740
gtgatggttg aaggtgtttt ccacaccctt tggcatacaa caaaggagc cgctttgatg   4800 agcgagagg gccgcctgga cccatactgg ggcagtgtca aggaggatcg actttgttac   4860
ggaggaccct ggaaattgca gcacaagtgg aacgggcagg atgaggtgca gatgattgtg   4920
gtggaacctg gcaggaacgt taagaacgtc cagacgaaac caggggtgtt caaaacacct   4980
gaaggagaaa tcggggccgt gactttggac ttccccactg gaacatcagg ctcaccaata   5040
gtggacaaaa acggtgatgt gattgggctt tatggcaatg gagtcataat gcccaacggc   5100
tcatacataa gcgcgatagt gcagggtgaa aggatggatg agccaatccc agccggattc   5160
gaacctgaga tgctgaggaa aaaacagatc actgtactgg atctccatcc cggcgccggt   5220
aaaacaagga ggattctgcc acagatcatc aaagaggcca taaacagaag actgagaaca   5280
gccgtgctag caccaaccag ggttgtggct gctgagatgg ctgaagcact gagaggactg   5340
cccatccggt accagacatc cgcagtgccc agagaacata atggaaatga gattgttgat   5400
gtcatgtgtc atgctaccct cacccacagg ctgatgtctc ctcacagggt gccgaactac   5460
aacctgttcg tgatggatga ggctcatttc accgacccag ctagcattgc agcaagaggt   5520
tacatttcca caaaggtcga gctagggag cggcggcaa tattcatgac agccacccca   5580
ccaggcactt cagatccatt cccagagtcc aattcaccaa tttccgactt acagactgag   5640
atcccggatc gagcttggaa ctctggatac gaatggatca cagaatacac cgggaagacg   5700 gtttggttg tgcctagtgt caagatgggg aatgagattg ccctttgcct acaacgtgct   5760
ggaaagaaag tagtccaatt gaacagaaag tcgtacgaga cggagtaccc aaaatgtaag   5820
aacgatgatt gggactttgt tatcacaaca gacatatctg aaatggggc taacttcaag   5880 gcgagcaggg tgattgacag ccggaagagt gtgaaccaa ccatcataac agaaggagaa   5940
gggagagtga tcctgggaga accatctgca gtgcagcgca ctagtgccgc ccagagacgt   6000
ggacgtatcg gtagaaatcc gtcgcaagtt ggtgatgagt actgttatgg ggggcacacg   6060
aatgaagacg actcgaactt cgcccattgg actgaggcac gaatcatgct ggacaacatc   6120
aacatgccaa acggactgat cgctcaattc taccaaccag agcgtgagaa ggtatatacc   6180
atggatgggg aataccggct cagaggagaa gagagaaaaa actttctgga actgttgagg   6240
actgcagatc tgccagtttg gctggcttac aaggttgcag cggctggagt gtcataccac   6300
gaccggaggt ggtgctttga tggtcctagg acaaacacaa ttttagaaga caacaacgaa   6360
gtggaagtca tcacgaagct tggtgaaagg aagattctga ggccgcgctg gattgacgcc   6420
agggtgtact cggatcacca ggcactaaag gcgttcaagg acttcgcctc gggaaaacgt   6480
tctcagatag ggctcattga ggttctggga aagatgcctg agcacttcat ggggaagaca   6540
tgggaagcac ttgacaccat gtacgttgtg gccactgcag agaaaggagg aagagctcac   6600
```

```
agaatggccc tggaggaact gccagatgct cttcagacaa ttgccttgat tgccttattg   6660
agtgtgatga ccatgggagt attcttcctc ctcatgcagc ggaagggcat tggaaagata   6720
ggtttgggag gcgctgtctt gggagtcgcg acctttttct gttggatggc tgaagttcca   6780
ggaacgaaga tcgccggaat gttgctgctc tcccttctct tgatgattgt gctaattcct   6840
gagccagaga agcaacgttc gcagacagac aaccagctag ccgtgttcct gatttgtgtc   6900
atgacccttg tgagcgcagt ggcagccaac gagatgggtt ggctagataa gaccaagagt   6960
gacataagca gtttgtttgg gcaaagaatt gaggtcaagg agaatttcag catgggagag   7020
tttcttttgg acttgaggcc tgcaacagcc tggtcactgt acgctgtgac aacagcggtc   7080
ctcactccac tgctaaagca tttgatcacg tcagattaca tcaacacctc attgacctca   7140
ataaacgttc aggcaagtgc actattcaca ctcgcgcgag gcttcccctt cgtcgatgtt   7200
ggagtgtcgg ctctcctgct agcagccgga tgctgggac aagtcaccct caccgttacg   7260
gtaacagcgg caacactcct tttttgccac tatgcctaca tggttcccgg ttggcaagct   7320
gaggcaatgc gctcagccca gcggcggaca gcggccggaa tcatgaagaa cgctgtagtg   7380
gatggcatcg tggccacgga cgtcccagaa ttagagcgca ccacacccat catgcagaag   7440
aaagttggac agatcatgct gatcttggtg tctctagctg cagtagtagt gaacccgtct   7500
gtgaagacag tacgagagc cggaattttg atcacggccg cagcggtgac gctttgggag   7560
aatggagcaa gctctgtttg gaacgcaaca actgccatcg gactctgcca catcatgcgt   7620
gggggttggt tgtcatgtct atccataaca tggacactca taagaacat ggaaaaacca   7680
ggactaaaaa gaggtggggc aaaaggacgc accttgggag aggtttggaa agaaagactc   7740
aaccagatga caaaagaaga gttcactagg taccgcaaag aggccatcat cgaagtcgat   7800
cgctcagcgg caaaacacgc caggaaagaa ggcaatgtca ctggagggca tccagtctct   7860
aggggcacag caaaactgag atggctggtc gaacggaggt ttctcgaacc ggtcggaaaa   7920
gtgattgacc ttggatgtgg aagaggcggt tggtgttact atatggcaac ccaaaaaaga   7980
gtccaagaag tcagagggta cacaaagggc ggtcccggac atgaagagcc caactagtg   8040
caaagttatg gatggaacat tgtcaccatg aagagtggga tggatgtgtt ctacagacct   8100
tctgagtgtt gtgacaccct cctttgtgac atcggagagt cctcgtcaag tgctgaggtt   8160
gaagagcata ggacgattcg ggtccttgaa atggttgagg actggctgca ccgagggcca   8220
agggaatttt gcgtgaaggt gctctgcccc tacatgccga aagtcataga gaagatggag   8280
ctgctccaac gccggtatgg ggggggactg gtcagaaacc cactctcacg gaattccacg   8340
cacgagatgt attgggtgag tcgagcttca ggcaatgtgg tacattcagt gaatatgacc   8400
agccaggtgc tcctaggaag aatggaaaaa ggacctgga agggaccca atacgaggaa   8460
gatgtaaact tgggaagtgg aaccagggcg gtgggaaaac ccctgctcaa ctcagacacc   8520
agtaaaatca gaacaggat tgaacgactc aggcgtgagt acagttcgac gtggcaccac   8580
gatgagaacc acccatatag aacctggaac tatcacggca gttatgatgt gaagcccaca   8640
ggctccgcca gttcgctggt caatggagtg gtcaggctcc tctcaaaacc atgggacacc   8700
atcacgaatg ttaccaccat ggccatgact gacactactc ccttcgggca gcagcgagtg   8760
ttcaaagaga aggtggacac gaaagctcct gaaccgccag aaggagtgaa gtacgtgctc   8820
aacgagacca ccaactggtt gtgggcgttt ttggccagag aaaaacgtcc cagaatgtgc   8880
tctcgagagg aattcataag aaaggtcaac agcaatgcag ctttgggtgc catgtttgaa   8940
gagcagaatc aatggaggag cgccagagaa gcagttgaag atccaaaatt tgggagatg   9000
```

```
gtggatgagg agcgcgaggc acatctgcgg ggggaatgtc acacttgcat ttacaacatg   9060
atgggaaaga gagagaaaaa acccggagag ttcggaaagg ccaagggaag cagagccatt   9120
tggttcatgt ggctcggagc tcgctttctg gagttcgagg ctctgggttt tctcaatgaa   9180
gaccactggc ttgaagaaa gaactcagga ggaggtgtcg agggcttggg cctccaaaaa   9240
ctgggttaca tcctgcgtga agttggcacc cggcctgggg gcaagatcta tgctgatgac   9300
acagctggct gggacacccg catcacgaga gctgacttgg aaaatgaagc taaggtgctt   9360
gagctgcttg atgggaaca tcggcgtctt gccagggcca tcattgagct cacctatcgt   9420
cacaaagttg tgaaagtgat gcgcccggct gctgatggaa gaaccgtcat ggatgttatc   9480
tccagagaag atcagagggg gagtggacaa gttgtcacct acgccctaaa cactttcacc   9540
aacctggccg tccagctggt gaggatgatg aaggggaag gagtgattgg cccagatgat   9600
gtggagaaac tcacaaaagg gaaaggaccc aaagtcagga cctggctgtt tgagaatggg   9660
gaagaaagac tcagccgcat ggctgtcagt ggagatgact gtgtggtaaa gcccctggac   9720
gatcgctttg ccacctcgct ccacttcctc aatgctatgt caaaggttcg caaagacatc   9780
caagagtgga aaccgtcaac tggatggtat gattggcagc aggttccatt ttgctcaaac   9840
catttcactg aattgatcat gaaagatgga agaacactgg tggttccatg ccgaggacag   9900
gatgaattgg taggcagagc tcgcatatct ccaggggccg gatggaacgt ccgcgacact   9960
gcttgtctgg ctaagtctta tgcccagatg tggctgcttc tgtacttcca cagaagagac  10020
ctgcggctca tggccaacgc catttgctcc gctgtccctg tgaattgggt ccctaccgga  10080
agaaccacgt ggtccatcca tgcaggagga gagtggatga acagagga catgttggag  10140 gtctggaacc gtgtttggat agaggagaat gaatggatgg aagacaaaac cccagtggag  10200
aaatggagtg acgtcccata ttcaggaaaa cgagaggaca tctggtgtgg cagcctgatt  10260
ggcacaagag cccgagccac gtgggcagaa aacatccagg tggctatcaa ccaagtcaga  10320
gcaatcatcg gagatgagaa gtatgtggat tacatgagtt cactaaagag atatgaagac  10380
acaactttgg ttgaggacac agtactgtag atatttaatc aattgtaaat agacaatata  10440
agtatgcata aaagtgtagt ttttatagtag tatttagtgg tgttagtgta aatagttaag  10500
aaaattttga ggagaaagtc aggccgggaa gttcccgcca ccggaagttg agtagacggt  10560
gctgcctgcg actcaacccc aggaggactg ggtgaacaaa gccgcgaagt gatccatgta  10620
agccctcaga accgtctcgg aaggaggacc ccacatgttg taacttcaaa gcccaatgtc  10680
agaccacgct acgcgtgct actctgcgga gagtgcagtc tgcgatagtg ccccaggagg  10740
actgggttaa caaaggcaaa ccaacgcccc acgcggccct agccccggta atggtgttaa  10800
ccagggcgaa aggactagag gttagaggag accccgcggt ttaaagtgca cggcccagcc  10860
tggctgaagc tgtaggtcag gggaaggact agaggttagt ggagaccccg tgccacaaaa  10920
caccacaaca aaacagcata ttgacacctg ggatagacta ggagatcttc tgctctgcac  10980
aaccagccac acggcacagt gcgccgacaa tggtggctgg tggtgcgaga acacaggatc  11040
t                                                                  11041
```

<210> SEQ ID NO 6
<211> LENGTH: 3437
<212> TYPE: PRT
<213> ORGANISM: Artificial Sequence
<220> FEATURE:
<223> OTHER INFORMATION: Synthetic polypeptide

```
<400> SEQUENCE: 6

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
            35                  40                  45

Ala Leu Leu Ala Phe Phe Arg Phe Thr Ala Ile Ala Pro Thr Arg Ala
        50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Thr Thr Ala Met Ala Ala Glu Val Thr Arg
            115                 120                 125

Arg Gly Ser Ala Tyr Tyr Met Tyr Leu Asp Arg Asn Asp Ala Gly Glu
        130                 135                 140

Ala Ile Ser Phe Pro Thr Thr Leu Gly Met Asn Lys Cys Tyr Ile Gln
145                 150                 155                 160

Ile Met Asp Leu Gly His Met Cys Asp Ala Thr Met Ser Tyr Glu Cys
                165                 170                 175

Pro Met Leu Asp Glu Gly Val Glu Pro Asp Asp Val Asp Cys Trp Cys
            180                 185                 190

Asn Thr Thr Ser Thr Trp Val Val Tyr Gly Thr Cys His His Lys Lys
        195                 200                 205

Gly Glu Ala Arg Arg Ser Arg Arg Ala Val Thr Leu Pro Ser His Ser
210                 215                 220

Thr Arg Lys Leu Gln Thr Arg Ser Gln Thr Trp Leu Glu Ser Arg Glu
225                 230                 235                 240

Tyr Thr Lys His Leu Ile Arg Val Glu Asn Trp Ile Phe Arg Asn Pro
                245                 250                 255

Gly Phe Ala Leu Ala Ala Ala Ala Ile Ala Trp Leu Leu Gly Ser Ser
            260                 265                 270

Thr Ser Gln Lys Val Ile Tyr Leu Val Met Ile Leu Leu Ile Ala Pro
        275                 280                 285

Ala Tyr Ser Ile Arg Cys Ile Gly Val Ser Asn Arg Asp Phe Val Glu
290                 295                 300

Gly Met Ser Gly Gly Thr Trp Val Asp Ile Val Leu Glu His Gly Gly
305                 310                 315                 320

Cys Val Thr Val Met Ala Gln Asp Lys Pro Thr Val Asp Ile Glu Leu
                325                 330                 335

Val Thr Thr Thr Val Ser Asn Met Ala Glu Val Arg Ser Tyr Cys Tyr
            340                 345                 350

Glu Ala Ser Ile Ser Asp Met Ala Ser Asp Ser Arg Cys Pro Thr Gln
        355                 360                 365

Gly Glu Ala Tyr Leu Asp Lys Gln Ser Asp Thr Gln Tyr Val Cys Lys
370                 375                 380

Arg Thr Leu Val Asp Arg Gly Trp Gly Asn Gly Cys Gly Leu Phe Gly
385                 390                 395                 400

Lys Gly Ser Leu Val Thr Cys Ala Lys Phe Ala Cys Ser Lys Lys Met
                405                 410                 415
```

```
Thr Gly Lys Ser Ile Gln Pro Glu Asn Leu Glu Tyr Arg Ile Met Leu
            420                 425                 430

Ser Val His Gly Ser Gln His Ser Gly Met Ile Val Asn Asp Thr Gly
            435                 440                 445

His Glu Thr Asp Glu Asn Arg Ala Lys Val Glu Ile Thr Pro Asn Ser
450                 455                 460

Pro Arg Ala Glu Ala Thr Leu Gly Gly Phe Gly Ser Leu Gly Leu Asp
465                 470                 475                 480

Cys Glu Pro Arg Thr Gly Leu Asp Phe Ser Asp Leu Tyr Tyr Leu Thr
            485                 490                 495

Met Asn Asn Lys His Trp Leu Val His Lys Glu Trp Phe His Asp Ile
            500                 505                 510

Pro Leu Pro Trp His Ala Gly Ala Asp Thr Gly Thr Pro His Trp Asn
            515                 520                 525

Asn Lys Glu Ala Leu Val Glu Phe Lys Asp Ala His Ala Lys Arg Gln
            530                 535                 540

Thr Val Val Val Leu Gly Ser Gln Glu Gly Ala Val His Thr Ala Leu
545                 550                 555                 560

Ala Gly Ala Leu Glu Ala Glu Met Asp Gly Ala Lys Gly Arg Leu Ser
            565                 570                 575

Ser Gly His Leu Lys Cys Arg Leu Lys Met Asp Lys Leu Arg Leu Lys
            580                 585                 590

Gly Val Ser Tyr Ser Leu Cys Thr Ala Ala Phe Thr Phe Thr Lys Ile
            595                 600                 605

Pro Ala Glu Thr Leu His Gly Thr Val Thr Val Glu Val Gln Tyr Ala
            610                 615                 620

Gly Thr Asp Gly Pro Cys Lys Val Pro Ala Gln Met Ala Val Asp Met
625                 630                 635                 640

Gln Thr Leu Thr Pro Val Gly Arg Leu Ile Thr Ala Asn Pro Val Ile
            645                 650                 655

Thr Glu Ser Thr Glu Asn Ser Lys Met Met Leu Glu Leu Asp Pro Pro
            660                 665                 670

Phe Gly Asp Ser Tyr Ile Val Ile Gly Val Gly Glu Lys Lys Ile Thr
            675                 680                 685

His His Trp His Arg Ser Gly Ser Thr Ile Gly Lys Ala Phe Glu Ala
            690                 695                 700

Thr Val Arg Gly Ala Lys Arg Met Ala Val Leu Gly Asp Thr Ala Trp
705                 710                 715                 720

Asp Phe Gly Ser Val Gly Gly Ala Leu Asn Ser Leu Gly Lys Gly Ile
            725                 730                 735

His Gln Ile Phe Gly Ala Ala Phe Lys Ser Leu Phe Gly Gly Met Ser
            740                 745                 750

Trp Phe Ser Gln Ile Leu Ile Gly Thr Leu Leu Met Trp Leu Gly Leu
            755                 760                 765

Asn Thr Lys Asn Gly Ser Ile Ser Leu Met Cys Leu Ala Leu Gly Gly
            770                 775                 780

Val Leu Ile Phe Leu Ser Thr Ala Val Ser Ala Asp Ser Gly Cys Ala
785                 790                 795                 800

Ile Asp Ile Ser Arg Gln Glu Leu Arg Cys Gly Ser Gly Val Phe Ile
            805                 810                 815

His Asn Asp Val Glu Ala Trp Met Asp Arg Tyr Lys Tyr Tyr Pro Glu
            820                 825                 830
```

```
Thr Pro Gln Gly Leu Ala Lys Ile Ile Gln Lys Ala His Lys Glu Gly
            835                 840                 845

Val Cys Gly Leu Arg Ser Val Ser Arg Leu Glu His Gln Met Trp Glu
    850                 855                 860

Ala Val Lys Asp Glu Leu Asn Thr Leu Leu Lys Glu Asn Gly Val Asp
865                 870                 875                 880

Leu Ser Val Val Glu Lys Gln Glu Gly Met Tyr Lys Ser Ala Pro
                885                 890                 895

Lys Arg Leu Thr Ala Thr Thr Glu Lys Leu Glu Ile Gly Trp Lys Ala
            900                 905                 910

Trp Gly Lys Ser Ile Leu Phe Ala Pro Glu Leu Ala Asn Asn Thr Phe
        915                 920                 925

Val Val Asp Gly Pro Glu Thr Lys Glu Cys Pro Thr Gln Asn Arg Ala
    930                 935                 940

Trp Asn Ser Leu Glu Val Glu Asp Phe Gly Phe Gly Leu Thr Ser Thr
945                 950                 955                 960

Arg Met Phe Leu Lys Val Arg Glu Ser Asn Thr Thr Glu Cys Asp Ser
                965                 970                 975

Lys Ile Ile Gly Thr Ala Val Lys Asn Asn Leu Ala Ile His Ser Asp
            980                 985                 990

Leu Ser Tyr Trp Ile Glu Ser Arg  Leu Asn Asp Thr Trp  Lys Leu Glu
        995                 1000                1005

Arg Ala  Val Leu Gly Glu Val  Lys Ser Cys Thr Trp  Pro Glu Thr
    1010                1015                1020

His Thr  Leu Trp Gly Asp Gly  Ile Leu Glu Ser Asp  Leu Ile Ile
    1025                1030                1035

Pro Val  Thr Leu Ala Gly Pro  Arg Ser Asn His Asn  Arg Arg Pro
    1040                1045                1050

Gly Tyr  Lys Thr Gln Asn Gln  Gly Pro Trp Asp Glu  Gly Arg Val
    1055                1060                1065

Glu Ile  Asp Phe Asp Tyr Cys  Pro Gly Thr Thr Val  Thr Leu Ser
    1070                1075                1080

Glu Ser  Cys Gly His Arg Gly  Pro Ala Thr Arg Thr  Thr Thr Glu
    1085                1090                1095

Ser Gly  Lys Leu Ile Thr Asp  Trp Cys Cys Arg Ser  Cys Thr Leu
    1100                1105                1110

Pro Pro  Leu Arg Tyr Gln Thr  Asp Ser Gly Cys Trp  Tyr Gly Met
    1115                1120                1125

Glu Ile  Arg Pro Gln Arg His  Asp Glu Lys Thr Leu  Val Gln Ser
    1130                1135                1140

Gln Val  Asn Ala Tyr Asn Ala  Asp Met Ile Asp Pro  Phe Gln Leu
    1145                1150                1155

Gly Leu  Leu Val Val Phe Leu  Ala Thr Gln Glu Val  Leu Arg Lys
    1160                1165                1170

Arg Trp  Thr Ala Lys Ile Ser  Met Pro Ala Ile Leu  Ile Ala Leu
    1175                1180                1185

Leu Val  Leu Val Phe Gly Gly  Ile Thr Tyr Thr Asp  Val Leu Arg
    1190                1195                1200

Tyr Val  Ile Leu Val Gly Ala  Ala Phe Ala Glu Ser  Asn Ser Gly
    1205                1210                1215

Gly Asp  Val Val His Leu Ala  Leu Met Ala Thr Phe  Lys Ile Gln
    1220                1225                1230

Pro Val  Phe Met Val Ala Ser  Phe Leu Lys Ala Arg  Trp Thr Asn
```

-continued

```
             1235                1240                1245

Gln  Glu  Asn  Ile  Leu  Leu  Met  Leu  Ala  Ala  Val  Phe  Phe  Gln  Met
             1250                1255                1260

Ala  Tyr  Tyr  Asp  Ala  Arg  Gln  Ile  Leu  Leu  Trp  Glu  Ile  Pro  Asp
             1265                1270                1275

Val  Leu  Asn  Ser  Leu  Ala  Val  Ala  Trp  Met  Ile  Leu  Arg  Ala  Ile
             1280                1285                1290

Thr  Phe  Thr  Thr  Thr  Ser  Asn  Val  Val  Pro  Leu  Leu  Ala  Leu
             1295                1300                1305

Leu  Thr  Pro  Gly  Leu  Arg  Cys  Leu  Asn  Leu  Asp  Val  Tyr  Arg  Ile
             1310                1315                1320

Leu  Leu  Leu  Met  Val  Gly  Ile  Gly  Ser  Leu  Ile  Arg  Glu  Lys  Arg
             1325                1330                1335

Ser  Ala  Ala  Ala  Lys  Lys  Gly  Ala  Ser  Leu  Leu  Cys  Leu  Ala
             1340                1345                1350

Leu  Ala  Ser  Thr  Gly  Leu  Phe  Asn  Pro  Met  Ile  Leu  Ala  Ala  Gly
             1355                1360                1365

Leu  Ile  Ala  Cys  Asp  Pro  Asn  Arg  Lys  Arg  Gly  Trp  Pro  Ala  Thr
             1370                1375                1380

Glu  Val  Met  Thr  Ala  Val  Gly  Leu  Met  Phe  Ala  Ile  Val  Gly  Gly
             1385                1390                1395

Leu  Ala  Glu  Leu  Asp  Ile  Asp  Ser  Met  Ala  Ile  Pro  Met  Thr  Ile
             1400                1405                1410

Ala  Gly  Leu  Met  Phe  Ala  Ala  Phe  Val  Ile  Ser  Gly  Lys  Ser  Thr
             1415                1420                1425

Asp  Met  Trp  Ile  Glu  Arg  Thr  Ala  Asp  Ile  Ser  Trp  Glu  Ser  Asp
             1430                1435                1440

Ala  Glu  Ile  Thr  Gly  Ser  Ser  Glu  Arg  Val  Asp  Val  Arg  Leu  Asp
             1445                1450                1455

Asp  Asp  Gly  Asn  Phe  Gln  Leu  Met  Asn  Asp  Pro  Gly  Ala  Pro  Trp
             1460                1465                1470

Lys  Ile  Trp  Met  Leu  Arg  Met  Val  Cys  Leu  Ala  Ile  Ser  Ala  Tyr
             1475                1480                1485

Thr  Pro  Trp  Ala  Ile  Leu  Pro  Ser  Val  Val  Gly  Phe  Trp  Ile  Thr
             1490                1495                1500

Leu  Gln  Tyr  Thr  Lys  Arg  Gly  Gly  Val  Leu  Trp  Asp  Thr  Pro  Ser
             1505                1510                1515

Pro  Lys  Glu  Tyr  Lys  Lys  Gly  Asp  Thr  Thr  Gly  Val  Tyr  Arg
             1520                1525                1530

Ile  Met  Thr  Arg  Gly  Leu  Leu  Gly  Ser  Tyr  Gln  Ala  Gly  Ala  Gly
             1535                1540                1545

Val  Met  Val  Glu  Gly  Val  Phe  His  Thr  Leu  Trp  His  Thr  Thr  Lys
             1550                1555                1560

Gly  Ala  Ala  Leu  Met  Ser  Gly  Glu  Gly  Arg  Leu  Asp  Pro  Tyr  Trp
             1565                1570                1575

Gly  Ser  Val  Lys  Glu  Asp  Arg  Leu  Cys  Tyr  Gly  Gly  Pro  Trp  Lys
             1580                1585                1590

Leu  Gln  His  Lys  Trp  Asn  Gly  Gln  Asp  Glu  Val  Gln  Met  Ile  Val
             1595                1600                1605

Val  Glu  Pro  Gly  Arg  Asn  Val  Lys  Asn  Val  Gln  Thr  Lys  Pro  Gly
             1610                1615                1620

Val  Phe  Lys  Thr  Pro  Glu  Gly  Glu  Ile  Gly  Ala  Val  Thr  Leu  Asp
             1625                1630                1635
```

-continued

```
Phe Pro Thr Gly Thr Ser Gly Ser Pro Ile Val Asp Lys Asn Gly
1640                1645                1650

Asp Val Ile Gly Leu Tyr Gly Asn Gly Val Ile Met Pro Asn Gly
1655                1660                1665

Ser Tyr Ile Ser Ala Ile Val Gln Gly Glu Arg Met Asp Glu Pro
1670                1675                1680

Ile Pro Ala Gly Phe Glu Pro Glu Met Leu Arg Lys Lys Gln Ile
1685                1690                1695

Thr Val Leu Asp Leu His Pro Gly Ala Gly Lys Thr Arg Arg Ile
1700                1705                1710

Leu Pro Gln Ile Ile Lys Glu Ala Ile Asn Arg Arg Leu Arg Thr
1715                1720                1725

Ala Val Leu Ala Pro Thr Arg Val Val Ala Ala Glu Met Ala Glu
1730                1735                1740

Ala Leu Arg Gly Leu Pro Ile Arg Tyr Gln Thr Ser Ala Val Pro
1745                1750                1755

Arg Glu His Asn Gly Asn Glu Ile Val Asp Val Met Cys His Ala
1760                1765                1770

Thr Leu Thr His Arg Leu Met Ser Pro His Arg Val Pro Asn Tyr
1775                1780                1785

Asn Leu Phe Val Met Asp Glu Ala His Phe Thr Asp Pro Ala Ser
1790                1795                1800

Ile Ala Ala Arg Gly Tyr Ile Ser Thr Lys Val Glu Leu Gly Glu
1805                1810                1815

Ala Ala Ala Ile Phe Met Thr Ala Thr Pro Pro Gly Thr Ser Asp
1820                1825                1830

Pro Phe Pro Glu Ser Asn Ser Pro Ile Ser Asp Leu Gln Thr Glu
1835                1840                1845

Ile Pro Asp Arg Ala Trp Asn Ser Gly Tyr Glu Trp Ile Thr Glu
1850                1855                1860

Tyr Thr Gly Lys Thr Val Trp Phe Val Pro Ser Val Lys Met Gly
1865                1870                1875

Asn Glu Ile Ala Leu Cys Leu Gln Arg Ala Gly Lys Lys Val Val
1880                1885                1890

Gln Leu Asn Arg Lys Ser Tyr Glu Thr Glu Tyr Pro Lys Cys Lys
1895                1900                1905

Asn Asp Asp Trp Asp Phe Val Ile Thr Thr Asp Ile Ser Glu Met
1910                1915                1920

Gly Ala Asn Phe Lys Ala Ser Arg Val Ile Asp Ser Arg Lys Ser
1925                1930                1935

Val Lys Pro Thr Ile Ile Thr Glu Gly Glu Gly Arg Val Ile Leu
1940                1945                1950

Gly Glu Pro Ser Ala Val Thr Ala Ala Ser Ala Ala Gln Arg Arg
1955                1960                1965

Gly Arg Ile Gly Arg Asn Pro Ser Gln Val Gly Asp Glu Tyr Cys
1970                1975                1980

Tyr Gly Gly His Thr Asn Glu Asp Asp Ser Asn Phe Ala His Trp
1985                1990                1995

Thr Glu Ala Arg Ile Met Leu Asp Asn Ile Asn Met Pro Asn Gly
2000                2005                2010

Leu Ile Ala Gln Phe Tyr Gln Pro Glu Arg Glu Lys Val Tyr Thr
2015                2020                2025
```

```
Met Asp Gly Glu Tyr Arg Leu Arg Gly Glu Glu Arg Lys Asn Phe
2030            2035                2040

Leu Glu Leu Leu Arg Thr Ala Asp Leu Pro Val Trp Leu Ala Tyr
2045            2050                2055

Lys Val Ala Ala Ala Gly Val Ser Tyr His Asp Arg Arg Trp Cys
2060            2065                2070

Phe Asp Gly Pro Arg Thr Asn Thr Ile Leu Glu Asp Asn Asn Glu
2075            2080                2085

Val Glu Val Ile Thr Lys Leu Gly Glu Arg Lys Ile Leu Arg Pro
2090            2095                2100

Arg Trp Ile Asp Ala Arg Val Tyr Ser Asp His Gln Ala Leu Lys
2105            2110                2115

Ala Phe Lys Asp Phe Ala Ser Gly Lys Arg Ser Gln Ile Gly Leu
2120            2125                2130

Ile Glu Val Leu Gly Lys Met Pro Glu His Phe Met Gly Lys Thr
2135            2140                2145

Trp Glu Ala Leu Asp Thr Met Tyr Val Val Ala Thr Ala Glu Lys
2150            2155                2160

Gly Gly Arg Ala His Arg Met Ala Leu Glu Glu Leu Pro Asp Ala
2165            2170                2175

Leu Gln Thr Ile Ala Leu Ile Ala Leu Leu Ser Val Met Thr Met
2180            2185                2190

Gly Val Phe Phe Leu Leu Met Gln Arg Lys Gly Ile Gly Lys Ile
2195            2200                2205

Gly Leu Gly Gly Ala Val Leu Gly Val Ala Thr Phe Phe Cys Trp
2210            2215                2220

Met Ala Glu Val Pro Gly Thr Lys Ile Ala Gly Met Leu Leu Leu
2225            2230                2235

Ser Leu Leu Leu Met Ile Val Leu Ile Pro Glu Pro Glu Lys Gln
2240            2245                2250

Arg Ser Gln Thr Asp Asn Gln Leu Ala Val Phe Leu Ile Cys Val
2255            2260                2265

Met Thr Leu Val Ser Ala Val Ala Ala Asn Glu Met Gly Trp Leu
2270            2275                2280

Asp Lys Thr Lys Ser Asp Ile Ser Ser Leu Phe Gly Gln Arg Ile
2285            2290                2295

Glu Val Lys Glu Asn Phe Ser Met Gly Glu Phe Leu Leu Asp Leu
2300            2305                2310

Arg Pro Ala Thr Ala Trp Ser Leu Tyr Ala Val Thr Thr Ala Val
2315            2320                2325

Leu Thr Pro Leu Leu Lys His Leu Ile Thr Ser Asp Tyr Ile Asn
2330            2335                2340

Thr Ser Leu Thr Ser Ile Asn Val Gln Ala Ser Ala Leu Phe Thr
2345            2350                2355

Leu Ala Arg Gly Phe Pro Phe Val Asp Val Gly Val Ser Ala Leu
2360            2365                2370

Leu Leu Ala Ala Gly Cys Trp Gly Gln Val Thr Leu Thr Val Thr
2375            2380                2385

Val Thr Ala Ala Thr Leu Leu Phe Cys His Tyr Ala Tyr Met Val
2390            2395                2400

Pro Gly Trp Gln Ala Glu Ala Met Arg Ser Ala Gln Arg Arg Thr
2405            2410                2415

Ala Ala Gly Ile Met Lys Asn Ala Val Val Asp Gly Ile Val Ala
```

```
                2420              2425              2430
Thr Asp Val Pro Glu Leu Glu Arg Thr Thr Pro Ile Met Gln Lys
    2435              2440              2445
Lys Val Gly Gln Ile Met Leu Ile Leu Val Ser Leu Ala Ala Val
    2450              2455              2460
Val Val Asn Pro Ser Val Lys Thr Val Arg Glu Ala Gly Ile Leu
    2465              2470              2475
Ile Thr Ala Ala Ala Val Thr Leu Trp Glu Asn Gly Ala Ser Ser
    2480              2485              2490
Val Trp Asn Ala Thr Thr Ala Ile Gly Leu Cys His Ile Met Arg
    2495              2500              2505
Gly Gly Trp Leu Ser Cys Leu Ser Ile Thr Trp Thr Leu Ile Lys
    2510              2515              2520
Asn Met Glu Lys Pro Gly Leu Lys Arg Gly Gly Ala Lys Gly Arg
    2525              2530              2535
Thr Leu Gly Glu Val Trp Lys Glu Arg Leu Asn Gln Met Thr Lys
    2540              2545              2550
Glu Glu Phe Thr Arg Tyr Arg Lys Glu Ala Ile Ile Glu Val Asp
    2555              2560              2565
Arg Ser Ala Ala Lys His Ala Arg Lys Glu Gly Asn Val Thr Gly
    2570              2575              2580
Gly His Pro Val Ser Arg Gly Thr Ala Lys Leu Arg Trp Leu Val
    2585              2590              2595
Glu Arg Arg Phe Leu Glu Pro Val Gly Lys Val Ile Asp Leu Gly
    2600              2605              2610
Cys Gly Arg Gly Gly Trp Cys Tyr Tyr Met Ala Thr Gln Lys Arg
    2615              2620              2625
Val Gln Glu Val Arg Gly Tyr Thr Lys Gly Gly Pro Gly His Glu
    2630              2635              2640
Glu Pro Gln Leu Val Gln Ser Tyr Gly Trp Asn Ile Val Thr Met
    2645              2650              2655
Lys Ser Gly Val Asp Val Phe Tyr Arg Pro Ser Glu Cys Cys Asp
    2660              2665              2670
Thr Leu Leu Cys Asp Ile Gly Glu Ser Ser Ser Ala Glu Val
    2675              2680              2685
Glu Glu His Arg Thr Ile Arg Val Leu Glu Met Val Glu Asp Trp
    2690              2695              2700
Leu His Arg Gly Pro Arg Glu Phe Cys Val Lys Val Leu Cys Pro
    2705              2710              2715
Tyr Met Pro Lys Val Ile Glu Lys Met Glu Leu Leu Gln Arg Arg
    2720              2725              2730
Tyr Gly Gly Gly Leu Val Arg Asn Pro Leu Ser Arg Asn Ser Thr
    2735              2740              2745
His Glu Met Tyr Trp Val Ser Arg Ala Ser Gly Asn Val Val His
    2750              2755              2760
Ser Val Asn Met Thr Ser Gln Val Leu Leu Gly Arg Met Glu Lys
    2765              2770              2775
Arg Thr Trp Lys Gly Pro Gln Tyr Glu Glu Asp Val Asn Leu Gly
    2780              2785              2790
Ser Gly Thr Arg Ala Val Gly Lys Pro Leu Leu Asn Ser Asp Thr
    2795              2800              2805
Ser Lys Ile Lys Asn Arg Ile Glu Arg Leu Arg Arg Glu Tyr Ser
    2810              2815              2820
```

-continued

```
Ser Thr Trp His His Asp Glu Asn His Pro Tyr Arg Thr Trp Asn
2825                2830                2835

Tyr His Gly Ser Tyr Asp Val Lys Pro Thr Gly Ser Ala Ser Ser
2840                2845                2850

Leu Val Asn Gly Val Val Arg Leu Leu Ser Lys Pro Trp Asp Thr
2855                2860                2865

Ile Thr Asn Val Thr Thr Met Ala Met Thr Asp Thr Thr Pro Phe
2870                2875                2880

Gly Gln Gln Arg Val Phe Lys Glu Lys Val Asp Thr Lys Ala Pro
2885                2890                2895

Glu Pro Pro Glu Gly Val Lys Tyr Val Leu Asn Glu Thr Thr Asn
2900                2905                2910

Trp Leu Trp Ala Phe Leu Ala Arg Glu Lys Arg Pro Arg Met Cys
2915                2920                2925

Ser Arg Glu Glu Phe Ile Arg Lys Val Asn Ser Asn Ala Ala Leu
2930                2935                2940

Gly Ala Met Phe Glu Glu Gln Asn Gln Trp Arg Ser Ala Arg Glu
2945                2950                2955

Ala Val Glu Asp Pro Lys Phe Trp Glu Met Val Asp Glu Glu Arg
2960                2965                2970

Glu Ala His Leu Arg Gly Glu Cys His Thr Cys Ile Tyr Asn Met
2975                2980                2985

Met Gly Lys Arg Glu Lys Lys Pro Gly Glu Phe Gly Lys Ala Lys
2990                2995                3000

Gly Ser Arg Ala Ile Trp Phe Met Trp Leu Gly Ala Arg Phe Leu
3005                3010                3015

Glu Phe Glu Ala Leu Gly Phe Leu Asn Glu Asp His Trp Leu Gly
3020                3025                3030

Arg Lys Asn Ser Gly Gly Gly Val Glu Gly Leu Gly Leu Gln Lys
3035                3040                3045

Leu Gly Tyr Ile Leu Arg Glu Val Gly Thr Arg Pro Gly Gly Lys
3050                3055                3060

Ile Tyr Ala Asp Asp Thr Ala Gly Trp Asp Thr Arg Ile Thr Arg
3065                3070                3075

Ala Asp Leu Glu Asn Glu Ala Lys Val Leu Glu Leu Leu Asp Gly
3080                3085                3090

Glu His Arg Arg Leu Ala Arg Ala Ile Ile Glu Leu Thr Tyr Arg
3095                3100                3105

His Lys Val Val Lys Val Met Arg Pro Ala Ala Asp Gly Arg Thr
3110                3115                3120

Val Met Asp Val Ile Ser Arg Glu Asp Gln Arg Gly Ser Gly Gln
3125                3130                3135

Val Val Thr Tyr Ala Leu Asn Thr Phe Thr Asn Leu Ala Val Gln
3140                3145                3150

Leu Val Arg Met Met Glu Gly Glu Gly Val Ile Gly Pro Asp Asp
3155                3160                3165

Val Glu Lys Leu Thr Lys Gly Lys Gly Pro Lys Val Arg Thr Trp
3170                3175                3180

Leu Phe Glu Asn Gly Glu Glu Arg Leu Ser Arg Met Ala Val Ser
3185                3190                3195

Gly Asp Asp Cys Val Val Lys Pro Leu Asp Asp Arg Phe Ala Thr
3200                3205                3210
```

```
Ser Leu His Phe Leu Asn Ala Met Ser Lys Val Arg Lys Asp Ile
3215                3220                3225

Gln Glu Trp Lys Pro Ser Thr Gly Trp Tyr Asp Trp Gln Gln Val
3230                3235                3240

Pro Phe Cys Ser Asn His Phe Thr Glu Leu Ile Met Lys Asp Gly
3245                3250                3255

Arg Thr Leu Val Val Pro Cys Arg Gly Gln Asp Glu Leu Val Gly
3260                3265                3270

Arg Ala Arg Ile Ser Pro Gly Ala Gly Trp Asn Val Arg Asp Thr
3275                3280                3285

Ala Cys Leu Ala Lys Ser Tyr Ala Gln Met Trp Leu Leu Leu Tyr
3290                3295                3300

Phe His Arg Arg Asp Leu Arg Leu Met Ala Asn Ala Ile Cys Ser
3305                3310                3315

Ala Val Pro Val Asn Trp Val Pro Thr Gly Arg Thr Thr Trp Ser
3320                3325                3330

Ile His Ala Gly Gly Glu Trp Met Thr Thr Glu Asp Met Leu Glu
3335                3340                3345

Val Trp Asn Arg Val Trp Ile Glu Glu Asn Glu Trp Met Glu Asp
3350                3355                3360

Lys Thr Pro Val Glu Lys Trp Ser Asp Val Pro Tyr Ser Gly Lys
3365                3370                3375

Arg Glu Asp Ile Trp Cys Gly Ser Leu Ile Gly Thr Arg Ala Arg
3380                3385                3390

Ala Thr Trp Ala Glu Asn Ile Gln Val Ala Ile Asn Gln Val Arg
3395                3400                3405

Ala Ile Ile Gly Asp Glu Lys Tyr Val Asp Tyr Met Ser Ser Leu
3410                3415                3420

Lys Arg Tyr Glu Asp Thr Thr Leu Val Glu Asp Thr Val Leu
3425                3430                3435

<210> SEQ ID NO 7
<211> LENGTH: 11041
<212> TYPE: DNA
<213> ORGANISM: Artificial Sequence
<220> FEATURE:
<223> OTHER INFORMATION: Synthetic construct

<400> SEQUENCE: 7
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agttcgaaac aaaagaaaag aggaggaaag     420
actagtgtcg gaattgttgg cctcctgctg accacagcta tggcagcgga ggtcactaga     480
cgtgggagtg catactatat gtacttggac agaaacgatg ctggggaggc catatctttt     540
ccaaccacat ggggatgaa taagtgttat atacagatca tggatcttgg acacatgtgt     600
gatgccacca tgagctatga atgccctatg ctggatgagg gggtggaacc agatgacgtc     660
gattgttggt gcaacacgac gtcaacttgg gttgtgtacg gaacctgcca tcacaaaaaa     720
```

-continued

```
ggtgaagcac ggagaagtag aagagctgtg acgctcccct cccattccac taggaagctg    780
caaacgcggt cgcaaacctg gttggaatca agagaataca caaagcactt gattagagtc    840
gaaaattgga tattcaggaa ccctggcttc gcgttagcag cagctgccat cgcttggctt    900
ttgggaagct caacgagcca aaaagtcata tacttggtca tgatactgct gattgccccg    960
gcatacagca tcaggtgcat aggagtcagc aatagggact ttgtggaagg tatgtcaggt   1020
gggacttggg ttgatattgt cttggaacat ggaggttgtg tcaccgtaat ggcacaggac   1080
aaaccgactg tcgacataga gctggttaca acaacagtca gcaacatggc ggaggtaaga   1140
tcctactgct atgaggcatc aatatcagac atggcttcgg acagccgctg cccaacacaa   1200
ggtgaagcct accttgacaa gcaatcagac actcaatatg tctgcaaaag aacgttagtg   1260
gacagaggct ggggaaatgg atgtggactt tttggcaaag ggagtctggt gacatgcgct   1320
aagtttgcat gctccaagaa aatgaccggg aagagcatcc agccagagaa tctggagtac   1380
cggataatgc tgtcagttca tggctcccag cacagtggga tgatcgttaa tgacacagga   1440
catgaaactg atgagaatag agcgaaggtt gagataacgc ccaattcacc aagagccgaa   1500
gccacccctg ggggttttgg aagcctagga cttgattgtg aaccgaggac aggccttgac   1560
ttttcagatt tgtattactt gactatgaat aacaagcact ggttggttca caaggagtgg   1620
ttccacgaca ttccattacc ttggcacgct ggggcagaca ccggaactcc acactggaac   1680
aacaaagaag cactggtaga gttcaaggac gcacatgcca aaaggcaaac tgtcgtggtt   1740
ctagggagtc aagaaggagc agttcacacg gcccttgctg gagctctgga ggctgagatg   1800
gatggtgcaa agggaaggct gtcctctggc cacttgaaat gtcgcctgaa aatggataaa   1860
cttagattga agggcgtgtc atactccttg tgtaccgcag cgttcacatt caccaagatc   1920
ccggctgaaa cactgcacgg gacagtcaca gtggaggtac agtacgcagg acagatggaa   1980
ccttgcaagg ttccagctca gatggcggtg gacatgcaaa ctctgacccc agttgggagg   2040
ttgataaccg ctaaccccgt aatcactgaa agcactgaga actctaagat gatgctggaa   2100
cttgatccac catttgggga ctcttacatt gtcataggag tcggggagaa gaagatcacc   2160
caccactggc acaggagtgg cagcaccatt ggaaaagcat tgaagccac tgtgagaggt   2220 gccaagagaa tggcagtctt gggagacaca gcctgggact ttggatcagt tggaggcgct   2280
ctcaactcat tgggcaaggg catccatcaa atttttggag cagctttcaa atcattgttt   2340
ggaggaatgt cctggttctc acaaattctc attggaacgt tgctgatgtg gttgggtctg   2400
aacacaaaga atggatctat ttcccttatg tgcttggcct tagggggagt gttgatcttc   2460
ttatccacag ccgtctctgc tgattccgga tgtgccatag acatcagccg gcaagagctg   2520
agatgtggaa gtggagtgtt catacacaat gatgtggagg cttggatgga ccggtacaag   2580
tattaccctg aaacgccaca aggcctagcc aagatcattc agaaagctca taggaagga   2640 gtgtgcggtc tacgatcagt ttccagactg gagcatcaaa tgtgggaagc agtgaaggac   2700
gagctgaaca ctcttttgaa ggagaatggt gtggaccta tgtcgtggt tgagaaacag   2760 gagggaatgt acaagtcagc acctaaacgc ctcaccgcca ccacggaaaa attggaaatt   2820
ggctggaagg cctggggaaa gagtatttta tttgcaccag aactcgccaa caacaccttt   2880
gtggttgatg gtccggagac caaggaatgt ccgactcaga atcgcgcttg gaatagctta   2940
gaagtggagg attttggatt tggtctcacc agcactcgga tgttcctgaa ggtcagagag   3000
agcaacacaa ctgaatgtga ctcgaagatc attggaacgg ctgtcaagaa caacttggcg   3060
atccacagtg acctgtccta ttggattgaa agcaggctca atgatacgtg gaagcttgaa   3120
```

-continued

```
agggcagttc tgggtgaagt caaatcatgt acgtggcctg agacgcatac cttgtggggc    3180
gatggaatcc ttgagagtga cttgataata ccagtcacac tggcgggacc acgaagcaat    3240
cacaatcgga gacctgggta caagacacaa aaccagggcc catgggacga aggccgggta    3300
gagattgact tcgattactg cccaggaact acggtcaccc tgagtgagag ctgcggacac    3360
cgtggacctg ccactcgcac caccacagag agcggaaagt tgataacaga ttggtgctgc    3420
aggagctgca ccttaccacc actgcgctac caaactgaca gcggctgttg gtatggtatg    3480
gagatcagac cacagagaca tgatgaaaag accctcgtgc agtcacaagt gaatgcttat    3540
aatgctgata tgattgaccc ttttcagttg ggccttctgg tcgtgttctt ggccacccag    3600
gaggtccttc gcaagaggtg gacagccaag atcagcatgc cagctatact gattgctctg    3660
ctagtcctgg tgtttggggg cattacttac actgatgtgt tacgctatgt catcttggtg    3720
ggggcagctt tcgcagaatc taattcggga ggagacgtgg tacacttggc gctcatggcg    3780
accttcaaga tacaaccagt gtttatggtg gcatcgtttc tcaaagcgag atggaccaac    3840
caggagaaca ttttgttgat gttggcggct gttttctttc aaatggctta ttacgatgcc    3900
cgccaaattc tgctctggga gatccctgat gtgttgaatt cactggcggt agcttggatg    3960
atactgagag ccataacatt cacaacgaca tcaaacgtgg ttgttccgct gctagccctg    4020
ctaacacccg ggctgagatg cttgaatctg gatgtgtaca ggatactgct gttgatggtc    4080
ggaataggca gcttgatcag ggagaagagg agtgcagctg caaaaaagaa aggagcaagt    4140
ctgctatgct tggctctagc ctcaacagga cttttcaacc ccatgatcct tgctgctgga    4200
ctgattgcat gtgatcccaa ccgtaaacgc ggatggcccg caactgaagt gatgacagct    4260
gtcggcctaa tgtttgccat cgtcggaggg ctggcagagc ttgacattga ctccatggcc    4320
attccaatga ctatcgcggg gctcatgttt gctgctttcg tgatttctgg gaaatcaaca    4380
gatatgtgga ttgagagaac ggcggacatt tcctgggaaa gtgatgcaga aattacaggc    4440
tcgagcgaaa gagttgatgt gcggcttgat gatgatggaa acttccagct catgaatgat    4500
ccaggagcac cttggaagat atggatgctc agaatggtct gtctcgcgat tagtgcgtac    4560
acccctgggc aatcttgcc ctcagtagtt ggattttgga taactctcca atacacaaag    4620
agaggaggcg tgttgtggga cactccctca ccaaaggagt acaaaaaggg ggacacgacc    4680
accggcgtct acaggatcat gactcgtggg ctgctcggca gttatcaagc aggagcgggc    4740
gtgatggttg aaggtgtttt ccacaccctt tggcatacaa caaaggagc cgctttgatg    4800
agcggagagg gccgcctgga cccatactgg ggcagtgtca aggaggatcg actttgttac    4860
ggaggaccct ggaaattgca gcacaagtgg aacgggcagg atgaggtgca gatgattgtg    4920
gtggaacctg gcaggaacgt taagaacgtc cagacgaaac caggggtgtt caaaacacct    4980
gaaggagaaa tcggggccgt gactttggac ttccccactg gaacatcagg ctcaccaata    5040
gtggacaaaa acggtgatgt gattgggctt tatggcaatg gagtcataat gcccaacggc    5100
tcatacataa gcgcgatagt gcagggtgaa aggatggatg agccaatccc agccggattc    5160
gaacctgaga tgctgaggaa aaaacagatc actgtactgg atctccatcc cggcgccggt    5220
aaaacaagga ggattctgcc acagatcatc aaagaggcca taaacagaag actgagaaca    5280
gccgtgctag caccaaccag ggttgtggct gctgagatgg ctgaagcact gagaggactg    5340
cccatccggt accagacatc cgcagtgccc agagaacata tggaaatgat gattgttgat    5400
gtcatgtgtc atgctaccct cacccacagg ctgatgtctc ctcacagggt gccgaactac    5460
```

```
aacctgttcg tgatggatga ggctcatttc accgacccag ctagcattgc agcaagaggt    5520
tacatttcca caaggtcga gctaggggag gcggcggcaa tattcatgac agccacccca    5580
ccaggcactt cagatccatt cccagagtcc aattcaccaa tttccgactt acagactgag    5640
atcccggatc gagcttggaa ctctggatac gaatggatca cagaatacac cgggaagacg    5700
gtttggtttg tgcctagtgt caagatgggg aatgagattg ccctttgcct acaacgtgct    5760
ggaaagaaag tagtccaatt gaacagaaag tcgtacgaga cggagtaccc aaaatgtaag    5820
aacgatgatt gggactttgt tatcacaaca gacatatctg aaatgggggc taacttcaag    5880
gcgagcaggg tgattgacag ccggaagagt gtgaaaccaa ccatcataac agaaggagaa    5940
gggagagtga tcctgggaga accatctgca gtgacagcag ctagtgccgc ccagagacgt    6000
ggacgtatcg gtagaaatcc gtcgcaagtt ggtgatgagt actgttatgg ggggcacacg    6060
aatgaagacg actcgaactt cgcccattgg actgaggcac gaatcatgct ggacaacatc    6120
aacatgccaa acggactgat cgctcaattc taccaaccag agcgtgagaa ggtatatacc    6180
atggatgggg aataccggct cagaggagaa gagagaaaaa actttctgga actgttgagg    6240
actgcagatc tgccagtttg gctggcttac aaggttgcag cggctggagt gtcataccac    6300
gaccggaggt ggtgctttga tggtcctagg acaaacacaa ttttagaaga caacaacgaa    6360
gtggaagtca tcacgaagct tggtgaaagg aagattctga ggccgcgctg gattgacgcc    6420
agggtgtact cggatcacca ggcactaaag gcgttcaagg acttcgcctc gggaaaacgt    6480
tctcagatag ggctcattga ggttctggga agatgcctg agcacttcat ggggaagaca    6540
tgggaagcac ttgacaccat gtacgttgtg ccactgcag agaaaggagg aagagctcac    6600
agaatggccc tggaggaact gccagatgct cttcagacaa ttgccttgat tgccttattg    6660
agtgtgatga ccatgggagt attcttcctc ctcatgcagc ggaagggcat tggaaagata    6720
ggtttgggag cgctgtctt gggagtcgcg acctttttct gttggatggc tgaagttcca    6780
ggaacgaaga tcgccggaat gttgctgctc tcccttctct tgatgattgt gctaattcct    6840
gagccagaga agcaacgttc gcagacagac aaccagctag ccgtgttcct gatttgtgtc    6900
atgacccttg tgagcgcagt ggcagccaac gagatgggtt ggctagataa gaccaagagt    6960
gacataagca gtttgtttgg gcaaagaatt gaggtcaagg agaatttcag catgggagag    7020
tttcttttgg acttgaggcc tgcaacagcc tggtcactgt acgctgtgac aacagcggtc    7080
ctcactccac tgctaaagca tttgatcacg tcagattaca tcaacacctc attgacctca    7140
ataaacgttc aggcaagtgc actattcaca ctcgcgcgag gcttcccctt cgtcgatgtt    7200
ggagtgtcgg ctctcctgct agcagccgga tgctggggac aagtcaccct caccgttacg    7260
gtaacagcgg caacactcct ttttgccac tatgcctaca tggttcccgg ttggcaagct    7320
gaggcaatgc gctcagccca gcggcggaca gcggccggaa tcatgaagaa cgctgtagtg    7380
gatggcatcg tggccacgga cgtcccagaa ttagagcgca ccacacccat catgcagaag    7440
aaagttggac agatcatgct gatcttggtg tctctagctg cagtagtagt gaacccgtct    7500
gtgaagacag tacgagaagc cggaattttg atcacggccg cagcggtgac gctttgggag    7560 aatgagcaa gctctgtttg gaacgcaaca actgccatcg gactctgcca catcatgcgt    7620
gggggttggt tgtcatgtct atccataaca tggacactca taagaacat ggaaaaacca    7680 ggactaaaaa gaggtgggc aaaaggacgc accttgggag aggtttggaa agaaagactc    7740
aaccagatga caaaagaaga gttcactagg taccgcaaag aggccatcat cgaagtcgat    7800
cgctcagcgg caaaacacgc caggaaagaa ggcaatgtca ctggagggca tccagtctct    7860
```

| | |
|---|---|
| aggggcacag caaaactgag atggctggtc gaacggaggt ttctcgaacc ggtcggaaaa | 7920 |
| gtgattgacc ttggatgtgg aagaggcggt tggtgttact atatggcaac ccaaaaaaga | 7980 |
| gtccaagaag tcagagggta cacaaagggc ggtcccggac atgaagagcc ccaactagtg | 8040 |
| caaagttatg gatggaacat tgtcaccatg aagagtggag tggatgtgtt ctacagacct | 8100 |
| tctgagtgtt gtgacaccct cctttgtgac atcggagagt cctcgtcaag tgctgaggtt | 8160 |
| gaagagcata ggacgattcg ggtccttgaa atggttgagg actggctgca ccagggggcca | 8220 |
| agggaatttt gcgtgaaggt gctctgcccc tacatgccga aagtcataga aagatggag | 8280 |
| ctgctccaac gccggtatgg ggggggactg gtcagaaacc cactctcacg gaattccacg | 8340 |
| cacgagatgt attgggtgag tcgagcttca ggcaatgtgg tacattcagt gaatatgacc | 8400 |
| agccaggtgc tcctaggaag aatggaaaaa ggacctgga agggaccccca atacgaggaa | 8460 |
| gatgtaaact tgggaagtgg aaccagggcg gtgggaaaac ccctgctcaa ctcagacacc | 8520 |
| agtaaaatca gaacaggat tgaacgactc aggcgtgagt acagttcgac gtggcaccac | 8580 |
| gatgagaacc acccatatag aacctggaac tatcacggca gttatgatgt gaagcccaca | 8640 |
| ggctccgcca gttcgctggt caatggagtg gtcaggctcc tctcaaaacc atgggacacc | 8700 |
| atcacgaatg ttaccaccat ggccatgact gacactactc ccttcgggca gcagcgagtg | 8760 |
| ttcaaagaga aggtggacac gaaagctcct gaaccgccag aaggagtgaa gtacgtgctc | 8820 |
| aacgagacca ccaactggtt gtgggcgttt ttggccagag aaaaacgtcc cagaatgtgc | 8880 |
| tctcgagagg aattcataag aaaggtcaac agcaatgcag ctttgggtgc catgtttgaa | 8940 |
| gagcagaatc aatggaggag cgccagagaa gcagttgaag atccaaaatt ttgggagatg | 9000 |
| gtggatgagg agcgcgaggc acatctgcgg ggggaatgtc acacttgcat ttacaacatg | 9060 |
| atgggaaaga gagagaaaaa acccggagag ttcggaaagg ccaagggaag cagagccatt | 9120 |
| tggttcatgt ggctcggagc tcgctttctg gagttcgagg ctctgggttt tctcaatgaa | 9180 |
| gaccactggc ttgaagaaa gaactcagga ggaggtgtcg agggcttggg cctccaaaaa | 9240 |
| ctgggttaca tcctgcgtga agttggcacc cggcctgggg gcaagatcta tgctgatgac | 9300 |
| acagctggct gggacacccg catcacgaga gctgacttgg aaaatgaagc taaggtgctt | 9360 |
| gagctgcttg atggggaaca tcggcgtctt gccagggcca tcattgagct cacctatcgt | 9420 |
| cacaaagttg tgaaagtgat gcgcccggct gctgatggaa gaaccgtcat ggatgttatc | 9480 |
| tccagagaag atcagagggg gagtggacaa gttgtcacct acgccctaaa cactttcacc | 9540 |
| aacctggccg tccagctggt gaggatgatg gaagggggaag gagtgattgg cccagatgat | 9600 |
| gtggagaaac tcacaaaagg gaaaggaccc aaagtcagga cctggctgtt tgagaatggg | 9660 |
| gaagaaagac tcagccgcat ggctgtcagt ggagatgact gtgtggtaaa gcccctggac | 9720 |
| gatcgctttg ccacctcgct ccacttcctc aatgctatgt caaaggttcg caaagacatc | 9780 |
| caagagtgga aaccgtcaac tggatggtat gattggcagc aggttccatt ttgctcaaac | 9840 |
| catttcactg aattgatcat gaaagatgga agaacactgg tggttccatg ccgaggacag | 9900 |
| gatgaattgg taggcagagc tcgcatatct ccaggggccg gatggaacgt ccgcgacact | 9960 |
| gcttgtctgg ctaagtctta tgcccagatg tggctgcttc tgtacttcca cagaagagac | 10020 |
| ctgcggctca tggccaacgc catttgctcc gctgtccctg tgaattgggt ccctaccgga | 10080 |
| agaaccacgt ggtccatcca tgcaggagga gagtggatga acagagga catgttggag | 10140 |
| gtctggaacc gtgtttggat agaggagaat gaatggatgg aagacaaaac cccagtggag | 10200 |

```
aaatggagtg acgtcccata ttcaggaaaa cgagaggaca tctggtgtgg cagcctgatt    10260
ggcacaagag cccgagccac gtgggcagaa acatccagg tggctatcaa ccaagtcaga     10320
gcaatcatcg gagatgagaa gtatgtggat tacatgagtt cactaaagag atatgaagac    10380
acaactttgg ttgaggacac agtactgtag atatttaatc aattgtaaat agacaatata    10440
agtatgcata aaagtgtagt tttatagtag tatttagtgg tgttagtgta aatagttaag    10500
aaaattttga ggagaaagtc aggccgggaa gttcccgcca ccggaagttg agtagacggt    10560
gctgcctgcg actcaacccc aggaggactg ggtgaacaaa gccgcgaagt gatccatgta    10620
agccctcaga accgtctcgg aaggaggacc ccacatgttg taacttcaaa gcccaatgtc    10680
agaccacgct acggcgtgct actctgcgga gagtgcagtc tgcgatagtg ccccaggagg    10740
actgggttaa caaaggcaaa ccaacgcccc acgcggccct agccccggta atggtgttaa    10800
ccagggcgaa aggactagag gttagaggag accccgcggt ttaaagtgca cggcccagcc    10860
tggctgaagc tgtaggtcag gggaaggact agaggttagt ggagaccccg tgccacaaaa    10920
caccacaaca aaacagcata ttgacacctg ggatagacta ggagatcttc tgctctgcac    10980
aaccagccac acggcacagt gcgccgacaa tggtggctgg tggtgcgaga acacaggatc    11040
t                                                                   11041
```

<210> SEQ ID NO 8
<211> LENGTH: 3437
<212> TYPE: PRT
<213> ORGANISM: Artificial Sequence
<220> FEATURE:
<223> OTHER INFORMATION: Synthetic polypeptide

<400> SEQUENCE: 8

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Ser Val Gly
            100                 105                 110

Ile Val Gly Leu Leu Leu Thr Thr Ala Met Ala Ala Glu Val Thr Arg
        115                 120                 125

Arg Gly Ser Ala Tyr Tyr Met Tyr Leu Asp Arg Asn Asp Ala Gly Glu
    130                 135                 140

Ala Ile Ser Phe Pro Thr Thr Leu Gly Met Asn Lys Cys Tyr Ile Gln
145                 150                 155                 160

Ile Met Asp Leu Gly His Met Cys Asp Ala Thr Met Ser Tyr Glu Cys
                165                 170                 175

Pro Met Leu Asp Glu Gly Val Glu Pro Asp Asp Val Asp Cys Trp Cys
            180                 185                 190

Asn Thr Thr Ser Thr Trp Val Val Tyr Gly Thr Cys His His Lys Lys
        195                 200                 205
```

```
Gly Glu Ala Arg Arg Ser Arg Arg Ala Val Thr Leu Pro Ser His Ser
            210                 215                 220

Thr Arg Lys Leu Gln Thr Arg Ser Gln Thr Trp Leu Glu Ser Arg Glu
225                 230                 235                 240

Tyr Thr Lys His Leu Ile Arg Val Glu Asn Trp Ile Phe Arg Asn Pro
                245                 250                 255

Gly Phe Ala Leu Ala Ala Ala Ile Ala Trp Leu Leu Gly Ser Ser
            260                 265                 270

Thr Ser Gln Lys Val Ile Tyr Leu Val Met Ile Leu Leu Ile Ala Pro
            275                 280                 285

Ala Tyr Ser Ile Arg Cys Ile Gly Val Ser Asn Arg Asp Phe Val Glu
            290                 295                 300

Gly Met Ser Gly Gly Thr Trp Val Asp Ile Val Leu Glu His Gly Gly
305                 310                 315                 320

Cys Val Thr Val Met Ala Gln Asp Lys Pro Thr Val Asp Ile Glu Leu
                325                 330                 335

Val Thr Thr Thr Val Ser Asn Met Ala Glu Val Arg Ser Tyr Cys Tyr
            340                 345                 350

Glu Ala Ser Ile Ser Asp Met Ala Ser Asp Ser Arg Cys Pro Thr Gln
            355                 360                 365

Gly Glu Ala Tyr Leu Asp Lys Gln Ser Asp Thr Gln Tyr Val Cys Lys
            370                 375                 380

Arg Thr Leu Val Asp Arg Gly Trp Gly Asn Gly Cys Gly Leu Phe Gly
385                 390                 395                 400

Lys Gly Ser Leu Val Thr Cys Ala Lys Phe Ala Cys Ser Lys Lys Met
                405                 410                 415

Thr Gly Lys Ser Ile Gln Pro Glu Asn Leu Glu Tyr Arg Ile Met Leu
            420                 425                 430

Ser Val His Gly Ser Gln His Ser Gly Met Ile Val Asn Asp Thr Gly
            435                 440                 445

His Glu Thr Asp Glu Asn Arg Ala Lys Val Glu Ile Thr Pro Asn Ser
            450                 455                 460

Pro Arg Ala Glu Ala Thr Leu Gly Gly Phe Gly Ser Leu Gly Leu Asp
465                 470                 475                 480

Cys Glu Pro Arg Thr Gly Leu Asp Phe Ser Asp Leu Tyr Tyr Leu Thr
                485                 490                 495

Met Asn Asn Lys His Trp Leu Val His Lys Glu Trp Phe His Asp Ile
            500                 505                 510

Pro Leu Pro Trp His Ala Gly Ala Asp Thr Gly Thr Pro His Trp Asn
            515                 520                 525

Asn Lys Glu Ala Leu Val Glu Phe Lys Asp Ala His Ala Lys Arg Gln
530                 535                 540

Thr Val Val Leu Gly Ser Gln Glu Gly Ala Val His Thr Ala Leu
545                 550                 555                 560

Ala Gly Ala Leu Glu Ala Glu Met Asp Gly Ala Lys Gly Arg Leu Ser
                565                 570                 575

Ser Gly His Leu Lys Cys Arg Leu Lys Met Asp Lys Leu Arg Leu Lys
            580                 585                 590

Gly Val Ser Tyr Ser Leu Cys Thr Ala Ala Phe Thr Phe Thr Lys Ile
            595                 600                 605

Pro Ala Glu Thr Leu His Gly Thr Val Thr Val Glu Val Gln Tyr Ala
610                 615                 620

Gly Thr Asp Gly Pro Cys Lys Val Pro Ala Gln Met Ala Val Asp Met
```

-continued

```
            625                 630                 635                 640
        Gln Thr Leu Thr Pro Val Gly Arg Leu Ile Thr Ala Asn Pro Val Ile
                        645                 650                 655

Thr Glu Ser Thr Glu Asn Ser Lys Met Met Leu Glu Leu Asp Pro Pro
                        660                 665                 670

Phe Gly Asp Ser Tyr Ile Val Ile Gly Val Gly Glu Lys Ile Thr
                        675                 680                 685

His His Trp His Arg Ser Gly Ser Thr Ile Gly Lys Ala Phe Glu Ala
                        690                 695                 700

Thr Val Arg Gly Ala Lys Arg Met Ala Val Leu Gly Asp Thr Ala Trp
        705                 710                 715                 720

Asp Phe Gly Ser Val Gly Ala Leu Asn Ser Leu Gly Lys Gly Ile
                        725                 730                 735

His Gln Ile Phe Gly Ala Ala Phe Lys Ser Leu Phe Gly Gly Met Ser
                        740                 745                 750

Trp Phe Ser Gln Ile Leu Ile Gly Thr Leu Leu Met Trp Leu Gly Leu
                        755                 760                 765

Asn Thr Lys Asn Gly Ser Ile Ser Leu Met Cys Leu Ala Leu Gly Gly
                        770                 775                 780

Val Leu Ile Phe Leu Ser Thr Ala Val Ser Ala Asp Ser Gly Cys Ala
        785                 790                 795                 800

Ile Asp Ile Ser Arg Gln Glu Leu Arg Cys Gly Ser Gly Val Phe Ile
                        805                 810                 815

His Asn Asp Val Glu Ala Trp Met Asp Arg Tyr Lys Tyr Tyr Pro Glu
                        820                 825                 830

Thr Pro Gln Gly Leu Ala Lys Ile Ile Gln Lys Ala His Lys Glu Gly
                        835                 840                 845

Val Cys Gly Leu Arg Ser Val Ser Arg Leu Glu His Gln Met Trp Glu
                        850                 855                 860

Ala Val Lys Asp Glu Leu Asn Thr Leu Leu Lys Glu Asn Gly Val Asp
        865                 870                 875                 880

Leu Ser Val Val Val Glu Lys Gln Glu Gly Met Tyr Lys Ser Ala Pro
                        885                 890                 895

Lys Arg Leu Thr Ala Thr Thr Glu Lys Leu Glu Ile Gly Trp Lys Ala
                        900                 905                 910

Trp Gly Lys Ser Ile Leu Phe Ala Pro Glu Leu Ala Asn Asn Thr Phe
                        915                 920                 925

Val Val Asp Gly Pro Glu Thr Lys Glu Cys Pro Thr Gln Asn Arg Ala
        930                 935                 940

Trp Asn Ser Leu Glu Val Glu Asp Phe Gly Phe Gly Leu Thr Ser Thr
        945                 950                 955                 960

Arg Met Phe Leu Lys Val Arg Glu Ser Asn Thr Thr Glu Cys Asp Ser
                        965                 970                 975

Lys Ile Ile Gly Thr Ala Val Lys Asn Asn Leu Ala Ile His Ser Asp
                        980                 985                 990

Leu Ser Tyr Trp Ile Glu Ser Arg Leu Asn Asp Thr Trp Lys Leu Glu
                        995                 1000                1005

Arg Ala Val Leu Gly Glu Val Lys Ser Cys Thr Trp Pro Glu Thr
                        1010                1015                1020

His Thr Leu Trp Gly Asp Gly Ile Leu Glu Ser Asp Leu Ile Ile
                        1025                1030                1035

Pro Val Thr Leu Ala Gly Pro Arg Ser Asn His Asn Arg Arg Pro
                        1040                1045                1050
```

```
Gly Tyr Lys Thr Gln Asn Gln Gly Pro Trp Asp Glu Gly Arg Val
1055                1060            1065

Glu Ile Asp Phe Asp Tyr Cys Pro Gly Thr Thr Val Thr Leu Ser
1070                1075            1080

Glu Ser Cys Gly His Arg Gly Pro Ala Thr Arg Thr Thr Thr Glu
1085                1090            1095

Ser Gly Lys Leu Ile Thr Asp Trp Cys Cys Arg Ser Cys Thr Leu
1100                1105            1110

Pro Pro Leu Arg Tyr Gln Thr Asp Ser Gly Cys Trp Tyr Gly Met
1115                1120            1125

Glu Ile Arg Pro Gln Arg His Asp Glu Lys Thr Leu Val Gln Ser
1130                1135            1140

Gln Val Asn Ala Tyr Asn Ala Asp Met Ile Asp Pro Phe Gln Leu
1145                1150            1155

Gly Leu Leu Val Val Phe Leu Ala Thr Gln Glu Val Leu Arg Lys
1160                1165            1170

Arg Trp Thr Ala Lys Ile Ser Met Pro Ala Ile Leu Ile Ala Leu
1175                1180            1185

Leu Val Leu Val Phe Gly Gly Ile Thr Tyr Thr Asp Val Leu Arg
1190                1195            1200

Tyr Val Ile Leu Val Gly Ala Ala Phe Ala Glu Ser Asn Ser Gly
1205                1210            1215

Gly Asp Val Val His Leu Ala Leu Met Ala Thr Phe Lys Ile Gln
1220                1225            1230

Pro Val Phe Met Val Ala Ser Phe Leu Lys Ala Arg Trp Thr Asn
1235                1240            1245

Gln Glu Asn Ile Leu Leu Met Leu Ala Ala Val Phe Phe Gln Met
1250                1255            1260

Ala Tyr Tyr Asp Ala Arg Gln Ile Leu Leu Trp Glu Ile Pro Asp
1265                1270            1275

Val Leu Asn Ser Leu Ala Val Ala Trp Met Ile Leu Arg Ala Ile
1280                1285            1290

Thr Phe Thr Thr Thr Ser Asn Val Val Val Pro Leu Leu Ala Leu
1295                1300            1305

Leu Thr Pro Gly Leu Arg Cys Leu Asn Leu Asp Val Tyr Arg Ile
1310                1315            1320

Leu Leu Leu Met Val Gly Ile Gly Ser Leu Ile Arg Glu Lys Arg
1325                1330            1335

Ser Ala Ala Ala Lys Lys Lys Gly Ala Ser Leu Leu Cys Leu Ala
1340                1345            1350

Leu Ala Ser Thr Gly Leu Phe Asn Pro Met Ile Leu Ala Ala Gly
1355                1360            1365

Leu Ile Ala Cys Asp Pro Asn Arg Lys Arg Gly Trp Pro Ala Thr
1370                1375            1380

Glu Val Met Thr Ala Val Gly Leu Met Phe Ala Ile Val Gly Gly
1385                1390            1395

Leu Ala Glu Leu Asp Ile Asp Ser Met Ala Ile Pro Met Thr Ile
1400                1405            1410

Ala Gly Leu Met Phe Ala Ala Phe Val Ile Ser Gly Lys Ser Thr
1415                1420            1425

Asp Met Trp Ile Glu Arg Thr Ala Asp Ile Ser Trp Glu Ser Asp
1430                1435            1440
```

-continued

| | | | | | | | | | | | | |
|---|---|---|---|---|---|---|---|---|---|---|---|---|
| Ala | Glu | Ile | Thr | Gly | Ser | Ser | Glu | Arg | Val | Asp | Val | Arg | Leu | Asp |
| | 1445 | | | | | 1450 | | | | | 1455 | | | |
| Asp | Asp | Gly | Asn | Phe | Gln | Leu | Met | Asn | Asp | Pro | Gly | Ala | Pro | Trp |
| | 1460 | | | | | 1465 | | | | | 1470 | | | |
| Lys | Ile | Trp | Met | Leu | Arg | Met | Val | Cys | Leu | Ala | Ile | Ser | Ala | Tyr |
| | 1475 | | | | | 1480 | | | | | 1485 | | | |
| Thr | Pro | Trp | Ala | Ile | Leu | Pro | Ser | Val | Val | Gly | Phe | Trp | Ile | Thr |
| | 1490 | | | | | 1495 | | | | | 1500 | | | |
| Leu | Gln | Tyr | Thr | Lys | Arg | Gly | Gly | Val | Leu | Trp | Asp | Thr | Pro | Ser |
| | 1505 | | | | | 1510 | | | | | 1515 | | | |
| Pro | Lys | Glu | Tyr | Lys | Lys | Gly | Asp | Thr | Thr | Thr | Gly | Val | Tyr | Arg |
| | 1520 | | | | | 1525 | | | | | 1530 | | | |
| Ile | Met | Thr | Arg | Gly | Leu | Leu | Gly | Ser | Tyr | Gln | Ala | Gly | Ala | Gly |
| | 1535 | | | | | 1540 | | | | | 1545 | | | |
| Val | Met | Val | Glu | Gly | Val | Phe | His | Thr | Leu | Trp | His | Thr | Thr | Lys |
| | 1550 | | | | | 1555 | | | | | 1560 | | | |
| Gly | Ala | Ala | Leu | Met | Ser | Gly | Glu | Gly | Arg | Leu | Asp | Pro | Tyr | Trp |
| | 1565 | | | | | 1570 | | | | | 1575 | | | |
| Gly | Ser | Val | Lys | Glu | Asp | Arg | Leu | Cys | Tyr | Gly | Gly | Pro | Trp | Lys |
| | 1580 | | | | | 1585 | | | | | 1590 | | | |
| Leu | Gln | His | Lys | Trp | Asn | Gly | Gln | Asp | Glu | Val | Gln | Met | Ile | Val |
| | 1595 | | | | | 1600 | | | | | 1605 | | | |
| Val | Glu | Pro | Gly | Arg | Asn | Val | Lys | Asn | Val | Gln | Thr | Lys | Pro | Gly |
| | 1610 | | | | | 1615 | | | | | 1620 | | | |
| Val | Phe | Lys | Thr | Pro | Glu | Gly | Glu | Ile | Gly | Ala | Val | Thr | Leu | Asp |
| | 1625 | | | | | 1630 | | | | | 1635 | | | |
| Phe | Pro | Thr | Gly | Thr | Ser | Gly | Ser | Pro | Ile | Val | Asp | Lys | Asn | Gly |
| | 1640 | | | | | 1645 | | | | | 1650 | | | |
| Asp | Val | Ile | Gly | Leu | Tyr | Gly | Asn | Gly | Val | Ile | Met | Pro | Asn | Gly |
| | 1655 | | | | | 1660 | | | | | 1665 | | | |
| Ser | Tyr | Ile | Ser | Ala | Ile | Val | Gln | Gly | Glu | Arg | Met | Asp | Glu | Pro |
| | 1670 | | | | | 1675 | | | | | 1680 | | | |
| Ile | Pro | Ala | Gly | Phe | Glu | Pro | Glu | Met | Leu | Arg | Lys | Lys | Gln | Ile |
| | 1685 | | | | | 1690 | | | | | 1695 | | | |
| Thr | Val | Leu | Asp | Leu | His | Pro | Gly | Ala | Gly | Lys | Thr | Arg | Arg | Ile |
| | 1700 | | | | | 1705 | | | | | 1710 | | | |
| Leu | Pro | Gln | Ile | Ile | Lys | Glu | Ala | Ile | Asn | Arg | Arg | Leu | Arg | Thr |
| | 1715 | | | | | 1720 | | | | | 1725 | | | |
| Ala | Val | Leu | Ala | Pro | Thr | Arg | Val | Val | Ala | Ala | Glu | Met | Ala | Glu |
| | 1730 | | | | | 1735 | | | | | 1740 | | | |
| Ala | Leu | Arg | Gly | Leu | Pro | Ile | Arg | Tyr | Gln | Thr | Ser | Ala | Val | Pro |
| | 1745 | | | | | 1750 | | | | | 1755 | | | |
| Arg | Glu | His | Asn | Gly | Asn | Glu | Ile | Val | Asp | Val | Met | Cys | His | Ala |
| | 1760 | | | | | 1765 | | | | | 1770 | | | |
| Thr | Leu | Thr | His | Arg | Leu | Met | Ser | Pro | His | Arg | Val | Pro | Asn | Tyr |
| | 1775 | | | | | 1780 | | | | | 1785 | | | |
| Asn | Leu | Phe | Val | Met | Asp | Glu | Ala | His | Phe | Thr | Asp | Pro | Ala | Ser |
| | 1790 | | | | | 1795 | | | | | 1800 | | | |
| Ile | Ala | Ala | Arg | Gly | Tyr | Ile | Ser | Thr | Lys | Val | Glu | Leu | Gly | Glu |
| | 1805 | | | | | 1810 | | | | | 1815 | | | |
| Ala | Ala | Ala | Ile | Phe | Met | Thr | Ala | Thr | Pro | Pro | Gly | Thr | Ser | Asp |
| | 1820 | | | | | 1825 | | | | | 1830 | | | |
| Pro | Phe | Pro | Glu | Ser | Asn | Ser | Pro | Ile | Ser | Asp | Leu | Gln | Thr | Glu |

```
                        1835                    1840                    1845

Ile  Pro  Asp  Arg  Ala  Trp  Asn  Ser  Gly  Tyr  Glu  Trp  Ile  Thr  Glu
     1850                    1855                    1860

Tyr  Thr  Gly  Lys  Thr  Val  Trp  Phe  Val  Pro  Ser  Val  Lys  Met  Gly
     1865                    1870                    1875

Asn  Glu  Ile  Ala  Leu  Cys  Leu  Gln  Arg  Ala  Gly  Lys  Lys  Val  Val
     1880                    1885                    1890

Gln  Leu  Asn  Arg  Lys  Ser  Tyr  Glu  Thr  Glu  Tyr  Pro  Lys  Cys  Lys
     1895                    1900                    1905

Asn  Asp  Asp  Trp  Asp  Phe  Val  Ile  Thr  Thr  Asp  Ile  Ser  Glu  Met
     1910                    1915                    1920

Gly  Ala  Asn  Phe  Lys  Ala  Ser  Arg  Val  Ile  Asp  Ser  Arg  Lys  Ser
     1925                    1930                    1935

Val  Lys  Pro  Thr  Ile  Ile  Thr  Glu  Gly  Glu  Gly  Arg  Val  Ile  Leu
     1940                    1945                    1950

Gly  Glu  Pro  Ser  Ala  Val  Thr  Ala  Ala  Ser  Ala  Ala  Gln  Arg  Arg
     1955                    1960                    1965

Gly  Arg  Ile  Gly  Arg  Asn  Pro  Ser  Gln  Val  Gly  Asp  Glu  Tyr  Cys
     1970                    1975                    1980

Tyr  Gly  Gly  His  Thr  Asn  Glu  Asp  Asp  Ser  Asn  Phe  Ala  His  Trp
     1985                    1990                    1995

Thr  Glu  Ala  Arg  Ile  Met  Leu  Asp  Asn  Ile  Asn  Met  Pro  Asn  Gly
     2000                    2005                    2010

Leu  Ile  Ala  Gln  Phe  Tyr  Gln  Pro  Glu  Arg  Glu  Lys  Val  Tyr  Thr
     2015                    2020                    2025

Met  Asp  Gly  Glu  Tyr  Arg  Leu  Arg  Gly  Glu  Glu  Arg  Lys  Asn  Phe
     2030                    2035                    2040

Leu  Glu  Leu  Leu  Arg  Thr  Ala  Asp  Leu  Pro  Val  Trp  Leu  Ala  Tyr
     2045                    2050                    2055

Lys  Val  Ala  Ala  Ala  Gly  Val  Ser  Tyr  His  Asp  Arg  Arg  Trp  Cys
     2060                    2065                    2070

Phe  Asp  Gly  Pro  Arg  Thr  Asn  Thr  Ile  Leu  Glu  Asp  Asn  Asn  Glu
     2075                    2080                    2085

Val  Glu  Val  Ile  Thr  Lys  Leu  Gly  Glu  Arg  Lys  Ile  Leu  Arg  Pro
     2090                    2095                    2100

Arg  Trp  Ile  Asp  Ala  Arg  Val  Tyr  Ser  Asp  His  Gln  Ala  Leu  Lys
     2105                    2110                    2115

Ala  Phe  Lys  Asp  Phe  Ala  Ser  Gly  Lys  Arg  Ser  Gln  Ile  Gly  Leu
     2120                    2125                    2130

Ile  Glu  Val  Leu  Gly  Lys  Met  Pro  Glu  His  Phe  Met  Gly  Lys  Thr
     2135                    2140                    2145

Trp  Glu  Ala  Leu  Asp  Thr  Met  Tyr  Val  Val  Ala  Thr  Ala  Glu  Lys
     2150                    2155                    2160

Gly  Gly  Arg  Ala  His  Arg  Met  Ala  Leu  Glu  Glu  Leu  Pro  Asp  Ala
     2165                    2170                    2175

Leu  Gln  Thr  Ile  Ala  Leu  Ile  Ala  Leu  Leu  Ser  Val  Met  Thr  Met
     2180                    2185                    2190

Gly  Val  Phe  Phe  Leu  Leu  Met  Gln  Arg  Lys  Gly  Ile  Gly  Lys  Ile
     2195                    2200                    2205

Gly  Leu  Gly  Gly  Ala  Val  Leu  Gly  Val  Ala  Thr  Phe  Phe  Cys  Trp
     2210                    2215                    2220

Met  Ala  Glu  Val  Pro  Gly  Thr  Lys  Ile  Ala  Gly  Met  Leu  Leu  Leu
     2225                    2230                    2235
```

```
Ser Leu Leu Leu Met Ile Val Leu Ile Pro Glu Pro Glu Lys Gln
    2240                2245                2250
Arg Ser Gln Thr Asp Asn Gln Leu Ala Val Phe Leu Ile Cys Val
    2255                2260                2265
Met Thr Leu Val Ser Ala Val Ala Ala Asn Glu Met Gly Trp Leu
    2270                2275                2280
Asp Lys Thr Lys Ser Asp Ile Ser Ser Leu Phe Gly Gln Arg Ile
    2285                2290                2295
Glu Val Lys Glu Asn Phe Ser Met Gly Glu Phe Leu Leu Asp Leu
    2300                2305                2310
Arg Pro Ala Thr Ala Trp Ser Leu Tyr Ala Val Thr Thr Ala Val
    2315                2320                2325
Leu Thr Pro Leu Leu Lys His Leu Ile Thr Ser Asp Tyr Ile Asn
    2330                2335                2340
Thr Ser Leu Thr Ser Ile Asn Val Gln Ala Ser Ala Leu Phe Thr
    2345                2350                2355
Leu Ala Arg Gly Phe Pro Phe Val Asp Val Gly Val Ser Ala Leu
    2360                2365                2370
Leu Leu Ala Ala Gly Cys Trp Gly Gln Val Thr Leu Thr Val Thr
    2375                2380                2385
Val Thr Ala Ala Thr Leu Leu Phe Cys His Tyr Ala Tyr Met Val
    2390                2395                2400
Pro Gly Trp Gln Ala Glu Ala Met Arg Ser Ala Gln Arg Arg Thr
    2405                2410                2415
Ala Ala Gly Ile Met Lys Asn Ala Val Val Asp Gly Ile Val Ala
    2420                2425                2430
Thr Asp Val Pro Glu Leu Glu Arg Thr Thr Pro Ile Met Gln Lys
    2435                2440                2445
Lys Val Gly Gln Ile Met Leu Ile Leu Val Ser Leu Ala Ala Val
    2450                2455                2460
Val Val Asn Pro Ser Val Lys Thr Val Arg Glu Ala Gly Ile Leu
    2465                2470                2475
Ile Thr Ala Ala Ala Val Thr Leu Trp Glu Asn Gly Ala Ser Ser
    2480                2485                2490
Val Trp Asn Ala Thr Thr Ala Ile Gly Leu Cys His Ile Met Arg
    2495                2500                2505
Gly Gly Trp Leu Ser Cys Leu Ser Ile Thr Trp Thr Leu Ile Lys
    2510                2515                2520
Asn Met Glu Lys Pro Gly Leu Lys Arg Gly Gly Ala Lys Gly Arg
    2525                2530                2535
Thr Leu Gly Glu Val Trp Lys Glu Arg Leu Asn Gln Met Thr Lys
    2540                2545                2550
Glu Glu Phe Thr Arg Tyr Arg Lys Glu Ala Ile Ile Glu Val Asp
    2555                2560                2565
Arg Ser Ala Ala Lys His Ala Arg Lys Glu Gly Asn Val Thr Gly
    2570                2575                2580
Gly His Pro Val Ser Arg Gly Thr Ala Lys Leu Arg Trp Leu Val
    2585                2590                2595
Glu Arg Arg Phe Leu Glu Pro Val Gly Lys Val Ile Asp Leu Gly
    2600                2605                2610
Cys Gly Arg Gly Gly Trp Cys Tyr Tyr Met Ala Thr Gln Lys Arg
    2615                2620                2625
```

| | | | | | | | | | | | |
|---|---|---|---|---|---|---|---|---|---|---|---|
| Val | Gln | Glu | Val | Arg | Gly | Tyr | Thr | Lys | Gly | Gly | Pro | Gly | His | Glu |
| | | 2630 | | | | 2635 | | | | 2640 | |

Val Gln Glu Val Arg Gly Tyr Thr Lys Gly Gly Pro Gly His Glu
         2630              2635              2640

Glu Pro Gln Leu Val Gln Ser Tyr Gly Trp Asn Ile Val Thr Met
         2645              2650              2655

Lys Ser Gly Val Asp Val Phe Tyr Arg Pro Ser Glu Cys Cys Asp
         2660              2665              2670

Thr Leu Leu Cys Asp Ile Gly Glu Ser Ser Ser Ala Glu Val
         2675              2680              2685

Glu Glu His Arg Thr Ile Arg Val Leu Glu Met Val Glu Asp Trp
         2690              2695              2700

Leu His Arg Gly Pro Arg Glu Phe Cys Val Lys Val Leu Cys Pro
         2705              2710              2715

Tyr Met Pro Lys Val Ile Glu Lys Met Glu Leu Leu Gln Arg Arg
         2720              2725              2730

Tyr Gly Gly Gly Leu Val Arg Asn Pro Leu Ser Arg Asn Ser Thr
         2735              2740              2745

His Glu Met Tyr Trp Val Ser Arg Ala Ser Gly Asn Val Val His
         2750              2755              2760

Ser Val Asn Met Thr Ser Gln Val Leu Leu Gly Arg Met Glu Lys
         2765              2770              2775

Arg Thr Trp Lys Gly Pro Gln Tyr Glu Glu Asp Val Asn Leu Gly
         2780              2785              2790

Ser Gly Thr Arg Ala Val Gly Lys Pro Leu Leu Asn Ser Asp Thr
         2795              2800              2805

Ser Lys Ile Lys Asn Arg Ile Glu Arg Leu Arg Arg Glu Tyr Ser
         2810              2815              2820

Ser Thr Trp His His Asp Glu Asn His Pro Tyr Arg Thr Trp Asn
         2825              2830              2835

Tyr His Gly Ser Tyr Asp Val Lys Pro Thr Gly Ser Ala Ser Ser
         2840              2845              2850

Leu Val Asn Gly Val Val Arg Leu Leu Ser Lys Pro Trp Asp Thr
         2855              2860              2865

Ile Thr Asn Val Thr Thr Met Ala Met Thr Asp Thr Thr Pro Phe
         2870              2875              2880

Gly Gln Gln Arg Val Phe Lys Glu Lys Val Asp Thr Lys Ala Pro
         2885              2890              2895

Glu Pro Pro Glu Gly Val Lys Tyr Val Leu Asn Glu Thr Thr Asn
         2900              2905              2910

Trp Leu Trp Ala Phe Leu Ala Arg Glu Lys Arg Pro Arg Met Cys
         2915              2920              2925

Ser Arg Glu Glu Phe Ile Arg Lys Val Asn Ser Asn Ala Ala Leu
         2930              2935              2940

Gly Ala Met Phe Glu Glu Gln Asn Gln Trp Arg Ser Ala Arg Glu
         2945              2950              2955

Ala Val Glu Asp Pro Lys Phe Trp Glu Met Val Asp Glu Glu Arg
         2960              2965              2970

Glu Ala His Leu Arg Gly Glu Cys His Thr Cys Ile Tyr Asn Met
         2975              2980              2985

Met Gly Lys Arg Glu Lys Lys Pro Gly Glu Phe Gly Lys Ala Lys
         2990              2995              3000

Gly Ser Arg Ala Ile Trp Phe Met Trp Leu Gly Ala Arg Phe Leu
         3005              3010              3015

Glu Phe Glu Ala Leu Gly Phe Leu Asn Glu Asp His Trp Leu Gly

-continued

```
            3020              3025              3030
Arg Lys Asn Ser Gly Gly Gly Val Glu Gly Leu Gly Leu Gln Lys
        3035              3040              3045
Leu Gly Tyr Ile Leu Arg Glu Val Gly Thr Arg Pro Gly Gly Lys
        3050              3055              3060
Ile Tyr Ala Asp Asp Thr Ala Gly Trp Asp Thr Arg Ile Thr Arg
        3065              3070              3075
Ala Asp Leu Glu Asn Glu Ala Lys Val Leu Glu Leu Leu Asp Gly
        3080              3085              3090
Glu His Arg Arg Leu Ala Arg Ala Ile Ile Glu Leu Thr Tyr Arg
        3095              3100              3105
His Lys Val Val Lys Val Met Arg Pro Ala Ala Asp Gly Arg Thr
        3110              3115              3120
Val Met Asp Val Ile Ser Arg Glu Asp Gln Arg Gly Ser Gly Gln
        3125              3130              3135
Val Val Thr Tyr Ala Leu Asn Thr Phe Thr Asn Leu Ala Val Gln
        3140              3145              3150
Leu Val Arg Met Met Glu Gly Glu Gly Val Ile Gly Pro Asp Asp
        3155              3160              3165
Val Glu Lys Leu Thr Lys Gly Lys Gly Pro Lys Val Arg Thr Trp
        3170              3175              3180
Leu Phe Glu Asn Gly Glu Glu Arg Leu Ser Arg Met Ala Val Ser
        3185              3190              3195
Gly Asp Asp Cys Val Val Lys Pro Leu Asp Asp Arg Phe Ala Thr
        3200              3205              3210
Ser Leu His Phe Leu Asn Ala Met Ser Lys Val Arg Lys Asp Ile
        3215              3220              3225
Gln Glu Trp Lys Pro Ser Thr Gly Trp Tyr Asp Trp Gln Gln Val
        3230              3235              3240
Pro Phe Cys Ser Asn His Phe Thr Glu Leu Ile Met Lys Asp Gly
        3245              3250              3255
Arg Thr Leu Val Val Pro Cys Arg Gly Gln Asp Glu Leu Val Gly
        3260              3265              3270
Arg Ala Arg Ile Ser Pro Gly Ala Gly Trp Asn Val Arg Asp Thr
        3275              3280              3285
Ala Cys Leu Ala Lys Ser Tyr Ala Gln Met Trp Leu Leu Leu Tyr
        3290              3295              3300
Phe His Arg Arg Asp Leu Arg Leu Met Ala Asn Ala Ile Cys Ser
        3305              3310              3315
Ala Val Pro Val Asn Trp Val Pro Thr Gly Arg Thr Thr Trp Ser
        3320              3325              3330
Ile His Ala Gly Gly Glu Trp Met Thr Thr Glu Asp Met Leu Glu
        3335              3340              3345
Val Trp Asn Arg Val Trp Ile Glu Glu Asn Glu Trp Met Glu Asp
        3350              3355              3360
Lys Thr Pro Val Glu Lys Trp Ser Asp Val Pro Tyr Ser Gly Lys
        3365              3370              3375
Arg Glu Asp Ile Trp Cys Gly Ser Leu Ile Gly Thr Arg Ala Arg
        3380              3385              3390
Ala Thr Trp Ala Glu Asn Ile Gln Val Ala Ile Asn Gln Val Arg
        3395              3400              3405
Ala Ile Ile Gly Asp Glu Lys Tyr Val Asp Tyr Met Ser Ser Leu
        3410              3415              3420
```

Lys Arg Tyr Glu Asp Thr Thr Leu Val Glu Asp Thr Val Leu
    3425              3430                3435

<210> SEQ ID NO 9
<211> LENGTH: 11905
<212> TYPE: DNA
<213> ORGANISM: Artificial Sequence
<220> FEATURE:
<223> OTHER INFORMATION: Synthetic construct

<400> SEQUENCE: 9

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcaa | tatgctaaaa | cgcggaatgc | cccgcgtgtt | gtccttgatt | 180 |
| ggactgaaga | gggctatgtt | gatggctcag | tcaaagcacg | gtctaacaaa | agaaatgaca | 240 |
| atgaaatacc | gtatggaagg | gtgcgtcgat | ggacataaat | ttgtgatcac | gggagagggc | 300 |
| attggatatc | cgttcaaagg | gaaacaggct | attaatctgt | gtgtggtcga | aggtggacca | 360 |
| ttgccatttg | ccgaagacat | attgtcagct | gcctttatgt | acggaaacag | gttttcact | 420 |
| gaatatcctc | aagacatagc | tgactatttc | aagaactcgt | gtcctgctgg | ttatacatgg | 480 |
| gacaggtctt | ttctctttga | ggatggagca | gtttgcatat | gtaatgcaga | tataacagtg | 540 |
| agtgttgaag | aaaactgcat | gtatcatgag | tccaaatttt | atgagtgaa | ttttcctgct | 600 |
| gatggacctg | tgatgaaaaa | gatgacagat | aactgggagc | catcctgcga | aagatcata | 660 |
| ccagtaccta | agcaggggat | attgaaaggg | gatgtctcca | tgtacctcct | tctgaaggat | 720 |
| ggtgggcgtt | tacggtgcca | attcgacaca | gtttacaaag | caaagtctgt | gccaagaaag | 780 |
| atgccggact | ggcacttcat | ccagcataag | ctcacccgtg | aagaccgcag | cgatgctaag | 840 |
| aatcagaaat | ggcatctgac | agaacatgct | attgcatccg | gatctgcatt | gcccggaagc | 900 |
| ggagctacta | acttcagcct | gctgaagcag | gctggagacg | tggaggagaa | ccctggacct | 960 |
| atgtccaaaa | agcccggcgg | tcctgggaaa | tccagagccg | tgaacatgtt | gaaaaggggg | 1020 |
| atgccacggg | tactgagtct | gatcggcctc | aaaagagcca | tgttgagcct | gatcgacggc | 1080 |
| aaggggccaa | tacgatttgt | gttggctctc | ttggcgttct | tcaggttcac | agcaattgct | 1140 |
| ccgacccgag | cagtgctgga | tcgatggaga | ggtgtgaaca | acaaacagc | gatgaaacac | 1200 |
| cttctgagtt | ttaagaagga | actagggacc | ttgaccagtg | ctatcaatcg | gcggagttcg | 1260 |
| aaacaaaaga | aaagaggagg | aaagaccgga | attgcagtca | tgattggcct | gatcgccagc | 1320 |
| gctatggcag | cggaggtcac | tagacgtggg | agtgcatact | atatgtactt | ggacagaaac | 1380 |
| gatgctgggg | aggccatatc | ttttccaacc | acattgggga | tgaataagtg | ttatatacag | 1440 |
| atcatggatc | ttgacacat | gtgtgatgcc | accatgagct | atgaatgccc | tatgctggat | 1500 |
| gagggggtgg | aaccagatga | cgtcgattgt | tggtgcaaca | cgacgtcaac | ttgggttgtg | 1560 |
| tacggaacct | gccatcacaa | aaaggtgaa | gcacggagaa | gtagaagagc | tgtgacgctc | 1620 |
| ccctcccatt | ccactaggaa | gctgcaaacg | cggtcgcaaa | cctggttgga | atcaagagaa | 1680 |
| tacacaaagc | acttgattag | agtcgaaaat | tggatattca | ggaaccctgg | cttcgcgtta | 1740 |
| gcagcagctg | ccatcgcttg | gcttttggga | agctcaacga | gccaaaaagt | catatacttg | 1800 |
| gtcatgatac | tgctgattgc | cccggcatac | agcatcaggt | gcataggagt | cagcaatagg | 1860 |
| gactttgtgg | aaggtatgtc | aggtgggact | tgggttgata | ttgtcttgga | acatggaggt | 1920 |
| tgtgtcaccg | taatggcaca | ggacaaaccg | actgtcgaca | tagagctggt | tacaacaaca | 1980 |

```
gtcagcaaca tggcggaggt aagatcctac tgctatgagg catcaatatc agacatggct    2040
tcggacagcc gctgcccaac acaaggtgaa gcctaccttg acaagcaatc agacactcaa    2100
tatgtctgca aaagaacgtt agtggacaga ggctggggaa atggatgtgg acttttggc    2160 aaagggagtc tggtgacatg cgctaagttt gcatgctcca agaaaatgac cgggaagagc    2220
atccagccag agaatctgga gtaccggata atgctgtcag ttcatggctc ccagcacagt    2280
gggatgatcg ttaatgacac aggacatgaa actgatgaga atagagcgaa ggttgagata    2340
acgcccaatt caccaagagc cgaagccacc ctgggggtt ttggaagcct aggacttgat    2400
tgtgaaccga ggacaggcct tgacttttca gatttgtatt acttgactat gaataacaag    2460
cactggttgg ttcacaagga gtggttccac gacattccat taccttggca cgctggggca    2520
gacaccggaa ctccacactg gaacaacaaa gaagcactgg tagagttcaa ggacgcacat    2580
gccaaaaggc aaactgtcgt ggttctaggg agtcaagaag gagcagttca cacggccctt    2640
gctggagctc tggaggctga gatggatggt gcaaagggaa ggctgtcctc tggccacttg    2700
aaatgtcgcc tgaaaatgga taaacttaga ttgaagggcg tgtcatactc cttgtgtacc    2760
gcagcgttca cattcaccaa gatcccggct gaaacactgc acgggacagt cacagtggag    2820
gtacagtacg cagggacaga tggaccttgc aaggttccag ctcagatggc ggtggacatg    2880
caaactctga ccccagttgg gaggttgata accgctaacc ccgtaatcac tgaaagcact    2940
gagaactcta agatgatgct ggaacttgat ccaccatttg gggactctta cattgtcata    3000
ggagtcgggg agaagaagat cacccaccac tggcacagga gtggcagcac cattggaaaa    3060
gcatttgaag ccactgtgag aggtgccaag agaatggcag tcttgggaga cacagcctgg    3120
gactttggat cagttggagg cgctctcaac tcattgggca agggcatcca tcaaattttt    3180
ggagcagctt tcaaatcatt gtttggagga atgtcctggt tctcacaaat tctcattgga    3240
acgttgctga tgtggttggg tctgaacaca aagaatggat ctatttccct tatgtgcttg    3300
gccttagggg gagtgttgat cttcttatcc acagccgtct ctgctgattc cggatgtgcc    3360
atagacatca gccggcaaga gctgagatgt ggaagtggag tgttcataca caatgatgtg    3420
gaggcttgga tggaccggta caagtattac cctgaaacgc cacaaggcct agccaagatc    3480
attcagaaag ctcataagga aggagtgtgc ggtctacgat cagtttccag actggagcat    3540
caaatgtggg aagcagtgaa ggacgagctg aacactcttt tgaaggagaa tggtgtggac    3600
cttagtgtcg tggttgagaa acaggaggga atgtacaagt cagcacctaa acgcctcacc    3660
gccaccacgg aaaaattgga aattggctgg aaggcctggg aaagagtat tttatttgca    3720 ccagaactcg ccaacaacac ctttgtggtt gatggtccgg agaccaagga atgtccgact    3780
cagaatcgcc ttggaatag cttagaagtg gaggattttg gatttggtct caccagcact    3840
cggatgttcc tgaaggtcag agagagcaac acaactgaat gtgactcgaa gatcattgga    3900
acggctgtca agaacaactt ggcgatccac agtgacctgt cctattggat tgaaagcagg    3960
ctcaatgata cgtggaagct tgaaagggca gttctgggtg aagtcaaatc atgtacgtgg    4020
cctgagacgc ataccttgtg gggcgatgga atccttgaga gtgacttgat aataccagtc    4080
acactggcgg gaccacgaag caatcacaat cggagacctg gtacaagac acaaaaccag    4140 ggcccatggg acgaaggccg ggtagagatt gacttcgatt actgcccagg aactacggtc    4200
accctgagtg agagctgcgg acaccgtgga cctgccactc gcaccaccac agagagcgga    4260
aagttgataa cagattggtg ctgcaggagc tgcaccttac caccactgcg ctaccaaact    4320
```

```
gacagcggct gttggtatgg tatggagatc agaccacaga gacatgatga aaagaccctc    4380
gtgcagtcac aagtgaatgc ttataatgct gatatgattg acccttttca gttgggcctt    4440
ctggtcgtgt tcttggccac ccaggaggtc cttcgcaaga ggtggacagc caagatcagc    4500
atgccagcta tactgattgc tctgctagtc ctggtgtttg gggcattac ttacactgat     4560 gtgttacgct atgtcatctt ggtgggggca gctttcgcag aatctaattc gggaggagac    4620
gtggtacact tggcgctcat ggcgaccttc aagatacaac cagtgtttat ggtggcatcg    4680
tttctcaaag cgagatggac caaccaggag aacattttgt tgatgttggc ggctgttttc    4740
tttcaaatgg cttattacga tgcccgccaa attctgctct gggagatccc tgatgtgttg    4800
aattcactgg cggtagcttg gatgatactg agagccataa cattcacaac gacatcaaac    4860
gtggttgttc cgctgctagc cctgctaaca cccgggctga gatgcttgaa tctggatgtg    4920
tacaggatac tgctgttgat ggtcggaata ggcagcttga tcagggagaa gaggagtgca    4980
gctgcaaaaa agaaaggagc aagtctgcta tgcttggctc tagcctcaac aggacttttc    5040
aaccccatga tccttgctgc tggactgatt gcatgtgatc ccaaccgtaa acgcggatgg    5100
cccgcaactg aagtgatgac agctgtcggc ctaatgtttg ccatcgtcgg agggctggca    5160
gagcttgaca ttgactccat ggccattcca atgactatcg cggggctcat gtttgctgct    5220
ttcgtgattt ctgggaaatc aacagatatg tggattgaga acggcgga catttcctgg     5280 gaaagtgatg cagaaattac aggctcgagc gaaagagttg atgtgcggct tgatgatgat    5340
ggaaacttcc agctcatgaa tgatccagga gcaccttgga agatatggat gctcagaatg    5400
gtctgtctcg cgattagtgc gtacaccccc tgggcaatct gccctcagt agttggattt      5460 tggataactc tccaatacac aaagagagga ggcgtgttgt gggacactcc ctcaccaaag    5520
gagtacaaaa aggggacac gaccaccggc gtctacagga tcatgactcg tgggctgctc      5580
ggcagttatc aagcaggagc gggcgtgatg gttgaaggtg ttttccacac cctttggcat    5640
acaacaaaag gagccgcttt gatgagcgga gagggccgcc tggacccata ctggggcagt    5700
gtcaaggagg atcgactttg ttacggagga ccctggaaat gcagcacaa gtggaacggg    5760 caggatgagg tgcagatgat tgtggtggaa cctggcagga acgttaagaa cgtccagacg    5820
aaaccagggg tgttcaaaac acctgaagga gaaatcgggg ccgtgactt tggacttcccc     5880 actggaacat caggctcacc aatagtggac aaaaacggtg atgtgattgg ctttatggc     5940 aatggagtca taatgcccaa cggctcatac ataagcgcga tagtgcaggg tgaaaggatg    6000
gatgagccaa tcccagccgg attcgaacct gagatgctga ggaaaaaaca gatcactgta    6060
ctggatctcc atcccggcgc cggtaaaaca aggaggattc tgccacagat catcaaagag    6120
gccataaaca gaagactgag aacagccgtg ctagcaccaa ccagggttgt ggctgctgag    6180
atggctgaag cactgagagg actgcccatc cggtaccaga catccgcagt gcccagagaa    6240
cataatggaa atgagattgt tgatgtcatg tgtcatgcta ccctcaccca caggctgatg    6300
tctcctcaca gggtgccgaa ctacaacctg ttcgtgatgg atgaggctca tttcaccgac    6360
ccagctagca ttgcagcaag aggttacatt tccacaaagg tcgagctagg ggaggcggcg    6420
gcaatattca tgacagccac cccaccaggc acttcagatc cattcccaga gtccaattca    6480
ccaatttccg acttacagac tgagatcccg gatcgagctt ggaactctgg atacgaatgg    6540
atcacagaat acaccgggaa gacggtttgg tttgtgccta gtgtcaagat ggggaatgag    6600
attgcccttt gcctacaacg tgctggaaag aaagtagtcc aattgaacag aaagtcgtac    6660
gagacggagt acccaaaatg taagaacgat gattgggact tgttatcac aacagacata    6720
```

```
tctgaaatgg gggctaactt caaggcgagc agggtgattg acagccggaa gagtgtgaaa    6780
ccaaccatca taacagaagg agaagggaga gtgatcctgg gagaaccatc tgcagtgaca    6840
gcagctagtg ccgcccagag acgtggacgt atcggtagaa atccgtcgca agttggtgat    6900
gagtactgtt atgggggca cacgaatgaa gacgactcga acttcgccca ttggactgag    6960
gcacgaatca tgctggacaa catcaacatg ccaaacggac tgatcgctca attctaccaa    7020
ccagagcgtg agaaggtata taccatggat ggggaatacc ggctcagagg agaagagaga    7080
aaaaactttc tggaactgtt gaggactgca gatctgccag tttggctggc ttacaaggtt    7140
gcagcggctg gagtgtcata ccacgaccgg aggtggtgct tgatggtcc taggacaaac    7200 acaattttag aagacaacaa cgaagtggaa gtcatcacga agcttggtga aggaagatt    7260 ctgaggccgc gctggattga cgccagggtg tactcggatc accaggcact aaaggcgttc    7320
aaggacttcg cctcgggaaa acgttctcag atagggctca ttgaggttct gggaaagatg    7380
cctgagcact tcatggggaa gacatgggaa gcacttgaca ccatgtacgt tgtggccact    7440
gcagagaaag gaggaagagc tcacagaatg gccctggagg aactgccaga tgctcttcag    7500
acaattgcct tgattgcctt attgagtgtg atgaccatgg gagtattctt cctcctcatg    7560
cagcggaagg gcattggaaa gataggtttg ggaggcgctg tcttgggagt cgcgaccttt    7620
ttctgttgga tggctgaagt tccaggaacg aagatcgccg gaatgttgct gctctccctt    7680
ctcttgatga ttgtgctaat tcctgagcca gagaagcaac gttcgcagac agacaaccag    7740
ctagccgtgt tcctgatttg tgtcatgacc cttgtgagcg cagtggcagc caacgagatg    7800
ggttggctag ataagaccaa gagtgacata agcagtttgt ttgggcaaag aattgaggtc    7860
aaggagaatt tcagcatggg agagtttctt ttggacttga ggcctgcaac agcctggtca    7920
ctgtacgctg tgacaacagc ggtcctcact ccactgctaa agcatttgat cacgtcagat    7980
tacatcaaca cctcattgac ctcaataaac gttcaggcaa gtgcactatt cacactcgcg    8040
cgaggcttcc ccttcgtcga tgttggagtg tcggctctcc tgctagcagc cggatgctgg    8100
ggacaagtca ccctcaccgt tacggtaaca gcggcaacac tccttttttg ccactatgcc    8160
tacatggttc ccggttggca agctgaggca atgcgctcag cccagcggcg gacagcggcc    8220
ggaatcatga agaacgctgt agtggatggc atcgtggcca cggacgtccc agaattagag    8280
cgcaccacac ccatcatgca gaagaaagtt ggacagatca tgctgatctt ggtgtctcta    8340
gctgcagtag tagtgaaccc gtctgtgaag acagtacgag aagccggaat tttgatcacg    8400
gccgcagcgg tgacgctttg ggagaatgga gcaagctctg tttggaacgc aacaactgcc    8460
atcggactct gccacatcat gcgtgggggt tggttgtcat gtctatccat aacatggaca    8520
ctcataaaga acatggaaaa accaggacta aaaagaggtg gggcaaaagg acgcaccttg    8580
ggagaggttt ggaaagaaag actcaaccag atgacaaaag aagagttcac taggtaccgc    8640
aaagaggcca tcatcgaagt cgatcgctca gcggcaaaac acgccaggaa agaaggcaat    8700
gtcactggag ggcatccagt ctctagggc acagcaaaac tgagatggct ggtcgaacgg    8760
aggtttctcg aaccggtcgg aaaagtgatt gaccttggat gtggaagagg cggttggtgt    8820
tactatatgg caacccaaaa aagagtccaa gaagtcagag gtacacaaa gggcggtccc    8880 ggacatgaag agcccaact agtgcaaagt tatggatgga acattgtcac catgaagagt    8940
ggagtggatg tgttctacag accttctgag tgttgtgaca ccctcctttg tgacatcgga    9000
gagtcctcgt caagtgctga ggttgaagag cataggacga ttcgggtcct tgaaatggtt    9060
```

```
gaggactggc tgcaccgagg gccaagggaa ttttgcgtga aggtgctctg cccctacatg   9120
ccgaaagtca tagagaagat ggagctgctc caacgccggt atggggggggg actggtcaga   9180 aacccactct cacggaattc cacgcacgag atgtattggg tgagtcgagc ttcaggcaat   9240
gtggtacatt cagtgaatat gaccagccag gtgctcctag gaagaatgga aaaaaggacc   9300
tggaagggac cccaatacga ggaagatgta aacttgggaa gtggaaccag ggcggtggga   9360
aaaccnctgc tcaactcaga caccagtaaa atcaagaaca ggattgaacg actcaggcgt   9420
gagtacagtt cgacgtggca ccacgatgag aaccacccat atagaacctg gaactatcac   9480
ggcagttatg atgtgaagcc cacaggctcc gccagttcgc tggtcaatgg agtggtcagg   9540
ctcctctcaa aaccatggga caccatcacg aatgttacca ccatggccat gactgacact   9600
actcccttcg ggcagcagcg agtgttcaaa gagaaggtgg acacgaaagc tcctgaaccg   9660
ccagaaggag tgaagtacgt gctcaacgag accaccaact ggttgtgggc gttttttggcc   9720 agagaaaaac gtcccagaat gtgctctcga gaggaattca taagaaaggt caacagcaat   9780
gcagctttgg gtgccatgtt tgaagagcag aatcaatgga gagcgccag agaagcagtt     9840 gaagatccaa aattttggga gatggtggat gaggagcgcg aggcacatct gcgggggggaa   9900 tgtcacactt gcatttacaa catgatggga aagagagaga aaaaacccgg agagttcgga   9960
aaggccaagg gaagcagagc catttggttc atgtggctcg gagctcgctt tctggagttc  10020
gaggctctgg gttttctcaa tgaagaccac tggcttggaa gaaagaactc aggaggaggt  10080
gtcgagggct tgggcctcca aaaactgggt tacatcctgc gtgaagttgg caccaggcct  10140
gggggcaaga tctatgctga tgacacagct ggctgggaca cccgcatcac gagagctgac  10200
ttggaaaatg aagctaaggt gcttgagctg cttgatgggg aacatcggcg tcttgccagg  10260
gccatcattg agctcaccta tcgtcacaaa gttgtgaaag tgatgcgccc ggctgctgat  10320
ggaagaaccg tcatggatgt tatctccaga gaagatcaga gggggagtgg acaagttgtc  10380
acctacgccc taaacacttt caccaacctg gccgtccagc tggtgaggat gatggaaggg  10440
gaaggagtga ttggcccaga tgatgtggag aaactcacaa aagggaaagg acccaaagtc  10500
aggacctggc tgtttgagaa tggggaagaa agactcagcc gcatggctgt cagtggagat  10560
gactgtgtgg taaagccct ggacgatcgc tttgccacct cgctccactt cctcaatgct  10620
atgtcaaagg ttcgcaaaga catccaagag tggaaaccgt caactggatg gtatgattgg  10680
cagcaggttc catttgctc aaaccatttc actgaattga tcatgaaaga tggaagaaca  10740
ctggtggttc catgccgagg acaggatgaa ttggtaggca gagctcgcat atctccaggg  10800
gccggatgga acgtccgcga cactgcttgt ctggctaagt cttatgccca gatgtggctg  10860
cttctgtact tccacagaag agacctgcgg ctcatggcca acgccatttg ctccgctgtc  10920
cctgtgaatt gggtccctac cggaagaacc acgtggtcca tccatgcagg aggagagtgg  10980
atgacaacag aggacatgtt ggaggtctgg aaccgtgttt ggatagagga gaatgaatgg  11040
atggaagaca aacccccagt ggagaaatgg agtgacgtcc catattcagg aaaacgagag  11100
gacatctggt gtggcagcct gattggcaca agagcccgag ccacgtgggc agaaaacatc  11160
caggtggcta tcaaccaagt cagagcaatc atcgagatg agaagtatgt ggattacatg  11220
agttcactaa agagatatga agacacaact ttggttgagg acacagtact gtagatattt  11280
aatcaattgt aaatagacaa tataagtatg cataaaagtg tagttttata gtagtattta  11340
gtggtgttag tgtaaatagt taagaaaatt ttgaggagaa agtcaggccg ggaagttccc  11400
gccaccggaa gttgagtaga cggtgctgcc tgcgactcaa ccccaggagg actgggtgaa  11460
```

-continued

```
caaagccgcg aagtgatcca tgtaagccct cagaaccgtc tcggaaggag gacccacat    11520 gttgtaactt caaagcccaa tgtcagacca cgctacggcg tgctactctg cggagagtgc   11580
agtctgcgat agtgcccag gaggactggg ttaacaaagg caaaccaacg ccccacgcgg    11640
ccctagcccc ggtaatggtg ttaaccaggg cgaaaggact agaggttaga ggagacccg    11700 cggtttaaag tgcacggccc agcctggctg aagctgtagg tcaggggaag gactagaggt   11760
tagtggagac cccgtgccac aaaacaccac aacaaaacag catattgaca cctgggatag   11820
actaggagat cttctgctct gcacaaccag ccacacggca cagtgcgccg acaatggtgg   11880
ctggtggtgc gagaacacag gatct                                        11905
```

<210> SEQ ID NO 10
<211> LENGTH: 3725
<212> TYPE: PRT
<213> ORGANISM: Artificial Sequence
<220> FEATURE:
<223> OTHER INFORMATION: Synthetic polypeptide

<400> SEQUENCE: 10

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Met Ala Gln Ser Lys His Gly Leu Thr Lys Glu Met Thr
        35                  40                  45

Met Lys Tyr Arg Met Glu Gly Cys Val Asp Gly His Lys Phe Val Ile
    50                  55                  60

Thr Gly Glu Gly Ile Gly Tyr Pro Phe Lys Gly Lys Gln Ala Ile Asn
65                  70                  75                  80

Leu Cys Val Val Glu Gly Gly Pro Leu Pro Phe Ala Glu Asp Ile Leu
                85                  90                  95

Ser Ala Ala Phe Met Tyr Gly Asn Arg Val Phe Thr Glu Tyr Pro Gln
            100                 105                 110

Asp Ile Ala Asp Tyr Phe Lys Asn Ser Cys Pro Ala Gly Tyr Thr Trp
        115                 120                 125

Asp Arg Ser Phe Leu Phe Glu Asp Gly Ala Val Cys Ile Cys Asn Ala
    130                 135                 140

Asp Ile Thr Val Ser Val Glu Glu Asn Cys Met Tyr His Glu Ser Lys
145                 150                 155                 160

Phe Tyr Gly Val Asn Phe Pro Ala Asp Gly Pro Val Met Lys Lys Met
                165                 170                 175

Thr Asp Asn Trp Glu Pro Ser Cys Glu Lys Ile Ile Pro Val Pro Lys
            180                 185                 190

Gln Gly Ile Leu Lys Gly Asp Val Ser Met Tyr Leu Leu Leu Lys Asp
        195                 200                 205

Gly Gly Arg Leu Arg Cys Gln Phe Asp Thr Val Tyr Lys Ala Lys Ser
    210                 215                 220

Val Pro Arg Lys Met Pro Asp Trp His Phe Ile Gln His Lys Leu Thr
225                 230                 235                 240

Arg Glu Asp Arg Ser Asp Ala Lys Asn Gln Lys Trp His Leu Thr Glu
                245                 250                 255

His Ala Ile Ala Ser Gly Ser Ala Leu Pro Gly Ser Gly Ala Thr Asn
            260                 265                 270

Phe Ser Leu Leu Lys Gln Ala Gly Asp Val Glu Glu Asn Pro Gly Pro

```
              275                 280                 285
Met Ser Lys Lys Pro Gly Gly Pro Gly Lys Ser Arg Ala Val Asn Met
290                 295                 300

Leu Lys Arg Gly Met Pro Arg Val Leu Ser Leu Ile Gly Leu Lys Arg
305                 310                 315                 320

Ala Met Leu Ser Leu Ile Asp Gly Lys Gly Pro Ile Arg Phe Val Leu
                325                 330                 335

Ala Leu Leu Ala Phe Phe Arg Phe Thr Ala Ile Ala Pro Thr Arg Ala
            340                 345                 350

Val Leu Asp Arg Trp Arg Gly Val Asn Lys Gln Thr Ala Met Lys His
        355                 360                 365

Leu Leu Ser Phe Lys Lys Glu Leu Gly Thr Leu Thr Ser Ala Ile Asn
    370                 375                 380

Arg Arg Ser Ser Lys Gln Lys Arg Gly Gly Lys Thr Gly Ile Ala
385                 390                 395                 400

Val Met Ile Gly Leu Ile Ala Ser Ala Met Ala Ala Glu Val Thr Arg
                405                 410                 415

Arg Gly Ser Ala Tyr Tyr Met Tyr Leu Asp Arg Asn Asp Ala Gly Glu
            420                 425                 430

Ala Ile Ser Phe Pro Thr Thr Leu Gly Met Asn Lys Cys Tyr Ile Gln
        435                 440                 445

Ile Met Asp Leu Gly His Met Cys Asp Ala Thr Met Ser Tyr Glu Cys
    450                 455                 460

Pro Met Leu Asp Glu Gly Val Glu Pro Asp Asp Val Asp Cys Trp Cys
465                 470                 475                 480

Asn Thr Thr Ser Thr Trp Val Val Tyr Gly Thr Cys His His Lys Lys
                485                 490                 495

Gly Glu Ala Arg Arg Ser Arg Arg Ala Val Thr Leu Pro Ser His Ser
            500                 505                 510

Thr Arg Lys Leu Gln Thr Arg Ser Gln Thr Trp Leu Glu Ser Arg Glu
        515                 520                 525

Tyr Thr Lys His Leu Ile Arg Val Glu Asn Trp Ile Phe Arg Asn Pro
    530                 535                 540

Gly Phe Ala Leu Ala Ala Ala Ala Ile Ala Trp Leu Leu Gly Ser Ser
545                 550                 555                 560

Thr Ser Gln Lys Val Ile Tyr Leu Val Met Ile Leu Leu Ile Ala Pro
                565                 570                 575

Ala Tyr Ser Ile Arg Cys Ile Gly Val Ser Asn Arg Asp Phe Val Glu
            580                 585                 590

Gly Met Ser Gly Gly Thr Trp Val Asp Ile Val Leu Glu His Gly Gly
        595                 600                 605

Cys Val Thr Val Met Ala Gln Asp Lys Pro Thr Val Asp Ile Glu Leu
    610                 615                 620

Val Thr Thr Thr Val Ser Asn Met Ala Glu Val Arg Ser Tyr Cys Tyr
625                 630                 635                 640

Glu Ala Ser Ile Ser Asp Met Ala Ser Asp Ser Arg Cys Pro Thr Gln
                645                 650                 655

Gly Glu Ala Tyr Leu Asp Lys Gln Ser Asp Thr Gln Tyr Val Cys Lys
            660                 665                 670

Arg Thr Leu Val Asp Arg Gly Trp Gly Asn Gly Cys Gly Leu Phe Gly
        675                 680                 685

Lys Gly Ser Leu Val Thr Cys Ala Lys Phe Ala Cys Ser Lys Lys Met
    690                 695                 700
```

-continued

```
Thr Gly Lys Ser Ile Gln Pro Glu Asn Leu Glu Tyr Arg Ile Met Leu
705                 710                 715                 720

Ser Val His Gly Ser Gln His Ser Gly Met Ile Val Asn Asp Thr Gly
            725                 730                 735

His Glu Thr Asp Glu Asn Arg Ala Lys Val Glu Ile Thr Pro Asn Ser
                740                 745                 750

Pro Arg Ala Glu Ala Thr Leu Gly Gly Phe Gly Ser Leu Gly Leu Asp
            755                 760                 765

Cys Glu Pro Arg Thr Gly Leu Asp Phe Ser Asp Leu Tyr Tyr Leu Thr
770                 775                 780

Met Asn Asn Lys His Trp Leu Val His Lys Glu Trp Phe His Asp Ile
785                 790                 795                 800

Pro Leu Pro Trp His Ala Gly Ala Asp Thr Gly Thr Pro His Trp Asn
                805                 810                 815

Asn Lys Glu Ala Leu Val Glu Phe Lys Asp Ala His Ala Lys Arg Gln
                    820                 825                 830

Thr Val Val Val Leu Gly Ser Gln Glu Gly Ala Val His Thr Ala Leu
            835                 840                 845

Ala Gly Ala Leu Glu Ala Glu Met Asp Gly Ala Lys Gly Arg Leu Ser
850                 855                 860

Ser Gly His Leu Lys Cys Arg Leu Lys Met Asp Lys Leu Arg Leu Lys
865                 870                 875                 880

Gly Val Ser Tyr Ser Leu Cys Thr Ala Ala Phe Thr Phe Thr Lys Ile
                885                 890                 895

Pro Ala Glu Thr Leu His Gly Thr Val Thr Val Glu Val Gln Tyr Ala
            900                 905                 910

Gly Thr Asp Gly Pro Cys Lys Val Pro Ala Gln Met Ala Val Asp Met
            915                 920                 925

Gln Thr Leu Thr Pro Val Gly Arg Leu Ile Thr Ala Asn Pro Val Ile
930                 935                 940

Thr Glu Ser Thr Glu Asn Ser Lys Met Met Leu Glu Leu Asp Pro Pro
945                 950                 955                 960

Phe Gly Asp Ser Tyr Ile Val Ile Gly Val Gly Glu Lys Lys Ile Thr
                965                 970                 975

His His Trp His Arg Ser Gly Ser Thr Ile Gly Lys Ala Phe Glu Ala
            980                 985                 990

Thr Val Arg Gly Ala Lys Arg Met  Ala Val Leu Gly Asp  Thr Ala Trp
        995                 1000                1005

Asp Phe  Gly Ser Val Gly  Gly Ala Leu Asn Ser Leu  Gly Lys Gly
    1010                1015                1020

Ile His  Gln Ile Phe Gly Ala  Ala Phe Lys Ser Leu  Phe Gly Gly
    1025                1030                1035

Met Ser  Trp Phe Ser Gln Ile  Leu Ile Gly Thr Leu  Leu Met Trp
    1040                1045                1050

Leu Gly  Leu Asn Thr Lys Asn  Gly Ser Ile Ser Leu  Met Cys Leu
    1055                1060                1065

Ala Leu  Gly Gly Val Leu Ile  Phe Leu Ser Thr Ala  Val Ser Ala
    1070                1075                1080

Asp Ser  Gly Cys Ala Ile Asp  Ile Ser Arg Gln Glu  Leu Arg Cys
    1085                1090                1095

Gly Ser  Gly Val Phe Ile His  Asn Asp Val Glu Ala  Trp Met Asp
    1100                1105                1110
```

```
Arg  Tyr  Lys  Tyr  Tyr  Pro  Glu  Thr  Pro  Gln  Gly  Leu  Ala  Lys  Ile
1115                1120                1125

Ile  Gln  Lys  Ala  His  Lys  Glu  Gly  Val  Cys  Gly  Leu  Arg  Ser  Val
1130                1135                1140

Ser  Arg  Leu  Glu  His  Gln  Met  Trp  Glu  Ala  Val  Lys  Asp  Glu  Leu
1145                1150                1155

Asn  Thr  Leu  Leu  Lys  Glu  Asn  Gly  Val  Asp  Leu  Ser  Val  Val  Val
1160                1165                1170

Glu  Lys  Gln  Glu  Gly  Met  Tyr  Lys  Ser  Ala  Pro  Lys  Arg  Leu  Thr
1175                1180                1185

Ala  Thr  Thr  Glu  Lys  Leu  Glu  Ile  Gly  Trp  Lys  Ala  Trp  Gly  Lys
1190                1195                1200

Ser  Ile  Leu  Phe  Ala  Pro  Glu  Leu  Ala  Asn  Asn  Thr  Phe  Val  Val
1205                1210                1215

Asp  Gly  Pro  Glu  Thr  Lys  Glu  Cys  Pro  Thr  Gln  Asn  Arg  Ala  Trp
1220                1225                1230

Asn  Ser  Leu  Glu  Val  Glu  Asp  Phe  Gly  Phe  Gly  Leu  Thr  Ser  Thr
1235                1240                1245

Arg  Met  Phe  Leu  Lys  Val  Arg  Glu  Ser  Asn  Thr  Thr  Glu  Cys  Asp
1250                1255                1260

Ser  Lys  Ile  Ile  Gly  Thr  Ala  Val  Lys  Asn  Asn  Leu  Ala  Ile  His
1265                1270                1275

Ser  Asp  Leu  Ser  Tyr  Trp  Ile  Glu  Ser  Arg  Leu  Asn  Asp  Thr  Trp
1280                1285                1290

Lys  Leu  Glu  Arg  Ala  Val  Leu  Gly  Glu  Val  Lys  Ser  Cys  Thr  Trp
1295                1300                1305

Pro  Glu  Thr  His  Thr  Leu  Trp  Gly  Asp  Gly  Ile  Leu  Glu  Ser  Asp
1310                1315                1320

Leu  Ile  Ile  Pro  Val  Thr  Leu  Ala  Gly  Pro  Arg  Ser  Asn  His  Asn
1325                1330                1335

Arg  Arg  Pro  Gly  Tyr  Lys  Thr  Gln  Asn  Gln  Gly  Pro  Trp  Asp  Glu
1340                1345                1350

Gly  Arg  Val  Glu  Ile  Asp  Phe  Asp  Tyr  Cys  Pro  Gly  Thr  Thr  Val
1355                1360                1365

Thr  Leu  Ser  Glu  Ser  Cys  Gly  His  Arg  Gly  Pro  Ala  Thr  Arg  Thr
1370                1375                1380

Thr  Thr  Glu  Ser  Gly  Lys  Leu  Ile  Thr  Asp  Trp  Cys  Cys  Arg  Ser
1385                1390                1395

Cys  Thr  Leu  Pro  Pro  Leu  Arg  Tyr  Gln  Thr  Asp  Ser  Gly  Cys  Trp
1400                1405                1410

Tyr  Gly  Met  Glu  Ile  Arg  Pro  Gln  Arg  His  Asp  Glu  Lys  Thr  Leu
1415                1420                1425

Val  Gln  Ser  Gln  Val  Asn  Ala  Tyr  Asn  Ala  Asp  Met  Ile  Asp  Pro
1430                1435                1440

Phe  Gln  Leu  Gly  Leu  Leu  Val  Val  Phe  Leu  Ala  Thr  Gln  Glu  Val
1445                1450                1455

Leu  Arg  Lys  Arg  Trp  Thr  Ala  Lys  Ile  Ser  Met  Pro  Ala  Ile  Leu
1460                1465                1470

Ile  Ala  Leu  Leu  Val  Leu  Val  Phe  Gly  Gly  Ile  Thr  Tyr  Thr  Asp
1475                1480                1485

Val  Leu  Arg  Tyr  Val  Ile  Leu  Val  Gly  Ala  Ala  Phe  Ala  Glu  Ser
1490                1495                1500

Asn  Ser  Gly  Gly  Asp  Val  Val  His  Leu  Ala  Leu  Met  Ala  Thr  Phe
```

```
            1505                1510                1515

Lys Ile Gln Pro Val Phe Met Val Ala Ser Phe Leu Lys Ala Arg
    1520                1525                1530

Trp Thr Asn Gln Glu Asn Ile Leu Leu Met Leu Ala Ala Val Phe
    1535                1540                1545

Phe Gln Met Ala Tyr Tyr Asp Ala Arg Gln Ile Leu Leu Trp Glu
    1550                1555                1560

Ile Pro Asp Val Leu Asn Ser Leu Ala Val Ala Trp Met Ile Leu
    1565                1570                1575

Arg Ala Ile Thr Phe Thr Thr Ser Asn Val Val Pro Leu
    1580                1585                1590

Leu Ala Leu Leu Thr Pro Gly Leu Arg Cys Leu Asn Leu Asp Val
    1595                1600                1605

Tyr Arg Ile Leu Leu Leu Met Val Gly Ile Gly Ser Leu Ile Arg
    1610                1615                1620

Glu Lys Arg Ser Ala Ala Ala Lys Lys Lys Gly Ala Ser Leu Leu
    1625                1630                1635

Cys Leu Ala Leu Ala Ser Thr Gly Leu Phe Asn Pro Met Ile Leu
    1640                1645                1650

Ala Ala Gly Leu Ile Ala Cys Asp Pro Asn Arg Lys Arg Gly Trp
    1655                1660                1665

Pro Ala Thr Glu Val Met Thr Ala Val Gly Leu Met Phe Ala Ile
    1670                1675                1680

Val Gly Gly Leu Ala Glu Leu Asp Ile Asp Ser Met Ala Ile Pro
    1685                1690                1695

Met Thr Ile Ala Gly Leu Met Phe Ala Ala Phe Val Ile Ser Gly
    1700                1705                1710

Lys Ser Thr Asp Met Trp Ile Glu Arg Thr Ala Asp Ile Ser Trp
    1715                1720                1725

Glu Ser Asp Ala Glu Ile Thr Gly Ser Ser Glu Arg Val Asp Val
    1730                1735                1740

Arg Leu Asp Asp Asp Gly Asn Phe Gln Leu Met Asn Asp Pro Gly
    1745                1750                1755

Ala Pro Trp Lys Ile Trp Met Leu Arg Met Val Cys Leu Ala Ile
    1760                1765                1770

Ser Ala Tyr Thr Pro Trp Ala Ile Leu Pro Ser Val Val Gly Phe
    1775                1780                1785

Trp Ile Thr Leu Gln Tyr Thr Lys Arg Gly Gly Val Leu Trp Asp
    1790                1795                1800

Thr Pro Ser Pro Lys Glu Tyr Lys Lys Gly Asp Thr Thr Thr Gly
    1805                1810                1815

Val Tyr Arg Ile Met Thr Arg Gly Leu Leu Gly Ser Tyr Gln Ala
    1820                1825                1830

Gly Ala Gly Val Met Val Glu Gly Val Phe His Thr Leu Trp His
    1835                1840                1845

Thr Thr Lys Gly Ala Ala Leu Met Ser Gly Glu Gly Arg Leu Asp
    1850                1855                1860

Pro Tyr Trp Gly Ser Val Lys Glu Asp Arg Leu Cys Tyr Gly Gly
    1865                1870                1875

Pro Trp Lys Leu Gln His Lys Trp Asn Gly Gln Asp Glu Val Gln
    1880                1885                1890

Met Ile Val Val Glu Pro Gly Arg Asn Val Lys Asn Val Gln Thr
    1895                1900                1905
```

```
Lys Pro Gly Val Phe Lys Thr Pro Glu Gly Glu Ile Gly Ala Val
    1910            1915               1920

Thr Leu Asp Phe Pro Thr Gly Thr Ser Gly Ser Pro Ile Val Asp
    1925            1930               1935

Lys Asn Gly Asp Val Ile Gly Leu Tyr Gly Asn Gly Val Ile Met
    1940            1945               1950

Pro Asn Gly Ser Tyr Ile Ser Ala Ile Val Gln Gly Glu Arg Met
    1955            1960               1965

Asp Glu Pro Ile Pro Ala Gly Phe Glu Pro Glu Met Leu Arg Lys
    1970            1975               1980

Lys Gln Ile Thr Val Leu Asp Leu His Pro Gly Ala Gly Lys Thr
    1985            1990               1995

Arg Arg Ile Leu Pro Gln Ile Ile Lys Glu Ala Ile Asn Arg Arg
    2000            2005               2010

Leu Arg Thr Ala Val Leu Ala Pro Thr Arg Val Val Ala Ala Glu
    2015            2020               2025

Met Ala Glu Ala Leu Arg Gly Leu Pro Ile Arg Tyr Gln Thr Ser
    2030            2035               2040

Ala Val Pro Arg Glu His Asn Gly Asn Glu Ile Val Asp Val Met
    2045            2050               2055

Cys His Ala Thr Leu Thr His Arg Leu Met Ser Pro His Arg Val
    2060            2065               2070

Pro Asn Tyr Asn Leu Phe Val Met Asp Glu Ala His Phe Thr Asp
    2075            2080               2085

Pro Ala Ser Ile Ala Ala Arg Gly Tyr Ile Ser Thr Lys Val Glu
    2090            2095               2100

Leu Gly Glu Ala Ala Ala Ile Phe Met Thr Ala Thr Pro Pro Gly
    2105            2110               2115

Thr Ser Asp Pro Phe Pro Glu Ser Asn Ser Pro Ile Ser Asp Leu
    2120            2125               2130

Gln Thr Glu Ile Pro Asp Arg Ala Trp Asn Ser Gly Tyr Glu Trp
    2135            2140               2145

Ile Thr Glu Tyr Thr Gly Lys Thr Val Trp Phe Val Pro Ser Val
    2150            2155               2160

Lys Met Gly Asn Glu Ile Ala Leu Cys Leu Gln Arg Ala Gly Lys
    2165            2170               2175

Lys Val Val Gln Leu Asn Arg Lys Ser Tyr Glu Thr Glu Tyr Pro
    2180            2185               2190

Lys Cys Lys Asn Asp Asp Trp Asp Phe Val Ile Thr Thr Asp Ile
    2195            2200               2205

Ser Glu Met Gly Ala Asn Phe Lys Ala Ser Arg Val Ile Asp Ser
    2210            2215               2220

Arg Lys Ser Val Lys Pro Thr Ile Ile Thr Glu Gly Glu Gly Arg
    2225            2230               2235

Val Ile Leu Gly Glu Pro Ser Ala Val Thr Ala Ala Ser Ala Ala
    2240            2245               2250

Gln Arg Arg Gly Arg Ile Gly Arg Asn Pro Ser Gln Val Gly Asp
    2255            2260               2265

Glu Tyr Cys Tyr Gly Gly His Thr Asn Glu Asp Asp Ser Asn Phe
    2270            2275               2280

Ala His Trp Thr Glu Ala Arg Ile Met Leu Asp Asn Ile Asn Met
    2285            2290               2295
```

-continued

```
Pro Asn Gly Leu Ile Ala Gln Phe Tyr Gln Pro Glu Arg Glu Lys
2300                    2305                2310

Val Tyr Thr Met Asp Gly Glu Tyr Arg Leu Arg Gly Glu Glu Arg
2315                    2320                2325

Lys Asn Phe Leu Glu Leu Leu Arg Thr Ala Asp Leu Pro Val Trp
2330                    2335                2340

Leu Ala Tyr Lys Val Ala Ala Gly Val Ser Tyr His Asp Arg
2345                    2350                2355

Arg Trp Cys Phe Asp Gly Pro Arg Thr Asn Thr Ile Leu Glu Asp
2360                    2365                2370

Asn Asn Glu Val Glu Val Ile Thr Lys Leu Gly Glu Arg Lys Ile
2375                    2380                2385

Leu Arg Pro Arg Trp Ile Asp Ala Arg Val Tyr Ser Asp His Gln
2390                    2395                2400

Ala Leu Lys Ala Phe Lys Asp Phe Ala Ser Gly Lys Arg Ser Gln
2405                    2410                2415

Ile Gly Leu Ile Glu Val Leu Gly Lys Met Pro Glu His Phe Met
2420                    2425                2430

Gly Lys Thr Trp Glu Ala Leu Asp Thr Met Tyr Val Val Ala Thr
2435                    2440                2445

Ala Glu Lys Gly Gly Arg Ala His Arg Met Ala Leu Glu Glu Leu
2450                    2455                2460

Pro Asp Ala Leu Gln Thr Ile Ala Leu Ile Ala Leu Leu Ser Val
2465                    2470                2475

Met Thr Met Gly Val Phe Phe Leu Leu Met Gln Arg Lys Gly Ile
2480                    2485                2490

Gly Lys Ile Gly Leu Gly Gly Ala Val Leu Gly Val Ala Thr Phe
2495                    2500                2505

Phe Cys Trp Met Ala Glu Val Pro Gly Thr Lys Ile Ala Gly Met
2510                    2515                2520

Leu Leu Leu Ser Leu Leu Leu Met Ile Val Leu Ile Pro Glu Pro
2525                    2530                2535

Glu Lys Gln Arg Ser Gln Thr Asp Asn Gln Leu Ala Val Phe Leu
2540                    2545                2550

Ile Cys Val Met Thr Leu Val Ser Ala Val Ala Ala Asn Glu Met
2555                    2560                2565

Gly Trp Leu Asp Lys Thr Lys Ser Asp Ile Ser Ser Leu Phe Gly
2570                    2575                2580

Gln Arg Ile Glu Val Lys Glu Asn Phe Ser Met Gly Glu Phe Leu
2585                    2590                2595

Leu Asp Leu Arg Pro Ala Thr Ala Trp Ser Leu Tyr Ala Val Thr
2600                    2605                2610

Thr Ala Val Leu Thr Pro Leu Leu Lys His Leu Ile Thr Ser Asp
2615                    2620                2625

Tyr Ile Asn Thr Ser Leu Thr Ser Ile Asn Val Gln Ala Ser Ala
2630                    2635                2640

Leu Phe Thr Leu Ala Arg Gly Phe Pro Phe Val Asp Val Gly Val
2645                    2650                2655

Ser Ala Leu Leu Leu Ala Ala Gly Cys Trp Gly Gln Val Thr Leu
2660                    2665                2670

Thr Val Thr Val Thr Ala Ala Thr Leu Leu Phe Cys His Tyr Ala
2675                    2680                2685

Tyr Met Val Pro Gly Trp Gln Ala Glu Ala Met Arg Ser Ala Gln
```

-continued

```
            2690                2695                2700
Arg Arg Thr Ala Ala Gly Ile Met Lys Asn Ala Val Val Asp Gly
    2705                2710                2715
Ile Val Ala Thr Asp Val Pro Glu Leu Glu Arg Thr Thr Pro Ile
    2720                2725                2730
Met Gln Lys Lys Val Gly Gln Ile Met Leu Ile Leu Val Ser Leu
    2735                2740                2745
Ala Ala Val Val Val Asn Pro Ser Val Lys Thr Val Arg Glu Ala
    2750                2755                2760
Gly Ile Leu Ile Thr Ala Ala Val Thr Leu Trp Glu Asn Gly
    2765                2770                2775
Ala Ser Ser Val Trp Asn Ala Thr Thr Ala Ile Gly Leu Cys His
    2780                2785                2790
Ile Met Arg Gly Gly Trp Leu Ser Cys Leu Ser Ile Thr Trp Thr
    2795                2800                2805
Leu Ile Lys Asn Met Glu Lys Pro Gly Leu Lys Arg Gly Gly Ala
    2810                2815                2820
Lys Gly Arg Thr Leu Gly Glu Val Trp Lys Glu Arg Leu Asn Gln
    2825                2830                2835
Met Thr Lys Glu Glu Phe Thr Arg Tyr Arg Lys Glu Ala Ile Ile
    2840                2845                2850
Glu Val Asp Arg Ser Ala Ala Lys His Ala Arg Lys Glu Gly Asn
    2855                2860                2865
Val Thr Gly Gly His Pro Val Ser Arg Gly Thr Ala Lys Leu Arg
    2870                2875                2880
Trp Leu Val Glu Arg Arg Phe Leu Glu Pro Val Gly Lys Val Ile
    2885                2890                2895
Asp Leu Gly Cys Gly Arg Gly Gly Trp Cys Tyr Tyr Met Ala Thr
    2900                2905                2910
Gln Lys Arg Val Gln Glu Val Arg Gly Tyr Thr Lys Gly Gly Pro
    2915                2920                2925
Gly His Glu Glu Pro Gln Leu Val Gln Ser Tyr Gly Trp Asn Ile
    2930                2935                2940
Val Thr Met Lys Ser Gly Val Asp Val Phe Tyr Arg Pro Ser Glu
    2945                2950                2955
Cys Cys Asp Thr Leu Leu Cys Asp Ile Gly Glu Ser Ser Ser Ser
    2960                2965                2970
Ala Glu Val Glu Glu His Arg Thr Ile Arg Val Leu Glu Met Val
    2975                2980                2985
Glu Asp Trp Leu His Arg Gly Pro Arg Glu Phe Cys Val Lys Val
    2990                2995                3000
Leu Cys Pro Tyr Met Pro Lys Val Ile Glu Lys Met Glu Leu Leu
    3005                3010                3015
Gln Arg Arg Tyr Gly Gly Gly Leu Val Arg Asn Pro Leu Ser Arg
    3020                3025                3030
Asn Ser Thr His Glu Met Tyr Trp Val Ser Arg Ala Ser Gly Asn
    3035                3040                3045
Val Val His Ser Val Asn Met Thr Ser Gln Val Leu Leu Gly Arg
    3050                3055                3060
Met Glu Lys Arg Thr Trp Lys Gly Pro Gln Tyr Glu Glu Asp Val
    3065                3070                3075
Asn Leu Gly Ser Gly Thr Arg Ala Val Gly Lys Pro Leu Leu Asn
    3080                3085                3090
```

```
Ser Asp Thr Ser Lys Ile Lys Asn Arg Ile Glu Arg Leu Arg Arg
3095            3100                3105

Glu Tyr Ser Ser Thr Trp His His Asp Glu Asn His Pro Tyr Arg
3110            3115                3120

Thr Trp Asn Tyr His Gly Ser Tyr Asp Val Lys Pro Thr Gly Ser
3125            3130                3135

Ala Ser Ser Leu Val Asn Gly Val Val Arg Leu Leu Ser Lys Pro
3140            3145                3150

Trp Asp Thr Ile Thr Asn Val Thr Thr Met Ala Met Thr Asp Thr
3155            3160                3165

Thr Pro Phe Gly Gln Gln Arg Val Phe Lys Glu Lys Val Asp Thr
3170            3175                3180

Lys Ala Pro Glu Pro Pro Glu Gly Val Lys Tyr Val Leu Asn Glu
3185            3190                3195

Thr Thr Asn Trp Leu Trp Ala Phe Leu Ala Arg Glu Lys Arg Pro
3200            3205                3210

Arg Met Cys Ser Arg Glu Glu Phe Ile Arg Lys Val Asn Ser Asn
3215            3220                3225

Ala Ala Leu Gly Ala Met Phe Glu Glu Gln Asn Gln Trp Arg Ser
3230            3235                3240

Ala Arg Glu Ala Val Glu Asp Pro Lys Phe Trp Glu Met Val Asp
3245            3250                3255

Glu Glu Arg Glu Ala His Leu Arg Gly Glu Cys His Thr Cys Ile
3260            3265                3270

Tyr Asn Met Met Gly Lys Arg Glu Lys Lys Pro Gly Glu Phe Gly
3275            3280                3285

Lys Ala Lys Gly Ser Arg Ala Ile Trp Phe Met Trp Leu Gly Ala
3290            3295                3300

Arg Phe Leu Glu Phe Glu Ala Leu Gly Phe Leu Asn Glu Asp His
3305            3310                3315

Trp Leu Gly Arg Lys Asn Ser Gly Gly Gly Val Glu Gly Leu Gly
3320            3325                3330

Leu Gln Lys Leu Gly Tyr Ile Leu Arg Glu Val Gly Thr Arg Pro
3335            3340                3345

Gly Gly Lys Ile Tyr Ala Asp Asp Thr Ala Gly Trp Asp Thr Arg
3350            3355                3360

Ile Thr Arg Ala Asp Leu Glu Asn Glu Ala Lys Val Leu Glu Leu
3365            3370                3375

Leu Asp Gly Glu His Arg Arg Leu Ala Arg Ala Ile Ile Glu Leu
3380            3385                3390

Thr Tyr Arg His Lys Val Val Lys Val Met Arg Pro Ala Ala Asp
3395            3400                3405

Gly Arg Thr Val Met Asp Val Ile Ser Arg Glu Asp Gln Arg Gly
3410            3415                3420

Ser Gly Gln Val Val Thr Tyr Ala Leu Asn Thr Phe Thr Asn Leu
3425            3430                3435

Ala Val Gln Leu Val Arg Met Met Glu Gly Glu Gly Val Ile Gly
3440            3445                3450

Pro Asp Asp Val Glu Lys Leu Thr Lys Gly Lys Gly Pro Lys Val
3455            3460                3465

Arg Thr Trp Leu Phe Glu Asn Gly Glu Glu Arg Leu Ser Arg Met
3470            3475                3480
```

| Ala | Val | Ser | Gly | Asp | Asp | Cys | Val | Val | Lys | Pro | Leu | Asp | Asp | Arg |
|---|---|---|---|---|---|---|---|---|---|---|---|---|---|---|
| | 3485 | | | | 3490 | | | | 3495 | | | | | |

Phe Ala Thr Ser Leu His Phe Leu Asn Ala Met Ser Lys Val Arg
3500 3505 3510

Lys Asp Ile Gln Glu Trp Lys Pro Ser Thr Gly Trp Tyr Asp Trp
3515 3520 3525

Gln Gln Val Pro Phe Cys Ser Asn His Phe Thr Glu Leu Ile Met
3530 3535 3540

Lys Asp Gly Arg Thr Leu Val Val Pro Cys Arg Gly Gln Asp Glu
3545 3550 3555

Leu Val Gly Arg Ala Arg Ile Ser Pro Gly Ala Gly Trp Asn Val
3560 3565 3570

Arg Asp Thr Ala Cys Leu Ala Lys Ser Tyr Ala Gln Met Trp Leu
3575 3580 3585

Leu Leu Tyr Phe His Arg Arg Asp Leu Arg Leu Met Ala Asn Ala
3590 3595 3600

Ile Cys Ser Ala Val Pro Val Asn Trp Val Pro Thr Gly Arg Thr
3605 3610 3615

Thr Trp Ser Ile His Ala Gly Gly Glu Trp Met Thr Thr Glu Asp
3620 3625 3630

Met Leu Glu Val Trp Asn Arg Val Trp Ile Glu Glu Asn Glu Trp
3635 3640 3645

Met Glu Asp Lys Thr Pro Val Glu Lys Trp Ser Asp Val Pro Tyr
3650 3655 3660

Ser Gly Lys Arg Glu Asp Ile Trp Cys Gly Ser Leu Ile Gly Thr
3665 3670 3675

Arg Ala Arg Ala Thr Trp Ala Glu Asn Ile Gln Val Ala Ile Asn
3680 3685 3690

Gln Val Arg Ala Ile Ile Gly Asp Glu Lys Tyr Val Asp Tyr Met
3695 3700 3705

Ser Ser Leu Lys Arg Tyr Glu Asp Thr Thr Leu Val Glu Asp Thr
3710 3715 3720

Val Leu
3725

<210> SEQ ID NO 11
<211> LENGTH: 11905
<212> TYPE: DNA
<213> ORGANISM: Artificial Sequence
<220> FEATURE:
<223> OTHER INFORMATION: Synthetic construct

<400> SEQUENCE: 11
agtagttcgc ctgtgtgagc tgacaaactt agtagtgttt gtgaggatta acaacaatta    60
acacagtgcg agctgtttct tagcacgaag atctcgatgt ctaagaaacc aggagggccc   120
ggcaagagcc gggctgtcaa tatgctaaaa cgcggaatgc cccgcgtgtt gtccttgatt   180
ggactgaaga gggctatgtt gatggcccag tccaagcacg gcctgaccaa ggagatgacc   240
atgaagtacc gcatggaggg ctgcgtggac ggccacaagt tcgtgatcac cggcgagggc   300
atcggctacc ccttcaaggg caagcaggcc atcaacctgt gcgtggtgga gggcggcccc   360
ttgcccttcg ccgaggacat cttgtccgcc gccttcatgt acggcaaccg cgtgttcacc   420
gagtaccccc aggacatcgt cgactacttc aagaactcct gccccgcagg ctacacctgg   480
gaccgctcct tcctgttcga ggacggcgcc gtgtgcatct gcaacgccga catcaccgtg   540

```
agcgtggagg agaactgcat gtaccacgag tccaagttct acggcgtgaa cttccccgcc    600
gacggccccg tgatgaagaa gatgaccgac aactgggagc cctcctgcga gaagatcatc    660
cccgtgccca agcagggcat cttgaagggc gacgtgagca tgtacctgct gctgaaggac    720
ggtggccgct tgcgctgcca gttcgacacc gtgtacaagg ccaagtccgt gccccgcaag    780
atgcccgact ggcacttcat ccagcacaag ctgacccgcg aggaccgcag cgacgccaag    840
aaccagaagt ggcacctgac cgagcacgcc atcgcctccg gctccgcctt gcccggaagc    900
ggagctacta acttcagcct gctgaagcag gctggagacg tggaggagaa ccctggacct    960
atgtccaaaa agcccggcgg tcctgggaaa tccagagccg tgaacatgtt gaaaaggggg   1020
atgccacggg tactgagtct gatcggcctc aaaagagcca tgttgagcct gatcgacggc   1080
aaggggccaa tacgatttgt gttggctctc ttggcgttct tcaggttcac agcaattgct   1140
ccgacccgag cagtgctgga tcgatggaga ggtgtgaaca aacaaacagc gatgaaacac   1200
cttctgagtt ttaagaagga actagggacc ttgaccagtg ctatcaatcg gcggagttcg   1260
aaacaaaaga aaagaggagg aaagaccgga attgcagtca tgattggcct gatcgccagc   1320
gctatggcag cggaggtcac tagacgtggg agtgcatact atatgtactt ggacagaaac   1380
gatgctgggg aggccatatc ttttccaacc acattgggga tgaataagtg ttatatacag   1440
atcatggatc ttggacacat gtgtgatgcc accatgagct atgaatgccc tatgctggat   1500
gagggggtgg aaccagatga cgtcgattgt tggtgcaaca cgacgtcaac ttgggttgtg   1560
tacggaacct gccatcacaa aaaaggtgaa gcacggagaa gtagaagagc tgtgacgctc   1620
ccctcccatt ccactaggaa gctgcaaacg cggtcgcaaa cctggttgga atcaagagaa   1680
tacacaaagc acttgattag agtcgaaaat tggatattca ggaaccctgg cttcgcgtta   1740
gcagcagctg ccatcgcttg gcttttggga agctcaacga gccaaaaagt catatacttg   1800
gtcatgatac tgctgattgc cccggcatac agcatcaggt gcataggagt cagcaatagg   1860
gactttgtgg aaggtatgtc agtgggact tgggttgata ttgtcttgga acatggaggt   1920
tgtgtcaccg taatggcaca ggacaaaccg actgtcgaca tagagctggt tacaacaaca   1980
gtcagcaaca tggcggaggt aagatcctac tgctatgagg catcaatatc agacatggct   2040
tcggacagcc gctgcccaac acaaggtgaa gcctaccttg acaagcaatc agacactcaa   2100
tatgtctgca aaagaacgtt agtggacaga ggctggggaa atggatgtgg acttttggc   2160
aaagggagtc tggtgacatg cgctaagttt gcatgctcca gaaaaatgac cgggaagagc   2220
atccagccag agaatctgga gtaccggata atgctgtcag ttcatggctc ccagcacagt   2280
gggatgatcg ttaatgacac aggacatgaa actgatgaga atagagcgaa ggttgagata   2340
acgcccaatt caccaagagc cgaagccacc ctgggggggtt ttggaagcct aggacttgat   2400
tgtgaaccga ggacaggcct tgacttttca gatttgtatt acttgactat gaataacaag   2460
cactggttgg ttcacaagga gtggttccac gacattccat accttggcca cgctggggca   2520
gacaccggaa ctccacactg gaacaacaaa gaagcactgg tagagttcaa ggacgcacat   2580
gccaaaaggc aaactgtcgt ggttctaggg agtcaagaag gagcagttca cacggccctt   2640
gctggagctc tggaggctga gatggatggt gcaagggaa ggctgtcctc tggccacttg   2700
aaatgtcgcc tgaaaatgga taaacttaga ttgaagggcg tgtcatactc cttgtgtacc   2760
gcagcgttca cattcaccaa gatcccggct gaaacactgc acgggacagt cacagtggag   2820
gtacagtacg cagggacaga tggaccttgc aaggttccag ctcagatggc ggtggacatg   2880
caaactctga ccccagttgg gaggttgata accgctaacc ccgtaatcac tgaaagcact   2940
```

| | |
|---|---|
| gagaactcta agatgatgct ggaacttgat ccaccatttg gggactctta cattgtcata | 3000 |
| ggagtcgggg agaagaagat cacccaccac tggcacagga gtggcagcac cattggaaaa | 3060 |
| gcatttgaag ccactgtgag aggtgccaag agaatggcag tcttgggaga cacagcctgg | 3120 |
| gactttggat cagttggagg cgctctcaac tcattgggca agggcatcca tcaaattttt | 3180 |
| ggagcagctt tcaaatcatt gtttggagga atgtcctggt tctcacaaat tctcattgga | 3240 |
| acgttgctga tgtggttggg tctgaacaca aagaatggat ctatttccct tatgtgcttg | 3300 |
| gccttagggg gagtgttgat cttcttatcc acagccgtct ctgctgattc cggatgtgcc | 3360 |
| atagacatca gccggcaaga gctgagatgt ggaagtggag tgttcataca aatgatgtg | 3420 |
| gaggcttgga tggaccggta caagtattac cctgaaacgc cacaaggcct agccaagatc | 3480 |
| attcagaaag ctcataagga aggagtgtgc ggtctacgat cagtttccag actggagcat | 3540 |
| caaatgtggg aagcagtgaa ggacgagctg aacactcttt tgaaggagaa tggtgtggac | 3600 |
| cttagtgtcg tggttgagaa acaggaggga atgtacaagt cagcacctaa acgcctcacc | 3660 |
| gccaccacgg aaaaattgga aattggctgg aaggcctggg gaaagagtat tttatttgca | 3720 |
| ccagaactcg ccaacaacac ctttgtggtt gatggtccgg agaccaagga atgtccgact | 3780 |
| cagaatcgcg cttggaatag cttagaagtg gaggattttg gatttggtct caccagcact | 3840 |
| cggatgttcc tgaaggtcag agagagcaac acaactgaat gtgactcgaa gatcattgga | 3900 |
| acggctgtca agaacaactt ggcgatccac agtgacctgt cctattggat tgaaagcagg | 3960 |
| ctcaatgata cgtggaagct tgaaagggca gttctgggtg aagtcaaatc atgtacgtgg | 4020 |
| cctgagacgc ataccttgtg gggcgatgga atccttgaga gtgacttgat aataccagtc | 4080 |
| acactggcgg gaccacgaag caatcacaat cggagacctg gtacaagac acaaaaccag | 4140 |
| ggcccatggg acgaaggccg ggtagagatt gacttcgatt actgcccagg aactacggtc | 4200 |
| accctgagtg agagctgcgg acaccgtgga cctgccactc gcaccaccac agagagcgga | 4260 |
| aagttgataa cagattggtg ctgcaggagc tgcaccttac caccactgcg ctaccaaact | 4320 |
| gacagcggct gttggtatgg tatggagatc agaccacaga gacatgatga aaagaccctc | 4380 |
| gtgcagtcac aagtgaatgc ttataatgct gatatgattg acccttttca gttgggcctt | 4440 |
| ctggtcgtgt tcttggccac ccaggaggtc cttcgcaaga ggtggacagc caagatcagc | 4500 |
| atgccagcta tactgattgc tctgctagtc ctggtgtttg ggcattac ttacactgat | 4560 |
| gtgttacgct atgtcatctt ggtggggca gctttcgcag aatctaattc gggaggagac | 4620 |
| gtggtacact tggcgctcat ggcgaccttc aagatacaac cagtgtttat ggtggcatcg | 4680 |
| tttctcaaag cgagatggac caaccaggag aacattttgt tgatgttggc ggctgttttc | 4740 |
| tttcaaatgg cttattacga tgcccgccaa attctgctct gggagatccc tgatgtgttg | 4800 |
| aattcactgg cggtagcttg gatgatactg agagccataa cattcacaac gacatcaaac | 4860 |
| gtggttgttc cgctgctagc cctgctaaca cccgggctga gatgcttgaa tctggatgtg | 4920 |
| tacaggatac tgctgttgat ggtcggaata ggcagcttga tcaggagaa gaggagtgca | 4980 |
| gctgcaaaaa agaaaggagc aagtctgcta tgcttggctc tagcctcaac aggactttc | 5040 |
| aaccccatga tccttgctgc tggactgatt gcatgtgatc ccaaccgtaa acgcggatgg | 5100 |
| cccgcaactg aagtgatgac agctgtcggc ctaatgtttg ccatcgtcgg agggctggca | 5160 |
| gagcttgaca ttgactccat ggccattcca atgactatcg cggggctcat gtttgctgct | 5220 |
| ttcgtgattt ctgggaaatc aacagatatg tggattgaga gaacggcgga catttcctgg | 5280 |

```
gaaagtgatg cagaaattac aggctcgagc gaaagagttg atgtgcggct tgatgatgat    5340
ggaaacttcc agctcatgaa tgatccagga gcaccttgga agatatggat gctcagaatg    5400
gtctgtctcg cgattagtgc gtacaccccc tgggcaatct tgccctcagt agttggattt    5460
tggataactc tccaatacac aaagagagga ggcgtgttgt gggacactcc ctcaccaaag    5520
gagtacaaaa aggggacaca gaccaccggc gtctacagga tcatgactcg tgggctgctc    5580
ggcagttatc aagcaggagc gggcgtgatg gttgaaggtg ttttccacac cctttggcat    5640
acaacaaaag gagccgcttt gatgagcgga gagggccgcc tggacccata ctggggcagt    5700
gtcaaggagg atcgactttg ttacggagga ccctggaaat tgcagcacaa gtggaacggg    5760
caggatgagg tgcagatgat tgtggtggaa cctggcagga acgttaagaa cgtccagacg    5820
aaaccagggg tgttcaaaac acctgaagga gaaatcgggg ccgtgacttt ggacttcccc    5880 actgaacat caggctcacc aatagtggac aaaaacggtg atgtgattgg gctttatggc    5940
aatggagtca taatgcccaa cggctcatac ataagcgcga tagtgcaggg tgaaaggatg    6000
gatgagccaa tcccagccgg attcgaacct gagatgctga ggaaaaaaca gatcactgta    6060
ctggatctcc atcccggcgc cggtaaaaca aggaggattc tgccacagat catcaaagag    6120
gccataaaca gaagactgag aacagccgtg ctagcaccaa ccagggttgt ggctgctgag    6180
atggctgaag cactgagagg actgcccatc cggtaccaga catccgcagt gcccagagaa    6240
cataatggaa atgagattgt tgatgtcatg tgtcatgcta ccctcaccca caggctgatg    6300
tctcctcaca gggtgccgaa ctacaacctg ttcgtgatgg atgaggctca tttcaccgac    6360
ccagctagca ttgcagcaag aggttacatt tccacaaagg tcgagctagg ggaggcggcg    6420
gcaatattca tgacagccac cccaccaggc acttcagatc cattcccaga gtccaattca    6480
ccaatttccg acttcagac tgagatcccg gatcgagctt ggaactctgg atacgaatgg    6540
atcacagaat acaccgggaa gacggtttgg tttgtgccta gtgtcaagat ggggaatgag    6600
attgcccttt gcctacaacg tgctggaaag aaagtagtcc aattgaacag aaagtcgtac    6660
gagacggagt acccaaaatg taagaacgat gattgggact tgttatcac aacagacata    6720 tctgaaatgg gggctaactt caaggcgagc agggtgattg acagccggaa gagtgtgaaa    6780
ccaaccatca taacagaagg agaagggaga gtgatcctgg agaaccatc tgcagtgaca    6840 gcagctagtg ccgcccagag acgtggacgt atcggtagaa atccgtcgca agttggtgat    6900
gagtactgtt atgggggca cacgaatgaa gacgactcga acttcgccca ttggactgag    6960
gcacgaatca tgctggacaa catcaacatg ccaaacggac tgatcgctca attctaccaa    7020
ccagagcgtg agaaggtata taccatggat ggggaatacc ggctcagagg agaagagaga    7080
aaaaactttc tggaactgtt gaggactgca gatctgccag tttggctggc ttacaaggtt    7140
gcagcggctg gagtgtcata ccacgaccgg aggtggtgct tgatggtcc taggacaaac    7200 acaattttag aagacaacaa cgaagtgaa gtcatcacga agcttggtga aaggaagatt    7260
ctgaggccgc gctggattga cgccagggtg tactcggatc accaggcact aaaggcgttc    7320
aaggacttcg cctcgggaaa acgttctcag ataggctca ttgaggttct gggaaagatg    7380
cctgagcact tcatggggaa gacatgggaa gcacttgaca ccatgtacgt tgtggccact    7440
gcagagaaag gaggaagagc tcacagaatg gccctggagg aactgccaga tgctcttcag    7500
acaattgcct tgattgcctt attgagtgtg atgaccatgg gagtattctt cctcctcatg    7560
cagcggaagg gcattggaaa gataggtttg ggaggcgctg tcttgggagt cgcgaccttt    7620
ttctgttgga tggctgaagt tccaggaacg aagatcgccg gaatgttgct gctctccctt    7680
```

```
ctcttgatga ttgtgctaat tcctgagcca gagaagcaac gttcgcagac agacaaccag    7740
ctagccgtgt tcctgatttg tgtcatgacc cttgtgagcg cagtggcagc caacgagatg    7800
ggttggctag ataagaccaa gagtgacata agcagtttgt ttgggcaaag aattgaggtc    7860
aaggagaatt tcagcatggg agagtttctt ttggacttga ggcctgcaac agcctggtca    7920
ctgtacgctg tgacaacagc ggtcctcact ccactgctaa agcatttgat cacgtcagat    7980
tacatcaaca cctcattgac ctcaataaac gttcaggcaa gtgcactatt cacactcgcg    8040
cgaggcttcc ccttcgtcga tgttggagtg tcggctctcc tgctagcagc cggatgctgg    8100
ggacaagtca ccctcaccgt tacggtaaca gcggcaacac tcctttttg ccactatgcc     8160 tacatggttc ccggttggca agctgaggca atgcgctcag cccagcggcg gacagcggcc    8220
ggaatcatga agaacgctgt agtggatggc atcgtggcca cggacgtccc agaattagag    8280
cgcaccacac ccatcatgca gaagaaagtt ggacagatca tgctgatctt ggtgtctcta    8340
gctgcagtag tagtgaaccc gtctgtgaag acagtacgag aagccggaat tttgatcacg    8400
gccgcagcgg tgacgctttg ggagaatgga gcaagctctg tttggaacgc aacaactgcc    8460
atcggactct gccacatcat gcgtgggggt tggttgtcat gtctatccat aacatggaca    8520
ctcataaaga acatggaaaa accaggacta aaaagaggtg gggcaaaagg acgcaccttg    8580
ggagaggttt ggaaagaaag actcaaccag atgacaaaag aagagttcac taggtaccgc    8640
aaagaggcca tcatcgaagt cgatcgctca gcggcaaaac acgccaggaa agaaggcaat    8700
gtcactggag ggcatccagt ctctaggggc acagcaaaac tgagatggct ggtcgaacgg    8760
aggtttctcg aaccggtcgg aaaagtgatt gaccttggat gtggaagagg cggttggtgt    8820
tactatatgg caacccaaaa aagagtccaa gaagtcagag ggtacacaaa gggcggtccc    8880
ggacatgaag agccccaact agtgcaaagt tatggatgga acattgtcac catgaagagt    8940
ggagtggatg tgttctacag accttctgag tgttgtgaca ccctccttg tgacatcgga    9000 gagtcctcgt caagtgctga ggttgaagag cataggacga ttcgggtcct tgaaatggtt    9060
gaggactggc tgcaccgagg gccaagggaa ttttgcgtga aggtgctctg ccctacatg     9120 ccgaaagtca tagagaagat ggagctgctc caacgccggt atggggggg actggtcaga     9180 aacccactct cacggaattc cacgcacgag atgtattggg tgagtcgagc ttcaggcaat    9240
gtggtacatt cagtgaatat gaccagccag gtgctcctag gaagaatgga aaaaaggacc    9300
tggaagggac cccaatacga ggaagatgta aacttgggaa gtggaaccag ggcggtggga    9360
aaacccctgc tcaactcaga caccagtaaa atcaagaaca ggattgaacg actcaggcgt    9420
gagtacagtt cgacgtggca ccacgatgag aaccacccat atagaacctg gactatcac    9480 ggcagttatg atgtgaagcc cacaggctcc gccagttcgc tggtcaatgg agtggtcagg    9540
ctcctctcaa aaccatggga caccatcacg aatgttacca ccatggccat gactgacact    9600
actcccttcg ggcagcagcg agtgttcaaa gagaaggtgg acacgaaagc tcctgaaccg    9660
ccagaaggag tgaagtacgt gctcaacgag accaccaact ggttgtgggc gttttggcc    9720 agagaaaaac gtcccagaat gtgctctcga gaggaattca taagaaaggt caacagcaat    9780
gcagctttgg gtgccatgtt tgaagagcag aatcaatgga ggagcgccag agaagcagtt    9840
gaagatccaa aattttggga gatggtggat gaggagcgcg aggcacatct gcgggggaa     9900 tgtcacactt gcatttacaa catgatggga aagagagaga aaaacccgg agagttcgga     9960 aaggccaagg gaagcagagc catttggttc atgtggctcg gagctcgctt tctggagttc   10020
```

```
gaggctctgg gttttctcaa tgaagaccac tggcttggaa gaaagaactc aggaggaggt  10080
gtcgagggct tgggcctcca aaaactgggt tacatcctgc gtgaagttgg cacccggcct  10140
gggggcaaga tctatgctga tgacacagct ggctgggaca cccgcatcac gagagctgac  10200
ttggaaaatg aagctaaggt gcttgagctg cttgatgggg aacatcggcg tcttgccagg  10260
gccatcattg agctcaccta tcgtcacaaa gttgtgaaag tgatgcgccc ggctgctgat  10320
ggaagaaccg tcatggatgt tatctccaga gaagatcaga gggggagtgg acaagttgtc  10380
acctacgccc taaacacttt caccaacctg gccgtccagc tggtgaggat gatggaaggg  10440
gaaggagtga ttggcccaga tgatgtggag aaactcacaa aagggaaagg acccaaagtc  10500
aggacctggc tgtttgagaa tggggaagaa agactcagcc gcatggctgt cagtggagat  10560
gactgtgtgg taaagcccct ggacgatcgc tttgccacct cgctccactt cctcaatgct  10620
atgtcaaagg ttcgcaaaga catccaagag tggaaaccgt caactggatg gtatgattgg  10680
cagcaggttc cattttgctc aaaccatttc actgaattga tcatgaaaga tggaagaaca  10740
ctggtggttc catgccgagg acaggatgaa ttggtaggca gagctcgcat atctccaggg  10800
gccggatgga acgtccgcga cactgcttgt ctggctaagt cttatgccca gatgtggctg  10860
cttctgtact ccacagaag agacctgcgc ctcatggcca cgccatttg ctccgctgtc  10920
cctgtgaatt gggtccctac cggaagaacc acgtggtcca tcatgcagg aggagagtgg  10980
atgacaacag aggacatgtt ggaggtctgg aaccgtgttt ggatagagga gaatgaatgg  11040
atggaagaca aaaccccagt ggagaaatgg agtgacgtcc catattcagg aaaacgagag  11100
gacatctggt gtgcagcct gattggcaca agagcccgag ccacgtgggc agaaaacatc  11160
caggtggcta tcaaccaagt cagagcaatc atcggagatg agaagtatgt ggattacatg  11220
agttcactaa agagatatga agacacaact ttggttgagg acacagtact gtagatattt  11280
aatcaattgt aaatagacaa tataagtatg cataaaagtg tagttttata gtagtattta  11340
gtggtgttag tgtaaatagt taagaaaatt ttgaggagaa agtcaggccg ggaagttccc  11400
gccaccggaa gttgagtaga cggtgctgcc tgcgactcaa ccccaggagg actgggtgaa  11460
caaagccgcg aagtgatcca tgtaagccct cagaaccgtc tcggaaggag gaccccacat  11520
gttgtaactt caaagcccaa tgtcagacca cgctacggcg tgctactctg cggagagtgc  11580
agtctgcgat agtgccccag gaggactggg ttaacaaagg caaccaacg ccccacgcgg  11640
ccctagcccc ggtaatggtg ttaaccaggg cgaaaggact agaggttaga ggagaccccg  11700
cggtttaaag tgcacggccc agcctggctg aagctgtagg tcaggggaag gactagaggt  11760
tagtggagac cccgtgccac aaaacaccac aacaaaacag catattgaca cctgggatag  11820
actaggagat cttctgctct gcacaaccag ccacacggca cagtgcgccg acaatggtgg  11880
ctggtggtgc gagaacacag gatct                                         11905
```

<210> SEQ ID NO 12  
<211> LENGTH: 3725  
<212> TYPE: PRT  
<213> ORGANISM: Artificial Sequence  
<220> FEATURE:  
<223> OTHER INFORMATION: Synthetic polypeptide

<400> SEQUENCE: 12

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30
```

```
Ala Met Leu Met Ala Gln Ser Lys His Gly Leu Thr Lys Glu Met Thr
            35                  40                  45

Met Lys Tyr Arg Met Glu Gly Cys Val Asp Gly His Lys Phe Val Ile
 50                  55                  60

Thr Gly Glu Gly Ile Gly Tyr Pro Phe Lys Gly Lys Gln Ala Ile Asn
 65                  70                  75                  80

Leu Cys Val Val Glu Gly Gly Pro Leu Pro Phe Ala Glu Asp Ile Leu
                     85                  90                  95

Ser Ala Ala Phe Met Tyr Gly Asn Arg Val Phe Thr Glu Tyr Pro Gln
                100                 105                 110

Asp Ile Val Asp Tyr Phe Lys Asn Ser Cys Pro Ala Gly Tyr Thr Trp
            115                 120                 125

Asp Arg Ser Phe Leu Phe Glu Asp Gly Ala Val Cys Ile Cys Asn Ala
130                 135                 140

Asp Ile Thr Val Ser Val Glu Glu Asn Cys Met Tyr His Glu Ser Lys
145                 150                 155                 160

Phe Tyr Gly Val Asn Phe Pro Ala Asp Gly Pro Val Met Lys Lys Met
                165                 170                 175

Thr Asp Asn Trp Glu Pro Ser Cys Glu Lys Ile Ile Pro Val Pro Lys
            180                 185                 190

Gln Gly Ile Leu Lys Gly Asp Val Ser Met Tyr Leu Leu Leu Lys Asp
                195                 200                 205

Gly Gly Arg Leu Arg Cys Gln Phe Asp Thr Val Tyr Lys Ala Lys Ser
210                 215                 220

Val Pro Arg Lys Met Pro Asp Trp His Phe Ile Gln His Lys Leu Thr
225                 230                 235                 240

Arg Glu Asp Arg Ser Asp Ala Lys Asn Gln Lys Trp His Leu Thr Glu
                245                 250                 255

His Ala Ile Ala Ser Gly Ser Ala Leu Pro Gly Ser Gly Ala Thr Asn
            260                 265                 270

Phe Ser Leu Leu Lys Gln Ala Gly Asp Val Glu Glu Asn Pro Gly Pro
        275                 280                 285

Met Ser Lys Lys Pro Gly Gly Pro Gly Lys Ser Arg Ala Val Asn Met
    290                 295                 300

Leu Lys Arg Gly Met Pro Arg Val Leu Ser Leu Ile Gly Leu Lys Arg
305                 310                 315                 320

Ala Met Leu Ser Leu Ile Asp Gly Lys Gly Pro Ile Arg Phe Val Leu
                325                 330                 335

Ala Leu Leu Ala Phe Phe Arg Phe Thr Ala Ile Ala Pro Thr Arg Ala
            340                 345                 350

Val Leu Asp Arg Trp Arg Gly Val Asn Lys Gln Thr Ala Met Lys His
        355                 360                 365

Leu Leu Ser Phe Lys Lys Glu Leu Gly Thr Leu Thr Ser Ala Ile Asn
    370                 375                 380

Arg Arg Ser Ser Lys Gln Lys Lys Arg Gly Gly Lys Thr Gly Ile Ala
385                 390                 395                 400

Val Met Ile Gly Leu Ile Ala Ser Ala Met Ala Ala Glu Val Thr Arg
                405                 410                 415

Arg Gly Ser Ala Tyr Tyr Met Tyr Leu Asp Arg Asn Asp Ala Gly Glu
            420                 425                 430

Ala Ile Ser Phe Pro Thr Thr Leu Gly Met Asn Lys Cys Tyr Ile Gln
        435                 440                 445
```

```
Ile Met Asp Leu Gly His Met Cys Asp Ala Thr Met Ser Tyr Glu Cys
    450             455                 460

Pro Met Leu Asp Glu Gly Val Glu Pro Asp Asp Val Asp Cys Trp Cys
465             470                 475                 480

Asn Thr Thr Ser Thr Trp Val Val Tyr Gly Thr Cys His His Lys Lys
                485                 490                 495

Gly Glu Ala Arg Arg Ser Arg Arg Ala Val Thr Leu Pro Ser His Ser
            500                 505                 510

Thr Arg Lys Leu Gln Thr Arg Ser Gln Thr Trp Leu Glu Ser Arg Glu
            515                 520                 525

Tyr Thr Lys His Leu Ile Arg Val Glu Asn Trp Ile Phe Arg Asn Pro
530                 535                 540

Gly Phe Ala Leu Ala Ala Ala Ile Ala Trp Leu Leu Gly Ser Ser
545                 550                 555                 560

Thr Ser Gln Lys Val Ile Tyr Leu Val Met Ile Leu Leu Ile Ala Pro
                565                 570                 575

Ala Tyr Ser Ile Arg Cys Ile Gly Val Ser Asn Arg Asp Phe Val Glu
            580                 585                 590

Gly Met Ser Gly Gly Thr Trp Val Asp Ile Val Leu Glu His Gly Gly
            595                 600                 605

Cys Val Thr Val Met Ala Gln Asp Lys Pro Thr Val Asp Ile Glu Leu
            610                 615                 620

Val Thr Thr Thr Val Ser Asn Met Ala Glu Val Arg Ser Tyr Cys Tyr
625                 630                 635                 640

Glu Ala Ser Ile Ser Asp Met Ala Ser Asp Ser Arg Cys Pro Thr Gln
                645                 650                 655

Gly Glu Ala Tyr Leu Asp Lys Gln Ser Asp Thr Gln Tyr Val Cys Lys
            660                 665                 670

Arg Thr Leu Val Asp Arg Gly Trp Gly Asn Gly Cys Gly Leu Phe Gly
            675                 680                 685

Lys Gly Ser Leu Val Thr Cys Ala Lys Phe Ala Cys Ser Lys Lys Met
690                 695                 700

Thr Gly Lys Ser Ile Gln Pro Glu Asn Leu Glu Tyr Arg Ile Met Leu
705                 710                 715                 720

Ser Val His Gly Ser Gln His Ser Gly Met Ile Val Asn Asp Thr Gly
                725                 730                 735

His Glu Thr Asp Glu Asn Arg Ala Lys Val Glu Ile Thr Pro Asn Ser
            740                 745                 750

Pro Arg Ala Glu Ala Thr Leu Gly Gly Phe Gly Ser Leu Gly Leu Asp
            755                 760                 765

Cys Glu Pro Arg Thr Gly Leu Asp Phe Ser Asp Leu Tyr Tyr Leu Thr
770                 775                 780

Met Asn Asn Lys His Trp Leu Val His Lys Glu Trp Phe His Asp Ile
785                 790                 795                 800

Pro Leu Pro Trp His Ala Gly Ala Asp Thr Gly Thr Pro His Trp Asn
                805                 810                 815

Asn Lys Glu Ala Leu Val Glu Phe Lys Asp Ala His Ala Lys Arg Gln
            820                 825                 830

Thr Val Val Val Leu Gly Ser Gln Glu Gly Ala Val His Thr Ala Leu
            835                 840                 845

Ala Gly Ala Leu Glu Ala Glu Met Asp Gly Ala Lys Gly Arg Leu Ser
850                 855                 860

Ser Gly His Leu Lys Cys Arg Leu Lys Met Asp Lys Leu Arg Leu Lys
```

```
                865                 870                 875                 880
        Gly Val Ser Tyr Ser Leu Cys Thr Ala Ala Phe Thr Phe Thr Lys Ile
                        885                 890                 895
        Pro Ala Glu Thr Leu His Gly Thr Val Thr Glu Val Gln Tyr Ala
                        900                 905                 910
        Gly Thr Asp Gly Pro Cys Lys Val Pro Ala Gln Met Ala Val Asp Met
                        915                 920                 925
        Gln Thr Leu Thr Pro Val Gly Arg Leu Ile Thr Ala Asn Pro Val Ile
                930                 935                 940
        Thr Glu Ser Thr Glu Asn Ser Lys Met Met Leu Glu Leu Asp Pro Pro
        945                 950                 955                 960
        Phe Gly Asp Ser Tyr Ile Val Ile Gly Val Gly Glu Lys Lys Ile Thr
                        965                 970                 975
        His His Trp His Arg Ser Gly Ser Thr Ile Gly Lys Ala Phe Glu Ala
                        980                 985                 990
        Thr Val Arg Gly Ala Lys Arg Met Ala Val Leu Gly Asp Thr Ala Trp
                        995                 1000                1005
        Asp Phe Gly Ser Val Gly Gly Ala Leu Asn Ser Leu Gly Lys Gly
                1010                1015                1020
        Ile His Gln Ile Phe Gly Ala Ala Phe Lys Ser Leu Phe Gly Gly
                1025                1030                1035
        Met Ser Trp Phe Ser Gln Ile Leu Ile Gly Thr Leu Leu Met Trp
                1040                1045                1050
        Leu Gly Leu Asn Thr Lys Asn Gly Ser Ile Ser Leu Met Cys Leu
                1055                1060                1065
        Ala Leu Gly Gly Val Leu Ile Phe Leu Ser Thr Ala Val Ser Ala
                1070                1075                1080
        Asp Ser Gly Cys Ala Ile Asp Ile Ser Arg Gln Glu Leu Arg Cys
                1085                1090                1095
        Gly Ser Gly Val Phe Ile His Asn Asp Val Glu Ala Trp Met Asp
                1100                1105                1110
        Arg Tyr Lys Tyr Tyr Pro Glu Thr Pro Gln Gly Leu Ala Lys Ile
                1115                1120                1125
        Ile Gln Lys Ala His Lys Glu Gly Val Cys Gly Leu Arg Ser Val
                1130                1135                1140
        Ser Arg Leu Glu His Gln Met Trp Glu Ala Val Lys Asp Glu Leu
                1145                1150                1155
        Asn Thr Leu Leu Lys Glu Asn Gly Val Asp Leu Ser Val Val Val
                1160                1165                1170
        Glu Lys Gln Glu Gly Met Tyr Lys Ser Ala Pro Lys Arg Leu Thr
                1175                1180                1185
        Ala Thr Thr Glu Lys Leu Glu Ile Gly Trp Lys Ala Trp Gly Lys
                1190                1195                1200
        Ser Ile Leu Phe Ala Pro Glu Leu Ala Asn Asn Thr Phe Val Val
                1205                1210                1215
        Asp Gly Pro Glu Thr Lys Glu Cys Pro Thr Gln Asn Arg Ala Trp
                1220                1225                1230
        Asn Ser Leu Glu Val Glu Asp Phe Gly Phe Gly Leu Thr Ser Thr
                1235                1240                1245
        Arg Met Phe Leu Lys Val Arg Glu Ser Asn Thr Thr Glu Cys Asp
                1250                1255                1260
        Ser Lys Ile Ile Gly Thr Ala Val Lys Asn Asn Leu Ala Ile His
                1265                1270                1275
```

-continued

```
Ser Asp Leu Ser Tyr Trp Ile Glu Ser Arg Leu Asn Asp Thr Trp
    1280            1285            1290

Lys Leu Glu Arg Ala Val Leu Gly Glu Val Lys Ser Cys Thr Trp
    1295            1300            1305

Pro Glu Thr His Thr Leu Trp Gly Asp Gly Ile Leu Glu Ser Asp
    1310            1315            1320

Leu Ile Ile Pro Val Thr Leu Ala Gly Pro Arg Ser Asn His Asn
    1325            1330            1335

Arg Arg Pro Gly Tyr Lys Thr Gln Asn Gln Gly Pro Trp Asp Glu
    1340            1345            1350

Gly Arg Val Glu Ile Asp Phe Asp Tyr Cys Pro Gly Thr Thr Val
    1355            1360            1365

Thr Leu Ser Glu Ser Cys Gly His Arg Gly Pro Ala Thr Arg Thr
    1370            1375            1380

Thr Thr Glu Ser Gly Lys Leu Ile Thr Asp Trp Cys Cys Arg Ser
    1385            1390            1395

Cys Thr Leu Pro Pro Leu Arg Tyr Gln Thr Asp Ser Gly Cys Trp
    1400            1405            1410

Tyr Gly Met Glu Ile Arg Pro Gln Arg His Asp Glu Lys Thr Leu
    1415            1420            1425

Val Gln Ser Gln Val Asn Ala Tyr Asn Ala Asp Met Ile Asp Pro
    1430            1435            1440

Phe Gln Leu Gly Leu Leu Val Val Phe Leu Ala Thr Gln Glu Val
    1445            1450            1455

Leu Arg Lys Arg Trp Thr Ala Lys Ile Ser Met Pro Ala Ile Leu
    1460            1465            1470

Ile Ala Leu Leu Val Leu Val Phe Gly Gly Ile Thr Tyr Thr Asp
    1475            1480            1485

Val Leu Arg Tyr Val Ile Leu Val Gly Ala Ala Phe Ala Glu Ser
    1490            1495            1500

Asn Ser Gly Gly Asp Val Val His Leu Ala Leu Met Ala Thr Phe
    1505            1510            1515

Lys Ile Gln Pro Val Phe Met Val Ala Ser Phe Leu Lys Ala Arg
    1520            1525            1530

Trp Thr Asn Gln Glu Asn Ile Leu Leu Met Leu Ala Ala Val Phe
    1535            1540            1545

Phe Gln Met Ala Tyr Tyr Asp Ala Arg Gln Ile Leu Leu Trp Glu
    1550            1555            1560

Ile Pro Asp Val Leu Asn Ser Leu Ala Val Ala Trp Met Ile Leu
    1565            1570            1575

Arg Ala Ile Thr Phe Thr Thr Thr Ser Asn Val Val Val Pro Leu
    1580            1585            1590

Leu Ala Leu Leu Thr Pro Gly Leu Arg Cys Leu Asn Leu Asp Val
    1595            1600            1605

Tyr Arg Ile Leu Leu Leu Met Val Gly Ile Gly Ser Leu Ile Arg
    1610            1615            1620

Glu Lys Arg Ser Ala Ala Ala Lys Lys Lys Gly Ala Ser Leu Leu
    1625            1630            1635

Cys Leu Ala Leu Ala Ser Thr Gly Leu Phe Asn Pro Met Ile Leu
    1640            1645            1650

Ala Ala Gly Leu Ile Ala Cys Asp Pro Asn Arg Lys Arg Gly Trp
    1655            1660            1665
```

```
Pro Ala Thr Glu Val Met Thr Ala Val Gly Leu Met Phe Ala Ile
    1670            1675                1680

Val Gly Gly Leu Ala Glu Leu Asp Ile Asp Ser Met Ala Ile Pro
    1685            1690                1695

Met Thr Ile Ala Gly Leu Met Phe Ala Ala Phe Val Ile Ser Gly
    1700            1705                1710

Lys Ser Thr Asp Met Trp Ile Glu Arg Thr Ala Asp Ile Ser Trp
    1715            1720                1725

Glu Ser Asp Ala Glu Ile Thr Gly Ser Ser Glu Arg Val Asp Val
    1730            1735                1740

Arg Leu Asp Asp Asp Gly Asn Phe Gln Leu Met Asn Asp Pro Gly
    1745            1750                1755

Ala Pro Trp Lys Ile Trp Met Leu Arg Met Val Cys Leu Ala Ile
    1760            1765                1770

Ser Ala Tyr Thr Pro Trp Ala Ile Leu Pro Ser Val Val Gly Phe
    1775            1780                1785

Trp Ile Thr Leu Gln Tyr Thr Lys Arg Gly Gly Val Leu Trp Asp
    1790            1795                1800

Thr Pro Ser Pro Lys Glu Tyr Lys Lys Gly Asp Thr Thr Thr Gly
    1805            1810                1815

Val Tyr Arg Ile Met Thr Arg Gly Leu Leu Gly Ser Tyr Gln Ala
    1820            1825                1830

Gly Ala Gly Val Met Val Glu Gly Val Phe His Thr Leu Trp His
    1835            1840                1845

Thr Thr Lys Gly Ala Ala Leu Met Ser Gly Glu Gly Arg Leu Asp
    1850            1855                1860

Pro Tyr Trp Gly Ser Val Lys Glu Asp Arg Leu Cys Tyr Gly Gly
    1865            1870                1875

Pro Trp Lys Leu Gln His Lys Trp Asn Gly Gln Asp Glu Val Gln
    1880            1885                1890

Met Ile Val Val Glu Pro Gly Arg Asn Val Lys Asn Val Gln Thr
    1895            1900                1905

Lys Pro Gly Val Phe Lys Thr Pro Glu Gly Glu Ile Gly Ala Val
    1910            1915                1920

Thr Leu Asp Phe Pro Thr Gly Thr Ser Gly Ser Pro Ile Val Asp
    1925            1930                1935

Lys Asn Gly Asp Val Ile Gly Leu Tyr Gly Asn Gly Val Ile Met
    1940            1945                1950

Pro Asn Gly Ser Tyr Ile Ser Ala Ile Val Gln Gly Glu Arg Met
    1955            1960                1965

Asp Glu Pro Ile Pro Ala Gly Phe Glu Pro Glu Met Leu Arg Lys
    1970            1975                1980

Lys Gln Ile Thr Val Leu Asp Leu His Pro Gly Ala Gly Lys Thr
    1985            1990                1995

Arg Arg Ile Leu Pro Gln Ile Ile Lys Glu Ala Ile Asn Arg Arg
    2000            2005                2010

Leu Arg Thr Ala Val Leu Ala Pro Thr Arg Val Val Ala Ala Glu
    2015            2020                2025

Met Ala Glu Ala Leu Arg Gly Leu Pro Ile Arg Tyr Gln Thr Ser
    2030            2035                2040

Ala Val Pro Arg Glu His Asn Gly Asn Glu Ile Val Asp Val Met
    2045            2050                2055

Cys His Ala Thr Leu Thr His Arg Leu Met Ser Pro His Arg Val
```

```
                    2060                2065                2070

Pro Asn Tyr Asn Leu Phe Val Met Asp Glu Ala His Phe Thr Asp
            2075                2080                2085

Pro Ala Ser Ile Ala Ala Arg Gly Tyr Ile Ser Thr Lys Val Glu
            2090                2095                2100

Leu Gly Glu Ala Ala Ala Ile Phe Met Thr Ala Thr Pro Pro Gly
            2105                2110                2115

Thr Ser Asp Pro Phe Pro Glu Ser Asn Ser Pro Ile Ser Asp Leu
            2120                2125                2130

Gln Thr Glu Ile Pro Asp Arg Ala Trp Asn Ser Gly Tyr Glu Trp
            2135                2140                2145

Ile Thr Glu Tyr Thr Gly Lys Thr Val Trp Phe Val Pro Ser Val
            2150                2155                2160

Lys Met Gly Asn Glu Ile Ala Leu Cys Leu Gln Arg Ala Gly Lys
            2165                2170                2175

Lys Val Val Gln Leu Asn Arg Lys Ser Tyr Glu Thr Glu Tyr Pro
            2180                2185                2190

Lys Cys Lys Asn Asp Asp Trp Asp Phe Val Ile Thr Thr Asp Ile
            2195                2200                2205

Ser Glu Met Gly Ala Asn Phe Lys Ala Ser Arg Val Ile Asp Ser
            2210                2215                2220

Arg Lys Ser Val Lys Pro Thr Ile Ile Thr Glu Gly Glu Gly Arg
            2225                2230                2235

Val Ile Leu Gly Glu Pro Ser Ala Val Thr Ala Ala Ser Ala Ala
            2240                2245                2250

Gln Arg Arg Gly Arg Ile Gly Arg Asn Pro Ser Gln Val Gly Asp
            2255                2260                2265

Glu Tyr Cys Tyr Gly Gly His Thr Asn Glu Asp Asp Ser Asn Phe
            2270                2275                2280

Ala His Trp Thr Glu Ala Arg Ile Met Leu Asp Asn Ile Asn Met
            2285                2290                2295

Pro Asn Gly Leu Ile Ala Gln Phe Tyr Gln Pro Glu Arg Glu Lys
            2300                2305                2310

Val Tyr Thr Met Asp Gly Glu Tyr Arg Leu Arg Gly Glu Glu Arg
            2315                2320                2325

Lys Asn Phe Leu Glu Leu Leu Arg Thr Ala Asp Leu Pro Val Trp
            2330                2335                2340

Leu Ala Tyr Lys Val Ala Ala Ala Gly Val Ser Tyr His Asp Arg
            2345                2350                2355

Arg Trp Cys Phe Asp Gly Pro Arg Thr Asn Thr Ile Leu Glu Asp
            2360                2365                2370

Asn Asn Glu Val Glu Val Ile Thr Lys Leu Gly Glu Arg Lys Ile
            2375                2380                2385

Leu Arg Pro Arg Trp Ile Asp Ala Arg Val Tyr Ser Asp His Gln
            2390                2395                2400

Ala Leu Lys Ala Phe Lys Asp Phe Ala Ser Gly Lys Arg Ser Gln
            2405                2410                2415

Ile Gly Leu Ile Glu Val Leu Gly Lys Met Pro Glu His Phe Met
            2420                2425                2430

Gly Lys Thr Trp Glu Ala Leu Asp Thr Met Tyr Val Val Ala Thr
            2435                2440                2445

Ala Glu Lys Gly Gly Arg Ala His Arg Met Ala Leu Glu Glu Leu
            2450                2455                2460
```

```
Pro Asp Ala Leu Gln Thr Ile Ala Leu Ile Ala Leu Leu Ser Val
    2465                2470                2475

Met Thr Met Gly Val Phe Phe Leu Leu Met Gln Arg Lys Gly Ile
    2480                2485                2490

Gly Lys Ile Gly Leu Gly Gly Ala Val Leu Gly Val Ala Thr Phe
    2495                2500                2505

Phe Cys Trp Met Ala Glu Val Pro Gly Thr Lys Ile Ala Gly Met
    2510                2515                2520

Leu Leu Leu Ser Leu Leu Leu Met Ile Val Leu Ile Pro Glu Pro
    2525                2530                2535

Glu Lys Gln Arg Ser Gln Thr Asp Asn Gln Leu Ala Val Phe Leu
    2540                2545                2550

Ile Cys Val Met Thr Leu Val Ser Ala Val Ala Ala Asn Glu Met
    2555                2560                2565

Gly Trp Leu Asp Lys Thr Lys Ser Asp Ile Ser Ser Leu Phe Gly
    2570                2575                2580

Gln Arg Ile Glu Val Lys Glu Asn Phe Ser Met Gly Glu Phe Leu
    2585                2590                2595

Leu Asp Leu Arg Pro Ala Thr Ala Trp Ser Leu Tyr Ala Val Thr
    2600                2605                2610

Thr Ala Val Leu Thr Pro Leu Leu Lys His Leu Ile Thr Ser Asp
    2615                2620                2625

Tyr Ile Asn Thr Ser Leu Thr Ser Ile Asn Val Gln Ala Ser Ala
    2630                2635                2640

Leu Phe Thr Leu Ala Arg Gly Phe Pro Phe Val Asp Val Gly Val
    2645                2650                2655

Ser Ala Leu Leu Leu Ala Ala Gly Cys Trp Gly Gln Val Thr Leu
    2660                2665                2670

Thr Val Thr Val Thr Ala Ala Thr Leu Leu Phe Cys His Tyr Ala
    2675                2680                2685

Tyr Met Val Pro Gly Trp Gln Ala Glu Ala Met Arg Ser Ala Gln
    2690                2695                2700

Arg Arg Thr Ala Ala Gly Ile Met Lys Asn Ala Val Val Asp Gly
    2705                2710                2715

Ile Val Ala Thr Asp Val Pro Glu Leu Glu Arg Thr Thr Pro Ile
    2720                2725                2730

Met Gln Lys Lys Val Gly Gln Ile Met Leu Ile Leu Val Ser Leu
    2735                2740                2745

Ala Ala Val Val Val Asn Pro Ser Val Lys Thr Val Arg Glu Ala
    2750                2755                2760

Gly Ile Leu Ile Thr Ala Ala Ala Val Thr Leu Trp Glu Asn Gly
    2765                2770                2775

Ala Ser Ser Val Trp Asn Ala Thr Thr Ala Ile Gly Leu Cys His
    2780                2785                2790

Ile Met Arg Gly Gly Trp Leu Ser Cys Leu Ser Ile Thr Trp Thr
    2795                2800                2805

Leu Ile Lys Asn Met Glu Lys Pro Gly Leu Lys Arg Gly Gly Ala
    2810                2815                2820

Lys Gly Arg Thr Leu Gly Glu Val Trp Lys Glu Arg Leu Asn Gln
    2825                2830                2835

Met Thr Lys Glu Glu Phe Thr Arg Tyr Arg Lys Glu Ala Ile Ile
    2840                2845                2850
```

-continued

| | | | | | | | | | | |
|---|---|---|---|---|---|---|---|---|---|---|
|Glu|Val|Asp|Arg|Ser|Ala|Ala|Lys|His|Ala|Arg|Lys|Glu|Gly|Asn|
|2855| | | | |2860| | | | |2865| | | | |

Val Thr Gly Gly His Pro Val Ser Arg Gly Thr Ala Lys Leu Arg
2870               2875                   2880

Trp Leu Val Glu Arg Arg Phe Leu Glu Pro Val Gly Lys Val Ile
2885               2890                   2895

Asp Leu Gly Cys Gly Arg Gly Gly Trp Cys Tyr Tyr Met Ala Thr
2900               2905                   2910

Gln Lys Arg Val Gln Glu Val Arg Gly Tyr Thr Lys Gly Gly Pro
2915               2920                   2925

Gly His Glu Glu Pro Gln Leu Val Gln Ser Tyr Gly Trp Asn Ile
2930               2935                   2940

Val Thr Met Lys Ser Gly Val Asp Val Phe Tyr Arg Pro Ser Glu
2945               2950                   2955

Cys Cys Asp Thr Leu Leu Cys Asp Ile Gly Glu Ser Ser Ser Ser
2960               2965                   2970

Ala Glu Val Glu Glu His Arg Thr Ile Arg Val Leu Glu Met Val
2975               2980                   2985

Glu Asp Trp Leu His Arg Gly Pro Arg Glu Phe Cys Val Lys Val
2990               2995                   3000

Leu Cys Pro Tyr Met Pro Lys Val Ile Glu Lys Met Glu Leu Leu
3005               3010                   3015

Gln Arg Arg Tyr Gly Gly Gly Leu Val Arg Asn Pro Leu Ser Arg
3020               3025                   3030

Asn Ser Thr His Glu Met Tyr Trp Val Ser Arg Ala Ser Gly Asn
3035               3040                   3045

Val Val His Ser Val Asn Met Thr Ser Gln Val Leu Leu Gly Arg
3050               3055                   3060

Met Glu Lys Arg Thr Trp Lys Gly Pro Gln Tyr Glu Glu Asp Val
3065               3070                   3075

Asn Leu Gly Ser Gly Thr Arg Ala Val Gly Lys Pro Leu Leu Asn
3080               3085                   3090

Ser Asp Thr Ser Lys Ile Lys Asn Arg Ile Glu Arg Leu Arg Arg
3095               3100                   3105

Glu Tyr Ser Ser Thr Trp His His Asp Glu Asn His Pro Tyr Arg
3110               3115                   3120

Thr Trp Asn Tyr His Gly Ser Tyr Asp Val Lys Pro Thr Gly Ser
3125               3130                   3135

Ala Ser Ser Leu Val Asn Gly Val Val Arg Leu Leu Ser Lys Pro
3140               3145                   3150

Trp Asp Thr Ile Thr Asn Val Thr Thr Met Ala Met Thr Asp Thr
3155               3160                   3165

Thr Pro Phe Gly Gln Gln Arg Val Phe Lys Glu Lys Val Asp Thr
3170               3175                   3180

Lys Ala Pro Glu Pro Pro Glu Gly Val Lys Tyr Val Leu Asn Glu
3185               3190                   3195

Thr Thr Asn Trp Leu Trp Ala Phe Leu Ala Arg Glu Lys Arg Pro
3200               3205                   3210

Arg Met Cys Ser Arg Glu Glu Phe Ile Arg Lys Val Asn Ser Asn
3215               3220                   3225

Ala Ala Leu Gly Ala Met Phe Glu Glu Gln Asn Gln Trp Arg Ser
3230               3235                   3240

Ala Arg Glu Ala Val Glu Asp Pro Lys Phe Trp Glu Met Val Asp

```
              3245                3250                3255
Glu  Glu  Arg  Glu  Ala  His  Leu  Arg  Gly  Glu  Cys  His  Thr  Cys  Ile
              3260                3265                3270
Tyr  Asn  Met  Met  Gly  Lys  Arg  Glu  Lys  Lys  Pro  Gly  Glu  Phe  Gly
              3275                3280                3285
Lys  Ala  Lys  Gly  Ser  Arg  Ala  Ile  Trp  Phe  Met  Trp  Leu  Gly  Ala
              3290                3295                3300
Arg  Phe  Leu  Glu  Phe  Glu  Ala  Leu  Gly  Phe  Leu  Asn  Glu  Asp  His
              3305                3310                3315
Trp  Leu  Gly  Arg  Lys  Asn  Ser  Gly  Gly  Gly  Val  Glu  Gly  Leu  Gly
              3320                3325                3330
Leu  Gln  Lys  Leu  Gly  Tyr  Ile  Leu  Arg  Glu  Val  Gly  Thr  Arg  Pro
              3335                3340                3345
Gly  Gly  Lys  Ile  Tyr  Ala  Asp  Asp  Thr  Ala  Gly  Trp  Asp  Thr  Arg
              3350                3355                3360
Ile  Thr  Arg  Ala  Asp  Leu  Glu  Asn  Glu  Ala  Lys  Val  Leu  Glu  Leu
              3365                3370                3375
Leu  Asp  Gly  Glu  His  Arg  Arg  Leu  Ala  Arg  Ala  Ile  Ile  Glu  Leu
              3380                3385                3390
Thr  Tyr  Arg  His  Lys  Val  Val  Lys  Val  Met  Arg  Pro  Ala  Ala  Asp
              3395                3400                3405
Gly  Arg  Thr  Val  Met  Asp  Val  Ile  Ser  Arg  Glu  Asp  Gln  Arg  Gly
              3410                3415                3420
Ser  Gly  Gln  Val  Val  Thr  Tyr  Ala  Leu  Asn  Thr  Phe  Thr  Asn  Leu
              3425                3430                3435
Ala  Val  Gln  Leu  Val  Arg  Met  Met  Glu  Gly  Glu  Gly  Val  Ile  Gly
              3440                3445                3450
Pro  Asp  Asp  Val  Glu  Lys  Leu  Thr  Lys  Gly  Lys  Gly  Pro  Lys  Val
              3455                3460                3465
Arg  Thr  Trp  Leu  Phe  Glu  Asn  Gly  Glu  Glu  Arg  Leu  Ser  Arg  Met
              3470                3475                3480
Ala  Val  Ser  Gly  Asp  Asp  Cys  Val  Val  Lys  Pro  Leu  Asp  Asp  Arg
              3485                3490                3495
Phe  Ala  Thr  Ser  Leu  His  Phe  Leu  Asn  Ala  Met  Ser  Lys  Val  Arg
              3500                3505                3510
Lys  Asp  Ile  Gln  Glu  Trp  Lys  Pro  Ser  Thr  Gly  Trp  Tyr  Asp  Trp
              3515                3520                3525
Gln  Gln  Val  Pro  Phe  Cys  Ser  Asn  His  Phe  Thr  Glu  Leu  Ile  Met
              3530                3535                3540
Lys  Asp  Gly  Arg  Thr  Leu  Val  Val  Pro  Cys  Arg  Gly  Gln  Asp  Glu
              3545                3550                3555
Leu  Val  Gly  Arg  Ala  Arg  Ile  Ser  Pro  Gly  Ala  Gly  Trp  Asn  Val
              3560                3565                3570
Arg  Asp  Thr  Ala  Cys  Leu  Ala  Lys  Ser  Tyr  Ala  Gln  Met  Trp  Leu
              3575                3580                3585
Leu  Leu  Tyr  Phe  His  Arg  Arg  Asp  Leu  Arg  Leu  Met  Ala  Asn  Ala
              3590                3595                3600
Ile  Cys  Ser  Ala  Val  Pro  Val  Asn  Trp  Val  Pro  Thr  Gly  Arg  Thr
              3605                3610                3615
Thr  Trp  Ser  Ile  His  Ala  Gly  Gly  Glu  Trp  Met  Thr  Thr  Glu  Asp
              3620                3625                3630
Met  Leu  Glu  Val  Trp  Asn  Arg  Val  Trp  Ile  Glu  Glu  Asn  Glu  Trp
              3635                3640                3645
```

```
Met Glu Asp Lys Thr Pro Val Glu Lys Trp Ser Asp Val Pro Tyr
    3650                3655                3660

Ser Gly Lys Arg Glu Asp Ile Trp Cys Gly Ser Leu Ile Gly Thr
    3665                3670                3675

Arg Ala Arg Ala Thr Trp Ala Glu Asn Ile Gln Val Ala Ile Asn
    3680                3685                3690

Gln Val Arg Ala Ile Ile Gly Asp Glu Lys Tyr Val Asp Tyr Met
    3695                3700                3705

Ser Ser Leu Lys Arg Tyr Glu Asp Thr Thr Leu Val Glu Asp Thr
    3710                3715                3720

Val Leu
    3725

<210> SEQ ID NO 13
<211> LENGTH: 10807
<212> TYPE: DNA
<213> ORGANISM: Zika virus strain R103451

<400> SEQUENCE: 13
```

| | | | | | |
|---|---|---|---|---|---|
| agttgttgat | ctgtgtgaat | cagactgcga | cagttcgagt | ttgaagcgaa | agctagcaac | 60 |
| agtatcaaca | ggttttattt | tggatttgga | acgagagtt | tctggtcatg | aaaaacccaa | 120 |
| aaaagaaatc | cggaggattc | cggattgtca | atatgctaaa | acgcggagta | gcccgtgtga | 180 |
| gccccttttgg | gggcttgaag | aggctgccag | ccggacttct | gctgggtcat | gggcccatca | 240 |
| ggatggtctt | ggcgattcta | gcctttttga | gattcacggc | aatcaagcca | tcactgggtc | 300 |
| tcatcaatag | atggggttca | gtggggaaaa | agaggctat | ggaaataata | aagaagttca | 360 |
| agaaagatct | ggctgccatg | ctgagaataa | tcaatgctag | aaggagaag | aagagacgag | 420 |
| gcgcagatac | tagtgtcgga | attgttggcc | tcctgctgac | cacagctatg | gcagcggagg | 480 |
| tcactagacg | tgggagtgca | tactatatgt | acttggacag | aaacgatgct | ggggaggcca | 540 |
| tatcttttcc | aaccacattg | gggatgaata | agtgttatat | acagatcatg | gatcttggac | 600 |
| acatgtgtga | tgccaccatg | agctatgaat | gccctatgct | ggatgagggg | gtggaaccag | 660 |
| atgacgtcga | ttgttggtgc | aacacgacgt | caacttgggt | tgtgtacgga | acctgccatc | 720 |
| acaaaaaagg | tgaagcacgg | agatctagaa | gagctgtgac | gctcccctcc | cattccacta | 780 |
| ggaagctgca | aacgcggtcg | caaacctggt | tggaatcaag | agaatacaca | aagcacttga | 840 |
| ttagagtcga | aaattggata | ttcaggaacc | ctggcttcgc | gttagcagca | gctgccatcg | 900 |
| cttggctttt | gggaagctca | acgagccaaa | aagtcatata | cttggtcatg | atactgctga | 960 |
| ttgccccggc | atacagcatc | aggtgcatag | gagtcagcaa | tagggacttt | gtggaaggta | 1020 |
| tgtcaggtgg | gacttgggtt | gatgttgtct | tggaacatgg | aggttgtgtc | accgtaatgg | 1080 |
| cacaggacaa | accgactgtc | gacatagagc | tggttacaac | aacagtcagc | aacatggcgg | 1140 |
| aggtaagatc | ctactgctat | gaggcatcaa | tatcagacat | ggcttcggac | agccgctgcc | 1200 |
| caacacaagg | tgaagcctac | cttgacaagc | aatcagacac | tcaatatgtc | tgcaaaagaa | 1260 |
| cgttagtgga | cagaggctgg | ggaaatggat | gtggactttt | tggcaaaggg | agcctggtga | 1320 |
| catgcgctaa | gtttgcatgc | tccaagaaaa | tgaccgggaa | gagcatccag | ccagagaatc | 1380 |
| tggagtaccg | gataatgctg | tcagttcatg | gctcccagca | cagtgggatg | atcgttaatg | 1440 |
| acacaggaca | tgaaactgat | gagaatagag | cgaaggtgga | gataacgccc | aattcaccaa | 1500 |
| gagccgaagc | caccctgggg | ggttttgaa | gcctaggact | tgattgtgaa | ccgaggacag | 1560 |

```
gccttgactt ttcagatttg tattacttga ctatgaataa caagcactgg ttggttcaca    1620
aggagtggtt ccacgacatt ccattacctt ggcacgctgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
ctgagatgga tggtgcaaag ggaaggctgt cctctggcca cttgaaatgt cgcctgaaaa    1860
tggataaact tagattgaag ggcgtgtcat actccttgtg taccgcagcg ttcacattca    1920
ccaagatccc ggctgaaaca ctgcacggga cagtcacagt ggaggtacag tacgcaggga    1980
cagatggacc ttgcaaggtt ccagctcaga tggcggtgga catgcaaact ctgaccccag    2040
ttgggaggtt gataaccgct aaccccgtaa tcactgaaag cactgagaac tctaagatga    2100
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caagagaatg gcagtcttgg gagacacagc ctgggactttggatcagttg    2280 gaggcgctct caactcattg ggcaagggca tccatcaaat ttttggagca gctttcaaat    2340
cattgttggg aggaatgtcc tggttctcac aaattctcat tggaacgttg ctgatgtggt    2400
tgggtctgaa cacaaagaat ggatctattt cccttatgtg cttggcctta ggggagtgt    2460 tgatcttctt atccacagcc gtctctgctg atgtggggtg ctcggtggac ttctcaaaga    2520
aggagacgag atgcggtaca ggggtgttcg tctataacga cgttgaagcc tggagggaca    2580
ggtacaagta ccatcctgac tcccccgta gattggcagc agcagtcaag caagcctggg    2640
aagatggtat ctgcgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagagctc acagagatt gcccgtgcct gtgaacgagc    2820
tgccccacgg ctggaaggct tgggggaaat cgtacttcgt cagagcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcatta gagtgtgatc cagccgttat ggaacagct gttaagggaa    3060 aggaggctgt acacagtgat ctaggctact ggattgagag tgagaagaat gacacatgga    3120
ggctgaagag ggcccatctg atcgagatga aacatgtga atggccaaag tcccacacat    3180
tgtggacaga tggaatagaa gagagtgatc tgatcatacc caagtcttta gctgggccac    3240
tcagccatca caataccaga gagggctaca ggacccaaat gaaagggcca tggcacagtg    3300
aagagcttga aattcggttt gaggaatgcc caggcactaa ggtccacgtg gaggaaacat    3360
gtggaacaag gaccatctct gagatcaa ccactgcaag cggaagggtg atcgaggaat    3420
ggtgctgcag ggagtgcaca atgcccccac tgtcgttccg ggctaaagat ggctgttggt    3480
atggaatgga gataaggccc aggaaagaac cagaaagcaa cttagtaagg tcaatggtga    3540
ctgcaggatc aactgatcac atggatcact tctcccttgg agtgcttgtg attctgctca    3600
tggtgcagga agggctaaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctactggcct tggcctcgtg tcttttgcaa actgcgatct    3900
ccgccttgga aggcgacctg atggttctca tcaatggttt tgctttggcc tggttggcaa    3960
```

```
tacgagcgat ggttgttcca cgcactgata acatcacctt ggcaatcctg ctgctctga      4020 caccactggc ccggggcaca ctgcttgtgg cgtggagagc aggccttgct acttgcgggg     4080
ggtttatgct cctctctctg aagggaaaag gcagtgtgaa gaagaactta ccatttgtca     4140
tggccctggg actaaccgct gtgaggctgg tcgaccccat caacgtggtg ggactgctgt     4200
tgctcacaag gagtgggaag cggagctggc cccctagcga agtactcaca gctgttggcc     4260
tgatatgcgc attggctgga ggttcgcca aggcagatat agagatggct gggcccatgg      4320
ccgcggtcgg tctgctaatt gtcagttacg tggtctcagg aaagagtgtg gacatgtaca     4380
ttgaaagagc aggtgacatc acatgggaaa aagatgcgga agtcactgga aacagtcccc    4440
ggctcgatgt ggcgctagat gagagtggtg atttctccct ggtggaggat gacggtcccc    4500
ccatgagaga gatcatactc aaggtggtcc tgatgaccat ctgtggcatg aacccaatag    4560
ccataccctt cgcagctgga gcgtggtacg tatacgtgaa gactggaaaa aggagtggtg    4620
ctctatggga tgtgcctgct cccaaggaag taaaaaggg ggagaccaca gatggagtgt     4680
acagagtaat gactcgtaga ctgctaggtt caacacaagt tggagtggga gttatgcaag    4740 aggggtctt tcacactatg tggcacgtca caaaaggatc cgcactgaga agcggtgaag     4800
ggagacttga tccatactgg ggagatgtca agcaggatct ggtgtcatac tgtggtccat    4860
ggaagctaga tgccgcctgg gacgggcaca gcgaggtgca gctcttggcc gtgcccccg     4920 gagagagagc gaggaacatc cagactctgc ccggaatatt aagacaaag gatggggaca     4980 ttggagcggt tgcgctggat tacccagcag gaacttcagg atctccaatc ctagacaagt    5040
gtgggagagt gataggactt tatggcaatg gggtcgtgat caaaaatggg agttatgtta    5100
gtgccatcac ccaagggagg agggaggaag agactcctgt tgagtgcttc gagccttcga    5160
tgctgaagaa gaagcagcta actgtcttag acttacatcc tggagctggg aaaaccagga    5220
gagttcttcc tgaaatagtc cgtgaagcca taaaaacaag actccgtact gtgatcttag    5280
ctccaaccag ggttgtcgct gctgaaatgg aggaggccct tagagggctt ccagtgcgtt    5340
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag actttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gagggggcgc ataggcagga    6000
atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
```

```
ttgatggcac gaccaacaac accatactgg aagacagcgt gccggcagag gtgtggacca    6360
gacacggaga gaaaagagtg ctcaaaccga ggtggatgga cgccagagtt tgttcagatc    6420
atgcggccct gaagtcattc aaggagtttg ccgctgggaa aagaggagcg cttttggag     6480 tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacccta gagaccatta tgcttttggg gttgctggga acagtctcgc    6660
tgggaatctt tttcgtcttg atgaggaaca agggcatagg gaagatgggc tttggaatgg    6720
tgacccttgg ggccagtgca tggctcatgt ggctctcgga aattgagcca gccagaattg    6780
catgcgtcct cattgttgtg ttcctattgc tggtggtgct cataccgag ccagaaaagc     6840 aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag gagagaggag ggggcaacca taggattctc aatggacatt gacctgcggc    7020
cagcctcagc ttgggccatc tatgctgcct tgacaacttt cattacccca gccgtccaac    7080
atgcagtgac cacttcatac aacaactact cctaatggc gatggccacg caagctggag     7140
tgttgtttgg tatgggcaaa gggatgccat tctacgcatg ggactttgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc cgtctccagc gccatactgt cgcggaccgc ctgggggtgg ggggaggctg    7500 gggcctgat cacagccgca acttccactt tgtgggaagg ctctccgaac aagtactgga    7560
actcctctac agccacttca ctgtgtaaca ttttaggg aagttacttg gctggagcct     7620
ctctaatcta cacagtaaca agaaacgctg cttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga agaggccgc cgcgccctca    7800 aggacggtgt ggcaacggga ggccatgctg tgtcccgagg aagtgcaaag ctgagatggt    7860
tggtggagcg gggataccig cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacattgtcc    8040
gtcttaagag tgggggtgga ctcttcata tggcggctga gccgtgtgac acgttgctgt     8100
gtgacatagg tgagtcatca tctagtcctg aagtggaaga agcacggacg ctcagagtcc    8160
tctccatggt gggggattgg cttgaaaaaa gaccaggagc ctttgtata aaagtgttgt      8220 gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gccccacac aagggtcagc gtcctctcta ataaacgggg      8640
ttgtcaggct cctgtcaaaa ccctgggatg tggtgactgg agtcacagga atagccatga    8700
```

```
ccgacaccac accgtatggt cagcaaagag ttttcaagga aaaagtggac actagggtgc    8760
cagaccccca agaaggcact cgtcaggtta tgagcatggt ctcttcctgg ttgtggaaag    8820
agctaggcaa acacaaacgg ccacgagtct gtaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagttgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtt    9240
gcataccagg aggaaggatg tatgcagatg acactgctgg ctgggacacc cgcatcagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacatttt ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960
agctccttta tttccacaga agggaccctc gactgatggc caatgccatt tgttcatctg   10020
tgccagttga ctgggttcca actgggagaa ctacctggtc aatccatgga aagggagaat   10080
ggatgaccac tgaagacatg cttgtggtgt ggaacagagt gtggattgag agaacgacc   10140 acatggaaga caagaccccca gttacgaaat ggacagacat tccctatttg gaaaaaggg   10200 aagacttgtg gtgtggatct ctcatagggc acagaccgcg caccacctgg gctgagaaca   10260
ttaaaaacac agtcaacatg gtgcgcagga tcataggtgt tgaagaaaag tacatggact   10320
acctatccac ccaagttcgc tacttgggtg aagaagggtc tacacctgga gtgctgtaag   10380
caccaatctt aacgttgtca ggcctgctag tcagccacag cttggggaaa gctgtgcagc   10440
ctgtgacccc cccaggagaa gctgggaaac aagcctata gtcaggccga aacgccatg   10500 gcacggaaga agccatgctg cctgtgagcc cctcagagga cactgagtca aaaaccccca   10560
cgcgcttgga ggcgcaggat gggaaaagaa ggtggcgacc ttccccaccc ttcaatctgg   10620
ggcctgaact ggagatcagc tgtggatctc cagaagaggg actagtggtt agaggagacc   10680
ccccggaaaa cgcaaaacag catattgacg ctgggaaaga ccagagactc catgagtttc   10740
caccacgctg ccgccaggc acagatcgcc gaatagcggc ggccggtgtg gggaaatcca   10800
tgggtct                                                            10807
```

<210> SEQ ID NO 14
<211> LENGTH: 3423
<212> TYPE: PRT
<213> ORGANISM: Zika virus strain R103451

<400> SEQUENCE: 14

```
Met Lys Asn Pro Lys Lys Ser Gly Gly Phe Arg Ile Val Asn Met
1               5                   10                  15
Leu Lys Arg Gly Val Ala Arg Val Ser Pro Phe Gly Gly Leu Lys Arg
                20                  25                  30
Leu Pro Ala Gly Leu Leu Gly His Gly Pro Ile Arg Met Val Leu
            35                  40                  45
Ala Ile Leu Ala Phe Leu Arg Phe Thr Ala Ile Lys Pro Ser Leu Gly
50                  55                  60
Leu Ile Asn Arg Trp Gly Ser Val Gly Lys Lys Glu Ala Met Glu Ile
65                  70                  75                  80
Ile Lys Lys Phe Lys Lys Asp Leu Ala Ala Met Leu Arg Ile Ile Asn
                85                  90                  95
Ala Arg Lys Glu Lys Lys Arg Arg Gly Ala Asp Thr Ser Val Gly Ile
                100                 105                 110
Val Gly Leu Leu Leu Thr Thr Ala Met Ala Ala Glu Val Thr Arg Arg
            115                 120                 125
Gly Ser Ala Tyr Tyr Met Tyr Leu Asp Arg Asn Asp Ala Gly Glu Ala
130                 135                 140
Ile Ser Phe Pro Thr Thr Leu Gly Met Asn Lys Cys Tyr Ile Gln Ile
145                 150                 155                 160
Met Asp Leu Gly His Met Cys Asp Ala Thr Met Ser Tyr Glu Cys Pro
                165                 170                 175
Met Leu Asp Glu Gly Val Glu Pro Asp Asp Val Asp Cys Trp Cys Asn
                180                 185                 190
Thr Thr Ser Thr Trp Val Val Tyr Gly Thr Cys His His Lys Lys Gly
            195                 200                 205
Glu Ala Arg Arg Ser Arg Arg Ala Val Thr Leu Pro Ser His Ser Thr
210                 215                 220
Arg Lys Leu Gln Thr Arg Ser Gln Thr Trp Leu Glu Ser Arg Glu Tyr
225                 230                 235                 240
Thr Lys His Leu Ile Arg Val Glu Asn Trp Ile Phe Arg Asn Pro Gly
                245                 250                 255
Phe Ala Leu Ala Ala Ala Ala Ile Ala Trp Leu Leu Gly Ser Ser Thr
                260                 265                 270
Ser Gln Lys Val Ile Tyr Leu Val Met Ile Leu Leu Ile Ala Pro Ala
            275                 280                 285
Tyr Ser Ile Arg Cys Ile Gly Val Ser Asn Arg Asp Phe Val Glu Gly
290                 295                 300
Met Ser Gly Gly Thr Trp Val Asp Val Val Leu Glu His Gly Gly Cys
305                 310                 315                 320
Val Thr Val Met Ala Gln Asp Lys Pro Thr Val Asp Ile Glu Leu Val
                325                 330                 335
Thr Thr Thr Val Ser Asn Met Ala Glu Val Arg Ser Tyr Cys Tyr Glu
                340                 345                 350
Ala Ser Ile Ser Asp Met Ala Ser Asp Ser Arg Cys Pro Thr Gln Gly
            355                 360                 365
Glu Ala Tyr Leu Asp Lys Gln Ser Asp Thr Gln Tyr Val Cys Lys Arg
370                 375                 380
Thr Leu Val Asp Arg Gly Trp Gly Asn Gly Cys Gly Leu Phe Gly Lys
385                 390                 395                 400
Gly Ser Leu Val Thr Cys Ala Lys Phe Ala Cys Ser Lys Lys Met Thr
                405                 410                 415
```

```
Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
            610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
            690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
            770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830
```

```
Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Ala Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
        995                 1000                1005

Ala His Leu Ile Glu Met Lys Thr Cys Glu Trp Pro Lys Ser His
        1010                1015                1020

Thr Leu Trp Thr Asp Gly Ile Glu Glu Ser Asp Leu Ile Ile Pro
        1025                1030                1035

Lys Ser Leu Ala Gly Pro Leu Ser His His Asn Thr Arg Glu Gly
        1040                1045                1050

Tyr Arg Thr Gln Met Lys Gly Pro Trp His Ser Glu Glu Leu Glu
        1055                1060                1065

Ile Arg Phe Glu Glu Cys Pro Gly Thr Lys Val His Val Glu Glu
        1070                1075                1080

Thr Cys Gly Thr Arg Gly Pro Ser Leu Arg Ser Thr Thr Ala Ser
        1085                1090                1095

Gly Arg Val Ile Glu Glu Trp Cys Cys Arg Glu Cys Thr Met Pro
        1100                1105                1110

Pro Leu Ser Phe Arg Ala Lys Asp Gly Cys Trp Tyr Gly Met Glu
        1115                1120                1125

Ile Arg Pro Arg Lys Glu Pro Glu Ser Asn Leu Val Arg Ser Met
        1130                1135                1140

Val Thr Ala Gly Ser Thr Asp His Met Asp His Phe Ser Leu Gly
        1145                1150                1155

Val Leu Val Ile Leu Leu Met Val Gln Glu Gly Leu Lys Lys Arg
        1160                1165                1170

Met Thr Thr Lys Ile Ile Ile Ser Thr Ser Met Ala Val Leu Val
        1175                1180                1185

Ala Met Ile Leu Gly Gly Phe Ser Met Ser Asp Leu Ala Lys Leu
        1190                1195                1200

Ala Ile Leu Met Gly Ala Thr Phe Ala Glu Met Asn Thr Gly Gly
        1205                1210                1215

Asp Val Ala His Leu Ala Leu Ile Ala Ala Phe Lys Val Arg Pro
        1220                1225                1230

Ala Leu Leu Val Ser Phe Ile Phe Arg Ala Asn Trp Thr Pro Arg
```

-continued

```
            1235                1240                1245
Glu Ser Met Leu Leu Ala Leu Ala Ser Cys Leu Leu Gln Thr Ala
        1250                1255                1260
Ile Ser Ala Leu Glu Gly Asp Leu Met Val Leu Ile Asn Gly Phe
        1265                1270                1275
Ala Leu Ala Trp Leu Ala Ile Arg Ala Met Val Val Pro Arg Thr
        1280                1285                1290
Asp Asn Ile Thr Leu Ala Ile Leu Ala Ala Leu Thr Pro Leu Ala
        1295                1300                1305
Arg Gly Thr Leu Leu Val Ala Trp Arg Ala Gly Leu Ala Thr Cys
        1310                1315                1320
Gly Gly Phe Met Leu Leu Ser Leu Lys Gly Lys Gly Ser Val Lys
        1325                1330                1335
Lys Asn Leu Pro Phe Val Met Ala Leu Gly Leu Thr Ala Val Arg
        1340                1345                1350
Leu Val Asp Pro Ile Asn Val Val Gly Leu Leu Leu Leu Thr Arg
        1355                1360                1365
Ser Gly Lys Arg Ser Trp Pro Pro Ser Glu Val Leu Thr Ala Val
        1370                1375                1380
Gly Leu Ile Cys Ala Leu Ala Gly Gly Phe Ala Lys Ala Asp Ile
        1385                1390                1395
Glu Met Ala Gly Pro Met Ala Ala Val Gly Leu Leu Ile Val Ser
        1400                1405                1410
Tyr Val Val Ser Gly Lys Ser Val Asp Met Tyr Ile Glu Arg Ala
        1415                1420                1425
Gly Asp Ile Thr Trp Glu Lys Asp Ala Glu Val Thr Gly Asn Ser
        1430                1435                1440
Pro Arg Leu Asp Val Ala Leu Asp Glu Ser Gly Asp Phe Ser Leu
        1445                1450                1455
Val Glu Asp Asp Gly Pro Pro Met Arg Glu Ile Ile Leu Lys Val
        1460                1465                1470
Val Leu Met Thr Ile Cys Gly Met Asn Pro Ile Ala Ile Pro Phe
        1475                1480                1485
Ala Ala Gly Ala Trp Tyr Val Tyr Val Lys Thr Gly Lys Arg Ser
        1490                1495                1500
Gly Ala Leu Trp Asp Val Pro Ala Pro Lys Glu Val Lys Lys Gly
        1505                1510                1515
Glu Thr Thr Asp Gly Val Tyr Arg Val Met Thr Arg Arg Leu Leu
        1520                1525                1530
Gly Ser Thr Gln Val Gly Val Gly Val Met Gln Glu Gly Val Phe
        1535                1540                1545
His Thr Met Trp His Val Thr Lys Gly Ser Ala Leu Arg Ser Gly
        1550                1555                1560
Glu Gly Arg Leu Asp Pro Tyr Trp Gly Asp Val Lys Gln Asp Leu
        1565                1570                1575
Val Ser Tyr Cys Gly Pro Trp Lys Leu Asp Ala Ala Trp Asp Gly
        1580                1585                1590
His Ser Glu Val Gln Leu Leu Ala Val Pro Pro Gly Glu Arg Ala
        1595                1600                1605
Arg Asn Ile Gln Thr Leu Pro Gly Ile Phe Lys Thr Lys Asp Gly
        1610                1615                1620
Asp Ile Gly Ala Val Ala Leu Asp Tyr Pro Ala Gly Thr Ser Gly
        1625                1630                1635
```

-continued

```
Ser Pro Ile Leu Asp Lys Cys Gly Arg Val Ile Gly Leu Tyr Gly
    1640            1645                1650

Asn Gly Val Val Ile Lys Asn Gly Ser Tyr Val Ser Ala Ile Thr
    1655            1660                1665

Gln Gly Arg Arg Glu Glu Glu Thr Pro Val Glu Cys Phe Glu Pro
    1670            1675                1680

Ser Met Leu Lys Lys Lys Gln Leu Thr Val Leu Asp Leu His Pro
    1685            1690                1695

Gly Ala Gly Lys Thr Arg Arg Val Leu Pro Glu Ile Val Arg Glu
    1700            1705                1710

Ala Ile Lys Thr Arg Leu Arg Thr Val Ile Leu Ala Pro Thr Arg
    1715            1720                1725

Val Val Ala Ala Glu Met Glu Glu Ala Leu Arg Gly Leu Pro Val
    1730            1735                1740

Arg Tyr Met Thr Thr Ala Val Asn Val Thr His Ser Gly Thr Glu
    1745            1750                1755

Ile Val Asp Leu Met Cys His Ala Thr Phe Thr Ser Arg Leu Leu
    1760            1765                1770

Gln Pro Ile Arg Val Pro Asn Tyr Asn Leu Tyr Ile Met Asp Glu
    1775            1780                1785

Ala His Phe Thr Asp Pro Ser Ser Ile Ala Ala Arg Gly Tyr Ile
    1790            1795                1800

Ser Thr Arg Val Glu Met Gly Glu Ala Ala Ile Phe Met Thr
    1805            1810                1815

Ala Thr Pro Pro Gly Thr Arg Asp Ala Phe Pro Asp Ser Asn Ser
    1820            1825                1830

Pro Ile Met Asp Thr Glu Val Glu Val Pro Glu Arg Ala Trp Ser
    1835            1840                1845

Ser Gly Phe Asp Trp Val Thr Asp His Ser Gly Lys Thr Val Trp
    1850            1855                1860

Phe Val Pro Ser Val Arg Asn Gly Asn Glu Ile Ala Ala Cys Leu
    1865            1870                1875

Thr Lys Ala Gly Lys Arg Val Ile Gln Leu Ser Arg Lys Thr Phe
    1880            1885                1890

Glu Thr Glu Phe Gln Lys Thr Lys His Gln Glu Trp Asp Phe Val
    1895            1900                1905

Val Thr Thr Asp Ile Ser Glu Met Gly Ala Asn Phe Lys Ala Asp
    1910            1915                1920

Arg Val Ile Asp Ser Arg Arg Cys Leu Lys Pro Val Ile Leu Asp
    1925            1930                1935

Gly Glu Arg Val Ile Leu Ala Gly Pro Met Pro Val Thr His Ala
    1940            1945                1950

Ser Ala Ala Gln Arg Arg Gly Arg Ile Gly Arg Asn Pro Asn Lys
    1955            1960                1965

Pro Gly Asp Glu Tyr Leu Tyr Gly Gly Gly Cys Ala Glu Thr Asp
    1970            1975                1980

Glu Asp His Ala His Trp Leu Glu Ala Arg Met Leu Leu Asp Asn
    1985            1990                1995

Ile Tyr Leu Gln Asp Gly Leu Ile Ala Ser Leu Tyr Arg Pro Glu
    2000            2005                2010

Ala Asp Lys Val Ala Ala Ile Glu Gly Glu Phe Lys Leu Arg Thr
    2015            2020                2025
```

-continued

Glu Gln Arg Lys Thr Phe Val Glu Leu Met Lys Arg Gly Asp Leu
    2030            2035            2040

Pro Val Trp Leu Ala Tyr Gln Val Ala Ser Ala Gly Ile Thr Tyr
    2045            2050            2055

Thr Asp Arg Arg Trp Cys Phe Asp Gly Thr Thr Asn Asn Thr Ile
    2060            2065            2070

Leu Glu Asp Ser Val Pro Ala Glu Val Trp Thr Arg His Gly Glu
    2075            2080            2085

Lys Arg Val Leu Lys Pro Arg Trp Met Asp Ala Arg Val Cys Ser
    2090            2095            2100

Asp His Ala Ala Leu Lys Ser Phe Lys Glu Phe Ala Ala Gly Lys
    2105            2110            2115

Arg Gly Ala Ala Phe Gly Val Met Glu Ala Leu Gly Thr Leu Pro
    2120            2125            2130

Gly His Met Thr Glu Arg Phe Gln Glu Ala Ile Asp Asn Leu Ala
    2135            2140            2145

Val Leu Met Arg Ala Glu Thr Gly Ser Arg Pro Tyr Lys Ala Ala
    2150            2155            2160

Ala Ala Gln Leu Pro Glu Thr Leu Glu Thr Ile Met Leu Leu Gly
    2165            2170            2175

Leu Leu Gly Thr Val Ser Leu Gly Ile Phe Phe Val Leu Met Arg
    2180            2185            2190

Asn Lys Gly Ile Gly Lys Met Gly Phe Gly Met Val Thr Leu Gly
    2195            2200            2205

Ala Ser Ala Trp Leu Met Trp Leu Ser Glu Ile Glu Pro Ala Arg
    2210            2215            2220

Ile Ala Cys Val Leu Ile Val Val Phe Leu Leu Leu Val Val Leu
    2225            2230            2235

Ile Pro Glu Pro Glu Lys Gln Arg Ser Pro Gln Asp Asn Gln Met
    2240            2245            2250

Ala Ile Ile Ile Met Val Ala Val Gly Leu Leu Gly Leu Ile Thr
    2255            2260            2265

Ala Asn Glu Leu Gly Trp Leu Glu Arg Thr Lys Ser Asp Leu Ser
    2270            2275            2280

His Leu Met Gly Arg Arg Glu Glu Gly Ala Thr Ile Gly Phe Ser
    2285            2290            2295

Met Asp Ile Asp Leu Arg Pro Ala Ser Ala Trp Ala Ile Tyr Ala
    2300            2305            2310

Ala Leu Thr Thr Phe Ile Thr Pro Ala Val Gln His Ala Val Thr
    2315            2320            2325

Thr Ser Tyr Asn Asn Tyr Ser Leu Met Ala Met Ala Thr Gln Ala
    2330            2335            2340

Gly Val Leu Phe Gly Met Gly Lys Gly Met Pro Phe Tyr Ala Trp
    2345            2350            2355

Asp Phe Gly Val Pro Leu Leu Met Ile Gly Cys Tyr Ser Gln Leu
    2360            2365            2370

Thr Pro Leu Thr Leu Ile Val Ala Ile Ile Leu Leu Val Ala His
    2375            2380            2385

Tyr Met Tyr Leu Ile Pro Gly Leu Gln Ala Ala Ala Ala Arg Ala
    2390            2395            2400

Ala Gln Lys Arg Thr Ala Ala Gly Ile Met Lys Asn Pro Val Val
    2405            2410            2415

Asp Gly Ile Val Val Thr Asp Ile Asp Thr Met Thr Ile Asp Pro

```
                2420                2425                2430
Gln Val Glu Lys Lys Met Gly Gln Val Leu Leu Ile Ala Val Ala
    2435                2440                2445
Val Ser Ser Ala Ile Leu Ser Arg Thr Ala Trp Gly Trp Gly Glu
    2450                2455                2460
Ala Gly Ala Leu Ile Thr Ala Ala Thr Ser Thr Leu Trp Glu Gly
    2465                2470                2475
Ser Pro Asn Lys Tyr Trp Asn Ser Ser Thr Ala Thr Ser Leu Cys
    2480                2485                2490
Asn Ile Phe Arg Gly Ser Tyr Leu Ala Gly Ala Ser Leu Ile Tyr
    2495                2500                2505
Thr Val Thr Arg Asn Ala Gly Leu Val Lys Arg Arg Gly Gly Gly
    2510                2515                2520
Thr Gly Glu Thr Leu Gly Glu Lys Trp Lys Ala Arg Leu Asn Gln
    2525                2530                2535
Met Ser Ala Leu Glu Phe Tyr Ser Tyr Lys Lys Ser Gly Ile Thr
    2540                2545                2550
Glu Val Cys Arg Glu Glu Ala Arg Arg Ala Leu Lys Asp Gly Val
    2555                2560                2565
Ala Thr Gly Gly His Ala Val Ser Arg Gly Ser Ala Lys Leu Arg
    2570                2575                2580
Trp Leu Val Glu Arg Gly Tyr Leu Gln Pro Tyr Gly Lys Val Ile
    2585                2590                2595
Asp Leu Gly Cys Gly Arg Gly Gly Trp Ser Tyr Tyr Ala Ala Thr
    2600                2605                2610
Ile Arg Lys Val Gln Glu Val Lys Gly Tyr Thr Lys Gly Gly Pro
    2615                2620                2625
Gly His Glu Glu Pro Val Leu Val Gln Ser Tyr Gly Trp Asn Ile
    2630                2635                2640
Val Arg Leu Lys Ser Gly Val Asp Val Phe His Met Ala Ala Glu
    2645                2650                2655
Pro Cys Asp Thr Leu Leu Cys Asp Ile Gly Glu Ser Ser Ser Ser
    2660                2665                2670
Pro Glu Val Glu Glu Ala Arg Thr Leu Arg Val Leu Ser Met Val
    2675                2680                2685
Gly Asp Trp Leu Glu Lys Arg Pro Gly Ala Phe Cys Ile Lys Val
    2690                2695                2700
Leu Cys Pro Tyr Thr Ser Thr Met Met Glu Thr Leu Glu Arg Leu
    2705                2710                2715
Gln Arg Arg Tyr Gly Gly Gly Leu Val Arg Val Pro Leu Ser Arg
    2720                2725                2730
Asn Ser Thr His Glu Met Tyr Trp Val Ser Gly Ala Lys Ser Asn
    2735                2740                2745
Thr Ile Lys Ser Val Ser Thr Thr Ser Gln Leu Leu Leu Gly Arg
    2750                2755                2760
Met Asp Gly Pro Arg Arg Pro Val Lys Tyr Glu Glu Asp Val Asn
    2765                2770                2775
Leu Gly Ser Gly Thr Arg Ala Val Val Ser Cys Ala Glu Ala Pro
    2780                2785                2790
Asn Met Lys Ile Ile Gly Asn Arg Ile Glu Arg Ile Arg Ser Glu
    2795                2800                2805
His Ala Glu Thr Trp Phe Phe Asp Glu Asn His Pro Tyr Arg Thr
    2810                2815                2820
```

```
Trp Ala Tyr His Gly Ser Tyr Glu Ala Pro Thr Gln Gly Ser Ala
2825             2830                 2835

Ser Ser Leu Ile Asn Gly Val Val Arg Leu Leu Ser Lys Pro Trp
2840             2845                 2850

Asp Val Val Thr Gly Val Thr Gly Ile Ala Met Thr Asp Thr Thr
2855             2860                 2865

Pro Tyr Gly Gln Gln Arg Val Phe Lys Glu Lys Val Asp Thr Arg
2870             2875                 2880

Val Pro Asp Pro Gln Glu Gly Thr Arg Gln Val Met Ser Met Val
2885             2890                 2895

Ser Ser Trp Leu Trp Lys Glu Leu Gly Lys His Lys Arg Pro Arg
2900             2905                 2910

Val Cys Thr Lys Glu Glu Phe Ile Asn Lys Val Arg Ser Asn Ala
2915             2920                 2925

Ala Leu Gly Ala Ile Phe Glu Glu Lys Glu Trp Lys Thr Ala
2930             2935                 2940

Val Glu Ala Val Asn Asp Pro Arg Phe Trp Ala Leu Val Asp Lys
2945             2950                 2955

Glu Arg Glu His His Leu Arg Gly Glu Cys Gln Ser Cys Val Tyr
2960             2965                 2970

Asn Met Met Gly Lys Arg Glu Lys Lys Gln Gly Glu Phe Gly Lys
2975             2980                 2985

Ala Lys Gly Ser Arg Ala Ile Trp Tyr Met Trp Leu Gly Ala Arg
2990             2995                 3000

Phe Leu Glu Phe Glu Ala Leu Gly Phe Leu Asn Glu Asp His Trp
3005             3010                 3015

Met Gly Arg Glu Asn Ser Gly Gly Gly Val Glu Gly Leu Gly Leu
3020             3025                 3030

Gln Arg Leu Gly Tyr Val Leu Glu Glu Met Ser Cys Ile Pro Gly
3035             3040                 3045

Gly Arg Met Tyr Ala Asp Asp Thr Ala Gly Trp Asp Thr Arg Ile
3050             3055                 3060

Ser Arg Phe Asp Leu Glu Asn Glu Ala Leu Ile Thr Asn Gln Met
3065             3070                 3075

Glu Lys Gly His Arg Ala Leu Ala Leu Ala Ile Ile Lys Tyr Thr
3080             3085                 3090

Tyr Gln Asn Lys Val Val Lys Val Leu Arg Pro Ala Glu Lys Gly
3095             3100                 3105

Lys Thr Val Met Asp Ile Ile Ser Arg Gln Asp Gln Arg Gly Ser
3110             3115                 3120

Gly Gln Val Val Thr Tyr Ala Leu Asn Thr Phe Thr Asn Leu Val
3125             3130                 3135

Val Gln Leu Ile Arg Asn Met Glu Ala Glu Glu Val Leu Glu Met
3140             3145                 3150

Gln Asp Leu Trp Leu Leu Arg Arg Ser Glu Lys Val Thr Asn Trp
3155             3160                 3165

Leu Gln Ser Asn Gly Trp Asp Arg Leu Lys Arg Met Ala Val Ser
3170             3175                 3180

Gly Asp Asp Cys Val Val Lys Pro Ile Asp Asp Arg Phe Ala His
3185             3190                 3195

Ala Leu Arg Phe Leu Asn Asp Met Gly Lys Val Arg Lys Asp Thr
3200             3205                 3210
```

| | | | | | | | | | | |
|---|---|---|---|---|---|---|---|---|---|---|
| Gln | Glu | Trp | Lys | Pro | Ser | Thr | Gly | Trp | Asp | Asn | Trp | Glu | Glu | Val |
| | 3215 | | | | 3220 | | | | 3225 | |
| Pro | Phe | Cys | Ser | His | His | Phe | Asn | Lys | Leu | His | Leu | Lys | Asp | Gly |
| 3230 | | | | | 3235 | | | | | 3240 | |

Gln Glu Trp Lys Pro Ser Thr Gly Trp Asp Asn Trp Glu Glu Val
    3215                3220                3225
Pro Phe Cys Ser His His Phe Asn Lys Leu His Leu Lys Asp Gly
3230                3235                3240
Arg Ser Ile Val Val Pro Cys Arg His Gln Asp Glu Leu Ile Gly
    3245                3250                3255
Arg Ala Arg Val Ser Pro Gly Ala Gly Trp Ser Ile Arg Glu Thr
3260                3265                3270
Ala Cys Leu Ala Lys Ser Tyr Ala Gln Met Trp Gln Leu Leu Tyr
    3275                3280                3285
Phe His Arg Arg Asp Leu Arg Leu Met Ala Asn Ala Ile Cys Ser
3290                3295                3300
Ser Val Pro Val Asp Trp Val Pro Thr Gly Arg Thr Thr Trp Ser
    3305                3310                3315
Ile His Gly Lys Gly Glu Trp Met Thr Thr Glu Asp Met Leu Val
3320                3325                3330
Val Trp Asn Arg Val Trp Ile Glu Glu Asn Asp His Met Glu Asp
    3335                3340                3345
Lys Thr Pro Val Thr Lys Trp Thr Asp Ile Pro Tyr Leu Gly Lys
3350                3355                3360
Arg Glu Asp Leu Trp Cys Gly Ser Leu Ile Gly His Arg Pro Arg
    3365                3370                3375
Thr Thr Trp Ala Glu Asn Ile Lys Asn Thr Val Asn Met Val Arg
3380                3385                3390
Arg Ile Ile Gly Asp Glu Glu Lys Tyr Met Asp Tyr Leu Ser Thr
    3395                3400                3405
Gln Val Arg Tyr Leu Gly Glu Gly Ser Thr Pro Gly Val Leu
3410                3415                3420

<210> SEQ ID NO 15
<211> LENGTH: 10807
<212> TYPE: DNA
<213> ORGANISM: Zika virus strain PRVABC59

<400> SEQUENCE: 15

```
agttgttgat ctgtgtgaat cagactgcga cagttcgagt ttgaagcgaa agctagcaac     60
agtatcaaca ggttttattt tggatttgga acgagagtt tctggtcatg aaaaacccaa    120
aaaagaaatc cggaggattc cggattgtca atatgctaaa acgcggagta gcccgtgtga    180
gccccttggg gggcttgaag aggctgccag ccggacttct gctgggtcat gggcccatca    240
ggatggtctt ggcgattcta gccttttga gattcacggc aatcaagcca tcactgggtc    300
tcatcaatag atggggttca gtggggaaaa aagaggctat ggaaacaata aagaagttca    360
agaaagatct ggctgccatg ctgagaataa tcaatgctag gaaggagaag aagagacgag    420
gcgcagatac tagtgtcgga attgttggcc tcctgctgac cacagctatg gcagcggagg    480
tcactagacg tgggagtgca tactatatgt acttggacag aaacgatgct ggggaggcca    540
tatcttttcc aaccacattg gggatgaata gtgttatat acagatcatg gatcttggac    600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctccctcc cattccacca    780
ggaagctgca aacgcggtcg caaacctggt tggaatcaag agaatacaca aagcacttga    840
ttagagtcga aaattggata ttcaggaacc ctggcttcgc gttagcagca gctgccatcg    900
```

```
cttggctttt gggaagctca acgagccaaa aagtcatata cttggtcatg atactgctga      960
ttgccccggc atacagcatc aggtgcatag gagtcagcaa tagggacttt gtggaaggta     1020
tgtcaggtgg gacttgggtt gatgttgtct tggaacatgg aggttgtgtc accgtaatgg     1080
cacaggacaa accgactgtc gacatagagc tggttacaac aacagtcagc aacatggcgg     1140
aggtaagatc ctactgctat gaggcatcaa tatcagacat ggcttctgac agccgctgcc     1200
caacacaagg tgaagcctac cttgacaagc aatcagacac tcaatatgtc tgcaaaagaa     1260
cgttagtgga cagaggctgg ggaaatggat gtggactttt tggcaaaggg agcctggtga     1320
catgcgctaa gtttgcatgc tccaagaaaa tgaccgggaa gagcatccag ccagagaatc     1380
tggagtaccg gataatgctg tcagttcatg gctcccagca cagtgggatg atcgttaatg     1440
acacaggaca tgaaactgat gagaatagag cgaaagttga gataacgccc aattcaccga     1500
gagccgaagc caccctgggg ggttttggaa gcctaggact tgattgtgaa ccgaggacag     1560
gccttgactt ttcagatttg tattacttga ctatgaataa caagcactgg ttggttcaca     1620
aggagtggtt ccacgacatt ccattacctt ggcacgctgg ggcagacacc ggaactccac     1680
actggaacaa caaagaagca ctggtagagt tcaaggacgc acatgccaaa aggcaaactg     1740
tcgtggttct agggagtcaa gaaggagcag ttcacacggc ccttgctgga gctctggagg     1800
ctgagatgga tggtgcaaag ggaaggctgt cctctggcca cttgaaatgt cgcctgaaaa     1860
tggataaact tagattgaag ggcgtgtcat actccttgtg tactgcagcg ttcacattca     1920
ccaagatccc ggctgaaaca ctgcacggga cagtcacagt ggaggtacag tacgcaggga     1980
cagatggacc ttgcaaggtt ccagctcaga tggcggtgga catgcaaact ctgacccag     2040
ttgggaggtt gataaccgct aacccgtaa tcactgaaag cactgagaac tctaagatga     2100
tgctggaact tgatccacca tttgggact cttacattgt cataggagtc ggggagaaga     2160
agatcaccca ccactggcac aggagtggca gcaccattgg aaaagcattt gaagccactg     2220
tgagaggtgc caagagaatg gcagtcttgg gagacacagc ctgggacttt ggatcagttg     2280
gaggcgctct caactcattg ggcaagggca tccatcaaat tttttggagca gctttcaaat     2340
cattgtttgg aggaatgtcc tggttctcac aaattctcat tggaacgttg ctgatgtggt     2400
tgggtctgaa cacaaagaat ggatctattt cccttatgtg cttggcctta ggggagtgt     2460
tgatcttctt atccacagcc gtctctgctg atgtggggtg ctcggtggac ttctcaaaga     2520
aggagacgag atgcggtaca ggggtgttcg tctataacga cgttgaagcc tgagggaca     2580
ggtacaagta ccatcctgac tcccccccgta gattggcagc agcagtcaag caagcctggg     2640
aagatggtat ctgcgggatc tcctctgttt caagaatgga aaacatcatg tggagatcag     2700
tagaagggga gctcaacgca atcctggaag agaatgagt tcaactgacg gtcgttgtgg     2760
gatctgtaaa aaaccccatg tggagaggtc cacagagatt gcccgtgcct gtgaacgagc     2820
tgccccacgg ctggaaggct tgggggaaat cgtatttcgt cagagcagca agacaaata     2880
acagctttgt cgtggatggt gacacactga aggaatgccc actcaaacat agagcatgga     2940
acagctttct tgtggaggat catgggttcg gggtatttca cactagtgtc tggctcaagg     3000
ttagagaaga ttattcatta gagtgtgatc cagccgttat tggaacagct gttaagggaa     3060
aggaggctgt acacagtgat ctaggctact ggattgagag tgagaagaat gacacatgga     3120
ggctgaagag ggcccatctg atcgagatga aacatgtga atggccaaag tcccacacat     3180
tgtggacaga tggaatagaa gagagtgatc tgatcatacc caagtcttta gctgggccac     3240
```

```
tcagccatca caataccaga gagggctaca ggacccaaat gaaagggcca tggcacagtg    3300
aagagcttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttccg ggctaaagat ggctgttggt    3480
atggaatgga gataaggccc aggaaagaac cagaaagcaa cttagtaagg tcaatggtga    3540
ctgcaggatc aactgatcac atggaccact tctcccttgg agtgcttgtg atcctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcacctt ggcaatcctg gctgctctga    4020
caccactggc ccggggcaca ctgcttgtgg cgtggagagc aggccttgct acttgcgggg    4080
ggtttatgct cctctctctg aagggaaaag gcagtgtgaa gaagaactta ccatttgtca    4140
tggccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgg tctgctaatt gtcagttacg tggtctcagg aaagagtgtg acatgtaca    4380 ttgaaagagc aggtgacatc acatgggaaa agatgcggaa agtcactgga aacagtcccc    4440
ggctcgatgt ggcgctagat gagagtgtg atttctccct ggtggaggat gacggtcccc    4500
ccatgagaga gatcatactc aaggtggtcc tgatgaccat ctgtggcatg aacccaatag    4560
ccataccctt tgcagctgga gcgtggtacg tatacgtgaa gactggaaaa aggagtggtg    4620
ctctatggga tgtgcctgct cccaaggaag taaaaagggg ggagaccaca gatggagtgt    4680
acagagtaat gactcgtaga ctgctaggtt caacacaagt tggagtggga gttatgcaag    4740 aggggtctt tcacactatg tggcacgtca caaaaggatc cgcgctgaga gcggtgaag    4800 ggagacttga tccatactgg ggagatgtca agcaggatct ggtgtcatac tgtggtccat    4860
ggaagctaga tgccgcctgg gatgggcaca gcgaggtgca gctcttggcc gtgccccccg    4920
gagagagagc gaggaacatc cagactctgc ccggaatatt taagacaaag gatgggaca    4980 ttggagcggt tgcgctggat tacccagcag gaacttcagg atctccaatc ctagacaagt    5040
gtgggagagt gataggactt tatggcaatg gggtcgtgat caaaaacggg agttatgtta    5100
gtgccatcac ccaagggagg agggaggaag agactcctgt tgagtgcttc gagccctcga    5160
tgctgaagaa gaagcagcta actgtcttag acttgcatcc tggagctggg aaaaccagga    5220
gagttcttcc tgaaatagtc cgtgaagcca taaaaacaag actccgtact gtgatcttag    5280
ctccaaccag ggttgtcgct gctgaaatgg aggaggccct tagagggctt ccagtgcgtt    5340
atatgacaac agcagtcaat gtcacccact ctggaacaga atcgtcgac ttaatgtgcc    5400 atgccacctt cacttcacgt ctactacagc caatcagagt ccccaactat aatctgtata    5460
ttatggatga ggcccacttc acagatcct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
```

```
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000 atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaagagga gatcttcctg     6240 tttggctggc ctatcaggtt gcatctgccg gaataaccta cacagataga agatggtgct    6300
ttgatggcac gaccaacaac accataatgg aagacagtgt gccggcagag gtgtggacca    6360
gacacggaga gaaaagagtg ctcaaaccga ggtggatgga cgccagagtt tgttcagatc    6420
atgcggccct gaagtcattc aaggagtttg ccgctgggaa aagaggagcg cttttggag    6480 tgatggaagc cctgggaaca ctgccaggac acatgacaga gagattccag gaagccattg    6540
acaacctcgc tgtgctcatg cgggcagaga ctggaagcag gccttacaaa ccgcggcgg    6600 cccaattgcc ggagacccta gagaccataa tgcttttggg gttgctggga acagtctcgc    6660
tgggaatctt cttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaaagagtga ctaagccatc    6960
taatgggaag gagagaggag ggggcaacca taggattctc aatggacatt gacctgcggc    7020
cagcctcagc ttgggccatc tatgctgcct tgacaacttt cattaccca gccgtccaac    7080 atgcagtgac cacctcatac aacaactact ccttaatggc gatggccacg caagctggag    7140
tgttgtttgg catgggcaaa gggatgccat tctacgcatg ggacttgga gtcccgctgc    7200 taatgatagg ttgctactca caattaacac ccctgaccct aatagtggcc atcatttgc    7260 tcgtggcgca ctacatgtac ttgatcccag ggctgcaggc agcagctgcg cgtgctgccc    7320
agaagagaac ggcagctggc atcatgaaga accctgttgt ggatgaaata gtggtgactg    7380
acattgacac aatgacaatt gaccccaag tggagaaaaa gatgggacag gtgctactca    7440
tagcagtagc cgtctccagc gccatactgt cgcggaccgc ctggggtgg ggaggctg    7500 gggctctgat cacagccgca acttccactt tgtgggaagg ctctccgaac aagtactgga    7560
actcctctac agccacttca ctgtgtaaca tttttagggg aagttacttg gctggagctt    7620
ctctaatcta cacagtaaca agaaacgctg gcttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga gaggccccgc cgcgccctca    7800
aggacggtgt ggcaacggga ggccatgctg tgtcccgagg aagtgcaaag ctgagatggt    7860
tggtggagcg gggatacctg cagccctatg gaaaggtcat tgatcttgga gtgtgcagag    7920
ggggctggag ttactacgtc gccaccatcc gcaaagttca agaagtgaaa ggatacacaa    7980
```

```
aaggaggccc tggtcatgaa gaacccgtgt tggtgcaaag ctatgggtgg aacatagtcc    8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatggggag     8280 gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct tgacgagaa ccacccatat aggacatggg     8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaaagag ttttcaagga aaaagtggac actagggtgc   8760
cagaccccca agaaggcact cgtcaggtta tgagcatggt ctcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaaggc agccgcgcca tctggtatat gtggctaggg ctagatttc      9120 tagagttcga agcccttgga ttcttgaacg aggatcactg gatggggaga gagaactcag    9180
gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggttttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggccgc gtctctccag     9900 gggcgggatg gagcatccgg gagactgctt gcctagcaaa atcatatgcg caaatgtggc    9960
agctccttta tttccacaga agggacctcc gactgatggc caatgccatt tgttcatctg    10020
tgccagttga ctgggttcca actgggagaa ctacctggtc aatccatgga aagggagaat    10080
ggatgaccac tgaagacatg cttgtggtgt ggaacagagt gtggattgag agaacgacc     10140 acatggaaga caagaccca gttacgaaat ggacagacat tccctatttg ggaaaaaggg    10200
aagacttgtg tgtggatct ctcataggc acagaccgcg caccacctgg gctgagaaca     10260
ttaaaaacac agtcaacatg gtgcgcagga tcataggtga tgaagaaaag tacatggact    10320
acctatccac ccaagttcgc tacttgggtg aagaagggtc tacacctgga gtgctgtaag    10380
```

-continued

```
caccaatctt aatgttgtca ggcctgctag tcagccacag cttggggaaa gctgtgcagc    10440
ctgtgacccc cccaggagaa gctgggaaac caagcctata gtcaggccga aacgccatg     10500 gcacggaaga agccatgctg cctgtgagcc cctcagagga cactgagtca aaaaacccca    10560
cgcgcttgga ggcgcaggat gggaaaagaa ggtggcgacc ttccccaccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg ccgccaggc  acagatcgcc gaatagcggc ggccggtgtg gggaaatcca    10800
tgggtct                                                              10807
```

<210> SEQ ID NO 16
<211> LENGTH: 3423
<212> TYPE: PRT
<213> ORGANISM: Zika virus strain PRVABC59

<400> SEQUENCE: 16

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
        20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
        50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285
```

```
Tyr Ser Ile Arg Cys Ile Gly Val Ser Asn Arg Asp Phe Val Glu Gly
    290                 295                 300

Met Ser Gly Gly Thr Trp Val Asp Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
        420                 425                 430

Val His Gly Ser Gln His Ser Gly Met Ile Val Asn Asp Thr Gly His
    435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
        580                 585                 590

Val Ser Tyr Ser Leu Cys Thr Ala Ala Phe Thr Phe Thr Lys Ile Pro
    595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
```

```
                705                 710                 715                 720
        Phe Gly Ser Val Gly Gly Ala Leu Asn Ser Leu Gly Lys Gly Ile His
                        725                 730                 735

Gln Ile Phe Gly Ala Ala Phe Lys Ser Leu Phe Gly Gly Met Ser Trp
                        740                 745                 750

Phe Ser Gln Ile Leu Ile Gly Thr Leu Leu Met Trp Leu Gly Leu Asn
                        755                 760                 765

Thr Lys Asn Gly Ser Ile Ser Leu Met Cys Leu Ala Leu Gly Gly Val
                        770                 775                 780

Leu Ile Phe Leu Ser Thr Ala Val Ser Ala Asp Val Gly Cys Ser Val
        785                 790                 795                 800

Asp Phe Ser Lys Lys Glu Thr Arg Cys Gly Thr Gly Val Phe Val Tyr
                        805                 810                 815

Asn Asp Val Glu Ala Trp Arg Asp Arg Tyr Lys Tyr His Pro Asp Ser
                        820                 825                 830

Pro Arg Arg Leu Ala Ala Ala Val Lys Gln Ala Trp Glu Asp Gly Ile
                        835                 840                 845

Cys Gly Ile Ser Ser Val Ser Arg Met Glu Asn Ile Met Trp Arg Ser
        850                 855                 860

Val Glu Gly Glu Leu Asn Ala Ile Leu Glu Glu Asn Gly Val Gln Leu
        865                 870                 875                 880

Thr Val Val Val Gly Ser Val Lys Asn Pro Met Trp Arg Gly Pro Gln
                        885                 890                 895

Arg Leu Pro Val Pro Val Asn Glu Leu Pro His Gly Trp Lys Ala Trp
                        900                 905                 910

Gly Lys Ser Tyr Phe Val Arg Ala Ala Lys Thr Asn Asn Ser Phe Val
                        915                 920                 925

Val Asp Gly Asp Thr Leu Lys Glu Cys Pro Leu Lys His Arg Ala Trp
                        930                 935                 940

Asn Ser Phe Leu Val Glu Asp His Gly Phe Gly Val Phe His Thr Ser
        945                 950                 955                 960

Val Trp Leu Lys Val Arg Glu Asp Tyr Ser Leu Glu Cys Asp Pro Ala
                        965                 970                 975

Val Ile Gly Thr Ala Val Lys Gly Lys Glu Ala Val His Ser Asp Leu
                        980                 985                 990

Gly Tyr Trp Ile Glu Ser Glu Lys Asn Asp Thr Trp Arg Leu Lys Arg
                        995                 1000                1005

Ala His Leu Ile Glu Met Lys Thr Cys Glu Trp Pro Lys Ser His
                        1010                1015                1020

Thr Leu Trp Thr Asp Gly Ile Glu Glu Ser Asp Leu Ile Ile Pro
                        1025                1030                1035

Lys Ser Leu Ala Gly Pro Leu Ser His His Asn Thr Arg Glu Gly
                        1040                1045                1050

Tyr Arg Thr Gln Met Lys Gly Pro Trp His Ser Glu Glu Leu Glu
                        1055                1060                1065

Ile Arg Phe Glu Glu Cys Pro Gly Thr Lys Val His Val Glu Glu
                        1070                1075                1080

Thr Cys Gly Thr Arg Gly Pro Ser Leu Arg Ser Thr Thr Ala Ser
                        1085                1090                1095

Gly Arg Val Ile Glu Glu Trp Cys Cys Arg Glu Cys Thr Met Pro
                        1100                1105                1110

Pro Leu Ser Phe Arg Ala Lys Asp Gly Cys Trp Tyr Gly Met Glu
                        1115                1120                1125
```

```
Ile Arg Pro Arg Lys Glu Pro Glu Ser Asn Leu Val Arg Ser Met
    1130            1135                1140

Val Thr Ala Gly Ser Thr Asp His Met Asp His Phe Ser Leu Gly
    1145            1150                1155

Val Leu Val Ile Leu Leu Met Val Gln Glu Gly Leu Lys Lys Arg
    1160            1165                1170

Met Thr Thr Lys Ile Ile Ile Ser Thr Ser Met Ala Val Leu Val
    1175            1180                1185

Ala Met Ile Leu Gly Gly Phe Ser Met Ser Asp Leu Ala Lys Leu
    1190            1195                1200

Ala Ile Leu Met Gly Ala Thr Phe Ala Glu Met Asn Thr Gly Gly
    1205            1210                1215

Asp Val Ala His Leu Ala Leu Ile Ala Ala Phe Lys Val Arg Pro
    1220            1225                1230

Ala Leu Leu Val Ser Phe Ile Phe Arg Ala Asn Trp Thr Pro Arg
    1235            1240                1245

Glu Ser Met Leu Leu Ala Leu Ala Ser Cys Leu Leu Gln Thr Ala
    1250            1255                1260

Ile Ser Ala Leu Glu Gly Asp Leu Met Val Leu Ile Asn Gly Phe
    1265            1270                1275

Ala Leu Ala Trp Leu Ala Ile Arg Ala Met Val Val Pro Arg Thr
    1280            1285                1290

Asp Asn Ile Thr Leu Ala Ile Leu Ala Ala Leu Thr Pro Leu Ala
    1295            1300                1305

Arg Gly Thr Leu Leu Val Ala Trp Arg Ala Gly Leu Ala Thr Cys
    1310            1315                1320

Gly Gly Phe Met Leu Leu Ser Leu Lys Gly Lys Gly Ser Val Lys
    1325            1330                1335

Lys Asn Leu Pro Phe Val Met Ala Leu Gly Leu Thr Ala Val Arg
    1340            1345                1350

Leu Val Asp Pro Ile Asn Val Val Gly Leu Leu Leu Leu Thr Arg
    1355            1360                1365

Ser Gly Lys Arg Ser Trp Pro Pro Ser Glu Val Leu Thr Ala Val
    1370            1375                1380

Gly Leu Ile Cys Ala Leu Ala Gly Gly Phe Ala Lys Ala Asp Ile
    1385            1390                1395

Glu Met Ala Gly Pro Met Ala Ala Val Gly Leu Leu Ile Val Ser
    1400            1405                1410

Tyr Val Val Ser Gly Lys Ser Val Asp Met Tyr Ile Glu Arg Ala
    1415            1420                1425

Gly Asp Ile Thr Trp Glu Lys Asp Ala Glu Val Thr Gly Asn Ser
    1430            1435                1440

Pro Arg Leu Asp Val Ala Leu Asp Glu Ser Gly Asp Phe Ser Leu
    1445            1450                1455

Val Glu Asp Asp Gly Pro Pro Met Arg Glu Ile Ile Leu Lys Val
    1460            1465                1470

Val Leu Met Thr Ile Cys Gly Met Asn Pro Ile Ala Ile Pro Phe
    1475            1480                1485

Ala Ala Gly Ala Trp Tyr Val Tyr Val Lys Thr Gly Lys Arg Ser
    1490            1495                1500

Gly Ala Leu Trp Asp Val Pro Ala Pro Lys Glu Val Lys Lys Gly
    1505            1510                1515
```

-continued

| | | | | | | | | | | | | |
|---|---|---|---|---|---|---|---|---|---|---|---|---|
|Glu|Thr|Thr|Asp|Gly|Val|Tyr|Arg|Val|Met|Thr|Arg|Arg|Leu|Leu|
| |1520| | | | |1525| | | |1530| | | | |

Gly Ser Thr Gln Val Gly Val Gly Val Met Gln Glu Gly Val Phe
    1535              1540              1545

His Thr Met Trp His Val Thr Lys Gly Ser Ala Leu Arg Ser Gly
    1550              1555              1560

Glu Gly Arg Leu Asp Pro Tyr Trp Gly Asp Val Lys Gln Asp Leu
    1565              1570              1575

Val Ser Tyr Cys Gly Pro Trp Lys Leu Asp Ala Ala Trp Asp Gly
    1580              1585              1590

His Ser Glu Val Gln Leu Leu Ala Val Pro Pro Gly Glu Arg Ala
    1595              1600              1605

Arg Asn Ile Gln Thr Leu Pro Gly Ile Phe Lys Thr Lys Asp Gly
    1610              1615              1620

Asp Ile Gly Ala Val Ala Leu Asp Tyr Pro Ala Gly Thr Ser Gly
    1625              1630              1635

Ser Pro Ile Leu Asp Lys Cys Gly Arg Val Ile Gly Leu Tyr Gly
    1640              1645              1650

Asn Gly Val Val Ile Lys Asn Gly Ser Tyr Val Ser Ala Ile Thr
    1655              1660              1665

Gln Gly Arg Arg Glu Glu Glu Thr Pro Val Glu Cys Phe Glu Pro
    1670              1675              1680

Ser Met Leu Lys Lys Lys Gln Leu Thr Val Leu Asp Leu His Pro
    1685              1690              1695

Gly Ala Gly Lys Thr Arg Arg Val Leu Pro Glu Ile Val Arg Glu
    1700              1705              1710

Ala Ile Lys Thr Arg Leu Arg Thr Val Ile Leu Ala Pro Thr Arg
    1715              1720              1725

Val Val Ala Ala Glu Met Glu Glu Ala Leu Arg Gly Leu Pro Val
    1730              1735              1740

Arg Tyr Met Thr Thr Ala Val Asn Val Thr His Ser Gly Thr Glu
    1745              1750              1755

Ile Val Asp Leu Met Cys His Ala Thr Phe Thr Ser Arg Leu Leu
    1760              1765              1770

Gln Pro Ile Arg Val Pro Asn Tyr Asn Leu Tyr Ile Met Asp Glu
    1775              1780              1785

Ala His Phe Thr Asp Pro Ser Ser Ile Ala Ala Arg Gly Tyr Ile
    1790              1795              1800

Ser Thr Arg Val Glu Met Gly Glu Ala Ala Ala Ile Phe Met Thr
    1805              1810              1815

Ala Thr Pro Pro Gly Thr Arg Asp Ala Phe Pro Asp Ser Asn Ser
    1820              1825              1830

Pro Ile Met Asp Thr Glu Val Glu Val Pro Glu Arg Ala Trp Ser
    1835              1840              1845

Ser Gly Phe Asp Trp Val Thr Asp His Ser Gly Lys Thr Val Trp
    1850              1855              1860

Phe Val Pro Ser Val Arg Asn Gly Asn Glu Ile Ala Ala Cys Leu
    1865              1870              1875

Thr Lys Ala Gly Lys Arg Val Ile Gln Leu Ser Arg Lys Thr Phe
    1880              1885              1890

Glu Thr Glu Phe Gln Lys Thr Lys His Gln Glu Trp Asp Phe Val
    1895              1900              1905

Val Thr Thr Asp Ile Ser Glu Met Gly Ala Asn Phe Lys Ala Asp

-continued

```
            1910                1915                1920
Arg Val Ile Asp Ser Arg Arg Cys Leu Lys Pro Val Ile Leu Asp
            1925                1930                1935
Gly Glu Arg Val Ile Leu Ala Gly Pro Met Pro Val Thr His Ala
            1940                1945                1950
Ser Ala Ala Gln Arg Arg Gly Arg Ile Gly Arg Asn Pro Asn Lys
            1955                1960                1965
Pro Gly Asp Glu Tyr Leu Tyr Gly Gly Gly Cys Ala Glu Thr Asp
            1970                1975                1980
Glu Asp His Ala His Trp Leu Glu Ala Arg Met Leu Leu Asp Asn
            1985                1990                1995
Ile Tyr Leu Gln Asp Gly Leu Ile Ala Ser Leu Tyr Arg Pro Glu
            2000                2005                2010
Ala Asp Lys Val Ala Ala Ile Glu Gly Glu Phe Lys Leu Arg Thr
            2015                2020                2025
Glu Gln Arg Lys Thr Phe Val Glu Leu Met Lys Arg Gly Asp Leu
            2030                2035                2040
Pro Val Trp Leu Ala Tyr Gln Val Ala Ser Ala Gly Ile Thr Tyr
            2045                2050                2055
Thr Asp Arg Arg Trp Cys Phe Asp Gly Thr Thr Asn Asn Thr Ile
            2060                2065                2070
Met Glu Asp Ser Val Pro Ala Glu Val Trp Thr Arg His Gly Glu
            2075                2080                2085
Lys Arg Val Leu Lys Pro Arg Trp Met Asp Ala Arg Val Cys Ser
            2090                2095                2100
Asp His Ala Ala Leu Lys Ser Phe Lys Glu Phe Ala Ala Gly Lys
            2105                2110                2115
Arg Gly Ala Ala Phe Gly Val Met Glu Ala Leu Gly Thr Leu Pro
            2120                2125                2130
Gly His Met Thr Glu Arg Phe Gln Glu Ala Ile Asp Asn Leu Ala
            2135                2140                2145
Val Leu Met Arg Ala Glu Thr Gly Ser Arg Pro Tyr Lys Ala Ala
            2150                2155                2160
Ala Ala Gln Leu Pro Glu Thr Leu Glu Thr Ile Met Leu Leu Gly
            2165                2170                2175
Leu Leu Gly Thr Val Ser Leu Gly Ile Phe Phe Val Leu Met Arg
            2180                2185                2190
Asn Lys Gly Ile Gly Lys Met Gly Phe Gly Met Val Thr Leu Gly
            2195                2200                2205
Ala Ser Ala Trp Leu Met Trp Leu Ser Glu Ile Glu Pro Ala Arg
            2210                2215                2220
Ile Ala Cys Val Leu Ile Val Val Phe Leu Leu Leu Val Val Leu
            2225                2230                2235
Ile Pro Glu Pro Glu Lys Gln Arg Ser Pro Gln Asp Asn Gln Met
            2240                2245                2250
Ala Ile Ile Ile Met Val Ala Val Gly Leu Leu Gly Leu Ile Thr
            2255                2260                2265
Ala Asn Glu Leu Gly Trp Leu Glu Arg Thr Lys Ser Asp Leu Ser
            2270                2275                2280
His Leu Met Gly Arg Arg Glu Glu Gly Ala Thr Ile Gly Phe Ser
            2285                2290                2295
Met Asp Ile Asp Leu Arg Pro Ala Ser Ala Trp Ala Ile Tyr Ala
            2300                2305                2310
```

```
Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
2480                2485                2490

Asn Ile Phe Arg Gly Ser Tyr Leu Ala Gly Ala Ser Leu Ile Tyr
2495                2500                2505

Thr Val Thr Arg Asn Ala Gly Leu Val Lys Arg Arg Gly Gly Gly
2510                2515                2520

Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550

Glu Val Cys Arg Glu Glu Ala Arg Arg Ala Leu Lys Asp Gly Val
2555                2560                2565

Ala Thr Gly Gly His Ala Val Ser Arg Gly Ser Ala Lys Leu Arg
2570                2575                2580

Trp Leu Val Glu Arg Gly Tyr Leu Gln Pro Tyr Gly Lys Val Ile
2585                2590                2595

Asp Leu Gly Cys Gly Arg Gly Gly Trp Ser Tyr Tyr Val Ala Thr
2600                2605                2610

Ile Arg Lys Val Gln Glu Val Lys Gly Tyr Thr Lys Gly Gly Pro
2615                2620                2625

Gly His Glu Glu Pro Val Leu Val Gln Ser Tyr Gly Trp Asn Ile
2630                2635                2640

Val Arg Leu Lys Ser Gly Val Asp Val Phe His Met Ala Ala Glu
2645                2650                2655

Pro Cys Asp Thr Leu Leu Cys Asp Ile Gly Glu Ser Ser Ser Ser
2660                2665                2670

Pro Glu Val Glu Glu Ala Arg Thr Leu Arg Val Leu Ser Met Val
2675                2680                2685

Gly Asp Trp Leu Glu Lys Arg Pro Gly Ala Phe Cys Ile Lys Val
2690                2695                2700
```

```
Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970

Asn Met Met Gly Lys Arg Glu Lys Lys Gln Gly Glu Phe Gly Lys
    2975                2980                2985

Ala Lys Gly Ser Arg Ala Ile Trp Tyr Met Trp Leu Gly Ala Arg
    2990                2995                3000

Phe Leu Glu Phe Glu Ala Leu Gly Phe Leu Asn Glu Asp His Trp
    3005                3010                3015

Met Gly Arg Glu Asn Ser Gly Gly Gly Val Glu Gly Leu Gly Leu
    3020                3025                3030

Gln Arg Leu Gly Tyr Val Leu Glu Glu Met Ser Arg Ile Pro Gly
    3035                3040                3045

Gly Arg Met Tyr Ala Asp Asp Thr Ala Gly Trp Asp Thr Arg Ile
    3050                3055                3060

Ser Arg Phe Asp Leu Glu Asn Glu Ala Leu Ile Thr Asn Gln Met
    3065                3070                3075

Glu Lys Gly His Arg Ala Leu Ala Leu Ala Ile Ile Lys Tyr Thr
    3080                3085                3090

Tyr Gln Asn Lys Val Val Lys Val Leu Arg Pro Ala Glu Lys Gly
```

| | | | | | | | | | | | | |
|---|---|---|---|---|---|---|---|---|---|---|---|---|
| | | 3095 | | | | 3100 | | | | 3105 | | |
| Lys | Thr | Val | Met | Asp | Ile | Ile | Ser | Arg | Gln | Asp | Gln | Arg | Gly | Ser |
| | | 3110 | | | | 3115 | | | | 3120 | | |
| Gly | Gln | Val | Val | Thr | Tyr | Ala | Leu | Asn | Thr | Phe | Thr | Asn | Leu | Val |
| | | 3125 | | | | 3130 | | | | 3135 | | |
| Val | Gln | Leu | Ile | Arg | Asn | Met | Glu | Ala | Glu | Glu | Val | Leu | Glu | Met |
| | | 3140 | | | | 3145 | | | | 3150 | | |
| Gln | Asp | Leu | Trp | Leu | Leu | Arg | Arg | Ser | Glu | Lys | Val | Thr | Asn | Trp |
| | | 3155 | | | | 3160 | | | | 3165 | | |
| Leu | Gln | Ser | Asn | Gly | Trp | Asp | Arg | Leu | Lys | Arg | Met | Ala | Val | Ser |
| | | 3170 | | | | 3175 | | | | 3180 | | |
| Gly | Asp | Asp | Cys | Val | Val | Lys | Pro | Ile | Asp | Asp | Arg | Phe | Ala | His |
| | | 3185 | | | | 3190 | | | | 3195 | | |
| Ala | Leu | Arg | Phe | Leu | Asn | Asp | Met | Gly | Lys | Val | Arg | Lys | Asp | Thr |
| | | 3200 | | | | 3205 | | | | 3210 | | |
| Gln | Glu | Trp | Lys | Pro | Ser | Thr | Gly | Trp | Asp | Asn | Trp | Glu | Glu | Val |
| | | 3215 | | | | 3220 | | | | 3225 | | |
| Pro | Phe | Cys | Ser | His | His | Phe | Asn | Lys | Leu | His | Leu | Lys | Asp | Gly |
| | | 3230 | | | | 3235 | | | | 3240 | | |
| Arg | Ser | Ile | Val | Val | Pro | Cys | Arg | His | Gln | Asp | Glu | Leu | Ile | Gly |
| | | 3245 | | | | 3250 | | | | 3255 | | |
| Arg | Ala | Arg | Val | Ser | Pro | Gly | Ala | Gly | Trp | Ser | Ile | Arg | Glu | Thr |
| | | 3260 | | | | 3265 | | | | 3270 | | |
| Ala | Cys | Leu | Ala | Lys | Ser | Tyr | Ala | Gln | Met | Trp | Gln | Leu | Leu | Tyr |
| | | 3275 | | | | 3280 | | | | 3285 | | |
| Phe | His | Arg | Arg | Asp | Leu | Arg | Leu | Met | Ala | Asn | Ala | Ile | Cys | Ser |
| | | 3290 | | | | 3295 | | | | 3300 | | |
| Ser | Val | Pro | Val | Asp | Trp | Val | Pro | Thr | Gly | Arg | Thr | Thr | Trp | Ser |
| | | 3305 | | | | 3310 | | | | 3315 | | |
| Ile | His | Gly | Lys | Gly | Glu | Trp | Met | Thr | Thr | Glu | Asp | Met | Leu | Val |
| | | 3320 | | | | 3325 | | | | 3330 | | |
| Val | Trp | Asn | Arg | Val | Trp | Ile | Glu | Glu | Asn | Asp | His | Met | Glu | Asp |
| | | 3335 | | | | 3340 | | | | 3345 | | |
| Lys | Thr | Pro | Val | Thr | Lys | Trp | Thr | Asp | Ile | Pro | Tyr | Leu | Gly | Lys |
| | | 3350 | | | | 3355 | | | | 3360 | | |
| Arg | Glu | Asp | Leu | Trp | Cys | Gly | Ser | Leu | Ile | Gly | His | Arg | Pro | Arg |
| | | 3365 | | | | 3370 | | | | 3375 | | |
| Thr | Thr | Trp | Ala | Glu | Asn | Ile | Lys | Asn | Thr | Val | Asn | Met | Val | Arg |
| | | 3380 | | | | 3385 | | | | 3390 | | |
| Arg | Ile | Ile | Gly | Asp | Glu | Glu | Lys | Tyr | Met | Asp | Tyr | Leu | Ser | Thr |
| | | 3395 | | | | 3400 | | | | 3405 | | |
| Gln | Val | Arg | Tyr | Leu | Gly | Glu | Glu | Gly | Ser | Thr | Pro | Gly | Val | Leu |
| | | 3410 | | | | 3415 | | | | 3420 | | |

<210> SEQ ID NO 17
<211> LENGTH: 11029
<212> TYPE: DNA
<213> ORGANISM: West Nile virus

<400> SEQUENCE: 17

| | |
|---|---|
| agtagttcgc ctgtgtgagc tgacaaactt agtagtgttt gtgaggatta acaacaatta | 60 |
| acacagtgcg agctgtttct tagcacgaag atctcgatgt ctaagaaacc aggagggccc | 120 |
| ggcaagagcc gggctgtcaa tatgctaaaa cgcggaatgc ccgcgtgtt gtccttgatt | 180 |

```
ggactgaaga gggctatgtt gagcctgatc gacggcaagg ggccaatacg atttgtgttg    240
gctctcttgg cgttcttcag gttcacagca attgctccga cccgagcagt gctggatcga    300
tggagaggtg tgaacaaaca aacagcgatg aaacaccttc tgagttttaa gaaggaacta    360
gggaccttga ccagtgctat caatcggcgg agctcaaaac aaaagaaaag aggaggaaag    420
accggaattg cagtcatgat tggcctgatc gccagcgtag gagcagttac cctctctaac    480
ttccaaggga aggtgatgat gacggtaaat gctactgacg tcacagatgt catcacgatt    540
ccaacagctg ctggaaagaa cctatgcatt gtcagagcaa tggatgtggg atacatgtgc    600
gatgatacta tcacttatga atgcccagtg ctgtcggctg gtaatgatcc agaagacatc    660
gactgttggt gcacaaagtc agcagtctac gtcaggtatg gaagatgcac caagacacgc    720
cactcaagac gcagtcggag gtcactgaca gtgcagacac acggagaaag cactctagcg    780
aacaagaagg gggcttggat ggacagcacc aaggccacaa ggtatttggt aaaaacagaa    840
tcatggatct tgaggaaccc tggatatgcc ctggtggcag ccgtcattgg ttggatgctt    900
gggagcaaca ccatgcagag agttgtgttt gtcgtgctat tgcttttggt ggccccagct    960
tacagcttca actgccttgg aatgagcaac agagacttct tggaaggagt gtctggagca   1020
acatgggtgg atttggttct cgaaggcgac agctgcgtga ctatcatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc gaccatggga   1200
gaagctcaca tgacaaacg tgctgaccca gcttttgtgt gcagacaagg agtggtggac   1260
aggggctggg gcaacggctg cggactattt ggcaaaggaa gcattgacac atgcgccaaa   1320
tttgcctgct ctaccaaggc aataggaaga accatcttga agagaatat caagtacgaa   1380 gtggccattt ttgtccatgg accaactact gtggagtcgc acggaaacta ctccacacag   1440
gttggagcca ctcaggcagg agattcagc atcactcctg cggcgccttc atacacacta   1500
aagcttggag aatatggaga ggtgacagtg gactgtgaac cacggtcagg gattgacacc   1560
aatgcatact acgtgatgac tgttggaaca aagacgttct tggtccatcg tgagtggttc   1620
atggacctca acctcccttg gagcagtgct ggaagtactg tgtggaggaa cagagagacg   1680
ttaatggagt ttgaggaacc acacgccacg aagcagtctg tgatagcatt gggctcacaa   1740
gagggagctc tgcatcaagc tttggctgga gccattcctg tggaattttc aagcaacact   1800
gtcaagttga cgtcgggtca tttgaagtgt agagtgaaga tggaaaaatt gcagttgaag   1860
ggaacaacct atgcgtctg ttcaaaggct ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tgggcagatt ggtcactgtc   2040
aacccttttg tttcagtggc cacggccaac gctaaggtcc tgattgaatt ggaaccaccc   2100
tttggagact catacatagt ggtgggcaga ggagaacaac agatcaatca ccattggcac   2160
aagtctggaa gcagcattgg caaagccttt acaaccaccc tcaaaggagc gcagagacta   2220
gccgctctag agacacagc ttgggacttt ggatcagttg gagggggtgtt cacctcagtt   2280 gggaaggctc tccatcaagt gttcggagga gcattccgct cactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcacgctg acactgggtg tgccatagac atcagccggc aagagctgag atgtggaagt   2520
ggagtgttca tacacaatga tgtggaggct tggatggacc ggtacaagta ttaccctgaa   2580
```

```
acgccacaag gcctagccaa gatcattcag aaagctcata aggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca cacctttgt ggttgatggt     2880
ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat tggaacggct gtcaagaaca acttggcgat ccacagtgac    3060
ctgtcctatt ggattgaaag caggctcaat gatacgtgga agcttgaaag gcagttctg     3120
ggtgaagtca atcatgtac gtggcctgag acgcatacct tgtgggcga tggaatcctt      3180
gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc aggaactaca ggtcaccctg agtgagagct gcggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgacccct tcagttggg ccttctggtc gtgttcttgg ccacccagga ggtccttcgc     3600
aagaggtgga cagccaagat cagcatgcca gctatactga ttgctctgct agtcctggtg    3660
tttggggca ttacttacac tgatgtgtta cgctatgtca tcttggtggg ggcagctttc     3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagctgca aaaagaaag gagcaagtct gctatgcttg     4140
gctctagcct caacaggact tttcaacccc atgatccttg ctgctggact gattgcatgt    4200
gatcccaacc gtaaacgcgg atggcccgca actgaagtga tgacagctgt cggcctaatg    4260
tttgccatcg tcggagggct ggcagagctt gacattgact ccatggccat tccaatgact    4320
atcgcggggc tcatgtttgc tgctttcgtg atttctggga atcaacaga tatgtggatt     4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac cccctgggca    4560
atcttgccct cagtagttgg attttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag agcgggcgt gatggttgaa     4740
ggtgtttttc acaccctttg gcatacaaca aaaggagccg ctttgatgag cggagagggc    4800
cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
```

```
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa acaaggagg     5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc taggggaggc ggcggcaata ttcatgacag ccaccccacc aggcacttca    5580
gatccattcc cagagtccaa ttcaccaatt tccgacttac agactgagat cccggatcga    5640
gcttggaact ctggatacga atggatcaca gaatacaccg gaagacggt ttggtttgtg     5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atggggcta acttcaaggc gagcagggtg     5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggaa     6180
taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg gtgaaaggaa gattctgagg ccgcgctgga ttgacgccag ggtgtactcg    6420
gatcaccagg cactaaaggc gttcaaggac ttcgcctcgg aaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac ctttttctgt tggatggctg aagttccagg aacgaagatc    6780
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttttggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttcccccttc gtcgatgttgg agtgtcggct    7200
ctcctgctag cagccggatg ctgggggacaa gtcaccctca ccgttacggt aacagcggca    7260
acactccttt tttgccacta tgcctacatg gttcccggtt ggcaagctga ggcaatgcgc    7320
```

```
tcagcccagc ggcggacagc ggccggaatc atgaagaacg ctgtagtgga tggcatcgtg      7380
gccacggacg tcccagaatt agagcgcacc acacccatca tgcagaagaa agttggacag      7440
atcatgctga tcttggtgtc tctagctgca gtagtagtga acccgtctgt gaagacagta      7500
cgagaagccg gaattttgat cacggccgca gcggtgacgc tttgggagaa tggagcaagc      7560
tctgtttgga acgcaacaac tgccatcgga ctctgccaca tcatgcgtgg gggttggttg      7620
tcatgtctat ccataacatg gacactcata agaacatgg aaaaaccagg actaaaaga        7680
ggtggggcaa aaggacgcac cttgggagag gtttggaaag aaagactcaa ccagatgaca      7740
aaagaagagt tcactaggta ccgcaaagag gccatcatcg aagtcgatcg ctcagcggca      7800
aaacacgcca ggaaagaagg caatgtcact ggagggcatc cagtctctag ggcacagca       7860
aaactgagat ggctggtcga acggaggttt ctcgaaccgg tcggaaaagt gattgacctt      7920
ggatgtggaa gaggcggttg gtgttactat atggcaaccc aaaaaagagt ccaagaagtc      7980
agagggtaca caaagggcgg tcccggacat gaagagcccc aactagtgca aagttatgga      8040
tggaacattg tcaccatgaa gagtggagtg gatgtgttct acagaccttc tgagtgttgt      8100
gacaccctcc tttgtgacat cggagagtcc tcgtcaagtg ctgaggttga agagcatagg      8160
acgattcggg tccttgaaat ggttgaggac tggctgcacc gagggccaag ggaattttgc      8220
gtgaaggtgc tctgcccta catgccgaaa gtcatagaga gatggagct gctccaacgc        8280
cggtatgggg gggactggt cagaaaccca ctctcacgga attccacgca cgagatgtat       8340
tgggtgagtc gagcttcagg caatgtggta cattcagtga atatgaccag ccaggtgctc      8400
ctaggaagaa tggaaaaaag gacctggaag ggaccccaat acgaggaaga tgtaaacttg      8460
ggaagtggaa ccagggcggt gggaaaaccc ctgctcaact cagacaccag taaaatcaag      8520
aacaggattg aacgactcag gcgtgagtac agttcgacgt ggcaccacga tgagaaccac      8580
ccatatagaa cctggaacta tcacggcagt tatgatgtga agcccacagg ctccgccagt      8640
tcgctggtca atggagtggt caggctcctc tcaaaaccat gggacaccat cacgaatgtt      8700
accaccatgg ccatgactga cactactccc ttcgggcagc agcgagtgtt caaagagaag      8760
gtggacacga aagctcctga accgccagaa ggagtgaagt acgtgctcaa tgagaccacc      8820
aactggttgt gggcgttttt ggccagagaa aaacgtccca gaatgtgctc tcgagaggaa      8880
ttcataagaa aggtcaacag caatgcagct ttgggtgcca tgtttgaaga gcagaatcaa      8940
tggaggagcg ccagagaagc agttgaagat ccaaaatttt gggagatggt ggatgaggag      9000
cgcgaggcac atctgcgggg ggaatgtcac acttgcattt acaacatgat gggaaagaga      9060
gagaaaaaac ccggagagtt cggaaaggcc aagggaagca gagccatttg gttcatgtgg      9120
ctcgagctc gctttctgga gttcgaggct ctgggttttc tcaatgaaga ccactggctt       9180
ggaagaaaga actcaggagg aggtgtcgag ggcttgggcc tccaaaaact gggttacatc      9240
ctgcgtgaag ttggcacccg gcctggggc aagatctatg ctgatgacac agctggctgg       9300
gacacccgca tcacgagagc tgacttggaa aatgaagcta aggtgcttga gctgcttgat      9360
ggggaacatc ggcgtcttgc cagggccatc attgagctca cctatcgtca caagttgtg      9420
aaagtgatgc gcccggctgc tgatggaaga accgtcatgg atgttatctc cagagaagat      9480
cagagggga gtggacaagt tgtcacctac gccctaaaca cttttcaccaa cctggccgtc       9540
cagctggtga ggatgatgga aggggaagga gtgattggcc cagatgatgt ggagaaactc      9600
acaaagggga aaggacccaa agtcaggacc tggctgtttg agaatgggga agaaagactc      9660
```

```
agccgcatgg ctgtcagtgg agatgactgt gtggtaaagc ccctggacga tcgctttgcc  9720
acctcgctcc acttcctcaa tgctatgtca aaggttcgca aagacatcca agagtggaaa  9780
ccgtcaactg gatggtatga ttggcagcag gttccatttt gctcaaacca tttcactgaa  9840
ttgatcatga agatggaag aacactggtg gttccatgcc gaggacagga tgaattggta  9900
ggcagagctc gcatatctcc aggggccgga tggaacgtcc gcgacactgc ttgtctggct  9960
aagtcttatg cccagatgtg gctgcttctg tacttccaca gaagagacct gcggctcatg 10020
gccaacgcca tttgctccgc tgtccctgtg aattgggtcc ctaccggaag aaccacgtgg 10080
tccatccatg caggaggaga gtggatgaca acagaggaca tgttggaggt ctggaaccgt 10140
gtttggatag aggagaatga atggatggaa gacaaaaccc cagtggagaa atggagtgac 10200
gtcccatatt caggaaaacg agaggacatc tggtgtggca gcctgattgg cacaagagcc 10260
cgagccacgt gggcagaaaa catccaggtg gctatcaacc aagtcagagc aatcatcgga 10320
gatgagaagt atgtggatta catgagttca ctaaagagat atgaagacac aactttggtt 10380
gaggacacag tactgtagat atttaatcaa ttgtaaatag acaatataag tatgcataaa 10440
agtgtagttt tatagtagta tttagtggtg ttagtgtaaa tagttaagaa aatttgagg 10500
agaaagtcag gccgggaagt tcccgccacc ggaagttgag tagacggtgc tgcctgcgac 10560
tcaaccccag gaggactggg tgaacaaagc cgcgaagtga tccatgtaag ccctcagaac 10620
cgtctcggaa ggaggacccc acatgttgta acttcaaagc ccaatgtcag accacgctac 10680
ggcgtgctac tctgcggaga gtgcagtctg cgatagtgcc ccaggaggac tgggttaaca 10740
aaggcaaacc aacgccccac gcggccctag ccccggtaat ggtgttaacc agggcgaaag 10800
gactagaggt tagaggagac cccgcggttt aaagtgcacg gcccagcctg actgaagctg 10860
taggtcaggg gaaggactag aggttagtgg agaccccgtg ccacaaaaca ccacaacaaa 10920
acagcatatt gacacctggg atagactagg agatcttctg ctctgcacaa ccagccacac 10980
ggcacagtgc gccgacaatg gtggctggtg gtgcgagaac acaggatct              11029
```

<210> SEQ ID NO 18
<211> LENGTH: 3433
<212> TYPE: PRT
<213> ORGANISM: West Nile virus

<400> SEQUENCE: 18

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
```

```
            130                 135                 140
Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                    165                 170                 175

Pro Val Leu Ser Ala Gly Asn Asp Pro Glu Asp Ile Asp Cys Trp Cys
                180                 185                 190

Thr Lys Ser Ala Val Tyr Val Arg Tyr Gly Arg Cys Thr Lys Thr Arg
            195                 200                 205

His Ser Arg Arg Ser Arg Arg Ser Leu Thr Val Gln Thr His Gly Glu
        210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                    245                 250                 255

Tyr Ala Leu Val Ala Ala Val Ile Gly Trp Met Leu Gly Ser Asn Thr
                260                 265                 270

Met Gln Arg Val Val Phe Val Leu Leu Leu Val Ala Pro Ala
            275                 280                 285

Tyr Ser Phe Asn Cys Leu Gly Met Ser Asn Arg Asp Phe Leu Glu Gly
        290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                    325                 330                 335

Asn Met Glu Ala Ala Asn Leu Ala Glu Val Arg Ser Tyr Cys Tyr Leu
                340                 345                 350

Ala Thr Val Ser Asp Leu Ser Thr Lys Ala Ala Cys Pro Thr Met Gly
            355                 360                 365

Glu Ala His Asn Asp Lys Arg Ala Asp Pro Ala Phe Val Cys Arg Gln
        370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                    405                 410                 415

Gly Arg Thr Ile Leu Lys Glu Asn Ile Lys Tyr Glu Val Ala Ile Phe
                420                 425                 430

Val His Gly Pro Thr Thr Val Glu Ser His Gly Asn Tyr Ser Thr Gln
            435                 440                 445

Val Gly Ala Thr Gln Ala Gly Arg Phe Ser Ile Thr Pro Ala Ala Pro
        450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                    485                 490                 495

Gly Thr Lys Thr Phe Leu Val His Arg Glu Trp Phe Met Asp Leu Asn
                500                 505                 510

Leu Pro Trp Ser Ser Ala Gly Ser Thr Val Trp Arg Asn Arg Glu Thr
            515                 520                 525

Leu Met Glu Phe Glu Glu Pro His Ala Thr Lys Gln Ser Val Ile Ala
        530                 535                 540

Leu Gly Ser Gln Glu Gly Ala Leu His Gln Ala Leu Ala Gly Ala Ile
545                 550                 555                 560
```

```
Pro Val Glu Phe Ser Ser Asn Thr Val Lys Leu Thr Ser Gly His Leu
            565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
            595                 600                 605

Gly His Gly Thr Val Val Leu Glu Leu Gln Tyr Thr Gly Thr Asp Gly
            610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
            645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
            675                 680                 685

Lys Ser Gly Ser Ser Ile Gly Lys Ala Phe Thr Thr Thr Leu Lys Gly
            690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
            725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
            770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
            805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
            835                 840                 845

Arg Ser Val Ser Arg Leu Glu His Gln Met Trp Glu Ala Val Lys Asp
850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
            885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
            915                 920                 925

Pro Glu Thr Lys Glu Cys Pro Thr Gln Asn Arg Ala Trp Asn Ser Leu
930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
            965                 970                 975
```

```
Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp
            1010                1015                1020

Gly Asp Gly Ile Leu Glu Ser Asp Leu Ile Ile Pro Val Thr Leu
            1025                1030                1035

Ala Gly Pro Arg Ser Asn His Asn Arg Arg Pro Gly Tyr Lys Thr
            1040                1045                1050

Gln Asn Gln Gly Pro Trp Asp Glu Gly Arg Val Glu Ile Asp Phe
            1055                1060                1065

Asp Tyr Cys Pro Gly Thr Thr Val Thr Leu Ser Glu Ser Cys Gly
            1070                1075                1080

His Arg Gly Pro Ala Thr Arg Thr Thr Thr Glu Ser Gly Lys Leu
            1085                1090                1095

Ile Thr Asp Trp Cys Cys Arg Ser Cys Thr Leu Pro Pro Leu Arg
            1100                1105                1110

Tyr Gln Thr Asp Ser Gly Cys Trp Tyr Gly Met Glu Ile Arg Pro
            1115                1120                1125

Gln Arg His Asp Glu Lys Thr Leu Val Gln Ser Gln Val Asn Ala
            1130                1135                1140

Tyr Asn Ala Asp Met Ile Asp Pro Phe Gln Leu Gly Leu Leu Val
            1145                1150                1155

Val Phe Leu Ala Thr Gln Glu Val Leu Arg Lys Arg Trp Thr Ala
            1160                1165                1170

Lys Ile Ser Met Pro Ala Ile Leu Ile Ala Leu Leu Val Leu Val
            1175                1180                1185

Phe Gly Gly Ile Thr Tyr Thr Asp Val Leu Arg Tyr Val Ile Leu
            1190                1195                1200

Val Gly Ala Ala Phe Ala Glu Ser Asn Ser Gly Gly Asp Val Val
            1205                1210                1215

His Leu Ala Leu Met Ala Thr Phe Lys Ile Gln Pro Val Phe Met
            1220                1225                1230

Val Ala Ser Phe Leu Lys Ala Arg Trp Thr Asn Gln Glu Asn Ile
            1235                1240                1245

Leu Leu Met Leu Ala Ala Val Phe Phe Gln Met Ala Tyr His Asp
            1250                1255                1260

Ala Arg Gln Ile Leu Leu Trp Glu Ile Pro Asp Val Leu Asn Ser
            1265                1270                1275

Leu Ala Val Ala Trp Met Ile Leu Arg Ala Ile Thr Phe Thr Thr
            1280                1285                1290

Thr Ser Asn Val Val Pro Leu Leu Ala Leu Leu Thr Pro Gly
            1295                1300                1305

Leu Arg Cys Leu Asn Leu Asp Val Tyr Arg Ile Leu Leu Leu Met
            1310                1315                1320

Val Gly Ile Gly Ser Leu Ile Arg Glu Lys Arg Ser Ala Ala Ala
            1325                1330                1335

Lys Lys Lys Gly Ala Ser Leu Leu Cys Leu Ala Leu Ala Ser Thr
            1340                1345                1350

Gly Leu Phe Asn Pro Met Ile Leu Ala Ala Gly Leu Ile Ala Cys
            1355                1360                1365

Asp Pro Asn Arg Lys Arg Gly Trp Pro Ala Thr Glu Val Met Thr
```

```
            1370                1375                1380

Ala Val Gly Leu Met Phe Ala Ile Val Gly Gly Leu Ala Glu Leu
            1385                1390                1395

Asp Ile Asp Ser Met Ala Ile Pro Met Thr Ile Ala Gly Leu Met
            1400                1405                1410

Phe Ala Ala Phe Val Ile Ser Gly Lys Ser Thr Asp Met Trp Ile
            1415                1420                1425

Glu Arg Thr Ala Asp Ile Ser Trp Glu Ser Asp Ala Glu Ile Thr
            1430                1435                1440

Gly Ser Ser Glu Arg Val Asp Val Arg Leu Asp Asp Gly Asn
            1445                1450                1455

Phe Gln Leu Met Asn Asp Pro Gly Ala Pro Trp Lys Ile Trp Met
            1460                1465                1470

Leu Arg Met Val Cys Leu Ala Ile Ser Ala Tyr Thr Pro Trp Ala
            1475                1480                1485

Ile Leu Pro Ser Val Val Gly Phe Trp Ile Thr Leu Gln Tyr Thr
            1490                1495                1500

Lys Arg Gly Gly Val Leu Trp Asp Thr Pro Ser Pro Lys Glu Tyr
            1505                1510                1515

Lys Lys Gly Asp Thr Thr Thr Gly Val Tyr Arg Ile Met Thr Arg
            1520                1525                1530

Gly Leu Leu Gly Ser Tyr Gln Ala Gly Ala Gly Val Met Val Glu
            1535                1540                1545

Gly Val Phe His Thr Leu Trp His Thr Thr Lys Gly Ala Ala Leu
            1550                1555                1560

Met Ser Gly Glu Gly Arg Leu Asp Pro Tyr Trp Gly Ser Val Lys
            1565                1570                1575

Glu Asp Arg Leu Cys Tyr Gly Gly Pro Trp Lys Leu Gln His Lys
            1580                1585                1590

Trp Asn Gly Gln Asp Glu Val Gln Met Ile Val Val Glu Pro Gly
            1595                1600                1605

Lys Asn Val Lys Asn Val Gln Thr Lys Pro Gly Val Phe Lys Thr
            1610                1615                1620

Pro Glu Gly Glu Ile Gly Ala Val Thr Leu Asp Phe Pro Thr Gly
            1625                1630                1635

Thr Ser Gly Ser Pro Ile Val Asp Lys Asn Gly Asp Val Ile Gly
            1640                1645                1650

Leu Tyr Gly Asn Gly Val Ile Met Pro Asn Gly Ser Tyr Ile Ser
            1655                1660                1665

Ala Ile Val Gln Gly Glu Arg Met Asp Glu Pro Ile Pro Ala Gly
            1670                1675                1680

Phe Glu Pro Glu Met Leu Arg Lys Lys Gln Ile Thr Val Leu Asp
            1685                1690                1695

Leu His Pro Gly Ala Gly Lys Thr Arg Arg Ile Leu Pro Gln Ile
            1700                1705                1710

Ile Lys Glu Ala Ile Asn Arg Arg Leu Arg Thr Ala Val Leu Ala
            1715                1720                1725

Pro Thr Arg Val Val Ala Ala Glu Met Ala Glu Ala Leu Arg Gly
            1730                1735                1740

Leu Pro Ile Arg Tyr Gln Thr Ser Ala Val Pro Arg Glu His Asn
            1745                1750                1755

Gly Asn Glu Ile Val Asp Val Met Cys His Ala Thr Leu Thr His
            1760                1765                1770
```

```
Arg Leu Met Ser Pro His Arg Val Pro Asn Tyr Asn Leu Phe Val
1775                1780                1785

Met Asp Glu Ala His Phe Thr Asp Pro Ala Ser Ile Ala Ala Arg
1790                1795                1800

Gly Tyr Ile Ser Thr Lys Val Glu Leu Gly Glu Ala Ala Ala Ile
1805                1810                1815

Phe Met Thr Ala Thr Pro Pro Gly Thr Ser Asp Pro Phe Pro Glu
1820                1825                1830

Ser Asn Ser Pro Ile Ser Asp Leu Gln Thr Glu Ile Pro Asp Arg
1835                1840                1845

Ala Trp Asn Ser Gly Tyr Glu Trp Ile Thr Glu Tyr Thr Gly Lys
1850                1855                1860

Thr Val Trp Phe Val Pro Ser Val Lys Met Gly Asn Glu Ile Ala
1865                1870                1875

Leu Cys Leu Gln Arg Ala Gly Lys Lys Val Val Gln Leu Asn Arg
1880                1885                1890

Lys Ser Tyr Glu Thr Glu Tyr Pro Lys Cys Lys Asn Asp Asp Trp
1895                1900                1905

Asp Phe Val Ile Thr Thr Asp Ile Ser Glu Met Gly Ala Asn Phe
1910                1915                1920

Lys Ala Ser Arg Val Ile Asp Ser Arg Lys Ser Val Lys Pro Thr
1925                1930                1935

Ile Ile Thr Glu Gly Glu Gly Arg Val Ile Leu Gly Glu Pro Ser
1940                1945                1950

Ala Val Thr Ala Ala Ser Ala Ala Gln Arg Arg Gly Arg Ile Gly
1955                1960                1965

Arg Asn Pro Ser Gln Val Gly Asp Glu Tyr Cys Tyr Gly Gly His
1970                1975                1980

Thr Asn Glu Asp Asp Ser Asn Phe Ala His Trp Thr Glu Ala Arg
1985                1990                1995

Ile Met Leu Asp Asn Ile Asn Met Pro Asn Gly Leu Ile Ala Gln
2000                2005                2010

Phe Tyr Gln Pro Glu Arg Glu Lys Val Tyr Thr Met Asp Gly Glu
2015                2020                2025

Tyr Arg Leu Arg Gly Glu Glu Arg Lys Asn Phe Leu Glu Leu Leu
2030                2035                2040

Arg Thr Ala Asp Leu Pro Val Trp Leu Ala Tyr Lys Val Ala Ala
2045                2050                2055

Ala Gly Val Ser Tyr His Asp Arg Arg Trp Cys Phe Asp Gly Pro
2060                2065                2070

Arg Thr Asn Thr Ile Leu Glu Asp Asn Asn Glu Val Glu Val Ile
2075                2080                2085

Thr Lys Leu Gly Glu Arg Lys Ile Leu Arg Pro Arg Trp Ile Asp
2090                2095                2100

Ala Arg Val Tyr Ser Asp His Gln Ala Leu Lys Ala Phe Lys Asp
2105                2110                2115

Phe Ala Ser Gly Lys Arg Ser Gln Ile Gly Leu Ile Glu Val Leu
2120                2125                2130

Gly Lys Met Pro Glu His Phe Met Gly Lys Thr Trp Glu Ala Leu
2135                2140                2145

Asp Thr Met Tyr Val Val Ala Thr Ala Glu Lys Gly Gly Arg Ala
2150                2155                2160
```

```
His Arg Met Ala Leu Glu Glu Leu Pro Asp Ala Leu Gln Thr Ile
2165                2170                2175

Ala Leu Ile Ala Leu Leu Ser Val Met Thr Met Gly Val Phe Phe
2180                2185                2190

Leu Leu Met Gln Arg Lys Gly Ile Gly Lys Ile Gly Leu Gly Gly
2195                2200                2205

Ala Val Leu Gly Val Ala Thr Phe Phe Cys Trp Met Ala Glu Val
2210                2215                2220

Pro Gly Thr Lys Ile Ala Gly Met Leu Leu Ser Leu Leu Leu
2225                2230                2235

Met Ile Val Leu Ile Pro Glu Pro Glu Lys Gln Arg Ser Gln Thr
2240                2245                2250

Asp Asn Gln Leu Ala Val Phe Leu Ile Cys Val Met Thr Leu Val
2255                2260                2265

Ser Ala Val Ala Ala Asn Glu Met Gly Trp Leu Asp Lys Thr Lys
2270                2275                2280

Ser Asp Ile Ser Ser Leu Phe Gly Gln Arg Ile Glu Val Lys Glu
2285                2290                2295

Asn Phe Ser Met Gly Glu Phe Leu Leu Asp Leu Arg Pro Ala Thr
2300                2305                2310

Ala Trp Ser Leu Tyr Ala Val Thr Thr Ala Val Leu Thr Pro Leu
2315                2320                2325

Leu Lys His Leu Ile Thr Ser Asp Tyr Ile Asn Thr Ser Leu Thr
2330                2335                2340

Ser Ile Asn Val Gln Ala Ser Ala Leu Phe Thr Leu Ala Arg Gly
2345                2350                2355

Phe Pro Phe Val Asp Val Gly Val Ser Ala Leu Leu Leu Ala Ala
2360                2365                2370

Gly Cys Trp Gly Gln Val Thr Leu Thr Val Thr Val Thr Ala Ala
2375                2380                2385

Thr Leu Leu Phe Cys His Tyr Ala Tyr Met Val Pro Gly Trp Gln
2390                2395                2400

Ala Glu Ala Met Arg Ser Ala Gln Arg Arg Thr Ala Ala Gly Ile
2405                2410                2415

Met Lys Asn Ala Val Val Asp Gly Ile Val Ala Thr Asp Val Pro
2420                2425                2430

Glu Leu Glu Arg Thr Thr Pro Ile Met Gln Lys Lys Val Gly Gln
2435                2440                2445

Ile Met Leu Ile Leu Val Ser Leu Ala Ala Val Val Val Asn Pro
2450                2455                2460

Ser Val Lys Thr Val Arg Glu Ala Gly Ile Leu Ile Thr Ala Ala
2465                2470                2475

Ala Val Thr Leu Trp Glu Asn Gly Ala Ser Ser Val Trp Asn Ala
2480                2485                2490

Thr Thr Ala Ile Gly Leu Cys His Ile Met Arg Gly Gly Trp Leu
2495                2500                2505

Ser Cys Leu Ser Ile Thr Trp Thr Leu Ile Lys Asn Met Glu Lys
2510                2515                2520

Pro Gly Leu Lys Arg Gly Gly Ala Lys Gly Arg Thr Leu Gly Glu
2525                2530                2535

Val Trp Lys Glu Arg Leu Asn Gln Met Thr Lys Glu Glu Phe Thr
2540                2545                2550

Arg Tyr Arg Lys Glu Ala Ile Ile Glu Val Asp Arg Ser Ala Ala
```

```
              2555                2560                2565
Lys His Ala Arg Lys Glu Gly Asn Val Thr Gly Gly His Pro Val
    2570                2575                2580

Ser Arg Gly Thr Ala Lys Leu Arg Trp Leu Val Glu Arg Arg Phe
    2585                2590                2595

Leu Glu Pro Val Gly Lys Val Ile Asp Leu Gly Cys Gly Arg Gly
    2600                2605                2610

Gly Trp Cys Tyr Tyr Met Ala Thr Gln Lys Arg Val Gln Glu Val
    2615                2620                2625

Arg Gly Tyr Thr Lys Gly Gly Pro Gly His Glu Glu Pro Gln Leu
    2630                2635                2640

Val Gln Ser Tyr Gly Trp Asn Ile Val Thr Met Lys Ser Gly Val
    2645                2650                2655

Asp Val Phe Tyr Arg Pro Ser Glu Cys Cys Asp Thr Leu Leu Cys
    2660                2665                2670

Asp Ile Gly Glu Ser Ser Ser Ser Ala Glu Val Glu Glu His Arg
    2675                2680                2685

Thr Ile Arg Val Leu Glu Met Val Glu Asp Trp Leu His Arg Gly
    2690                2695                2700

Pro Arg Glu Phe Cys Val Lys Val Leu Cys Pro Tyr Met Pro Lys
    2705                2710                2715

Val Ile Glu Lys Met Glu Leu Leu Gln Arg Arg Tyr Gly Gly Gly
    2720                2725                2730

Leu Val Arg Asn Pro Leu Ser Arg Asn Ser Thr His Glu Met Tyr
    2735                2740                2745

Trp Val Ser Arg Ala Ser Gly Asn Val Val His Ser Val Asn Met
    2750                2755                2760

Thr Ser Gln Val Leu Leu Gly Arg Met Glu Lys Arg Thr Trp Lys
    2765                2770                2775

Gly Pro Gln Tyr Glu Glu Asp Val Asn Leu Gly Ser Gly Thr Arg
    2780                2785                2790

Ala Val Gly Lys Pro Leu Leu Asn Ser Asp Thr Ser Lys Ile Lys
    2795                2800                2805

Asn Arg Ile Glu Arg Leu Arg Arg Glu Tyr Ser Ser Thr Trp His
    2810                2815                2820

His Asp Glu Asn His Pro Tyr Arg Thr Trp Asn Tyr His Gly Ser
    2825                2830                2835

Tyr Asp Val Lys Pro Thr Gly Ser Ala Ser Ser Leu Val Asn Gly
    2840                2845                2850

Val Val Arg Leu Leu Ser Lys Pro Trp Asp Thr Ile Thr Asn Val
    2855                2860                2865

Thr Thr Met Ala Met Thr Asp Thr Thr Pro Phe Gly Gln Gln Arg
    2870                2875                2880

Val Phe Lys Glu Lys Val Asp Thr Lys Ala Pro Glu Pro Pro Glu
    2885                2890                2895

Gly Val Lys Tyr Val Leu Asn Glu Thr Thr Asn Trp Leu Trp Ala
    2900                2905                2910

Phe Leu Ala Arg Glu Lys Arg Pro Arg Met Cys Ser Arg Glu Glu
    2915                2920                2925

Phe Ile Arg Lys Val Asn Ser Asn Ala Ala Leu Gly Ala Met Phe
    2930                2935                2940

Glu Glu Gln Asn Gln Trp Arg Ser Ala Arg Glu Ala Val Glu Asp
    2945                2950                2955
```

-continued

```
Pro Lys Phe Trp Glu Met Val Asp Glu Arg Glu Ala His Leu
    2960                2965            2970

Arg Gly Glu Cys His Thr Cys Ile Tyr Asn Met Met Gly Lys Arg
    2975                2980            2985

Glu Lys Lys Pro Gly Glu Phe Gly Lys Ala Lys Gly Ser Arg Ala
    2990                2995            3000

Ile Trp Phe Met Trp Leu Gly Ala Arg Phe Leu Glu Phe Glu Ala
    3005                3010            3015

Leu Gly Phe Leu Asn Glu Asp His Trp Leu Gly Arg Lys Asn Ser
    3020                3025            3030

Gly Gly Gly Val Glu Gly Leu Gly Leu Gln Lys Leu Gly Tyr Ile
    3035                3040            3045

Leu Arg Glu Val Gly Thr Arg Pro Gly Gly Lys Ile Tyr Ala Asp
    3050                3055            3060

Asp Thr Ala Gly Trp Asp Thr Arg Ile Thr Arg Ala Asp Leu Glu
    3065                3070            3075

Asn Glu Ala Lys Val Leu Glu Leu Leu Asp Gly Glu His Arg Arg
    3080                3085            3090

Leu Ala Arg Ala Ile Ile Glu Leu Thr Tyr Arg His Lys Val Val
    3095                3100            3105

Lys Val Met Arg Pro Ala Ala Asp Gly Arg Thr Val Met Asp Val
    3110                3115            3120

Ile Ser Arg Glu Asp Gln Arg Gly Ser Gly Gln Val Val Thr Tyr
    3125                3130            3135

Ala Leu Asn Thr Phe Thr Asn Leu Ala Val Gln Leu Val Arg Met
    3140                3145            3150

Met Glu Gly Glu Gly Val Ile Gly Pro Asp Asp Val Glu Lys Leu
    3155                3160            3165

Thr Lys Gly Lys Gly Pro Lys Val Arg Thr Trp Leu Phe Glu Asn
    3170                3175            3180

Gly Glu Glu Arg Leu Ser Arg Met Ala Val Ser Gly Asp Asp Cys
    3185                3190            3195

Val Val Lys Pro Leu Asp Asp Arg Phe Ala Thr Ser Leu His Phe
    3200                3205            3210

Leu Asn Ala Met Ser Lys Val Arg Lys Asp Ile Gln Glu Trp Lys
    3215                3220            3225

Pro Ser Thr Gly Trp Tyr Asp Trp Gln Gln Val Pro Phe Cys Ser
    3230                3235            3240

Asn His Phe Thr Glu Leu Ile Met Lys Asp Gly Arg Thr Leu Val
    3245                3250            3255

Val Pro Cys Arg Gly Gln Asp Glu Leu Val Gly Arg Ala Arg Ile
    3260                3265            3270

Ser Pro Gly Ala Gly Trp Asn Val Arg Asp Thr Ala Cys Leu Ala
    3275                3280            3285

Lys Ser Tyr Ala Gln Met Trp Leu Leu Leu Tyr Phe His Arg Arg
    3290                3295            3300

Asp Leu Arg Leu Met Ala Asn Ala Ile Cys Ser Ala Val Pro Val
    3305                3310            3315

Asn Trp Val Pro Thr Gly Arg Thr Thr Trp Ser Ile His Ala Gly
    3320                3325            3330

Gly Glu Trp Met Thr Thr Glu Asp Met Leu Glu Val Trp Asn Arg
    3335                3340            3345
```

| | | | | | | | | | | |
|---|---|---|---|---|---|---|---|---|---|---|
|Val|Trp|Ile|Glu|Glu|Asn|Glu|Trp|Met|Glu|Asp|Lys|Thr|Pro|Val|
| |3350| | | | |3355| | | |3360| | | | |
|Glu|Lys|Trp|Ser|Asp|Val|Pro|Tyr|Ser|Gly|Lys|Arg|Glu|Asp|Ile|
| |3365| | | | |3370| | | |3375| | | | |
|Trp|Cys|Gly|Ser|Leu|Ile|Gly|Thr|Arg|Ala|Arg|Ala|Thr|Trp|Ala|
| |3380| | | | |3385| | | |3390| | | | |
|Glu|Asn|Ile|Gln|Val|Ala|Ile|Asn|Gln|Val|Arg|Ala|Ile|Ile|Gly|
| |3395| | | | |3400| | | |3405| | | | |
|Asp|Glu|Lys|Tyr|Val|Asp|Tyr|Met|Ser|Ser|Leu|Lys|Arg|Tyr|Glu|
| |3410| | | | |3415| | | |3420| | | | |
|Asp|Thr|Thr|Leu|Val|Glu|Asp|Thr|Val|Leu| | | | | |
| |3425| | | | |3430| | | | | | | | |

<210> SEQ ID NO 19
<211> LENGTH: 11905
<212> TYPE: DNA
<213> ORGANISM: Artificial Sequence
<220> FEATURE:
<223> OTHER INFORMATION: Synthetic construct

<400> SEQUENCE: 19

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gatggctcag tcaaagcacg gtctaacaaa agaaatgaca     240
atgaaatacc gtatggaagg gtgcgtcgat ggacataaat tgtgatcac gggagagggc      300
attggatatc cgttcaaagg gaaacaggct attaatctgt gtgtggtcga aggtggacca     360
ttgccatttg ccgaagacat attgtcagct gcctttatgt acggaaacag gttttcact      420
gaatatcctc aagacatagc tgactatttc aagaactcgt gtcctgctgg ttatacatgg     480
gacaggtctt ttctctttga ggatggagca gtttgcatat gtaatgcaga tataacagtg     540
agtgttgaag aaaactgcat gtatcatgag tccaaatttt atggagtgaa ttttcctgct     600
gatggacctg tgatgaaaaa gatgacagat aactgggagc catcctgcga aagatcata      660
ccagtaccta agcagggat attgaaaggg gatgtctcca tgtacctcct tctgaaggat     720
ggtgggcgtt tacggtgcca attcgacaca gtttacaaag caaagtctgt gccaagaaag     780
atgccggact ggcacttcat ccagcataag ctcacccgtg aagaccgcag cgatgctaag     840
aatcagaaat ggcatctgac agaacatgct attgcatccg gatctgcatt gcccggaagc     900
ggagctacta acttcagcct gctgaagcag gctggagacg tggaggagaa ccctggacct     960
atgtccaaaa agcccggcgg tcctgggaaa tccagagccg tgaacatgtt gaaaaggggg    1020
atgccacggg tactgagtct gatcggcctc aaaagagcca tgttgagcct gatcgacggc    1080
aaggggccaa tacgatttgt gttggctctc ttggcgttct tcaggttcac agcaattgct    1140
ccgacccgag cagtgctgga tcgatggaga ggtgtgaaca acaaacagc gatgaaacac    1200
cttctgagtt ttaagaagga actagggacc ttgaccagtg ctatcaatcg gcggagttcg    1260
aaacaaaaga aaagaggagg aaagaccgga attgcagtca tgattggcct gatcgccagc    1320
gctatggcag cggaggtcac tagacgtggg agtgcatact atatgtactt ggacagaaac    1380
gatgctgggg aggccatatc ttttccaacc acatttggga tgaataagtg ttatatacag    1440
atcatggatc ttggacacat gtgtgatgcc accatgagct atgaatgccc tatgctggat    1500
gaggggggtgg aaccagatga cgtcgattgt tggtgcaaca cgacgtcaac ttgggttgtg    1560
```

```
tacggaacct gccatcacaa aaaaggtgaa gcacggagaa gtagaagagc tgtgacgctc   1620
ccctcccatt ccactaggaa gctgcaaacg cggtcgcaaa cctggttgga atcaagagaa   1680
tacacaaagc acttgattag agtcgaaaat tggatattca ggaaccctgg cttcgcgtta   1740
gcagcagctg ccatcgcttg gcttttggga agctcaacga gccaaaaagt catatacttg   1800
gtcatgatac tgctgattgc cccggcatac agcatcaggt gcataggagt cagcaatagg   1860
gactttgtgg aaggtatgtc aggtgggact tgggttgatg ttgtcttgga acatggaggt   1920
tgtgtcaccg taatggcaca ggacaaaccg actgtcgaca tagagctggt tacaacaaca   1980
gtcagcaaca tggcggaggt aagatcctac tgctatgagg catcaatatc agacatggct   2040
tcggacagcc gctgcccaac acaaggtgaa gcctaccttg acaagcaatc agacactcaa   2100
tatgtctgca aaagaacgtt agtggacaga ggctggggaa atggatgtgg actttttggc   2160
aaagggagtc tggtgacatg cgctaagttt gcatgctcca agaaaatgac cgggaagagc   2220
atccagccag agaatctgga gtaccggata atgctgtcag ttcatggctc ccagcacagt   2280
gggatgatcg ttaatgacac aggacatgaa actgatgaga atagagcgaa ggttgagata   2340
acgcccaatt caccaagagc cgaagccacc ctgggggggtt ttggaagcct aggacttgat   2400
tgtgaaccga ggacaggcct tgactttttca gatttgtatt acttgactat gaataacaag   2460
cactggttgg ttcacaagga gtggttccac gacattccat taccttgca cgctggggca   2520 gacaccggaa ctccacactg gaacaacaaa gaagcactgg tagagttcaa ggacgcacat   2580 gccaaaggc aaactgtcgt ggttctaggg agtcaagaag gagcagttca cacggccctt   2640
gctggagctc tggaggctga gatggatggt gcaagggaa ggctgtcctc tggccacttg   2700
aaatgtcgcc tgaaaatgga taaacttaga ttgaagggcg tgtcatactc cttgtgtacc   2760
gcagcgttca cattcaccaa gatcccggct gaaacactgc acgggacagt cacagtggag   2820
gtacagtacg cagggacaga tggaccttgc aaggttccag ctcagatggc ggtgacatg    2880 caaactctga ccccagttgg gaggttgata accgctaacc ccgtaatcac tgaaagcact   2940
gagaactcta agatgatgct ggaacttgat ccaccatttg gggactctta cattgtcata   3000
ggagtcgggg agaagaagat cacccaccac tggcacagga gtggcagcac cattggaaaa   3060
gcatttgaag ccactgtgag aggtgccaag agaatggcag tcttgggaga cacagcctgg   3120
gactttggat cagttggagg cgctctcaac tcattgggca agggcatcca tcaaattttt   3180
ggagcagctt tcaaatcatt gtttggagga atgtcctggt tctcacaaat tctcattgga   3240
acgttgctga tgtggttggg tctgaacaca agaatggat ctatttccct tatgtgcttg   3300
gccttagggg gagtgttgat cttcttatcc acagccgtct ctgctgattc cggatgtgcc   3360
atagacatca gccggcaaga gctgagatgt ggaagtggag tgttcatcca caatgatgtg   3420
gaggcttgga tggaccggta caagtattac cctgaaacgc acaaggcct agccaagatc   3480 attcagaaag ctcataagga aggagtgtgc ggtctacgat cagttccag actgagcat    3540 caaatgtggg aagcagtgaa ggacgagctg aacactcttt tgaaggagaa tggtgtggac   3600
cttagtgtcg tggttgagaa acaggaggga atgtacaagt cagcacctaa acgcctcacc   3660
gccaccacgg aaaaattgga aattggctgg aaggcctggg gaaagagtat tttatttgca   3720
ccagaactcg ccaacaacac ctttgtggtt gatggtccgg agaccaagga atgtccgact   3780
cagaatcgcg cttggaatag cttagaagtg gaggatttttg gatttggtct caccagcact   3840
cggatgttcc tgaaggtcag agagagcaac acaactgaat gtgactcgaa gatcattgga   3900
```

```
acggctgtca agaacaactt ggcgatccac agtgacctgt cctattggat tgaaagcagg    3960
ctcaatgata cgtggaagct tgaaagggca gttctgggtg aagtcaaatc atgtacgtgg    4020
cctgagacgc ataccttgtg gggcgatgga atccttgaga gtgacttgat ataccagtc    4080 acactggcgg gaccacgaag caatcacaat cggagacctg ggtacaagac acaaaaccag    4140
ggcccatggg acgaaggccg ggtagagatt gacttcgatt actgcccagg aactacggtc    4200
accctgagtg agagctgcgg acaccgtgga cctgccactc gcaccaccac agagagcgga    4260
aagttgataa cagattggtg ctgcaggagc tgcaccttac caccactgcg ctaccaaact    4320
gacagcggct gttggtatgg tatggagatc agaccacaga gacatgatga aaagaccctc    4380
gtgcagtcac aagtgaatgc ttataatgct gatatgattg accctttca gttgggcctt    4440 ctggtcgtgt tcttggccac ccaggaggtc cttcgcaaga ggtggacagc caagatcagc    4500
atgccagcta tactgattgc tctgctagtc ctggtgtttg ggggcattac ttacactgat    4560
gtgttacgct atgtcatctt ggtgggggca gctttcgcag aatctaattc gggaggagac    4620
gtggtacact tggcgctcat ggcgaccttc aagatacaac cagtgtttat ggtggcatcg    4680
tttctcaaag cgagatggac caaccaggag aacattttgt tgatgttggc ggctgttttc    4740
tttcaaatgg cttattacga tgcccgccaa attctgctct gggagatccc tgatgtgttg    4800
aattcactgg cggtagcttg gatgatactg agagccataa cattcacaac gacatcaaac    4860
gtggttgttc cgctgctagc cctgctaaca cccgggctga gatgcttgaa tctggatgtg    4920
tacaggatac tgctgttgat ggtcggaata ggcagcttga tcagggagaa gaggagtgca    4980
gctgcaaaaa agaaaggagc aagtctgcta tgcttggctc tagcctcaac aggacttttc    5040
aaccccatga tccttgctgc tggactgatt gcatgtgatc ccaaccgtaa acgcggatgg    5100
cccgcaactg aagtgatgac agctgtcggc ctaatgtttg ccatcgtcgg agggctggca    5160
gagcttgaca ttgactccat ggccattcca atgactatcg cggggctcat gtttgctgct    5220
ttcgtgattt ctgggaaatc aacagatatg tggattgaga aacggcgga catttcctgg    5280 gaaagtgatg cagaaattac aggctcgagc gaaagagttg atgtgcggct tgatgatgat    5340
ggaaacttcc agctcatgaa tgatccagga gcaccttgga gatatggat gctcagaatg    5400 gtctgtctcg cgattagtgc gtacacccc tgggcaatct tgccctcagt agttggattt    5460
tggataactc tccaatacac aaagagagga ggcgtgttgt gggacactcc ctcaccaaag    5520
gagtacaaaa aggggacac gaccaccggc gtctacagga tcatgactcg tgggctgctc    5580
ggcagttatc aagcaggagc gggcgtgatg gttgaaggtg ttttccacac cctttggcat    5640
acaacaaaag gagccgcttt gatgagcgga gagggccgcc tggacccata ctggggcagt    5700
gtcaaggagg atcgactttg ttacggagga ccctggaaat gcagcacaa gtggaacggg    5760 caggatgagg tgcagatgat tgtggtggaa cctggcagga acgttaagaa cgtccagacg    5820
aaaccagggg tgttcaaaac acctgaagga gaaatcgggg ccgtgacttt ggacttcccc    5880
actggaacat caggctcacc aatagtggac aaaaacggtg atgtgattgg ctttatggc    5940 aatggagtca taatgcccaa cggctcatac ataagcgcga tagtgcaggg tgaaaggatg    6000
gatgagccaa tccagccgg attcgaacct gagatgctga ggaaaaaca gatcactgta    6060 ctggatctcc atcccggcgc cggtaaaaca aggaggattc tgccacagat catcaaagag    6120
gccataaaca gaagactgag aacagccgtg ctagcaccaa ccagggttgt ggctgctgag    6180
atggctgaag cactgagagg actgcccatc cggtaccaga catccgcagt gcccagagaa    6240
cataatggaa atgagattgt tgatgtcatg tgtcatgcta ccctcaccca caggctgatg    6300
```

```
tctcctcaca gggtgccgaa ctacaacctg ttcgtgatgg atgaggctca tttcaccgac   6360
ccagctagca ttgcagcaag aggttacatt tccacaaagg tcgagctagg ggaggcggcg   6420
gcaatattca tgacagccac cccaccaggc acttcagatc cattcccaga gtccaattca   6480
ccaatttccg acttacagac tgagatcccg gatcgagctt ggaactctgg atacgaatgg   6540
atcacagaat acaccgggaa gacggtttgg tttgtgccta gtgtcaagat ggggaatgag   6600
attgcccttt gcctacaacg tgctggaaag aaagtagtcc aattgaacag aaagtcgtac   6660
gagacggagt acccaaaatg taagaacgat gattgggact tgttatcac aacagacata    6720 tctgaaatgg gggctaactt caaggcgagc agggtgattg acagccggaa gagtgtgaaa   6780
ccaaccatca taacagaagg agaagggaga gtgatcctgg agaaccatc tgcagtgaca    6840 gcagctagtg ccgcccagag acgtggacgt atccgtagaa atccgtcgca agttggtgat   6900
gagtactgtt atggggggca cacgaatgaa gacgactcga acttcgccca ttggactgag   6960
gcacgaatca tgctggacaa catcaacatg ccaaacggac tgatcgctca attctaccaa   7020
ccagagcgtg agaaggtata ccatggat ggggaatacc ggctcagagg agaagagaga     7080
aaaaactttc tggaactgtt gaggactgca gatctgccag tttggctggc ttacaaggtt   7140
gcagcggctg gagtgtcata ccacgaccgg aggtggtgct ttgatggtcc taggacaaac   7200 acaatttag aagacaacaa cgaagtggaa gtcatcacga agcttggtga aggaagatt     7260 ctgaggccgc gctggattga cgccagggtg tactcggatc accaggcact aaaggcgttc   7320
aaggacttcg cctcgggaaa acgttctcag atagggctca ttgaggttct gggaaagatg   7380
cctgagcact tcatggggaa gacatgggaa gcacttgaca ccatgtacgt tgtggccact   7440
gcagagaaag gaggaagagc tcacagaatg gccctggagg aactgccaga tgctcttcag   7500
acaattgcct tgattgcctt attgagtgtg atgaccatgg gagtattctt cctcctcatg   7560
cagcggaagg gcattggaaa gataggtttg ggaggcgctg tcttgggagt cgcgaccttt   7620
ttctgttgga tggctgaagt tccaggaacg aagatcgccg gaatgttgct gctctccctt   7680
ctcttgatga ttgtgctaat tcctgagcca gagaagcaac gttcgcagac agacaaccag   7740
ctagccgtgt tcctgatttg tgtcatgacc cttgtgagcg cagtggcagc caacgagatg   7800
ggttggctag ataagaccaa gagtgacata agcagtttgt ttgggcaaag aattgaggtc   7860
aaggagaatt tcagcatggg agagtttctt ttggacttga ggcctgcaac agcctggtca   7920
ctgtacgctg tgacaacagc ggtcctcact ccactgctaa agcatttgat cacgtcagat   7980
tacatcaaca cctcattgac ctcaataaac gttcaggcaa gtgcactatt cacactcgcg   8040
cgaggcttcc ccttcgtcga tgttggagtg tcggctctcc tgctagcagc cggatgctgg   8100
ggacaagtca ccctcaccgt tacggtaaca gcggcaacac tccttttttg ccactatgcc   8160
tacatggttc ccggttggca agctgaggca atgcgctcag cccagcggcg gacagcggcc   8220
ggaatcatga agaacgctgt agtggatggc atcgtggcca cggacgtccc agaattagag   8280
cgcaccacac ccatcatgca agaaaagtt ggacagatca tgctgatctt ggtgtctcta    8340
gctgcagtag tagtgaaccc gtctgtgaag acagtacgag aagccggaat tttgatcacg   8400
gccgcagcgg tgacgcttg ggagaatgga gcaagctctg tttggaacgc aacaactgcc    8460
atcggactct gccacatcat gcgtgggggt tggttgtcat gtctatccat aacatggaca   8520
ctcataaaga acatgaaaa accaggacta aaaagaggtg gggcaaaagg acgcaccttg     8580
ggagaggttt ggaaagaaag actcaaccag atgacaaaag aagagttcac taggtaccgc   8640
```

```
aaagaggcca tcatcgaagt cgatcgctca gcggcaaaac acgccaggaa agaaggcaat    8700
gtcactggag ggcatccagt ctctagggc acagcaaaac tgagatggct ggtcgaacgg    8760
aggtttctcg aaccggtcgg aaaagtgatt gaccttggat gtggaagagg cggttggtgt    8820
tactatatgg caacccaaaa aagagtccaa gaagtcagag ggtacacaaa gggcggtccc    8880
ggacatgaag agccccaact agtgcaaagt tatggatgga acattgtcac catgaagagt    8940
ggagtggatg tgttctacag accttctgag tgttgtgaca ccctcctttg tgacatcgga    9000
gagtcctcgt caagtgctga ggttgaagag cataggacga ttcgggtcct tgaaatggtt    9060
gaggactggc tgcaccgagg gccaagggaa ttttgcgtga aggtgctctg cccctacatg    9120
ccgaaagtca tagagaagat ggagctgctc aacgccggt atgggggggg actggtcaga    9180
aacccactct cacggaattc cacgcacgag atgtattggg tgagtcgagc ttcaggcaat    9240
gtggtacatt cagtgaatat gaccagccag gtgctcctag aagaatgga aaaaggacc    9300 tggaagggac cccaatacga ggaagatgta aacttgggaa gtggaaccag ggcggtggga    9360 aaaccctgc tcaactcaga caccagtaaa atcaagaaca ggattgaacg actcaggcgt    9420
gagtacagtt cgacgtggca ccacgatgag aaccacccat atagaacctg gaactatcac    9480
ggcagttatg atgtgaagcc cacaggctcc gccagttcgc tggtcaatgg agtggtcagg    9540
ctcctctcaa aaccatggga caccatcacg aatgttacca ccatggccat gactgacact    9600
actcccttcg ggcagcagcg agtgttcaaa gagaaggtgg acacgaaagc tcctgaaccg    9660
ccagaaggag tgaagtacgt gctcaacgag accaccaact ggttgtgggc gttttttggcc    9720 agagaaaaac gtcccagaat gtgctctcga gaggaattca taagaaaggt caacagcaat    9780
gcagctttgg gtgccatgtt tgaagagcag aatcaatgga ggagcgccag agaagcagtt    9840
gaagatccaa aattttggga gatggtggat gaggagcgcg aggcacatct gcgggggaa    9900 tgtcacactt gcatttacaa catgatggga aagagagaga aaaacccgg agagttcgga    9960 aaggccaagg gaagcagagc catttggttc atgtggctcg gagctcgctt tctgaggttc    10020
gaggctctgg gttttctcaa tgaagaccac tggcttggaa gaaagaactc aggaggaggt    10080
gtcgagggct tgggcctcca aaaactgggt tacatcctgc gtgaagttgg caccccggcct    10140 ggggccaaga tctatgctga tgacacagct ggctgggaca cccgcatcac gagagctgac    10200
ttggaaaatg aagctaaggt gcttgagctg cttgatgggg aacatcggcg tcttgccagg    10260
gccatcattg agctcaccta tcgtcacaaa gttgtgaaag tgatgcgccc ggctgctgat    10320
ggaagaaccg tcatggatgt tatctccaga gaagatcaga gggggagtgg acaagttgtc    10380
acctacgccc taaacacttt caccaacctg gccgtccagc tggtgaggat gatggaaggg    10440
gaaggagtga ttggcccaga tgatgtggag aaactcacaa aagggaaagg acccaaagtc    10500
aggacctggc tgtttgagaa tggggaagaa agactcagcc gcatggctgt cagtggagat    10560
gactgtgtgg taaagcccct ggacgatcgc tttgccacct cgctccactt cctcaatgct    10620
atgtcaaagg ttcgcaaaga catccaagag tggaaaccgt caactggatg gtatgattgg    10680
cagcaggttc cattttgctc aaaccatttc actgaattga tcatgaaaga tggaagaaca    10740
ctggtggttc catgccgagg acaggatgaa ttggtaggca gagctcgcat atctccaggg    10800
gccggatgga acgtccgcga cactgcttgt ctggctaagt cttatgccca gatgtggctg    10860
cttctgtact ccacagaag agacctgcgc tcatggccca acgccatttg ctccgctgtc    10920
cctgtgaatt gggtccctac cggaagaacc acgtggtcca tccatgcagg aggagagtgg    10980
atgacaacag aggacatgtt ggaggtctgg aaccgtgttt ggatagagga gaatgaatgg    11040
```

```
atggaagaca aaacccagt ggagaaatgg agtgacgtcc catattcagg aaaacgagag    11100
gacatctggt gtggcagcct gattggcaca agagcccgag ccacgtgggc agaaaacatc    11160
caggtggcta tcaaccaagt cagagcaatc atcggagatg agaagtatgt ggattacatg    11220
agttcactaa agagatatga agacacaact ttggttgagg acacagtact gtagatattt    11280
aatcaattgt aaatagacaa tataagtatg cataaaagtg tagttttata gtagtattta    11340
gtggtgttag tgtaaatagt taagaaaatt ttgaggagaa agtcaggccg ggaagttccc    11400
gccaccggaa gttgagtaga cggtgctgcc tgcgactcaa ccccaggagg actgggtgaa    11460
caaagccgcg aagtgatcca tgtaagccct cagaaccgtc tcggaaggag daccccacat    11520
gttgtaactt caaagcccaa tgtcagacca cgctacggcg tgctactctg cggagagtgc    11580
agtctgcgat agtgccccag gaggactggg ttaacaaagg caaaccaacg ccccacgcgg    11640
ccctagcccc ggtaatggtg ttaaccaggg cgaaaggact agaggttaga ggagaccccg    11700
cggtttaaag tgcacggccc agcctggctg aagctgtagg tcaggggaag gactagaggt    11760
tagtggagac cccgtgccac aaaacaccac aacaaaacag catattgaca cctgggatag    11820
actaggagat cttctgctct gcacaaccag ccacacggca cagtgcgccg acaatggtgg    11880
ctggtggtgc gagaacacag gatct                                         11905
```

<210> SEQ ID NO 20
<211> LENGTH: 3725
<212> TYPE: PRT
<213> ORGANISM: Artificial Sequence
<220> FEATURE:
<223> OTHER INFORMATION: Synthetic polypeptide

<400> SEQUENCE: 20

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Met Ala Gln Ser Lys His Gly Leu Thr Lys Glu Met Thr
        35                  40                  45

Met Lys Tyr Arg Met Glu Gly Cys Val Asp Gly His Lys Phe Val Ile
    50                  55                  60

Thr Gly Glu Gly Ile Gly Tyr Pro Phe Lys Gly Lys Gln Ala Ile Asn
65                  70                  75                  80

Leu Cys Val Val Glu Gly Gly Pro Leu Pro Phe Ala Glu Asp Ile Leu
                85                  90                  95

Ser Ala Ala Phe Met Tyr Gly Asn Arg Val Phe Thr Glu Tyr Pro Gln
            100                 105                 110

Asp Ile Ala Asp Tyr Phe Lys Asn Ser Cys Pro Ala Gly Tyr Thr Trp
        115                 120                 125

Asp Arg Ser Phe Leu Phe Glu Asp Gly Ala Val Cys Ile Cys Asn Ala
    130                 135                 140

Asp Ile Thr Val Ser Val Glu Glu Asn Cys Met Tyr His Glu Ser Lys
145                 150                 155                 160

Phe Tyr Gly Val Asn Phe Pro Ala Asp Gly Pro Val Met Lys Lys Met
                165                 170                 175

Thr Asp Asn Trp Glu Pro Ser Cys Glu Lys Ile Ile Pro Val Pro Lys
            180                 185                 190

Gln Gly Ile Leu Lys Gly Asp Val Ser Met Tyr Leu Leu Leu Lys Asp
        195                 200                 205
```

```
Gly Gly Arg Leu Arg Cys Gln Phe Asp Thr Val Tyr Lys Ala Lys Ser
        210                 215                 220

Val Pro Arg Lys Met Pro Asp Trp His Phe Ile Gln His Lys Leu Thr
225                 230                 235                 240

Arg Glu Asp Arg Ser Asp Ala Lys Asn Gln Lys Trp His Leu Thr Glu
                245                 250                 255

His Ala Ile Ala Ser Gly Ser Ala Leu Pro Gly Ser Gly Ala Thr Asn
                260                 265                 270

Phe Ser Leu Leu Lys Gln Ala Gly Asp Val Glu Glu Asn Pro Gly Pro
            275                 280                 285

Met Ser Lys Lys Pro Gly Gly Pro Gly Lys Ser Arg Ala Val Asn Met
        290                 295                 300

Leu Lys Arg Gly Met Pro Arg Val Leu Ser Leu Ile Gly Leu Lys Arg
305                 310                 315                 320

Ala Met Leu Ser Leu Ile Asp Gly Lys Gly Pro Ile Arg Phe Val Leu
                325                 330                 335

Ala Leu Leu Ala Phe Phe Arg Phe Thr Ala Ile Ala Pro Thr Arg Ala
                340                 345                 350

Val Leu Asp Arg Trp Arg Gly Val Asn Lys Gln Thr Ala Met Lys His
                355                 360                 365

Leu Leu Ser Phe Lys Lys Glu Leu Gly Thr Leu Thr Ser Ala Ile Asn
        370                 375                 380

Arg Arg Ser Ser Lys Gln Lys Lys Arg Gly Gly Lys Thr Gly Ile Ala
385                 390                 395                 400

Val Met Ile Gly Leu Ile Ala Ser Ala Met Ala Ala Glu Val Thr Arg
                405                 410                 415

Arg Gly Ser Ala Tyr Tyr Met Tyr Leu Asp Arg Asn Asp Ala Gly Glu
                420                 425                 430

Ala Ile Ser Phe Pro Thr Thr Leu Gly Met Asn Lys Cys Tyr Ile Gln
        435                 440                 445

Ile Met Asp Leu Gly His Met Cys Asp Ala Thr Met Ser Tyr Glu Cys
450                 455                 460

Pro Met Leu Asp Glu Gly Val Glu Pro Asp Asp Val Asp Cys Trp Cys
465                 470                 475                 480

Asn Thr Thr Ser Thr Trp Val Val Tyr Gly Thr Cys His His Lys Lys
                485                 490                 495

Gly Glu Ala Arg Arg Ser Arg Arg Ala Val Thr Leu Pro Ser His Ser
                500                 505                 510

Thr Arg Lys Leu Gln Thr Arg Ser Gln Thr Trp Leu Glu Ser Arg Glu
        515                 520                 525

Tyr Thr Lys His Leu Ile Arg Val Glu Asn Trp Ile Phe Arg Asn Pro
530                 535                 540

Gly Phe Ala Leu Ala Ala Ala Ile Ala Trp Leu Leu Gly Ser Ser
545                 550                 555                 560

Thr Ser Gln Lys Val Ile Tyr Leu Val Met Ile Leu Leu Ile Ala Pro
                565                 570                 575

Ala Tyr Ser Ile Arg Cys Ile Gly Val Ser Asn Arg Asp Phe Val Glu
                580                 585                 590

Gly Met Ser Gly Gly Thr Trp Val Asp Val Val Leu Glu His Gly Gly
            595                 600                 605

Cys Val Thr Val Met Ala Gln Asp Lys Pro Thr Val Asp Ile Glu Leu
610                 615                 620
```

```
Val Thr Thr Thr Val Ser Asn Met Ala Glu Val Arg Ser Tyr Cys Tyr
625                 630                 635                 640

Glu Ala Ser Ile Ser Asp Met Ala Ser Asp Ser Arg Cys Pro Thr Gln
            645                 650                 655

Gly Glu Ala Tyr Leu Asp Lys Gln Ser Asp Thr Gln Tyr Val Cys Lys
            660                 665                 670

Arg Thr Leu Val Asp Arg Gly Trp Gly Asn Gly Cys Gly Leu Phe Gly
            675                 680                 685

Lys Gly Ser Leu Val Thr Cys Ala Lys Phe Ala Cys Ser Lys Lys Met
    690                 695                 700

Thr Gly Lys Ser Ile Gln Pro Glu Asn Leu Glu Tyr Arg Ile Met Leu
705                 710                 715                 720

Ser Val His Gly Ser Gln His Ser Gly Met Ile Val Asn Asp Thr Gly
                725                 730                 735

His Glu Thr Asp Glu Asn Arg Ala Lys Val Glu Ile Thr Pro Asn Ser
            740                 745                 750

Pro Arg Ala Glu Ala Thr Leu Gly Gly Phe Gly Ser Leu Gly Leu Asp
        755                 760                 765

Cys Glu Pro Arg Thr Gly Leu Asp Phe Ser Asp Leu Tyr Tyr Leu Thr
770                 775                 780

Met Asn Asn Lys His Trp Leu Val His Lys Glu Trp Phe His Asp Ile
785                 790                 795                 800

Pro Leu Pro Trp His Ala Gly Ala Asp Thr Gly Thr Pro His Trp Asn
                805                 810                 815

Asn Lys Glu Ala Leu Val Glu Phe Lys Asp Ala His Ala Lys Arg Gln
        820                 825                 830

Thr Val Val Leu Gly Ser Gln Glu Gly Ala Val His Thr Ala Leu
            835                 840                 845

Ala Gly Ala Leu Glu Ala Glu Met Asp Gly Ala Lys Gly Arg Leu Ser
850                 855                 860

Ser Gly His Leu Lys Cys Arg Leu Lys Met Asp Lys Leu Arg Leu Lys
865                 870                 875                 880

Gly Val Ser Tyr Ser Leu Cys Thr Ala Ala Phe Thr Phe Thr Lys Ile
                885                 890                 895

Pro Ala Glu Thr Leu His Gly Thr Val Thr Val Glu Val Gln Tyr Ala
            900                 905                 910

Gly Thr Asp Gly Pro Cys Lys Val Pro Ala Gln Met Ala Val Asp Met
        915                 920                 925

Gln Thr Leu Thr Pro Val Gly Arg Leu Ile Thr Ala Asn Pro Val Ile
930                 935                 940

Thr Glu Ser Thr Glu Asn Ser Lys Met Met Leu Glu Leu Asp Pro Pro
945                 950                 955                 960

Phe Gly Asp Ser Tyr Ile Val Ile Gly Val Gly Glu Lys Lys Ile Thr
                965                 970                 975

His His Trp His Arg Ser Gly Ser Thr Ile Gly Lys Ala Phe Glu Ala
            980                 985                 990

Thr Val Arg Gly Ala Lys Arg Met Ala Val Leu Gly Asp Thr Ala Trp
        995                 1000                1005

Asp Phe Gly Ser Val Gly Gly Ala Leu Asn Ser Leu Gly Lys Gly
    1010                1015                1020

Ile His Gln Ile Phe Gly Ala Ala Phe Lys Ser Leu Phe Gly Gly
    1025                1030                1035

Met Ser Trp Phe Ser Gln Ile Leu Ile Gly Thr Leu Leu Met Trp
```

-continued

```
            1040               1045               1050
Leu Gly Leu Asn Thr Lys Asn Gly Ser Ile Ser Leu Met Cys Leu
            1055               1060               1065
Ala Leu Gly Gly Val Leu Ile Phe Leu Ser Thr Ala Val Ser Ala
            1070               1075               1080
Asp Ser Gly Cys Ala Ile Asp Ile Ser Arg Gln Glu Leu Arg Cys
            1085               1090               1095
Gly Ser Gly Val Phe Ile His Asn Asp Val Glu Ala Trp Met Asp
            1100               1105               1110
Arg Tyr Lys Tyr Tyr Pro Glu Thr Pro Gln Gly Leu Ala Lys Ile
            1115               1120               1125
Ile Gln Lys Ala His Lys Glu Gly Val Cys Gly Leu Arg Ser Val
            1130               1135               1140
Ser Arg Leu Glu His Gln Met Trp Glu Ala Val Lys Asp Glu Leu
            1145               1150               1155
Asn Thr Leu Leu Lys Glu Asn Gly Val Asp Leu Ser Val Val Val
            1160               1165               1170
Glu Lys Gln Glu Gly Met Tyr Lys Ser Ala Pro Lys Arg Leu Thr
            1175               1180               1185
Ala Thr Thr Glu Lys Leu Glu Ile Gly Trp Lys Ala Trp Gly Lys
            1190               1195               1200
Ser Ile Leu Phe Ala Pro Glu Leu Ala Asn Asn Thr Phe Val Val
            1205               1210               1215
Asp Gly Pro Glu Thr Lys Glu Cys Pro Thr Gln Asn Arg Ala Trp
            1220               1225               1230
Asn Ser Leu Glu Val Glu Asp Phe Gly Phe Gly Leu Thr Ser Thr
            1235               1240               1245
Arg Met Phe Leu Lys Val Arg Glu Ser Asn Thr Thr Glu Cys Asp
            1250               1255               1260
Ser Lys Ile Ile Gly Thr Ala Val Lys Asn Asn Leu Ala Ile His
            1265               1270               1275
Ser Asp Leu Ser Tyr Trp Ile Glu Ser Arg Leu Asn Asp Thr Trp
            1280               1285               1290
Lys Leu Glu Arg Ala Val Leu Gly Glu Val Lys Ser Cys Thr Trp
            1295               1300               1305
Pro Glu Thr His Thr Leu Trp Gly Asp Gly Ile Leu Glu Ser Asp
            1310               1315               1320
Leu Ile Ile Pro Val Thr Leu Ala Gly Pro Arg Ser Asn His Asn
            1325               1330               1335
Arg Arg Pro Gly Tyr Lys Thr Gln Asn Gln Gly Pro Trp Asp Glu
            1340               1345               1350
Gly Arg Val Glu Ile Asp Phe Asp Tyr Cys Pro Gly Thr Thr Val
            1355               1360               1365
Thr Leu Ser Glu Ser Cys Gly His Arg Gly Pro Ala Thr Arg Thr
            1370               1375               1380
Thr Thr Glu Ser Gly Lys Leu Ile Thr Asp Trp Cys Cys Arg Ser
            1385               1390               1395
Cys Thr Leu Pro Pro Leu Arg Tyr Gln Thr Asp Ser Gly Cys Trp
            1400               1405               1410
Tyr Gly Met Glu Ile Arg Pro Gln Arg His Asp Glu Lys Thr Leu
            1415               1420               1425
Val Gln Ser Gln Val Asn Ala Tyr Asn Ala Asp Met Ile Asp Pro
            1430               1435               1440
```

-continued

```
Phe Gln Leu Gly Leu Leu Val Val Phe Leu Ala Thr Gln Glu Val
    1445                1450                1455

Leu Arg Lys Arg Trp Thr Ala Lys Ile Ser Met Pro Ala Ile Leu
    1460                1465                1470

Ile Ala Leu Leu Val Leu Val Phe Gly Gly Ile Thr Tyr Thr Asp
    1475                1480                1485

Val Leu Arg Tyr Val Ile Leu Val Gly Ala Ala Phe Ala Glu Ser
    1490                1495                1500

Asn Ser Gly Gly Asp Val Val His Leu Ala Leu Met Ala Thr Phe
    1505                1510                1515

Lys Ile Gln Pro Val Phe Met Val Ala Ser Phe Leu Lys Ala Arg
    1520                1525                1530

Trp Thr Asn Gln Glu Asn Ile Leu Leu Met Leu Ala Ala Val Phe
    1535                1540                1545

Phe Gln Met Ala Tyr Tyr Asp Ala Arg Gln Ile Leu Leu Trp Glu
    1550                1555                1560

Ile Pro Asp Val Leu Asn Ser Leu Ala Val Ala Trp Met Ile Leu
    1565                1570                1575

Arg Ala Ile Thr Phe Thr Thr Thr Ser Asn Val Val Val Pro Leu
    1580                1585                1590

Leu Ala Leu Leu Thr Pro Gly Leu Arg Cys Leu Asn Leu Asp Val
    1595                1600                1605

Tyr Arg Ile Leu Leu Leu Met Val Gly Ile Gly Ser Leu Ile Arg
    1610                1615                1620

Glu Lys Arg Ser Ala Ala Ala Lys Lys Lys Gly Ala Ser Leu Leu
    1625                1630                1635

Cys Leu Ala Leu Ala Ser Thr Gly Leu Phe Asn Pro Met Ile Leu
    1640                1645                1650

Ala Ala Gly Leu Ile Ala Cys Asp Pro Asn Arg Lys Arg Gly Trp
    1655                1660                1665

Pro Ala Thr Glu Val Met Thr Ala Val Gly Leu Met Phe Ala Ile
    1670                1675                1680

Val Gly Gly Leu Ala Glu Leu Asp Ile Asp Ser Met Ala Ile Pro
    1685                1690                1695

Met Thr Ile Ala Gly Leu Met Phe Ala Ala Phe Val Ile Ser Gly
    1700                1705                1710

Lys Ser Thr Asp Met Trp Ile Glu Arg Thr Ala Asp Ile Ser Trp
    1715                1720                1725

Glu Ser Asp Ala Glu Ile Thr Gly Ser Ser Glu Arg Val Asp Val
    1730                1735                1740

Arg Leu Asp Asp Asp Gly Asn Phe Gln Leu Met Asn Asp Pro Gly
    1745                1750                1755

Ala Pro Trp Lys Ile Trp Met Leu Arg Met Val Cys Leu Ala Ile
    1760                1765                1770

Ser Ala Tyr Thr Pro Trp Ala Ile Leu Pro Ser Val Val Gly Phe
    1775                1780                1785

Trp Ile Thr Leu Gln Tyr Thr Lys Arg Gly Gly Val Leu Trp Asp
    1790                1795                1800

Thr Pro Ser Pro Lys Glu Tyr Lys Lys Gly Asp Thr Thr Thr Gly
    1805                1810                1815

Val Tyr Arg Ile Met Thr Arg Gly Leu Leu Gly Ser Tyr Gln Ala
    1820                1825                1830
```

-continued

```
Gly Ala Gly Val Met Val Glu Gly Val Phe His Thr Leu Trp His
    1835            1840            1845

Thr Thr Lys Gly Ala Ala Leu Met Ser Gly Glu Gly Arg Leu Asp
    1850            1855            1860

Pro Tyr Trp Gly Ser Val Lys Glu Asp Arg Leu Cys Tyr Gly Gly
    1865            1870            1875

Pro Trp Lys Leu Gln His Lys Trp Asn Gly Gln Asp Glu Val Gln
    1880            1885            1890

Met Ile Val Val Glu Pro Gly Arg Asn Val Lys Asn Val Gln Thr
    1895            1900            1905

Lys Pro Gly Val Phe Lys Thr Pro Glu Gly Glu Ile Gly Ala Val
    1910            1915            1920

Thr Leu Asp Phe Pro Thr Gly Thr Ser Gly Ser Pro Ile Val Asp
    1925            1930            1935

Lys Asn Gly Asp Val Ile Gly Leu Tyr Gly Asn Gly Val Ile Met
    1940            1945            1950

Pro Asn Gly Ser Tyr Ile Ser Ala Ile Val Gln Gly Glu Arg Met
    1955            1960            1965

Asp Glu Pro Ile Pro Ala Gly Phe Glu Pro Glu Met Leu Arg Lys
    1970            1975            1980

Lys Gln Ile Thr Val Leu Asp Leu His Pro Gly Ala Gly Lys Thr
    1985            1990            1995

Arg Arg Ile Leu Pro Gln Ile Ile Lys Glu Ala Ile Asn Arg Arg
    2000            2005            2010

Leu Arg Thr Ala Val Leu Ala Pro Thr Arg Val Val Ala Ala Glu
    2015            2020            2025

Met Ala Glu Ala Leu Arg Gly Leu Pro Ile Arg Tyr Gln Thr Ser
    2030            2035            2040

Ala Val Pro Arg Glu His Asn Gly Asn Glu Ile Val Asp Val Met
    2045            2050            2055

Cys His Ala Thr Leu Thr His Arg Leu Met Ser Pro His Arg Val
    2060            2065            2070

Pro Asn Tyr Asn Leu Phe Val Met Asp Glu Ala His Phe Thr Asp
    2075            2080            2085

Pro Ala Ser Ile Ala Ala Arg Gly Tyr Ile Ser Thr Lys Val Glu
    2090            2095            2100

Leu Gly Glu Ala Ala Ala Ile Phe Met Thr Ala Thr Pro Pro Gly
    2105            2110            2115

Thr Ser Asp Pro Phe Pro Glu Ser Asn Ser Pro Ile Ser Asp Leu
    2120            2125            2130

Gln Thr Glu Ile Pro Asp Arg Ala Trp Asn Ser Gly Tyr Glu Trp
    2135            2140            2145

Ile Thr Glu Tyr Thr Gly Lys Thr Val Trp Phe Val Pro Ser Val
    2150            2155            2160

Lys Met Gly Asn Glu Ile Ala Leu Cys Leu Gln Arg Ala Gly Lys
    2165            2170            2175

Lys Val Val Gln Leu Asn Arg Lys Ser Tyr Glu Thr Glu Tyr Pro
    2180            2185            2190

Lys Cys Lys Asn Asp Asp Trp Asp Phe Val Ile Thr Thr Asp Ile
    2195            2200            2205

Ser Glu Met Gly Ala Asn Phe Lys Ala Ser Arg Val Ile Asp Ser
    2210            2215            2220

Arg Lys Ser Val Lys Pro Thr Ile Ile Thr Glu Gly Glu Gly Arg
```

```
                2225                2230                2235

Val Ile Leu Gly Glu Pro Ser Ala Val Thr Ala Ala Ser Ala Ala
    2240            2245                2250

Gln Arg Arg Gly Arg Ile Gly Arg Asn Pro Ser Gln Val Gly Asp
2255                2260                2265

Glu Tyr Cys Tyr Gly Gly His Thr Asn Glu Asp Asp Ser Asn Phe
2270                2275                2280

Ala His Trp Thr Glu Ala Arg Ile Met Leu Asp Asn Ile Asn Met
2285                2290                2295

Pro Asn Gly Leu Ile Ala Gln Phe Tyr Gln Pro Glu Arg Glu Lys
2300                2305                2310

Val Tyr Thr Met Asp Gly Glu Tyr Arg Leu Arg Gly Glu Glu Arg
2315                2320                2325

Lys Asn Phe Leu Glu Leu Leu Arg Thr Ala Asp Leu Pro Val Trp
2330                2335                2340

Leu Ala Tyr Lys Val Ala Ala Ala Gly Val Ser Tyr His Asp Arg
2345                2350                2355

Arg Trp Cys Phe Asp Gly Pro Arg Thr Asn Thr Ile Leu Glu Asp
2360                2365                2370

Asn Asn Glu Val Glu Val Ile Thr Lys Leu Gly Glu Arg Lys Ile
2375                2380                2385

Leu Arg Pro Arg Trp Ile Asp Ala Arg Val Tyr Ser Asp His Gln
2390                2395                2400

Ala Leu Lys Ala Phe Lys Asp Phe Ala Ser Gly Lys Arg Ser Gln
2405                2410                2415

Ile Gly Leu Ile Glu Val Leu Gly Lys Met Pro Glu His Phe Met
2420                2425                2430

Gly Lys Thr Trp Glu Ala Leu Asp Thr Met Tyr Val Val Ala Thr
2435                2440                2445

Ala Glu Lys Gly Gly Arg Ala His Arg Met Ala Leu Glu Glu Leu
2450                2455                2460

Pro Asp Ala Leu Gln Thr Ile Ala Leu Ile Ala Leu Leu Ser Val
2465                2470                2475

Met Thr Met Gly Val Phe Phe Leu Leu Met Gln Arg Lys Gly Ile
2480                2485                2490

Gly Lys Ile Gly Leu Gly Gly Ala Val Leu Gly Val Ala Thr Phe
2495                2500                2505

Phe Cys Trp Met Ala Glu Val Pro Gly Thr Lys Ile Ala Gly Met
2510                2515                2520

Leu Leu Leu Ser Leu Leu Leu Met Ile Val Leu Ile Pro Glu Pro
2525                2530                2535

Glu Lys Gln Arg Ser Gln Thr Asp Asn Gln Leu Ala Val Phe Leu
2540                2545                2550

Ile Cys Val Met Thr Leu Val Ser Ala Val Ala Ala Asn Glu Met
2555                2560                2565

Gly Trp Leu Asp Lys Thr Lys Ser Asp Ile Ser Ser Leu Phe Gly
2570                2575                2580

Gln Arg Ile Glu Val Lys Glu Asn Phe Ser Met Gly Glu Phe Leu
2585                2590                2595

Leu Asp Leu Arg Pro Ala Thr Ala Trp Ser Leu Tyr Ala Val Thr
2600                2605                2610

Thr Ala Val Leu Thr Pro Leu Leu Lys His Leu Ile Thr Ser Asp
2615                2620                2625
```

-continued

```
Tyr Ile Asn Thr Ser Leu Thr Ser Ile Asn Val Gln Ala Ser Ala
            2630                2635                2640

Leu Phe Thr Leu Ala Arg Gly Phe Pro Phe Val Asp Val Gly Val
            2645                2650                2655

Ser Ala Leu Leu Leu Ala Ala Gly Cys Trp Gly Gln Val Thr Leu
            2660                2665                2670

Thr Val Thr Val Thr Ala Ala Thr Leu Leu Phe Cys His Tyr Ala
            2675                2680                2685

Tyr Met Val Pro Gly Trp Gln Ala Glu Ala Met Arg Ser Ala Gln
            2690                2695                2700

Arg Arg Thr Ala Ala Gly Ile Met Lys Asn Ala Val Val Asp Gly
            2705                2710                2715

Ile Val Ala Thr Asp Val Pro Glu Leu Glu Arg Thr Thr Pro Ile
            2720                2725                2730

Met Gln Lys Lys Val Gly Gln Ile Met Leu Ile Leu Val Ser Leu
            2735                2740                2745

Ala Ala Val Val Val Asn Pro Ser Val Lys Thr Val Arg Glu Ala
            2750                2755                2760

Gly Ile Leu Ile Thr Ala Ala Ala Val Thr Leu Trp Glu Asn Gly
            2765                2770                2775

Ala Ser Ser Val Trp Asn Ala Thr Thr Ala Ile Gly Leu Cys His
            2780                2785                2790

Ile Met Arg Gly Gly Trp Leu Ser Cys Leu Ser Ile Thr Trp Thr
            2795                2800                2805

Leu Ile Lys Asn Met Glu Lys Pro Gly Leu Lys Arg Gly Gly Ala
            2810                2815                2820

Lys Gly Arg Thr Leu Gly Glu Val Trp Lys Glu Arg Leu Asn Gln
            2825                2830                2835

Met Thr Lys Glu Glu Phe Thr Arg Tyr Arg Lys Glu Ala Ile Ile
            2840                2845                2850

Glu Val Asp Arg Ser Ala Ala Lys His Ala Arg Lys Glu Gly Asn
            2855                2860                2865

Val Thr Gly Gly His Pro Val Ser Arg Gly Thr Ala Lys Leu Arg
            2870                2875                2880

Trp Leu Val Glu Arg Arg Phe Leu Glu Pro Val Gly Lys Val Ile
            2885                2890                2895

Asp Leu Gly Cys Gly Arg Gly Gly Trp Cys Tyr Tyr Met Ala Thr
            2900                2905                2910

Gln Lys Arg Val Gln Glu Val Arg Gly Tyr Thr Lys Gly Gly Pro
            2915                2920                2925

Gly His Glu Glu Pro Gln Leu Val Gln Ser Tyr Gly Trp Asn Ile
            2930                2935                2940

Val Thr Met Lys Ser Gly Val Asp Val Phe Tyr Arg Pro Ser Glu
            2945                2950                2955

Cys Cys Asp Thr Leu Leu Cys Asp Ile Gly Glu Ser Ser Ser Ser
            2960                2965                2970

Ala Glu Val Glu Glu His Arg Thr Ile Arg Val Leu Glu Met Val
            2975                2980                2985

Glu Asp Trp Leu His Arg Gly Pro Arg Glu Phe Cys Val Lys Val
            2990                2995                3000

Leu Cys Pro Tyr Met Pro Lys Val Ile Glu Lys Met Glu Leu Leu
            3005                3010                3015
```

-continued

| | | | | | | | | | | | |
|---|---|---|---|---|---|---|---|---|---|---|---|
| Gln | Arg | Arg | Tyr | Gly | Gly | Gly | Leu | Val | Arg | Asn | Pro | Leu | Ser | Arg |
| | 3020 | | | | | 3025 | | | | 3030 | |
| Asn | Ser | Thr | His | Glu | Met | Tyr | Trp | Val | Ser | Arg | Ala | Ser | Gly | Asn |
| | 3035 | | | | | 3040 | | | | 3045 | |
| Val | Val | His | Ser | Val | Asn | Met | Thr | Ser | Gln | Val | Leu | Leu | Gly | Arg |
| | 3050 | | | | | 3055 | | | | 3060 | |
| Met | Glu | Lys | Arg | Thr | Trp | Lys | Gly | Pro | Gln | Tyr | Glu | Glu | Asp | Val |
| | 3065 | | | | | 3070 | | | | 3075 | |
| Asn | Leu | Gly | Ser | Gly | Thr | Arg | Ala | Val | Gly | Lys | Pro | Leu | Leu | Asn |
| | 3080 | | | | | 3085 | | | | 3090 | |
| Ser | Asp | Thr | Ser | Lys | Ile | Lys | Asn | Arg | Ile | Glu | Arg | Leu | Arg | Arg |
| | 3095 | | | | | 3100 | | | | 3105 | |
| Glu | Tyr | Ser | Ser | Thr | Trp | His | His | Asp | Glu | Asn | His | Pro | Tyr | Arg |
| | 3110 | | | | | 3115 | | | | 3120 | |
| Thr | Trp | Asn | Tyr | His | Gly | Ser | Tyr | Asp | Val | Lys | Pro | Thr | Gly | Ser |
| | 3125 | | | | | 3130 | | | | 3135 | |
| Ala | Ser | Ser | Leu | Val | Asn | Gly | Val | Val | Arg | Leu | Leu | Ser | Lys | Pro |
| | 3140 | | | | | 3145 | | | | 3150 | |
| Trp | Asp | Thr | Ile | Thr | Asn | Val | Thr | Thr | Met | Ala | Met | Thr | Asp | Thr |
| | 3155 | | | | | 3160 | | | | 3165 | |
| Thr | Pro | Phe | Gly | Gln | Gln | Arg | Val | Phe | Lys | Glu | Lys | Val | Asp | Thr |
| | 3170 | | | | | 3175 | | | | 3180 | |
| Lys | Ala | Pro | Glu | Pro | Pro | Glu | Gly | Val | Lys | Tyr | Val | Leu | Asn | Glu |
| | 3185 | | | | | 3190 | | | | 3195 | |
| Thr | Thr | Asn | Trp | Leu | Trp | Ala | Phe | Leu | Ala | Arg | Glu | Lys | Arg | Pro |
| | 3200 | | | | | 3205 | | | | 3210 | |
| Arg | Met | Cys | Ser | Arg | Glu | Glu | Phe | Ile | Arg | Lys | Val | Asn | Ser | Asn |
| | 3215 | | | | | 3220 | | | | 3225 | |
| Ala | Ala | Leu | Gly | Ala | Met | Phe | Glu | Glu | Gln | Asn | Gln | Trp | Arg | Ser |
| | 3230 | | | | | 3235 | | | | 3240 | |
| Ala | Arg | Glu | Ala | Val | Glu | Asp | Pro | Lys | Phe | Trp | Glu | Met | Val | Asp |
| | 3245 | | | | | 3250 | | | | 3255 | |
| Glu | Glu | Arg | Glu | Ala | His | Leu | Arg | Gly | Glu | Cys | His | Thr | Cys | Ile |
| | 3260 | | | | | 3265 | | | | 3270 | |
| Tyr | Asn | Met | Met | Gly | Lys | Arg | Glu | Lys | Lys | Pro | Gly | Glu | Phe | Gly |
| | 3275 | | | | | 3280 | | | | 3285 | |
| Lys | Ala | Lys | Gly | Ser | Arg | Ala | Ile | Trp | Phe | Met | Trp | Leu | Gly | Ala |
| | 3290 | | | | | 3295 | | | | 3300 | |
| Arg | Phe | Leu | Glu | Phe | Glu | Ala | Leu | Gly | Phe | Leu | Asn | Glu | Asp | His |
| | 3305 | | | | | 3310 | | | | 3315 | |
| Trp | Leu | Gly | Arg | Lys | Asn | Ser | Gly | Gly | Gly | Val | Glu | Gly | Leu | Gly |
| | 3320 | | | | | 3325 | | | | 3330 | |
| Leu | Gln | Lys | Leu | Gly | Tyr | Ile | Leu | Arg | Glu | Val | Gly | Thr | Arg | Pro |
| | 3335 | | | | | 3340 | | | | 3345 | |
| Gly | Gly | Lys | Ile | Tyr | Ala | Asp | Asp | Thr | Ala | Gly | Trp | Asp | Thr | Arg |
| | 3350 | | | | | 3355 | | | | 3360 | |
| Ile | Thr | Arg | Ala | Asp | Leu | Glu | Asn | Glu | Ala | Lys | Val | Leu | Glu | Leu |
| | 3365 | | | | | 3370 | | | | 3375 | |
| Leu | Asp | Gly | Glu | His | Arg | Arg | Leu | Ala | Arg | Ala | Ile | Ile | Glu | Leu |
| | 3380 | | | | | 3385 | | | | 3390 | |
| Thr | Tyr | Arg | His | Lys | Val | Val | Lys | Val | Met | Arg | Pro | Ala | Ala | Asp |
| | 3395 | | | | | 3400 | | | | 3405 | |
| Gly | Arg | Thr | Val | Met | Asp | Val | Ile | Ser | Arg | Glu | Asp | Gln | Arg | Gly |

| | | | | | | | | | | |
|---|---|---|---|---|---|---|---|---|---|---|
| | | | 3410 | | | 3415 | | | 3420 | |
| Ser | Gly | Gln | Val | Val | Thr | Tyr | Ala | Leu | Asn | Thr | Phe | Thr | Asn | Leu |
| | 3425 | | | | 3430 | | | | 3435 | |
| Ala | Val | Gln | Leu | Val | Arg | Met | Met | Glu | Gly | Glu | Gly | Val | Ile | Gly |
| | 3440 | | | | 3445 | | | | 3450 | |
| Pro | Asp | Asp | Val | Glu | Lys | Leu | Thr | Lys | Gly | Lys | Gly | Pro | Lys | Val |
| | 3455 | | | | 3460 | | | | 3465 | |
| Arg | Thr | Trp | Leu | Phe | Glu | Asn | Gly | Glu | Glu | Arg | Leu | Ser | Arg | Met |
| | 3470 | | | | 3475 | | | | 3480 | |
| Ala | Val | Ser | Gly | Asp | Asp | Cys | Val | Val | Lys | Pro | Leu | Asp | Asp | Arg |
| | 3485 | | | | 3490 | | | | 3495 | |
| Phe | Ala | Thr | Ser | Leu | His | Phe | Leu | Asn | Ala | Met | Ser | Lys | Val | Arg |
| | 3500 | | | | 3505 | | | | 3510 | |
| Lys | Asp | Ile | Gln | Glu | Trp | Lys | Pro | Ser | Thr | Gly | Trp | Tyr | Asp | Trp |
| | 3515 | | | | 3520 | | | | 3525 | |
| Gln | Gln | Val | Pro | Phe | Cys | Ser | Asn | His | Phe | Thr | Glu | Leu | Ile | Met |
| | 3530 | | | | 3535 | | | | 3540 | |
| Lys | Asp | Gly | Arg | Thr | Leu | Val | Val | Pro | Cys | Arg | Gly | Gln | Asp | Glu |
| | 3545 | | | | 3550 | | | | 3555 | |
| Leu | Val | Gly | Arg | Ala | Arg | Ile | Ser | Pro | Gly | Ala | Gly | Trp | Asn | Val |
| | 3560 | | | | 3565 | | | | 3570 | |
| Arg | Asp | Thr | Ala | Cys | Leu | Ala | Lys | Ser | Tyr | Ala | Gln | Met | Trp | Leu |
| | 3575 | | | | 3580 | | | | 3585 | |
| Leu | Leu | Tyr | Phe | His | Arg | Arg | Asp | Leu | Arg | Leu | Met | Ala | Asn | Ala |
| | 3590 | | | | 3595 | | | | 3600 | |
| Ile | Cys | Ser | Ala | Val | Pro | Val | Asn | Trp | Val | Pro | Thr | Gly | Arg | Thr |
| | 3605 | | | | 3610 | | | | 3615 | |
| Thr | Trp | Ser | Ile | His | Ala | Gly | Gly | Glu | Trp | Met | Thr | Thr | Glu | Asp |
| | 3620 | | | | 3625 | | | | 3630 | |
| Met | Leu | Glu | Val | Trp | Asn | Arg | Val | Trp | Ile | Glu | Glu | Asn | Glu | Trp |
| | 3635 | | | | 3640 | | | | 3645 | |
| Met | Glu | Asp | Lys | Thr | Pro | Val | Glu | Lys | Trp | Ser | Asp | Val | Pro | Tyr |
| | 3650 | | | | 3655 | | | | 3660 | |
| Ser | Gly | Lys | Arg | Glu | Asp | Ile | Trp | Cys | Gly | Ser | Leu | Ile | Gly | Thr |
| | 3665 | | | | 3670 | | | | 3675 | |
| Arg | Ala | Arg | Ala | Thr | Trp | Ala | Glu | Asn | Ile | Gln | Val | Ala | Ile | Asn |
| | 3680 | | | | 3685 | | | | 3690 | |
| Gln | Val | Arg | Ala | Ile | Ile | Gly | Asp | Glu | Lys | Tyr | Val | Asp | Tyr | Met |
| | 3695 | | | | 3700 | | | | 3705 | |
| Ser | Ser | Leu | Lys | Arg | Tyr | Glu | Asp | Thr | Thr | Leu | Val | Glu | Asp | Thr |
| | 3710 | | | | 3715 | | | | 3720 | |
| Val | Leu | | | | | | | | | |
| | 3725 | | | | | | | | | |